(12) United States Patent
Jeschke et al.

(10) Patent No.: US 10,131,649 B2
(45) Date of Patent: Nov. 20, 2018

(54) BICYCLIC COMPOUNDS AS PEST CONTROL AGENTS

(71) Applicant: BAYER CROPSCIENCE AKTIENGESELLSCHAFT, Monheim am Rhein (DE)

(72) Inventors: Peter Jeschke, Bergisch Gladbach (DE); Alexander Arlt, Köln (DE); Silvia Cerezo-Galvez, Langenfeld (DE); Arnd Voerste, Köln (DE); Martin Füßlein, Düsseldorf (DE); Reiner Fischer, Monheim (DE); Thomas Bretschneider, Lohmar (DE); Kerstin Ilg, Köln (DE); Olga Malsam, Rösrath (DE); Peter Lösel, Leverkusen (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/531,793

(22) PCT Filed: Dec. 1, 2015

(86) PCT No.: PCT/EP2015/078164
§ 371 (c)(1),
(2) Date: May 31, 2017

(87) PCT Pub. No.: WO2016/087421
PCT Pub. Date: Jun. 9, 2016

(65) Prior Publication Data
US 2017/0327487 A1    Nov. 16, 2017

(30) Foreign Application Priority Data

Dec. 2, 2014 (EP) ..................... 14195937

(51) Int. Cl.
| | |
|---|---|
| C07D 403/04 | (2006.01) |
| C07D 401/14 | (2006.01) |
| C07D 401/04 | (2006.01) |
| A01N 43/56 | (2006.01) |
| A01N 43/60 | (2006.01) |
| A01N 43/84 | (2006.01) |

(52) U.S. Cl.
CPC ........... *C07D 403/04* (2013.01); *A01N 43/56* (2013.01); *A01N 43/60* (2013.01); *A01N 43/84* (2013.01); *C07D 401/04* (2013.01); *C07D 401/14* (2013.01)

(58) Field of Classification Search
CPC .. C07D 403/04; C07D 401/04; C07D 401/14; A01N 43/56; A01N 43/60; A01N 43/84
See application file for complete search history.

(56) References Cited

U.S. PATENT DOCUMENTS

| | | | |
|---|---|---|---|
| 8,865,622 | B2 | 10/2014 | Andersch et al. |
| 2008/0033020 | A1 | 2/2008 | Mansfield et al. |
| 2012/0165345 | A1 | 6/2012 | Bretschneider et al. |
| 2014/0249149 | A1 | 9/2014 | Greul et al. |
| 2014/0256728 | A1 | 9/2014 | Gruel et al. |

FOREIGN PATENT DOCUMENTS

| | | |
|---|---|---|
| CN | 103 450 152 A | 12/2013 |
| EP | 2 132 987 A1 | 12/2009 |
| WO | 2006/008191 A1 | 1/2006 |
| WO | 2012/000896 A2 | 1/2012 |
| WO | 2012/038476 A1 | 3/2012 |
| WO | 2012/118139 A1 | 9/2012 |
| WO | 2013/064460 A1 | 5/2013 |
| WO | 2013/064461 A2 | 5/2013 |
| WO | 2013/064521 A1 | 5/2013 |
| WO | 2014/126580 A1 | 8/2014 |
| WO | 2015/038503 A1 | 3/2015 |
| WO | 2016/071499 A1 | 5/2016 |

OTHER PUBLICATIONS

Wen et al. (Pesticide Biochemistry and Physiology 98 (2010) 248-253).*
Zhang et al. (European Journal of Medicinal Chemistry 126 (2017) 669-674).*
Singh et al. (Journal de Mycologie Médicale (2012) 22, 134-141).*
International Search Report of PCT/EP2015/078164 dated Jan. 2, 2016.
Vidyacharan et al. "A facile synthesis of 2H-indazoles under neat conditions and further transformation into aza-Y-carboline alkaloid analogues in a tandem one-pot fashion†", RSC Advances (2014), vol. 4, No. 65, p. 34232-34236.

* cited by examiner

*Primary Examiner* — Robert H Havlin
(74) *Attorney, Agent, or Firm* — McBee Moore Woodward & Vanik IP, LLC

(57) ABSTRACT

The present application relates to novel bicyclic compounds, to compositions comprising these compounds, to their use for controlling animal pests and to processes and intermediates for their preparation.

18 Claims, No Drawings

BICYCLIC COMPOUNDS AS PEST CONTROL AGENTS

CROSS REFERENCE TO RELATED APPLICATIONS

This application is a § 371 National State Application of PCT/EP2015/078164, filed Dec. 1, 2015, which claims priority to European Application No. 14195937.9 filed Dec. 2, 2014.

BACKGROUND OF THE INVENTION

Field of the Invention

The present application relates to novel bicyclic compounds, to compositions comprising these compounds, to their use for controlling animal pests and to processes and intermediates for their preparation.

Description of Related Art

Recently, bicyclic compounds having insecticidal properties have been disclosed (WO 2015/038503 A1).

WO 2003/090751 A1 describes the preparation and pharmaceutical use of MMP-13-selective metalloproteinase inhibitors containing, inter alia, a 4-[[2-(pyridin-3-yl)-2H-indazolyl-5-yl]oxy] fragment.

Modern crop protection compositions have to meet many demands, for example in relation to extent, persistence and spectrum of their action and possible use. Questions of toxicity and of combinability with other active compounds or formulation auxiliaries play a role, as does the question of the expense that the synthesis of an active compound requires. In addition, resistances can occur. For all these reasons alone, the search for novel crop protection compositions cannot be considered complete, and there is a constant need for novel compounds having improved properties compared to the known compounds, at least in relation to individual aspects.

SUMMARY

It was an object of the present invention to provide compounds which widen the spectrum of the pesticides under various aspects.

The object, and further objects which are not stated explicitly but can be discerned or derived from the connections discussed herein, are achieved by compounds of the formula (I)

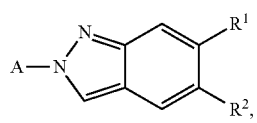

(I)

in which
A represents a radical from the group consisting of (A-b) to (A-f)

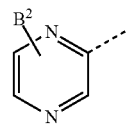
(A-b)

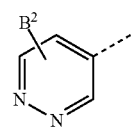
(A-c)

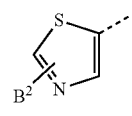
(A-d)

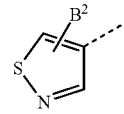
(A-e)

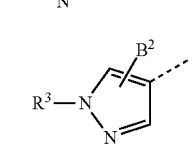
(A-f)

where the broken line represents the bond to the nitrogen atom of the bicycle of the formula (I) and $B^2$ represents a radical from the group consisting of hydrogen, halogen, cyano, nitro, alkyl, haloalkyl, alkoxy, haloalkoxy and in each case optionally substituted cycloalkyl and cycloalkenyl, $R^1$ represents a radical from the group consisting of hydrogen, alkyl, alkoxy and cyano, $R^2$ a) represents a B radical from the group consisting of

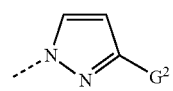
(B-1)

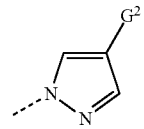
(B-2)

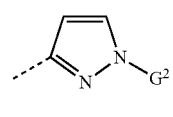
(B-3)

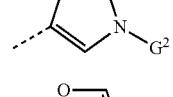
(B-4)

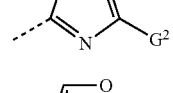
(B-5)

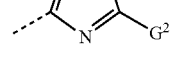
(B-6)

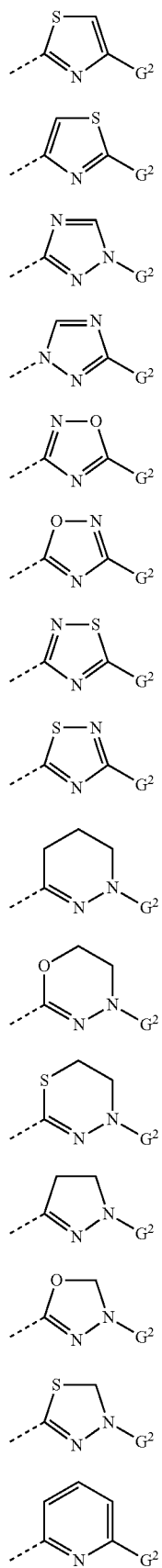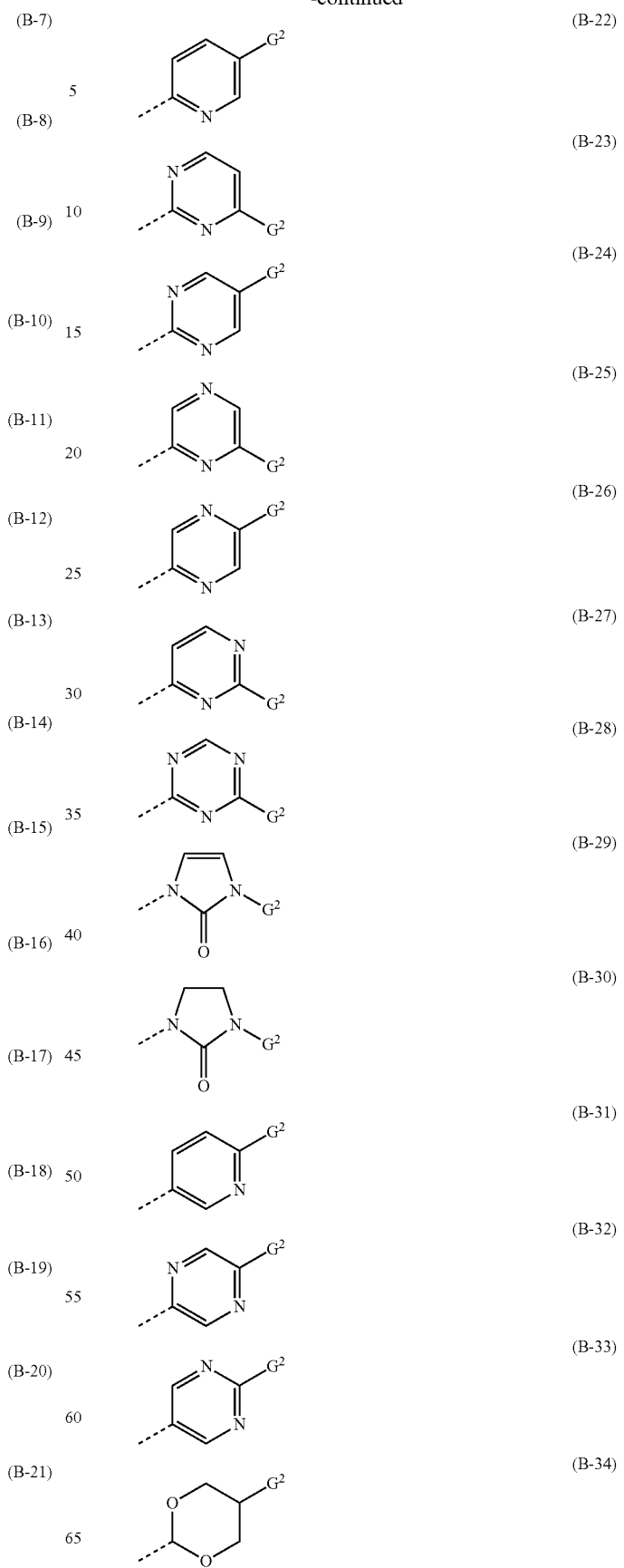

-continued

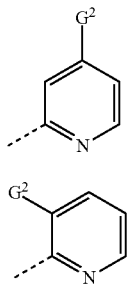 (B-35)

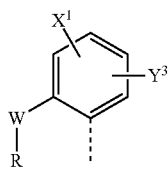 (B-36)

where the broken line represents the bond to the carbon atom of the bicycle of the formula (I) or R² b) represents a radical from the group consisting of (D-1) to (D-3)

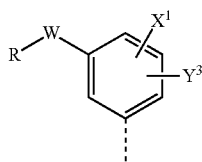 (D-1)

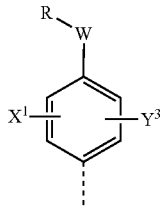 (D-2)

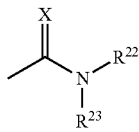 (D-3)

where the broken line represents the bond to the carbon atom of the bicycle of the formula (I) or R² c) represents a radical of the formula

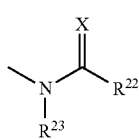

or

R² d) represents a radical of the formula

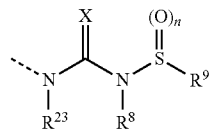

or

R² e) represents a radical from the group consisting of (F-1) to (F-11)

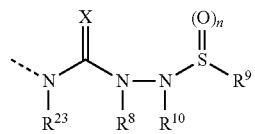 (F-1)

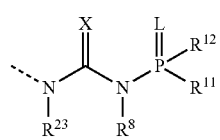 (F-2)

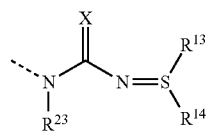 (F-3)

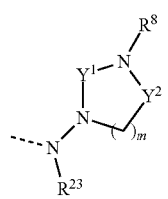 (F-4)

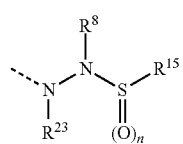 (F-5)

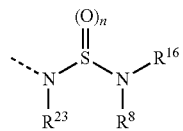 (F-6)

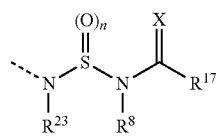 (F-7)

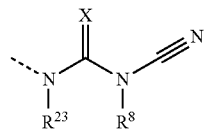 (F-8)

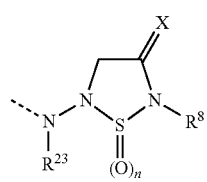 (F-9)

(F-10)

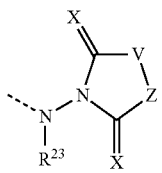
(F-11)

where the broken line represents the bond to the carbon atom in the formula (I) or $R^2$ f) represents a radical from the group consisting of haloalkyl, carboxyl and amino,
in which $G^2$ represents hydrogen or a radical from the group consisting of halogen, nitro, amino, cyano, alkylamino, haloalkylamino, dialkylamino, alkyl, haloalkyl, saturated or unsaturated cycloalkyl which is optionally substituted and optionally interrupted by one or more heteroatoms, cycloalkylalkyl, alkoxy, haloalkoxy, alkoxyalkyl, halogenated alkoxyalkyl, alkylthioalkyl, alkylsulphinylalkyl, alkylsulphonylalkyl, bis(alkoxy)alkyl, bis(haloalkoxy)alkyl, alkoxy(alkylsulphanyl)alkyl, alkoxy(alkylsulphinyl)alkyl, alkoxy(alkylsulphonyl)alkyl, bis(alkylsulphanyl)alkyl, bis(haloalkylsulphanyl)alkyl, bis(hydroxyalkylsulphanyl)alkyl, alkoxycarbonyl, alkoxycarbonylalkyl, alpha-hydroxyiminoalkoxycarbonylalkyl, alpha-alkoxyiminoalkoxycarbonylalkyl, $C(X^2)NR^3R^4$, $NR^6R^7$, alkylthio, alkylsulphinyl, alkylsulphonyl, haloalkylthio, haloalkylsulphinyl, haloalkylsulphonyl, the heterocyclyl radicals dioxanyl, dioxolanyl, dioxepanyl, dioxocanyl, oxathianyl, oxathiolanyl, oxathiepanyl, oxathiocanyl, dithianyl, dithiolanyl, dithiepanyl, dithiocanyl, oxathianyl oxide, oxathiolanyl oxide, oxathiepanyl oxide, oxathiocanyl oxide, oxathianyl dioxide, oxathiolanyl dioxide, oxathiepanyl dioxide, oxathiocanyl dioxide, morpholinyl, triazolinonyl, oxazolinyl, dihydrooxadiazinyl, dihydrodioxazinyl, dihydrooxazolyl, dihydrooxazinyl and pyrazolinonyl (which for their turn may be substituted by alkyl, haloalkyl, alkoxy and alkoxyalkyl), phenyl (which for its turn may be substituted by halogen, cyano, nitro, alkyl and haloalkyl), the heteroaryl radicals pyridyl, pyridyl N-oxide, pyrimidyl, imidazolyl, pyrazolyl, oxazolyl, thiazolyl, furanyl, thienyl, triazolyl, tetrazolyl, oxadiazolyl, thiadiazolyl, pyrazinyl, triazinyl, tetrazinyl and isoquinolinyl (which for their turn may be substituted by halogen, nitro, alkyl, haloalkyl, alkoxy, haloalkoxy, alkoxyalkyl, alkylthio, alkylthioalkyl and cycloalkyl) and the heteroarylalkyl radicals triazolylalkyl, pyridylalkyl, pyrimidylalkyl and oxadiazolylalkyl (which for their turn may be substituted by halogen and alkyl),
or $G^2$ represents a C radical from the group consisting of (C-1) to (C-9)

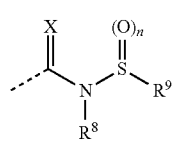
(C-1)

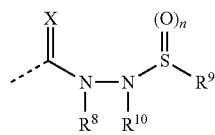
(C-2)

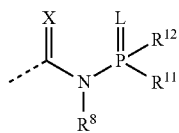
(C-3)

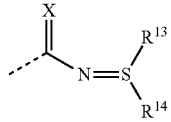
(C-4)

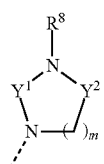
(C-5)

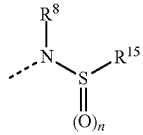
(C-6)

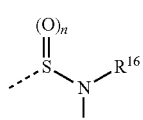
(C-7)

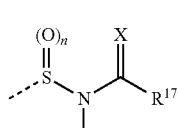
(C-8)

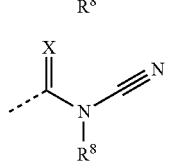
(C-9)

where the broken line represents the bond to the B radicals,

X represents oxygen or sulphur, $X^1$ represents a radical from the group consisting of hydrogen, halogen, cyano, nitro, alkyl, haloalkyl, cycloalkyl, alkoxy and haloalkoxy, $X^2$ represents oxygen, sulphur, $NR^5$ or NOH, L represents oxygen or sulphur, V—Z represents $R^{24}CH$—$CHR^{25}$ or $R^{24}C$=$CR^{25}$, n represents 1 or 2, m represents 1, 2, 3 or 4, R represents $NR^{18}R^{19}$, or represents an in each case optionally substituted radical from the group consisting of alkyl, alkenyl, alkynyl, alkoxyalkyl, alkyl-S-alkyl, alkyl-S(O)-alkyl, alkyl-S(O)$_2$-alkyl, $R^{18}$—CO-alkyl, $NR^{18}R^{19}$—CO-alkyl, cycloalkyl, cycloalkenyl, cycloalkylalkyl, cycloalkenylalkyl, heterocyclyl, heterocyclylalkyl, phenyl, phenylalkyl, hetaryl and hetarylalkyl, $R^3$ represents hydrogen or alkyl, $R^4$ represents a radical from the group consisting of hydrogen, alkyl, haloalkyl, cyanoalkyl, alkynyl, cycloalkyl, cycloalkylalkyl, alkoxyalkyl, alkoxycarbonyl, alkoxycarbonylalkyl, alkylthioalkyl, alkylsulphinylalkyl, alkylsulphonylalkyl, aryl, arylalkyl and hetarylalkyl, $R^5$ represents a radical from the group consisting of hydrogen, alkyl, haloalkyl, cyanoalkyl, alkynyl, cycloalkyl, cycloalkylalkyl, alkoxyalkyl, alkoxycarbonyl, alkoxycarbonylalkyl, alkylthioalkyl, aryl, arylalkyl and hetarylalkyl, or $R^3$ and $R^4$ together with the nitrogen atom to which they are attached form a ring which may contain one or more further heteroatoms from the group consisting of nitrogen, oxygen and sulphur, or $R^3$ and $R^5$ together with the nitrogen atoms to which they are attached form a ring, $R^6$ represents hydrogen or alkyl, $R^7$ represents a radical from the group consisting of hydrogen, alkyl, haloalkyl, cyanoalkyl, alkynyl, cycloalkyl, cycloalkylalkyl, alkoxy, haloalkoxy, alkoxyalkyl, alkylthioalkyl, alkylsulphinylalkyl, alkylsulphonylalkyl, alkoxycarbonyl, alkoxycarbonylalkyl, alkylthioalkyl, aryl, arylalkyl and hetarylalkyl, or $R^6$ and $R^7$ together with the nitrogen atom to which they are attached form a ring which may contain one or more further heteroatoms from the group consisting of nitrogen, oxygen and sulphur, $R^8$ represents a radical from the group consisting of hydrogen, alkyl, haloalkyl, cyanoalkyl, alkoxy, haloalkoxy, alkenyl, alkoxyalkyl, in each case optionally halogen-substituted alkylcarbonyl and alkylsulphonyl, optionally halogen-substituted alkoxycarbonyl, optionally halogen-, alkyl-, alkoxy-, haloalkyl- and cyano-substituted cycloalkylcarbonyl, or a cation, or an optionally alkyl- or arylalkyl-substituted ammonium ion, $R^9$ represents a radical from the group consisting of in each case optionally substituted alkyl, alkenyl and alkynyl, in each case optionally substituted cycloalkyl, cycloalkylalkyl and cycloalkenyl, in which the rings may contain at least one heteroatom from the group consisting of sulphur, oxygen (where oxygen atoms must not be directly adjacent to one another) and nitrogen, in each case optionally substituted aryl, heteroaryl, arylalkyl and heteroarylalkyl and an optionally substituted amino group, $R^8$ and $R^9$ in the radicals (C-1) and (F-1) may also form, together with the N—S(O)n group to which they are attached, a saturated or unsaturated and optionally substituted 4- to 8-membered ring which may contain one or more further heteroatoms from the group consisting of sulphur, oxygen (where oxygen atoms must not be directly adjacent to one another) and nitrogen and/or at least one carbonyl group, $R^{10}$ represents hydrogen or alkyl, $R^8$ and $R^{10}$ in the radicals (C-2) and (F-2) may also represent, together with the nitrogen atoms to which they are attached, a saturated or unsaturated and optionally substituted 4- to 8-membered ring which may contain at least one further heteroatom from the group consisting of sulphur, oxygen (where oxygen atoms must not be directly adjacent to one another) and nitrogen and/or at least one carbonyl group, $R^9$ and $R^{10}$ in the radicals (C-2) and (F-2) may also form, together with the N—S(O)n group to which they are attached, a saturated or unsaturated and optionally substituted 4- to 8-membered ring which may contain one or more further heteroatoms from the group consisting of sulphur, oxygen (where oxygen atoms must not be directly adjacent to one another) and nitrogen and/or at least one carbonyl group, $R^{11}$ represents an in each case optionally substituted radical from the group consisting of alkyl, alkenyl, alkynyl, alkoxy, alkenyloxy, alkynyloxy, cycloalkyl, cycloalkyloxy, cycloalkenyloxy, cycloalkylalkoxy, alkylthio, alkenylthio, phenoxy, phenylthio, benzyloxy, benzylthio, heteroaryloxy, heteroarylthio, heteroarylalkoxy and heteroarylalkylthio, $R^{12}$ represents an in each case optionally substituted radical from the group consisting of alkyl, alkenyl, alkynyl, alkoxy, alkenyloxy, alkynyloxy, cycloalkyl, cycloalkyloxy, cycloalkenyloxy, cycloalkylalkoxy, alkylthio, alkenylthio, phenoxy, phenylthio, benzyloxy, benzylthio, heteroaryloxy, heteroarylthio, heteroarylalkoxy and heteroarylalkylthio, $R^{11}$ and $R^{12}$ in the radicals (C-3) and (F-3) may also form, together with the phosphorus atom to which they are attached, a saturated or unsaturated and optionally substituted 5- to 7-membered ring which may contain one or two heteroatoms from the group consisting of oxygen (where oxygen atoms must not be directly adjacent to one another) and sulphur, $R^{13}$ represents an in each case optionally substituted radical from the group consisting of alkyl, alkenyl, alkynyl, phenyl and phenylalkyl, $R^{14}$ represents an in each case optionally substituted radical from the group consisting of alkyl, alkenyl, alkynyl, phenyl and phenylalkyl, $R^{15}$ represents a radical from the group consisting of in each case optionally substituted alkyl, alkenyl and alkynyl, in each case optionally substituted cycloalkyl, cycloalkylalkyl and cycloalkenyl, in which the rings may contain at least one heteroatom from the group consisting of sulphur, oxygen (where oxygen atoms must not be directly adjacent to one another) and nitrogen, in each case optionally substituted aryl, heteroaryl, arylalkyl and heteroarylalkyl and an optionally substituted amino group, $R^8$ and $R^{15}$ in the radicals (C-6) and (F-6) may also form, together with the N—S(O)n group to which they are attached, a saturated or unsaturated and optionally substituted 4- to 8-membered ring which may contain one or more further heteroatoms from the group consisting of sulphur, oxygen (where oxygen atoms must not be directly adjacent to one another) and nitrogen and/or at least one carbonyl group, $R^{16}$ represents a radical from the group consisting of hydrogen, in each case optionally substituted alkyl, alkoxy, alkenyl and alkynyl, in each case optionally substituted cycloalkyl, cycloalkylalkyl and cycloalkenyl, in which the rings may contain at least one heteroatom from the group consisting of sulphur, oxygen (where oxygen atoms must not be directly adjacent to one another) and nitrogen, in each case optionally substituted aryl, heteroaryl, arylalkyl and heteroarylalkyl and an optionally substituted amino group, $R^8$ and $R^{16}$ in the radicals (C-7) and (F-7) may also form, together with the nitrogen atom to which they are attached, a saturated or unsaturated and optionally substituted 4- to 8-membered ring which may contain one or more further heteroatoms from the group consisting of sulphur, oxygen (where oxygen atoms must not be directly adjacent to one another) and nitrogen and/or at least one carbonyl group, $R^{17}$ represents a radical from the group consisting of in each case optionally substituted alkyl, alkoxy, alkenyl and alkynyl, in each case optionally substituted cycloalkyl, cycloalkylalkyl and cycloalkenyl, in which the rings may contain at least one heteroatom from the group consisting of sulphur, oxygen (where oxygen atoms must not be directly adjacent to one another) and nitrogen, in each case optionally substituted aryl, heteroaryl, arylalkyl and heteroarylalkyl and an optionally substituted amino group, $R^8$ and $R^{17}$ in the radicals (C-8) and (F-8) may also form, together with the N—C(X) group to which they are attached, a saturated or unsaturated and optionally substituted 4- to 8-membered ring which may contain one or more further heteroatoms from the group consisting of sulphur, oxygen (where oxygen atoms must not be directly adjacent to one another) and nitrogen and/or at least one carbonyl group, $R^{18}$ represents a radical from the group consisting of hydrogen, hydroxy, in each case optionally substituted alkyl, alkoxy, alkoxyalkyl, alkylthioalkyl, alkylsulphinylalkyl, alkylsulphonylalkyl, alkylcarbonyl, alkoxycarbonyl, alkenyl and alkynyl, in each case optionally substituted cycloalkyl, cycloalkylalkyl, cycloalkenyl and cycloalkenylalkyl, in which the rings may contain at least one heteroatom from the group consisting of sulphur, oxygen (where oxygen atoms must not be directly adjacent to one another) and nitrogen, in each case optionally substituted aryl, arylalkyl, heteroaryl and heteroarylalkyl and an optionally substituted amino group, $R^{19}$ represents a radical from the group consisting of hydrogen, represents an alkali metal or alkaline earth metal ion or represents an ammonium ion which is optionally mono- to tetrasubstituted by $C_1$-$C_4$-alkyl or represents an in each case optionally halogen- or cyano-substituted alkyl, alkoxy, alkoxyalkyl, alkylthioalkyl, alkylsulphinylalkyl, alkylsulphonylalkyl radical, $Y^1$ and $Y^2$ independently of one another represent C=O or $S(O)_2$, $Y^3$ represents a radical from the group consisting of hydrogen, halogen, cyano, alkyl, cycloalkyl, haloalkyl, alkoxy, haloalkoxy and $NR^{20}R^{21}$, W represents a radical from the group consisting of O, S, SO and $SO_2$, $R^{22}$ represents a radical from the group consisting of alkyl, optionally halogen-, carbamoyl-, thiocarbamoyl- or cyano-substituted cycloalkyl, haloalkyl, alkoxy, haloalkoxy, alkoxyalkyloxy, alkylthio, alkylsulphinyl, alkylsulphonyl, haloalkylthio, haloalkylsulphinyl, haloalkylsulphonyl, alkylthioalkyl, alkylsulphinylalkyl, alkylsulphonylalkyl, alkylthioalkyloxy, alkylsulphinylalkyloxy, alkylsulphonylalkyloxy, haloalkylthioalkyl, haloalkylsulphinylalkyl, haloalkylsulphonylalkyl, alkylthioalkenyl, alkylsulphinylalkenyl, alkylsulphonylalkenyl, alkenylthioalkyl, alkenylsulphinylalkyl, alkenylsulphonylalkyl, alkylcarbonylalkyl, haloalkylcarbonylalkyl, alkoxyalkyl, haloalkoxyalkyl, alkoxycarbonylalkyl, haloalkoxycarbonylalkyl, alkylaminosulphonyl, di(alkylamino)sulphonyl, or, in the case $R^2$=d), $R^{22}$ also represents optionally substituted aryl or represents a radical from the group consisting of E-1 to E-51

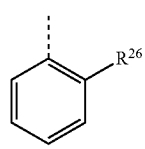

E-1

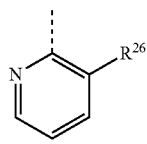

E-2

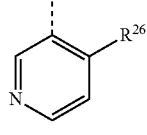

E-3

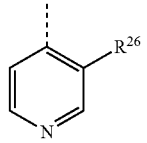

E-4

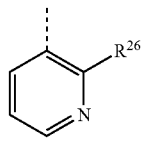

E-5

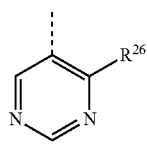

E-6

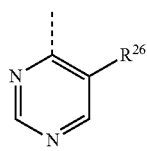

E-7

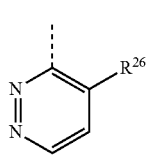

E-8

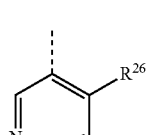

E-9

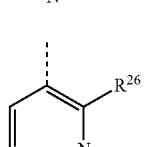

E-10

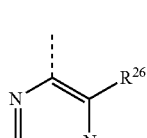

E-11

-continued
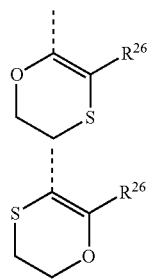
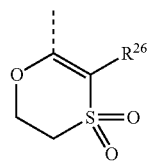
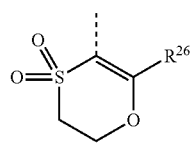
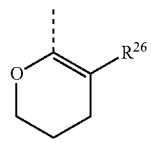
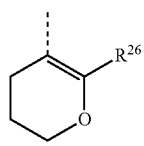
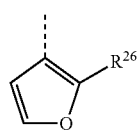
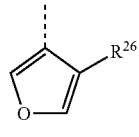
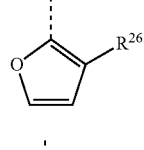
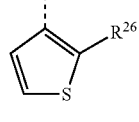
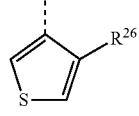
-continued
E-12
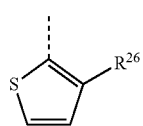
E-13
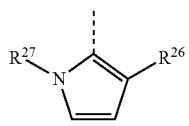
E-14
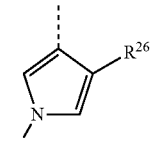
E-15
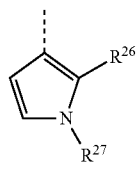
E-16
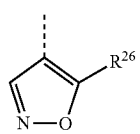
E-17
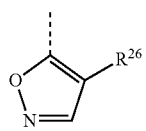
E-18
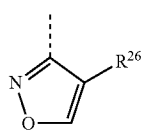
E-19
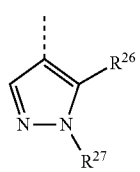
E-20
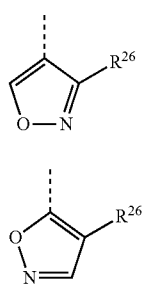
E-21
E-22
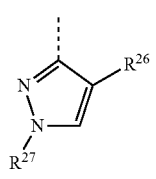
E-23
E-24
E-25
E-26
E-27
E-28
E-29
E-30
E-31
E-32

-continued

E-33 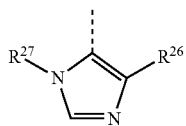

E-34 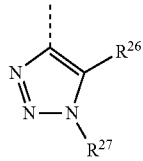

E-35 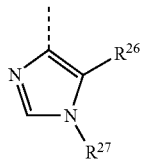

E-36 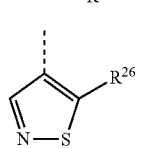

E-37 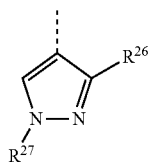

E-38 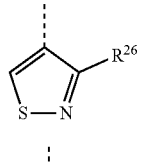

E-39 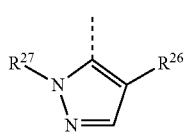

E-40 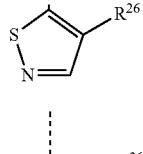

E-41 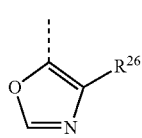

E-42 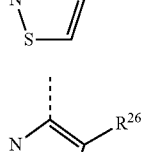

E-43 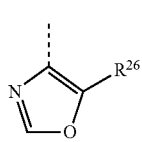

E-44 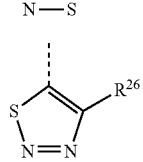

E-45 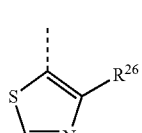

E-46 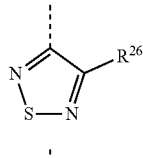

E-47 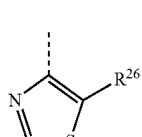

E-48 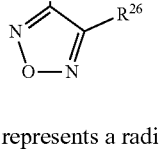

E-49 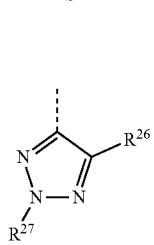

E-50 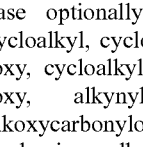

E-51 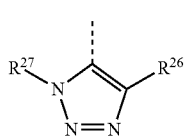

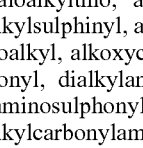

$R^{20}$ represents a radical from the group consisting of hydrogen, halogen, cyano, nitro, amino, hydroxy and in each case optionally substituted alkyl, alkenyl, alkynyl, cycloalkyl, cycloalkylalkyl, alkoxy, alkenyloxy, alkynyloxy, cycloalkyloxy, alkylcarbonyloxy, alkenylcarbonyloxy, alkynylcarbonyloxy, cycloalkylcarbonyloxy, alkoxycarbonyloxy, alkylsulphonyloxy, alkylamino, alkenylamino, alkynylamino, cycloalkylamino, alkylthio, haloalkylthio, alkenylthio, alkynylthio, cycloalkylthio, alkylsulphinyl, alkylsulphonyl, alkylcarbonyl, alkoxyiminoalkyl, alkoxycarbonyl, aminocarbonyl, alkylaminocarbonyl, dialkylaminocarbonyl, aminothiocarbonyl, alkylaminosulphonyl, alkylsulphonylamino, alkylcarbonylamino, alkenylcarbonylamino, alkynylcarbonylamino, cycloalkylcarbonylamino, alkoxycarbonylamino, alkylthiocarbonylamino, bicycloalkyl, aryl, aryloxy, heteroaryl and heteroaryloxy, where the substituents independently of one another are selected from the group consisting of halogen, cyano, nitro, hydroxy, amino, alkyl and haloalkyl, $R^{21}$ represents a radical from the group consisting of hydrogen, alkyl, cycloalkyl, haloalkyl, alkenyl, alkynyl, cycloalkylalkyl, cyanoalkyl, alkylcarbonyl, alkenylcarbonyl, haloalkylcarbonyl, haloalkenylcarbonyl, alkoxyalkyl, alkoxycarbonyl, alkylsulphonyl and haloalkylsulphonyl, $R^{23}$ represents a radical from the group consisting of hydrogen, alkyl, alkenyl, alkynyl, cycloalkyl, cycloalkenyl, alkoxy, alkenyloxy, alkynyloxy, cycloalkyloxy, alkylthioalkyl, alkenylthioalkyl, cyanoalkyl, alkoxyalkyl and $R^{24}$ represents hydrogen or an in each case optionally substituted radical from the group consisting of alkyl, alkenyl, alkynyl, phenyl and phenylalkyl and $R^{25}$ represents hydrogen or an in each case optionally substituted radical from the group consisting of alkyl, alkenyl, alkynyl, phenyl and phenylalkyl, $R^{27}$ represents hydrogen or alkyl and $R^{26}$ represents hydrogen, alkyl, haloalkyl, alkenyl, alkynyl, cycloalkyl, cycloalkylalkyl, alkoxyalkyl, alkylthioalkyl, alkylsulphinylalkyl, alkylsulphonylalkyl or cyanoalkyl and compounds of the formula (I) in which
A represents the A radical (A-a)

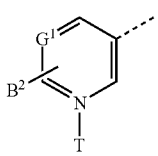

(A-a)

where the broken line represents the bond to the nitrogen atom of the bicycle of the formula (I) and $G^1$ represents N or C—$B^1$, $B^1$ represents a radical from the group consisting of hydrogen, halogen, cyano, nitro, alkyl, haloalkyl, alkoxy, haloalkoxy and in each case optionally substituted cycloalkyl and cycloalkenyl, $B^2$ represents a radical from the group consisting of hydrogen, halogen, cyano, nitro, alkyl, haloalkyl, alkoxy, haloalkoxy and in each case optionally substituted cycloalkyl and cycloalkenyl, T represents oxygen or an electron pair, $R^1$ represents a radical from the group consisting of hydrogen, alkyl, alkoxy and cyano, $R^2$ a) represents a B radical from the group consisting of

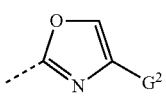

(B-5)

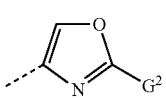

(B-6)

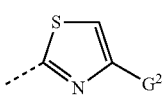

(B-7)

-continued

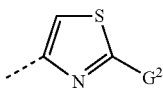

(B-8)

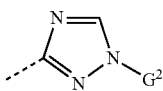

(B-9)

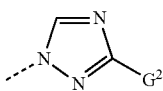

(B-10)

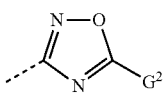

(B-11)

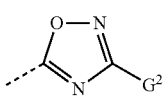

(B-12)

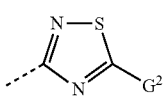

(B-13)

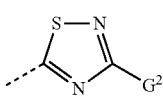

(B-14)

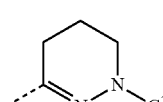

(B-15)

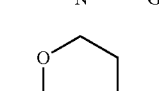

(B-16)

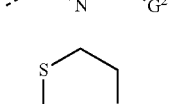

(B-17)

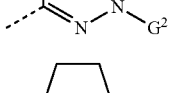

(B-18)

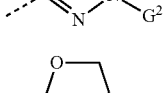

(B-19)

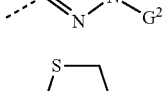

(B-20)

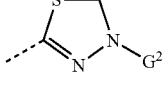

(B-28)

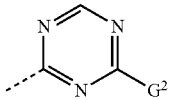

(B-29)

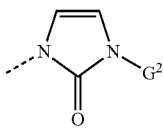

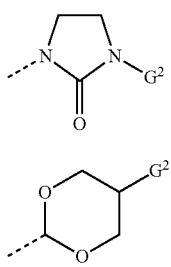
(B-30)

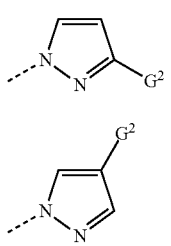
(B-34)

where the broken line represents the bond to the carbon atom of the bicycle of the formula (I), where
G² represents hydrogen or a radical from the group consisting of halogen, nitro, amino, cyano, alkylamino, haloalkylamino, dialkylamino, alkyl, haloalkyl, alkoxycarbonylalkyl, saturated or unsaturated cycloalkyl which is optionally substituted and optionally interrupted by one or more heteroatoms, cycloalkylalkyl, alkoxy, haloalkoxy, alkoxyalkyl, halogenated alkoxyalkyl, alkylthioalkyl, alkylsulphinylalkyl, alkylsulphonylalkyl, bis(alkoxy)alkyl, bis(haloalkoxy)alkyl, alkoxy(alkylsulphanyl)alkyl, alkoxy(alkylsulphinyl)alkyl, alkoxy(alkylsulphonyl)alkyl, bis(alkylsulphanyl)alkyl, bis(haloalkylsulphanyl)alkyl, bis(hydroxyalkylsulphanyl)alkyl, alkoxycarbonyl, alkoxycarbonylalkyl, alpha-hydroxyiminoalkoxycarbonylalkyl, alpha-alkoxyiminoalkoxycarbonylalkyl, C(X²)NR³R⁴, NR⁶R⁷, alkylthio, alkylsulphinyl, alkylsulphonyl, haloalkylthio, haloalkylsulphinyl, haloalkylsulphonyl, the heterocyclyl radicals dioxanyl, dioxolanyl, dioxepanyl, dioxocanyl, oxathianyl, oxathiolanyl, oxathiepanyl, oxathiocanyl, dithianyl, dithiolanyl, dithiepanyl, dithiocanyl, oxathianyl oxide, oxathiolanyl oxide, oxathiepanyl oxide, oxathiocanyl oxide, oxathianyl dioxide, oxathiolanyl dioxide, oxathiepanyl dioxide, oxathiocanyl dioxide, morpholinyl, triazolinonyl, oxazolinyl, dihydrooxadiazinyl, dihydrodioxazinyl, dihydrooxazolyl, dihydrooxazinyl and pyrazolinonyl (which for their turn may be substituted by alkyl, haloalkyl, alkoxy and alkoxyalkyl), phenyl (which for its turn may be substituted by halogen, cyano, nitro, alkyl and haloalkyl), the heteroaryl radicals pyridyl, pyridyl N-oxide, pyrimidyl, imidazolyl, pyrazolyl, oxazolyl, thiazolyl, furanyl, thienyl, triazolyl, tetrazolyl, oxadiazolyl, thiadiazolyl, pyrazinyl, triazinyl, tetrazinyl and isoquinolinyl (which for their turn may be substituted by halogen, nitro, alkyl, haloalkyl, alkoxy, haloalkoxy, alkoxyalkyl, alkylthio, alkylthioalkyl and cycloalkyl) and the heteroarylalkyl radicals triazolylalkyl, pyridylalkyl, pyrimidylalkyl and oxadiazolylalkyl (which for their turn may be substituted by halogen and alkyl), or R² aa) represents one of the B radicals below

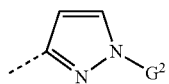
(B-1)

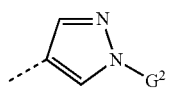
(B-2)

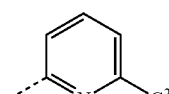
(B-3)

(B-4)

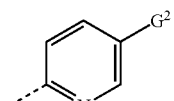
(B-21)

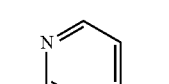
(B-22)

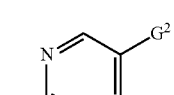
(B-23)

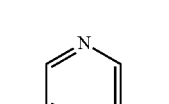
(B-24)

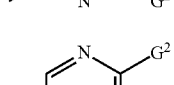
(B-25)

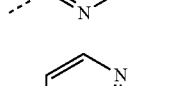
(B-26)

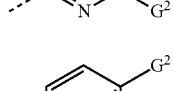
(B-27)

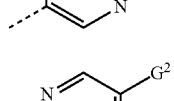
(B-31)

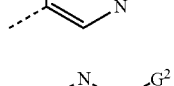
(B-32)

(B-33)

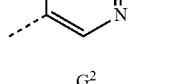
(B-35)

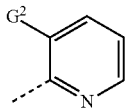
(B-36)

where the broken line represents the bond to the carbon atom of the bicycle of the formula (I), where G² represents a radical from the group consisting of halogen, nitro, amino, cyano, alkylamino, haloalkylamino, dialkylamino, saturated or unsaturated cycloalkyl which is optionally substituted and optionally interrupted by one or more heteroatoms, cycloalkylalkyl, haloalkoxy, alkoxyalkyl, halogenated alkoxyalkyl, alkylthioalkyl, alkylsulphinylalkyl, alkylsulphonylalkyl, haloalkylthioalkyl, haloalkylsulphinylalkyl, haloalkylsulphonylalkyl, bis(alkoxy)alkyl, bis(haloalkoxy)alkyl, alkoxy(alkylsulphanyl)alkyl, alkoxy(alkylsulphinyl)alkyl, alkoxy(alkylsulphonyl)alkyl, bis(alkylsulphanyl)alkyl, bis(haloalkylsulphanyl)alkyl, bis(hydroxyalkylsulphanyl)alkyl, alkoxycarbonyl, alkoxycarbonylalkyl, alpha-hydroxyiminoalkoxycarbonylalkyl, alpha-alkoxyiminoalkoxycarbonylalkyl, C(X²)NR³R⁴, NR⁶R⁷, alkylthio, alkylsulphinyl, alkylsulphonyl, haloalkylthio, haloalkylsulphinyl, haloalkylsulphonyl, the heterocyclyl radicals dioxanyl, dioxolanyl, dioxepanyl, dioxocanyl, oxathianyl, oxathiolanyl, oxathiepanyl, oxathiocanyl, dithianyl, dithiolanyl, dithiepanyl, dithiocanyl, oxathianyl oxide, oxathiolanyl oxide, oxathiepanyl oxide, oxathiocanyl oxide, oxathianyl dioxide, oxathiolanyl dioxide, oxathiepanyl dioxide, oxathiocanyl dioxide, morpholinyl, triazolinonyl, oxazolinyl, dihydrooxadiazinyl, dihydrodioxazinyl, dihydrooxazolyl, dihydrooxazinyl and pyrazolinonyl (which for their turn may be substituted by alkyl, haloalkyl, alkoxy and alkoxyalkyl), phenyl (which for its turn may be substituted by halogen, cyano, nitro, alkyl and haloalkyl), the heteroaryl radicals imidazolyl, pyrazolyl, oxazolyl, furanyl, thienyl, triazolyl, tetrazolyl, oxadiazolyl, thiadiazolyl, pyrazinyl, triazinyl, tetrazinyl and isoquinolinyl (which for their turn may be substituted by halogen, nitro, alkyl, haloalkyl, alkoxy, haloalkoxy, alkoxyalkyl, alkylthio, alkylthioalkyl and cycloalkyl) and the heteroarylalkyl radicals triazolylalkyl, pyridylalkyl, pyrimidylalkyl and oxadiazolylalkyl (which for their turn may be substituted by halogen and alkyl), or G², if R² represents one of the radicals listed under a) or aa), also represents a C radical from the group consisting of

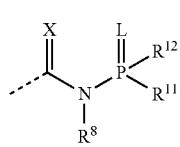
(C-2)

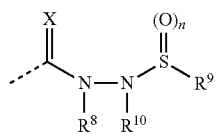
(C-3)

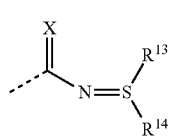
(C-4)

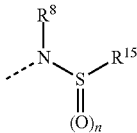
(C-6)

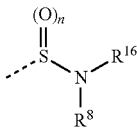
(C-7)

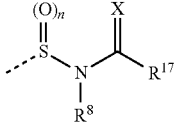
(C-8)

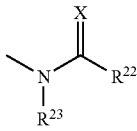
(C-9)

where the broken line represents the bond to the B radicals, or

R² c) represents a radical of the formula

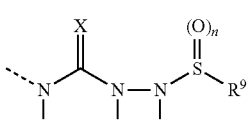

or

R² d) represents a radical of the formula

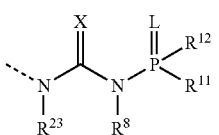

or

R² e) represents an F radical from the group consisting of

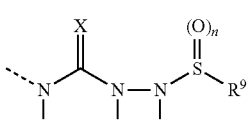
(F-2)

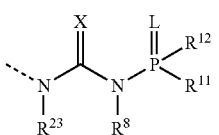
(F-3)

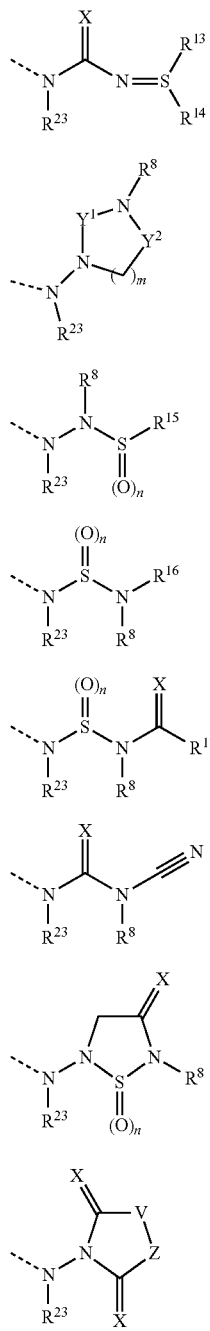

where the broken line represents the bond to the carbon atom in the formula (I) or R² f) represents a radical from the group consisting of haloalkyl, carboxyl and amino, X represents oxygen or sulphur, X² represents oxygen, sulphur, NR⁵ or NOH, L represents oxygen or sulphur, V—Z represents R²⁴CH—CHR²⁵ or R²⁴C=CR²⁵, n represents 1 or 2, m represents 1, 2, 3 or 4, R³ represents hydrogen or alkyl, R⁴ represents a radical from the group consisting of hydrogen, alkyl, haloalkyl, cyanoalkyl, alkynyl, cycloalkyl, cycloalkylalkyl, alkoxyalkyl, alkoxycarbonyl, alkoxycarbonylalkyl, alkylthioalkyl, alkylsulphinylalkyl, alkylsulphonylalkyl, aryl, arylalkyl and hetarylalkyl, R⁵ represents a radical from the group consisting of hydrogen, alkyl, haloalkyl, cyanoalkyl, alkynyl, cycloalkyl, cycloalkylalkyl, alkoxyalkyl, alkoxycarbonyl, alkoxycarbonylalkyl, alkylthioalkyl, aryl, arylalkyl and hetarylalkyl, or R³ and R⁴ together with the nitrogen atom to which they are attached form a ring which may contain one or more further heteroatoms from the group consisting of nitrogen, oxygen and sulphur, or R³ and R⁵ together with the nitrogen atoms to which they are attached form a ring, R⁶ represents hydrogen or alkyl, R⁷ represents a radical from the group consisting of hydrogen, alkyl, haloalkyl, cyanoalkyl, alkynyl, cycloalkyl, cycloalkylalkyl, alkoxy, haloalkoxy, alkoxyalkyl, alkylthioalkyl, alkylsulphinylalkyl, alkylsulphonylalkyl, alkoxycarbonyl, alkoxycarbonylalkyl, alkylthioalkyl, aryl, arylalkyl and hetarylalkyl, or R⁶ and R⁷ together with the nitrogen atom to which they are attached form a ring which may contain one or more further heteroatoms from the group consisting of nitrogen, oxygen and sulphur, R⁸ represents a radical from the group consisting of hydrogen, alkyl, haloalkyl, cyanoalkyl, alkoxy, haloalkoxy, alkenyl, alkoxyalkyl, in each case optionally halogen-substituted alkylcarbonyl and alkylsulphonyl, optionally halogen-substituted alkoxycarbonyl, optionally halogen-, alkyl-, alkoxy-, haloalkyl- and cyano-substituted cycloalkylcarbonyl, or a cation, or an optionally alkyl- or arylalkyl-substituted ammonium ion, R⁹ represents a radical from the group consisting of in each case optionally substituted alkyl, alkenyl and alkynyl, in each case optionally substituted cycloalkyl, cycloalkylalkyl and cycloalkenyl, in which the rings may contain at least one heteroatom from the group consisting of sulphur, oxygen (where oxygen atoms must not be directly adjacent to one another) and nitrogen, in each case optionally substituted aryl, heteroaryl, arylalkyl and heteroarylalkyl and an optionally substituted amino group, R¹⁰ represents hydrogen or alkyl, R⁸ and R¹⁰ in the radicals (C-2) and (F-2) may also represent, together with the nitrogen atoms to which they are attached, a saturated or unsaturated and optionally substituted 4- to 8-membered ring which may contain at least one further heteroatom from the group consisting of sulphur, oxygen (where oxygen atoms must not be directly adjacent to one another) and nitrogen and/or at least one carbonyl group, R⁹ and R¹⁰ in the radicals (C-2) and (F-2) may also form, together with the N—S(O)n group to which they are attached, a saturated or unsaturated and optionally substituted 4- to 8-membered ring which may contain one or more further heteroatoms from the group consisting of sulphur, oxygen (where oxygen atoms must not be directly adjacent to one another) and nitrogen and/or at least one carbonyl group, R¹¹ represents an in each case optionally substituted radical from the group consisting of alkyl, alkenyl, alkynyl, alkoxy, alkenyloxy, alkynyloxy, cycloalkyl, cycloalkyloxy, cycloalkenyloxy, cycloalkylalkoxy, alkylthio, alkenylthio, phenoxy, phenylthio, benzyloxy, benzylthio, heteroaryloxy, heteroarylthio, heteroarylalkoxy and heteroarylalkylthio, R¹² represents an in each case optionally substituted radical from the group consisting of alkyl, alkenyl, alkynyl, alkoxy, alkenyloxy, alkynyloxy, cycloalkyl, cycloalkyloxy, cycloalkenyloxy, cycloalkylalkoxy, alkylthio, alkenylthio, phenoxy, phenylthio, benzyloxy, benzylthio, heteroaryloxy, heteroarylthio, heteroarylalkoxy and heteroarylalkylthio, $R^{11}$ and $R^{12}$ in the radicals (C-3) and (F-3) may also form, together with the phosphorus atom to which they are attached, a saturated or unsaturated and optionally substituted 5- to 7-membered ring which may contain one or two heteroatoms from the group consisting of oxygen (where oxygen atoms must not be directly adjacent to one another) and sulphur, $R^{13}$ represents an in each case optionally substituted radical from the group consisting of alkyl, alkenyl, alkynyl, phenyl and phenylalkyl, $R^{14}$ represents an in each case optionally substituted radical from the group consisting of alkyl, alkenyl, alkynyl, phenyl and phenylalkyl, $R^{15}$ represents a radical from the group consisting of in each case optionally substituted alkyl, alkenyl and alkynyl, in each case optionally substituted cycloalkyl, cycloalkylalkyl and cycloalkenyl, in which the rings may contain at least one heteroatom from the group consisting of sulphur, oxygen (where oxygen atoms must not be directly adjacent to one another) and nitrogen, in each case optionally substituted aryl, heteroaryl, arylalkyl and heteroarylalkyl and an optionally substituted amino group, $R^8$ and $R^{15}$ in the radicals (C-6) and (F-6) may also form, together with the N—S(O)n group to which they are attached, a saturated or unsaturated and optionally substituted 4- to 8-membered ring which may contain one or more further heteroatoms from the group consisting of sulphur, oxygen (where oxygen atoms must not be directly adjacent to one another) and nitrogen and/or at least one carbonyl group, $R^{16}$ represents a radical from the group consisting of hydrogen, in each case optionally substituted alkyl, alkoxy, alkenyl and alkynyl, in each case optionally substituted cycloalkyl, cycloalkylalkyl and cycloalkenyl, in which the rings may contain at least one heteroatom from the group consisting of sulphur, oxygen (where oxygen atoms must not be directly adjacent to one another) and nitrogen, in each case optionally substituted aryl, heteroaryl, arylalkyl and heteroarylalkyl and an optionally substituted amino group, $R^8$ and $R^{16}$ in the radicals (C-7) and (F-7) may also form, together with the nitrogen atom to which they are attached, a saturated or unsaturated and optionally substituted 4- to 8-membered ring which may contain one or more further heteroatoms from the group consisting of sulphur, oxygen (where oxygen atoms must not be directly adjacent to one another) and nitrogen and/or at least one carbonyl group, $R^{17}$ represents a radical from the group consisting of in each case optionally substituted alkyl, alkoxy, alkenyl and alkynyl, in each case optionally substituted cycloalkyl, cycloalkylalkyl and cycloalkenyl, in which the rings may contain at least one heteroatom from the group consisting of sulphur, oxygen (where oxygen atoms must not be directly adjacent to one another) and nitrogen, in each case optionally substituted aryl, heteroaryl, arylalkyl and heteroarylalkyl and an optionally substituted amino group, $R^8$ and $R^{17}$ in the radicals (C-8) and (F-8) may also form, together with the N—C(X) group to which they are attached, a saturated or unsaturated and optionally substituted 4- to 8-membered ring which may contain one or more further heteroatoms from the group consisting of sulphur, oxygen (where oxygen atoms must not be directly adjacent to one another) and nitrogen and/or at least one carbonyl group, $Y^1$ and $Y^2$ independently of one another represent C=O or $S(O)_2$, $R^{22}$ represents a radical from the group consisting of (D-1) to (D-3)

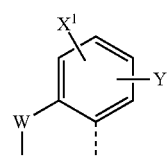

(D-1)

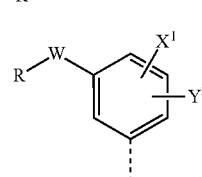

(D-2)

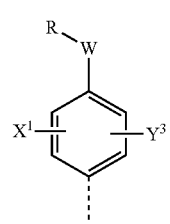

(D-3)

where the broken line represents the bond to the nitrogen atom in the radical c) or to the carbon atom in the radical d), $X^1$ represents a radical from the group consisting of hydrogen, halogen, cyano, nitro, alkyl, haloalkyl, cycloalkyl, alkoxy and haloalkoxy, $Y^3$ represents a radical from the group consisting of hydrogen, halogen, cyano, alkyl, cycloalkyl, haloalkyl, alkoxy, haloalkoxy and $NR^{20}R^{21}$, W represents a radical from the group consisting of S, SO and $SO_2$ and R represents $NR^{18}R^{19}$, or represents an in each case optionally substituted radical from the group consisting of alkyl, alkenyl, alkynyl, alkoxyalkyl, alkyl-S-alkyl, alkyl-S(O)-alkyl, alkyl-S(O)$_2$-alkyl, $R^{18}$—CO-alkyl, $NR^{18}R^{19}$—CO-alkyl, cycloalkyl, cycloalkenyl, cycloalkylalkyl, cycloalkenylalkyl, heterocyclyl, heterocyclylalkyl, phenyl, phenylalkyl, hetaryl and hetarylalkyl, $R^{18}$ represents a radical from the group consisting of hydrogen, hydroxy, in each case optionally substituted alkyl, alkoxy, alkoxyalkyl, alkylthioalkyl, alkylsulphinylalkyl, alkylsulphonylalkyl, alkylcarbonyl, alkoxycarbonyl, alkenyl and alkynyl, in each case optionally substituted cycloalkyl, cycloalkylalkyl, cycloalkenyl and cycloalkenylalkyl, in which the rings may contain at least one heteroatom from the group consisting of sulphur, oxygen (where oxygen atoms must not be directly adjacent to one another) and nitrogen, in each case optionally substituted aryl, arylalkyl, heteroaryl and heteroarylalkyl and an optionally substituted amino group, $R^{19}$ represents a radical from the group consisting of hydrogen, represents an alkali metal or alkaline earth metal ion or represents an ammonium ion which is optionally mono- to tetrasubstituted by $C_1$-$C_4$-alkyl or represents an in each case optionally halogen- or cyano-substituted alkyl, alkoxy, alkoxyalkyl, alkylthioalkyl, alkylsulphinylalkyl, alkylsulphonylalkyl radical, $R^{20}$ represents a radical from the group consisting of hydrogen, halogen, cyano, nitro, amino, hydroxy and in each case optionally substituted alkyl, alkenyl, alkynyl, cycloalkyl, cycloalkylalkyl, alkoxy, alkenyloxy, alkynyloxy, cycloalkyloxy, alkylcarbonyloxy, alkenylcarbonyloxy, alkynylcarbonyloxy, cycloalkylcarbonyloxy, alkoxycarbonyloxy, alkylsulphonyloxy, alkylamino, alkenylamino, alkynylamino, cycloalkylamino, alkylthio, haloalkylthio, alkenylthio, alkynylthio, cycloalkylthio, alkylsulphinyl, alkylsulphonyl, alkylcarbonyl, alkoxyiminoalkyl, alkoxycarbonyl, aminocarbonyl, alkylaminocarbonyl, dialkylaminocarbonyl, aminothiocarbonyl, alkylaminosulphonyl, alkylsulphonylamino, alkylcarbonylamino, alkenylcarbonylamino, alkynylcarbonylamino, cycloalkylcarbonylamino, alkoxycarbonylamino, alkylthiocarbonylamino, bicycloalkyl, aryl, aryloxy, heteroaryl and heteroaryloxy, where the substituents independently of one another are selected from the group consisting of halogen, cyano, nitro, hydroxy, amino, alkyl and haloalkyl, $R^{21}$ represents a radical from the group consisting of hydrogen, alkyl, cycloalkyl, haloalkyl, alkenyl, alkynyl, cycloalkylalkyl, cyanoalkyl, alkylcarbonyl, alkenylcarbonyl, haloalkylcarbonyl, haloalkenylcarbonyl, alkoxyalkyl, alkoxycarbonyl, alkylsulphonyl and haloalkylsulphonyl, or $R^{22}$ represents a radical from the group consisting of E-1 to E-51

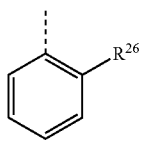

E-1

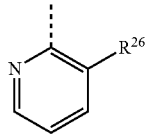

E-2

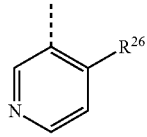

E-3

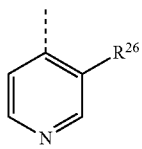

E-4

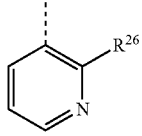

E-5

-continued

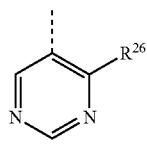

E-6

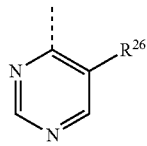

E-7

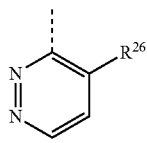

E-8

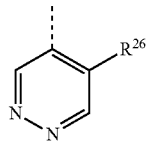

E-9

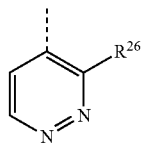

E-10

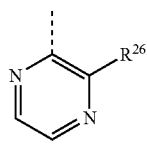

E-11

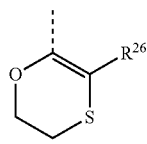

E-12

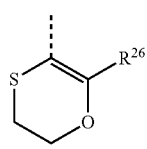

E-14

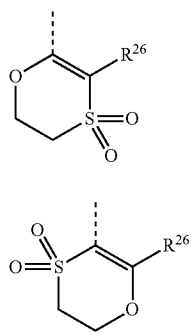

E-15

-continued
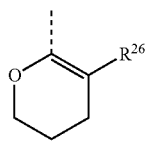 E-16
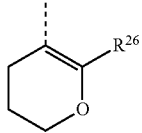 E-17
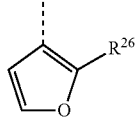 E-18
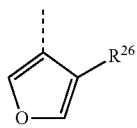 E-19
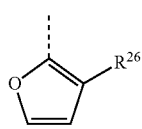 E-20
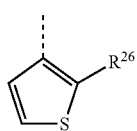 E-21
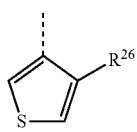 E-22
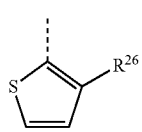 E-23
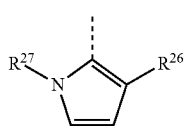 E-24
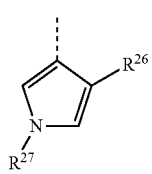 E-25
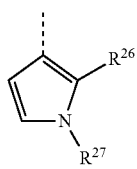 E-26
-continued
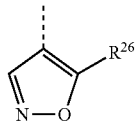 E-27
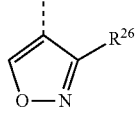 E-28
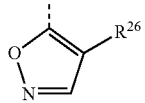 E-29
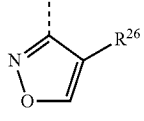 E-30
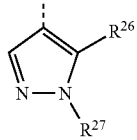 E-31
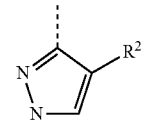 E-32
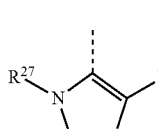 E-33
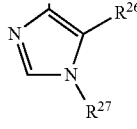 E-34
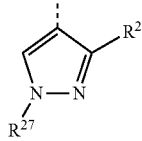 E-35
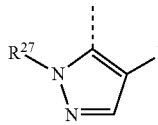 E-36

-continued

E-37 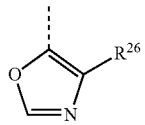

E-38 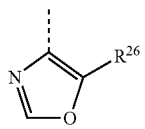

E-39 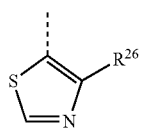

E-40 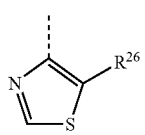

E-41 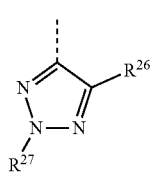

E-42 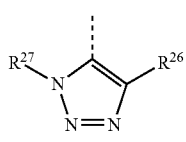

E-43 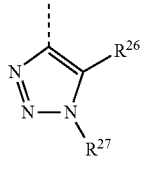

E-44 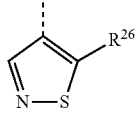

E-45 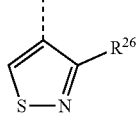

E-46 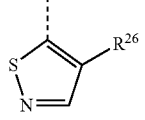

E-47 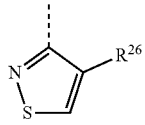

-continued

E-48 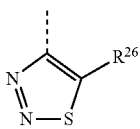

E-49 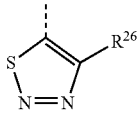

E-50 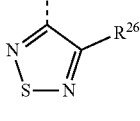

E-51 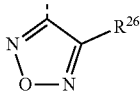

$R^{23}$ represents a radical from the group consisting of hydrogen, alkyl, alkenyl, alkynyl, cycloalkyl, cycloalkenyl, alkoxy, alkenyloxy, alkynyloxy, cycloalkyloxy, alkylthioalkyl, alkenylthioalkyl, cyanoalkyl, alkoxyalkyl, $R^{24}$ represents hydrogen or an in each case optionally substituted radical from the group consisting of alkyl, alkenyl, alkynyl, phenyl and phenylalkyl and $R^{25}$ represents hydrogen or an in each case optionally substituted radical from the group consisting of alkyl, alkenyl, alkynyl, phenyl and phenylalkyl, $R^{27}$ represents hydrogen or alkyl and $R^{26}$ represents hydrogen, alkyl, haloalkyl, alkenyl, alkynyl, cycloalkyl, cycloalkylalkyl, alkoxyalkyl, alkylthioalkyl, alkylsulphinylalkyl, alkylsulphonylalkyl or cyanoalkyl.

It has been additionally found that the compounds of the formula (I) and also the compounds listed in Table 1 which are not embraced by formula (I) have good efficacy as pesticides, for example against arthropods and especially insects, and additionally generally have very good compatibility with plants, especially crop plants, and/or have favourable toxicological and/or favourable environmentally relevant properties.

Preferred range (1): Preference is given to compounds of the formula (I) in which A represents an A radical from the group consisting of (A-b) and (A-f)

(A-b)

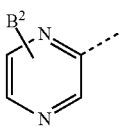

(A-f)

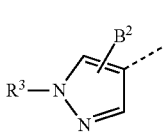

where the broken line represents the bond to the nitrogen atom of the bicycle of the formula (I) and B² represents a radical from the group consisting of hydrogen, halogen, C₁-C₆-alkyl and C₁-C₄-haloalkyl,
R¹ represents a radical from the group consisting of hydrogen, C₁-C₆-alkyl and C₁-C₆-alkoxy,
R² a) represents a B radical from the group consisting of
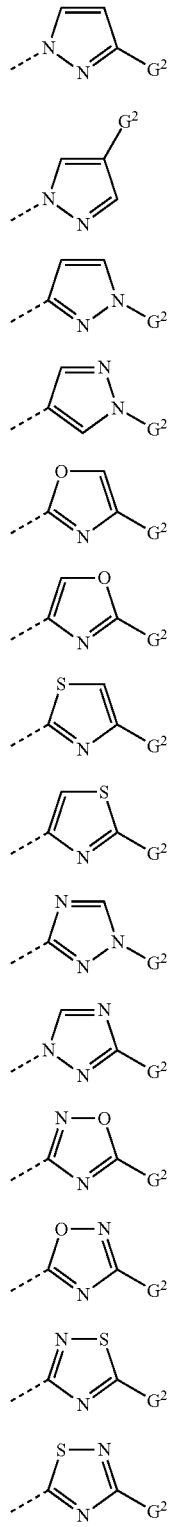
(B-1), (B-2), (B-3), (B-4), (B-5), (B-6), (B-7), (B-8), (B-9), (B-10), (B-11), (B-12), (B-13), (B-14)
-continued
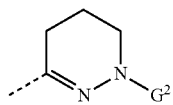 (B-15)
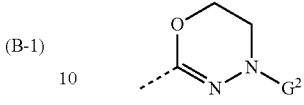 (B-16)
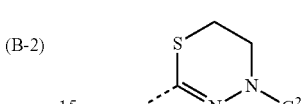 (B-17)
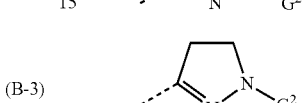 (B-18)
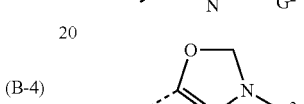 (B-19)
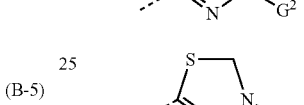 (B-20)
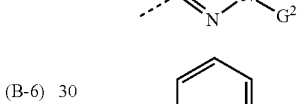 (B-21)
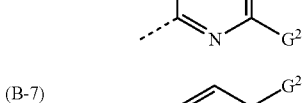 (B-22)
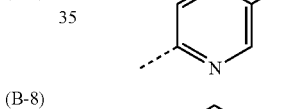 (B-23)
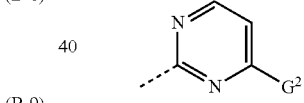 (B-24)
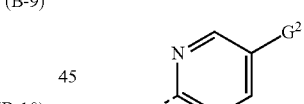 (B-25)
 (B-26)
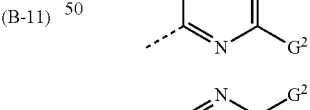 (B-27)
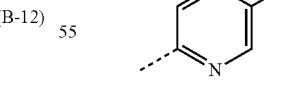 (B-28)
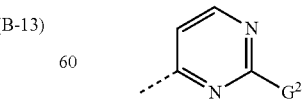

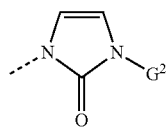 (B-29)

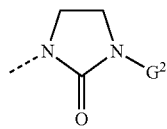 (B-30)

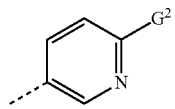 (B-31)

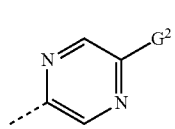 (B-32)

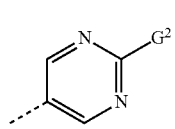 (B-33)

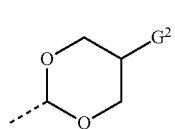 (B-34)

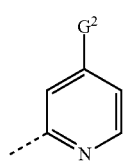 (B-35)

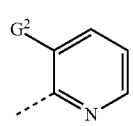 (B-36)

where the broken line represents the bond to the carbon atom of the bicycle of the formula (I) or $R^2$ b) represents a radical from the group consisting of (D-1) to (D-3)

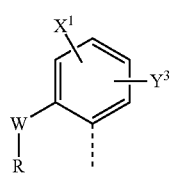 (D-1)

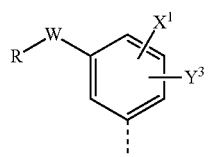 (D-2)

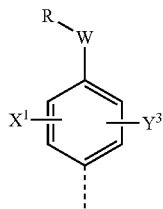 (D-3)

where the broken line represents the bond to the carbon atom of the bicycle of the formula (I) or $R^2$ c) represents a radical of the formula

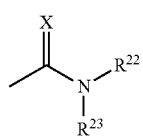

or $R^2$ d) represents a radical of the formula

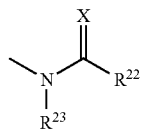

or $R^2$ e) represents a radical from the group consisting of (F-1), (F-8), (F-10) and (F-11)

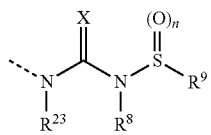 (F-1)

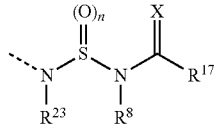 (F-8)

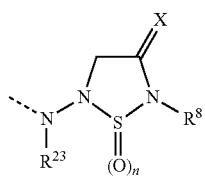 (F-10)

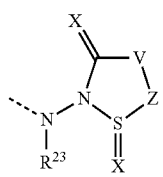 (F-11)

where the broken line represents the bond to the carbon atom in the formula (I) or R[2] f) represents a radical from the group consisting of $C_1$-$C_6$-haloalkyl, carboxyl and amino, where $G^2$ represents hydrogen or represents a radical from the group consisting of halogen, nitro, amino, cyano, $C_1$-$C_4$-alkylamino, halo-$C_1$-$C_4$-alkylamino, di-($C_1$-$C_4$-alkyl)-amino, $C_1$-$C_4$-alkyl, halo-$C_1$-$C_4$-alkyl, $C_1$-$C_4$-alkoxycarbonyl-$C_1$-$C_4$-alkyl, $C_3$-$C_6$-cycloalkyl, $C_3$-$C_6$-cycloalkenyl, $C_3$-$C_6$-cycloalkyl-$C_1$-$C_4$-alkyl, $C_1$-$C_4$-alkoxy, halo-$C_1$-$C_4$-alkoxy, $C_1$-$C_4$-alkoxy-$C_1$-$C_4$-alkyl, halogenated $C_1$-$C_4$-alkoxy-$C_1$-$C_4$-alkyl, bis($C_1$-$C_4$-alkoxy)-$C_1$-$C_4$-alkyl, bis(halo-$C_1$-$C_4$-alkoxy)-$C_1$-$C_4$-alkyl, $C_1$-$C_4$-alkoxy-($C_1$-$C_4$-alkylsulphanyl)-$C_1$-$C_4$-alkyl, $C_1$-$C_4$-alkoxy-($C_1$-$C_4$-alkylsulphinyl)-$C_1$-$C_4$-alkyl, $C_1$-$C_4$-alkoxy-($C_1$-$C_4$-alkylsulphonyl)-$C_1$-$C_4$-alkyl, bis ($C_1$-$C_4$-alkylsulphanyl)-$C_1$-$C_4$-alkyl, bis(halo-$C_1$-$C_4$-alkylsulphanyl)-$C_1$-$C_4$-alkyl, bis(hydroxy-$C_1$-$C_4$-alkylsulphanyl)-$C_1$-$C_4$-alkyl, $C_1$-$C_4$-alkoxycarbonyl, $C_1$-$C_4$-alkoxycarbonyl-$C_1$-$C_4$-alkyl, alpha-hydroxyimino-$C_1$-$C_4$-alkoxycarbonyl-$C_1$-$C_4$-alkyl, alpha-$C_1$-$C_4$-alkoxyimino-$C_1$-$C_4$-alkoxycarbonyl-$C_1$-$C_4$-alkyl, $C(X^2)NR^3R^4$, $NR^6R^7$, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, the heterocyclyl radicals dioxanyl, dioxolanyl, dioxepanyl, dioxocanyl, oxathianyl, oxathiolanyl, oxathiepanyl, oxathiocanyl, dithianyl, dithiolanyl, dithiepanyl, dithiocanyl, oxathianyl oxide, oxathiolanyl oxide, oxathiepanyl oxide, oxathiocanyl oxide, oxathianyl dioxide, oxathiolanyl dioxide, oxathiepanyl dioxide, oxathiocanyl dioxide, morpholinyl, triazolinonyl, oxazolinyl, dihydrooxadiazinyl, dihydrodioxazinyl, dihydrooxazolyl, dihydrooxazinyl and pyrazolinonyl (which for their part may be substituted by $C_1$-$C_4$-alkyl, halo-$C_1$-$C_4$-alkyl, $C_1$-$C_4$-alkoxy and $C_1$-$C_4$-alkoxy-$C_1$-$C_4$-alkyl), phenyl (which for its part may be substituted by halogen, cyano, nitro, $C_1$-$C_4$-alkyl and halo-$C_1$-$C_4$-alkyl), the heteroaryl radicals pyridyl, pyridyl N-oxide, pyrimidyl, imidazolyl, pyrazolyl, oxazolyl, thiazolyl, furanyl, thienyl, triazolyl, tetrazolyl, oxadiazolyl, thiadiazolyl, pyrazinyl, triazinyl, tetrazinyl and isoquinolinyl (which for their part may be substituted by halogen, nitro, $C_1$-$C_4$-alkyl, halo-$C_1$-$C_4$-alkyl, $C_1$-$C_4$-alkoxy, halo-$C_1$-$C_4$-alkoxy, $C_1$-$C_4$-alkoxy-$C_1$-$C_4$-alkyl, $C_1$-$C_4$-alkylthio, $C_1$-$C_4$-alkylthio-$C_1$-$C_4$-alkyl and $C_3$-$C_6$-cycloalkyl) and the heteroaryl-$C_1$-$C_4$-alkyl radicals triazolyl-$C_1$-$C_4$-alkyl, pyridyl-$C_1$-$C_4$-alkyl, pyrimidyl-$C_1$-$C_4$-alkyl and oxadiazolyl-$C_1$-$C_4$-alkyl (which for their part may be substituted by halogen and $C_1$-$C_4$-alkyl), or $G^2$ represents a radical from the group consisting of (C-1) and (C-6) to (C-9)

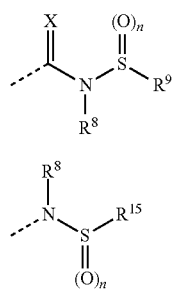

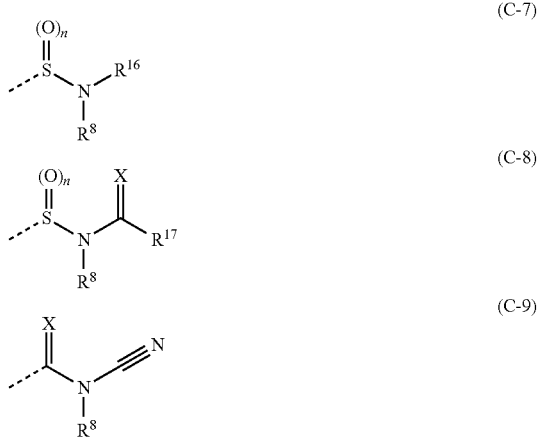

where the broken line represents the bond to the B radicals,

X represents oxygen or sulphur, $X^1$ represents a radical from the group consisting of hydrogen, halogen, cyano, nitro, $C_1$-$C_6$-alkyl, $C_1$-$C_6$-haloalkyl, $C_3$-$C_6$-cycloalkyl, $C_1$-$C_6$-alkoxy and $C_1$-$C_6$-haloalkoxy, $X^2$ represents oxygen, sulphur, $NR^5$ or NOH, V—Z represents $R^{24}$CH—CHR$^{25}$ or $R^{24}$C═CR$^{25}$, n represents 1 or 2, R represents $NR^{18}R^{19}$ or represents $C_1$-$C_6$-alkyl, $C_3$-$C_6$-alkenyl, $C_3$-$C_6$-alkynyl, $C_1$-$C_6$-alkoxy-$C_1$-$C_4$-alkyl, $C_1$-$C_6$-alkyl-S—$C_1$-$C_4$-alkyl, $C_1$-$C_6$-alkyl-S(O)—$C_1$-$C_4$-alkyl, $C_1$-$C_6$-alkyl-S(O)$_2$—$C_1$-$C_4$-alkyl, each of which is optionally mono- or disubstituted by halogen, oxygen (leads to C═O) or cyano, represents $R^{18}$—CO—$C_1$-$C_4$-alkyl, represents $NR^{18}R^{19}$—CO—$C_1$-$C_4$-alkyl, represents $C_3$-$C_6$-cycloalkyl which is optionally substituted by oxygen (leads to C═O), $C_1$-$C_4$-alkyl, $C_3$-$C_8$-cycloalkyl, $C_1$-$C_4$-alkoxy and $C_1$-$C_4$-haloalkyl, represents $C_3$-$C_8$-cycloalkenyl which is optionally mono- or disubstituted by oxygen (leads to C═O), $C_1$-$C_4$-alkyl, $C_3$-$C_6$-cycloalkyl, $C_1$-$C_4$-alkoxy and $C_1$-$C_4$-haloalkyl, represents $C_3$-$C_6$-cycloalkyl-$C_1$-$C_4$-alkyl which is optionally mono- or disubstituted by oxygen (leads to C═O), $C_1$-$C_4$-alkyl, $C_3$-$C_6$-cycloalkyl, $C_1$-$C_4$-alkoxy and $C_1$-$C_4$-haloalkyl, represents $C_3$-$C_6$-cycloalkenyl-$C_1$-$C_4$-alkyl which is optionally mono- or disubstituted by oxygen (leads to C═O), $C_1$-$C_4$-alkyl, $C_3$-$C_6$-cycloalkyl, $C_1$-$C_4$-alkoxy and $C_1$-$C_4$-haloalkyl, represents heterocyclyl which is optionally mono- or disubstituted by oxygen (leads to C═O), $C_1$-$C_4$-alkyl, $C_3$-$C_6$-cycloalkyl, $C_1$-$C_4$-alkoxy and $C_1$-$C_4$-haloalkyl, represents heterocyclyl-$C_1$-$C_4$-alkyl which is optionally mono- or disubstituted by oxygen (leads to C═O), $C_1$-$C_4$-alkyl, $C_3$-$C_6$-cycloalkyl, $C_1$-$C_4$-alkoxy and $C_1$-$C_4$-haloalkyl, or represents phenyl, phenyl-$C_1$-$C_4$-alkyl, hetaryl and hetaryl-$C_1$-$C_4$-alkyl, each of which is optionally mono- to trisubstituted by halogen, cyano, $C_1$-$C_4$-alkyl, $C_1$-$C_4$-haloalkyl, $C_3$-$C_6$-cycloalkyl, $C_1$-$C_4$-alkoxy or $C_1$-$C_4$-haloalkoxy, $R^3$ represents hydrogen or $C_1$-$C_6$-alkyl, $R^4$ represents a radical from the group consisting of hydrogen, $C_1$-$C_4$-alkyl, halo-$C_1$-$C_4$-alkyl, cyano-$C_1$-$C_4$-alkyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_4$-alkyl, $C_1$-$C_4$-alkoxycarbonyl, $C_1$-$C_4$-alkoxycarbonyl-$C_1$-$C_4$-alkyl, $C_1$-$C_4$-alkylthio-$C_1$-$C_4$-alkyl, aryl, aryl-$C_1$-$C_4$-alkyl and hetaryl-$C_1$-$C_4$-alkyl, $R^5$ represents a radical from the group consisting of hydrogen, $C_1$-$C_4$-alkyl, halo-$C_1$-$C_4$-alkyl, cyano-$C_1$-$C_4$-alkyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_4$-alkyl, $C_1$-$C_4$-alkoxycarbonyl, $C_1$-$C_4$-alkoxycarbonyl-$C_1$-$C_4$-alkyl, $C_1$-$C_4$-alkylthio-$C_1$-$C_4$-alkyl, aryl, aryl-$C_1$-$C_4$-alkyl and hetaryl-$C_1$-$C_4$-alkyl, or $R^3$ and $R^4$ together with the nitrogen atom to which they are attached form a 4- to 7-membered ring which may contain one or two further heteroatoms from the group consisting of nitrogen, oxygen and sulphur (where oxygen and sulphur atoms must not be directly adjacent to one another), $R^6$ represents hydrogen or $C_1$-$C_4$-alkyl, $R^7$ represents a radical from the group consisting of hydrogen, $C_1$-$C_4$-alkyl, halo-$C_1$-$C_4$-alkyl, cyano-$C_1$-$C_4$-alkyl, $C_2$-$C_4$-alkynyl, $C_3$-$C_6$-cycloalkyl, $C_3$-$C_4$-cycloalkyl-$C_1$-$C_4$-alkyl, $C_1$-$C_4$-alkoxy, halo-$C_1$-$C_4$-alkoxy, $C_1$-$C_4$-alkoxy-$C_1$-$C_4$-alkyl, $C_1$-$C_4$-alkoxycarbonyl, $C_1$-$C_4$-alkoxycarbonyl-$C_1$-$C_4$-alkyl, $C_1$-$C_4$-alkylthio-$C_1$-$C_4$-alkyl, aryl, aryl-$C_1$-$C_4$-alkyl and hetaryl-$C_1$-$C_4$-alkyl, or $R^6$ and $R^7$ together with the nitrogen atom to which they are attached form a 4- to 7-membered ring which may contain one or two further heteroatoms from the group consisting of nitrogen, oxygen and sulphur (where oxygen and sulphur atoms must not be directly adjacent to one another), $R^8$ represents a radical from the group consisting of hydrogen, $C_1$-$C_6$-alkyl, $C_1$-$C_6$-haloalkyl, cyano-$C_1$-$C_6$-alkyl, $C_1$-$C_6$-alkoxy, $C_1$-$C_6$-haloalkoxy, $C_2$-$C_6$-alkenyl, $C_1$-$C_6$-alkoxy-$C_1$-$C_6$-alkyl, in each case optionally halogen-substituted $C_1$-$C_6$-alkylcarbonyl and $C_1$-$C_6$-alkylsulphonyl, optionally halogen-substituted $C_1$-$C_6$-alkoxycarbonyl, optionally halogen-, $C_1$-$C_6$-alkyl-, $C_1$-$C_6$-alkoxy-, $C_1$-$C_6$-haloalkyl- and cyano-substituted $C_3$-$C_6$-cycloalkylcarbonyl, or represents a cation or an optionally $C_1$-$C_6$-alkyl- or aryl-$C_1$-$C_6$-alkyl-substituted ammonium ion, $R^9$ represents a radical from the group consisting of in each case optionally halogen-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-haloalkylsulphinyl-, $C_1$-$C_6$-alkylsulphonyl- and $C_1$-$C_6$-haloalkylsulphonyl-substituted $C_1$-$C_6$-alkyl, $C_2$-$C_6$-alkenyl and $C_2$-$C_6$-alkynyl, in each case optionally halogen-, $C_1$-$C_6$-alkyl-, $C_1$-$C_6$-haloalkyl-, $C_1$-$C_6$-alkoxy- or $C_1$-$C_6$-haloalkoxy-substituted $C_3$-$C_6$-cycloalkyl, $C_3$-$C_6$-cycloalkyl-$C_1$-$C_6$-alkyl and $C_3$-$C_6$-cycloalkenyl, in which one ring member may be replaced by a heteroatom from the group consisting of sulphur, oxygen (where oxygen atoms must not be directly adjacent to one another) and nitrogen (and here in particular represent

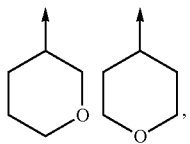

where the arrow in each case denotes the bond to the sulphur atom in the radical (C-1) and in the radical (F-1)), in each case optionally halogen-, cyano- (also in the alkyl moiety), nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-haloalkylsulphinyl-, $C_1$-$C_6$-alkylsulphonyl-, $C_1$-$C_6$-haloalkylsulphonyl-, amino-, $C_1$-$C_6$-alkylamino-, di-($C_1$-$C_6$-alkyl)amino-, $C_1$-$C_6$-alkylcarbonylamino-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_3$-$C_6$-cycloalkyl-$C_1$-$C_6$-alkyl-, $C_1$-$C_6$-alkylcarbonyl-, $C_1$-$C_6$-alkoxycarbonyl- or aminocarbonyl-substituted aryl, heteroaryl, aryl-$C_1$-$C_6$-alkyl, heteroaryl-$C_1$-$C_6$-alkyl or represents NR'R" in which R' and R" independently of one another represent a radical from the group consisting of hydrogen, $C_1$-$C_6$-alkyl, $C_1$-$C_6$-haloalkyl, $C_3$-$C_6$-cycloalkyl, $C_1$-$C_6$-alkoxy, $C_1$-$C_6$-alkylcarbonyl and $C_1$-$C_6$-alkoxylcarbonyl.

$R^8$ and $R^9$ in the radical (C-1) and in the radical (F-1) may also form, together with the N—S(O)$_n$ group to which they are attached, a saturated or unsaturated and optionally halogen-, $C_1$-$C_6$-alkyl-, $C_1$-$C_6$-haloalkyl-, $C_1$-$C_6$-alkoxy-, $C_1$-$C_6$-haloalkoxy-substituted 5- to 7-membered ring which may contain one or two heteroatoms from the group consisting of sulphur, oxygen (where oxygen atoms must not be directly adjacent to one another) and nitrogen and/or at least one and preferably one carbonyl group, in particular, $R^8$ and $R^9$ together with the N—S(O)$_n$ group to which they are attached may represent a radical from the group consisting of

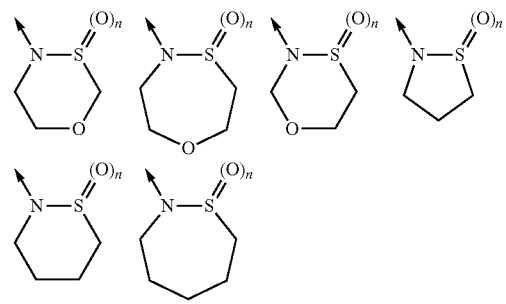

(in which the arrow in each case denotes the bond to the C(X) group), $R^{15}$ represents a radical from the group consisting of in each case optionally methyl-, cyano-, carbamoyl-substituted $C_1$-$C_6$-alkyl, $C_2$-$C_6$-alkenyl and $C_2$-$C_6$-alkynyl, in each case optionally methyl-, trifluoromethyl-, halogen-, cyano- or carbamoyl-substituted $C_3$-$C_6$-cycloalkyl, $C_3$-$C_6$-cycloalkyl-$C_1$-$C_2$-alkyl and $C_3$-$C_6$-cycloalkenyl, in which the rings may contain at least one heteroatom from the group consisting of sulphur, oxygen (where oxygen atoms must not be directly adjacent to one another) and nitrogen, in each case optionally $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-haloalkylsulphinyl-, $C_1$-$C_4$-haloalkylsulphonyl-, $C_1$-$C_4$-alkylamino-, di-($C_1$-$C_4$-alkyl)-amino-, halogen-, nitro- or cyano-substituted aryl, heteroaryl, aryl-$C_1$-$C_4$-alkyl and heteroaryl-$C_1$-$C_2$-alkyl and an optionally $C_1$-$C_4$-alkyl-, $C_1$-$C_4$-alkylcarbonyl-, $C_1$-$C_4$-alkyl-$C_1$-$C_4$-alkoxycarbonyl- or $C_1$-$C_4$-alkylsulphonyl-substituted amino group, $R^8$ and $R^{15}$ in the radical (C-6) may also form, together with the N—S(O)n group to which they are attached, a saturated or unsaturated and optionally substituted 4- to 8-membered ring which may contain one or two further heteroatoms from the group consisting of sulphur, oxygen (where oxygen and sulphur atoms must not be directly adjacent to one another) and nitrogen and/or at least one carbonyl group, $R^{16}$ represents a radical from the group consisting of hydrogen, in each case optionally methyl-, cyano-, carbamoyl- or carboxyl-substituted $C_1$-$C_6$-alkyl, $C_1$-$C_6$-alkoxy, $C_2$-$C_4$-alkenyl and $C_2$-$C_4$-alkynyl, in each case optionally halogen-, cyano-, nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-haloalkylsulphinyl-, $C_1$-$C_6$-alkylsulphonyl-, $C_1$-$C_6$-haloalkylsulphonyl-, amino-, $C_1$-$C_6$-alkylamino-, di-($C_1$-$C_6$-alkyl)amino-, $C_1$-$C_6$-alkylcarbonylamino-, $C_1$-$C_6$-alkoxycarbonylamino-, $C_2$-$C_6$-alkenyl-, $C_2$-$C_6$-alkynyl- or $C_1$-$C_6$-alkylcarbonyl-substituted $C_3$-$C_6$-cycloalkyl, $C_3$-$C_6$-cycloalkyl-$C_1$-$C_4$-alkyl and $C_3$-$C_6$-cycloalkenyl in which the rings may contain at least one heteroatom from the group consisting of sulphur, oxygen (where oxygen atoms must not be directly adjacent to one another) and nitrogen, in each case optionally halogen-, cyano-, nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-haloalkylsulphinyl-, $C_1$-$C_6$-alkylsulphonyl-, $C_1$-$C_6$-haloalkylsulphonyl-, amino-, $C_1$-$C_6$-alkylamino-, di-($C_1$-$C_6$-alkyl)amino-, $C_1$-$C_6$-alkylcarbonylamino-, $C_1$-$C_6$-alkoxycarbonylamino-, $C_2$-$C_6$-alkenyl-, $C_2$-$C_6$-alkynyl- or $C_1$-$C_6$-alkylcarbonyl-substituted aryl, heteroaryl, aryl-$C_1$-$C_2$-alkyl and heteroaryl-$C_1$-$C_2$-alkyl and an optionally $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-haloalkylsulphinyl-, $C_1$-$C_6$-alkylsulphonyl-, $C_1$-$C_6$-haloalkylsulphonyl-, $C_2$-$C_6$-alkenyl-, $C_2$-$C_6$-alkynyl- or $C_1$-$C_6$-alkylcarbonyl-substituted amino group, $R^{17}$ represents a radical from the group consisting of in each case optionally halogen-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-haloalkylsulphinyl-, $C_1$-$C_6$-alkylsulphonyl- or $C_1$-$C_6$-haloalkylsulphonyl-substituted $C_1$-$C_6$-alkyl, $C_1$-$C_6$-alkoxy, $C_2$-$C_6$-alkenyl and $C_2$-$C_6$-alkynyl, in each case optionally halogen-, $C_1$-$C_6$-alkyl-, $C_1$-$C_6$-haloalkyl-, $C_1$-$C_6$-alkoxy- or $C_1$-$C_6$-haloalkoxy-substituted $C_3$-$C_6$-cycloalkyl, $C_3$-$C_6$-cycloalkyl-$C_1$-$C_6$-alkyl and $C_3$-$C_6$-cycloalkenyl, N-pyrrolidinyl, N-piperidinyl, N-morpholinyl, N-thiomorpholinyl, N-thiomorpholinyl 1-oxide, N-thiomorpholinyl 1,1-dioxide, N-piperazinyl, N-1-methylpiperazinyl or N-2-oxo-1-methylpiperazinyl, in each case optionally halogen-, cyano- (also in the alkyl moiety), nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-haloalkylsulphinyl-, $C_1$-$C_6$-alkylsulphonyl-, $C_1$-$C_6$-haloalkylsulphonyl-, amino-, $C_1$-$C_6$-alkylamino-, di($C_1$-$C_6$-alkyl)amino-, $C_1$-$C_6$-alkylcarbonylamino-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_3$-$C_6$-cycloalkyl-$C_1$-$C_6$-alkyl-, $C_1$-$C_6$-alkylcarbonyl-, $C_1$-$C_6$-alkoxycarbonyl- or aminocarbonyl-substituted aryl, heteroaryl, aryl-$C_1$-$C_6$-alkyl, heteroaryl-$C_1$-$C_6$-alkyl or represents NR'R" in which R' and R" independently of one another each represent a radical from the group consisting of hydrogen, $C_1$-$C_6$-alkyl, $C_1$-$C_6$-haloalkyl, $C_3$-$C_6$-cycloalkyl, $C_1$-$C_6$-alkoxy, $C_1$-$C_6$-alkylcarbonyl and $C_1$-$C_6$-alkoxycarbonyl, $R^8$ and $R^{17}$ in the radical (C-8) and in the radical (F-8) may also form, together with the N—C(X) group to which they are attached, a saturated or unsaturated and optionally halogen-, $C_1$-$C_6$-alkyl-, $C_1$-$C_6$-haloalkyl-, $C_1$-$C_6$-alkoxy-, $C_1$-$C_6$-haloalkoxy-substituted 5- to 7-membered ring which may contain one or two further heteroatoms from the group consisting of sulphur, oxygen (where oxygen atoms must not be directly adjacent to one another) and nitrogen and/or one carbonyl group, in particular, $R^8$ and $R^{17}$ together with the N—C(X) group to which they are attached may represent a radical from the group consisting of

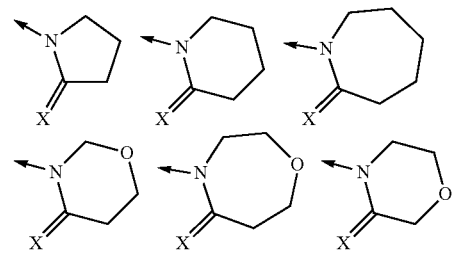

(where the arrow in each case denotes the bond to the sulphur atom in the radical (C-8) and in the radical (F-8)), $R^{18}$ represents a radical from the group consisting of hydrogen, hydroxy, of $C_1$-$C_6$-alkyl, $C_1$-$C_6$-alkoxy, $C_1$-$C_6$-alkoxy-$C_1$-$C_4$-alkyl, $C_1$-$C_6$-alkyl-S—$C_1$-$C_4$-alkyl, $C_1$-$C_6$-alkyl-S(O)—$C_1$-$C_4$-alkyl, $C_1$-$C_6$-alkyl-S(O)$_2$—$C_1$-$C_4$-alkyl, $C_1$-$C_6$-alkylcarbonyl, $C_1$-$C_6$-alkoxycarbonyl, $C_3$-$C_6$-cycloalkyl, $C_3$-$C_6$-cycloalkenyl, $C_3$-$C_6$-cycloalkyl-$C_1$-$C_3$-alkyl, $C_3$-$C_6$-cycloalkenyl-$C_1$-$C_3$-alkyl, heterocyclyl, heterocyclyl-$C_1$-$C_3$-alkyl, each of which is optionally mono- or polysubstituted by halogen or mono- or disubstituted by cyano, and phenyl, phenyl-$C_1$-$C_3$-alkyl, hetaryl and hetaryl-$C_1$-$C_3$-alkyl, each of which is optionally mono- to tetrasubstituted by $C_1$-$C_4$-alkyl, $C_1$-$C_4$-haloalkyl, $C_1$-$C_4$-alkoxy, $C_1$-$C_4$-haloalkoxy, $C_3$-$C_6$-cycloalkyl, halogen or cyano, $R^{19}$ represents hydrogen, an alkali or alkaline earth metal ion, or represents an ammonium ion which is optionally mono- to tetrasubstituted by $C_1$-$C_4$-alkyl, or represents a radical from the group consisting of $C_1$-$C_4$-alkyl, $C_1$-$C_4$-alkoxy, $C_1$-$C_4$-alkoxy-$C_1$-$C_4$-alkyl, $C_1$-$C_4$-alkyl-S—$C_1$-$C_4$-alkyl, $C_1$-$C_4$-alkyl-S(O)—$C_1$-$C_4$-alkyl and $C_1$-$C_4$-alkyl-S(O)$_2$—$C_1$-$C_4$-alkyl, each of which is optionally mono- or polysubstituted by halogen or mono- or disubstituted by cyano, $Y^3$ represents a radical from the group consisting of hydrogen, halogen, cyano, $C_1$-$C_6$-alkyl, $C_1$-$C_6$-haloalkyl, $C_3$-$C_6$-cycloalkyl, $C_1$-$C_6$-alkoxy, $C_1$-$C_6$-haloalkoxy and $NR^{20}R^{21}$, W represents a radical from the group consisting of O, S, SO and SO$_2$, $R^{22}$ represents a radical from the group consisting of $C_1$-$C_6$-alkyl, optionally halogen-, carbamoyl-, thiocarbamoyl- or cyano-substituted $C_3$-$C_6$-cycloalkyl, $C_1$-$C_6$-haloalkyl, $C_1$-$C_6$-alkoxy, $C_1$-$C_4$-haloalkoxy, $C_1$-$C_6$-alkoxy-$C_1$-$C_6$-alkyloxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylthio-$C_1$-$C_4$-alkyl, $C_1$-$C_4$-alkylsulphinyl-$C_1$-$C_4$-alkyl, $C_1$-$C_4$-alkylsulphonyl-$C_1$-$C_4$-alkyl, $C_1$-$C_4$-alkylthio-$C_1$-$C_4$-alkyloxy, $C_1$-$C_4$-alkylsulphinyl-$C_1$-$C_4$-alkyloxy, $C_1$-$C_4$- alkylsulphonyl-$C_1$-$C_4$-alkyloxy, $C_1$-$C_4$-haloalkylthio-$C_1$-$C_4$-alkyl, $C_1$-$C_4$-haloalkylsulphinyl-$C_1$-$C_4$-alkyl, $C_1$-$C_4$-haloalkylsulphonyl-$C_1$-$C_4$-alkyl, $C_1$-$C_4$-alkylthio-$C_2$-$C_4$-alkenyl, $C_1$-$C_4$-alkylsulphinyl-$C_2$-$C_4$-alkenyl, $C_1$-$C_4$-alkylsulphonyl-$C_2$-$C_4$-alkenyl, $C_2$-$C_4$-alkenylthio-$C_1$-$C_4$-alkyl, $C_2$-$C_4$-alkenylsulphinyl-$C_1$-$C_4$-alkyl, $C_2$-$C_4$-alkenylsulphonyl-$C_1$-$C_4$-alkyl, $C_1$-$C_4$-alkylcarbonyl-$C_1$-$C_4$-alkyl, $C_1$-$C_4$-haloalkylcarbonyl-$C_1$-$C_4$-alkyl, $C_1$-$C_4$-alkoxy-$C_1$-$C_4$-alkyl, $C_1$-$C_4$-haloalkoxy-$C_1$-$C_4$-alkyl, $C_1$-$C_4$-alkoxycarbonyl-$C_1$-$C_4$-alkyl, $C_1$-$C_4$-haloalkoxycarbonyl-$C_1$-$C_4$-alkyl, $C_1$-$C_4$-alkylaminosulphonyl, di($C_1$-$C_4$-alkyl)aminosulphonyl, in the case $R^2$=d), $R^{22}$ also represents optionally halogen-, cyano-, nitro-, amino-, hydroxy-, $C_1$-$C_6$-alkyl-, $C_1$-$C_6$-haloalkyl-, $C_2$-$C_6$-alkenyl-, $C_2$-$C_6$-alkynyl-, $C_3$-$C_6$-cycloalkyl-, $C_3$-$C_6$-alkenyloxy-, $C_3$-$C_6$-alkynyloxy-, $C_1$-$C_6$-alkoxy-, $C_1$-$C_4$-haloalkoxy-, $C_1$-$C_6$-alkoxycarbonyloxy-, $C_1$-$C_6$-alkylamino-, $C_3$-$C_6$-alkenylamino-, $C_3$-$C_6$-alkynylamino-, $C_3$-$C_6$-cycloalkylamino-, $C_1$-$C_6$-alkylthio-, $C_1$-$C_4$-alkylsulphinyl-, $C_1$-$C_4$-alkylsulphonyl-, $C_3$-$C_6$-alkenylthio-, $C_3$-$C_6$-alkynylthio-, $C_3$-$C_6$-cycloalkylthio-, $C_1$-$C_4$-haloalkylthio-, $C_1$-$C_4$-haloalkylsulphinyl-, $C_1$-$C_4$-haloalkylsulphonyl-, $C_1$-$C_6$-alkylcarbonyl-, aminocarbonyl-, $C_1$-$C_6$-alkylaminocarbonyl-, di-($C_1$-$C_6$)-alkylaminocarbonyl-, $C_1$-$C_6$-alkylcarbonylamino-, $C_1$-$C_6$-alkylamino- or di-($C_1$-$C_6$-alkyl)-amino-substituted aryl or represents a radical from the group consisting of E-1 to E-51

E-1

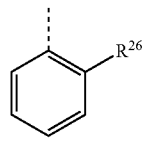

E-2

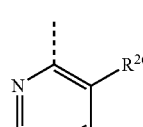

E-3

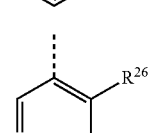

E-4

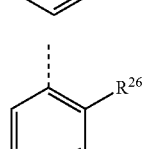

E-5

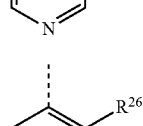

E-6

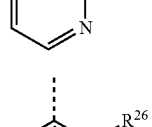

E-7

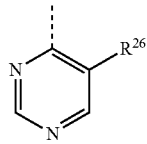

E-8

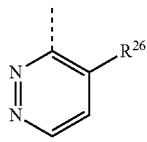

E-9

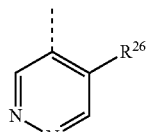

E-10

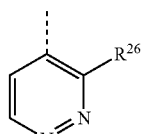

E-11

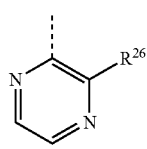

E-12

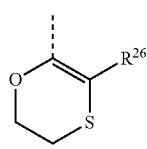

E-13

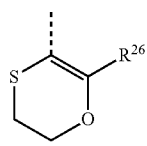

E-14

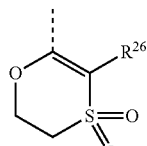

E-15

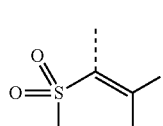

E-16

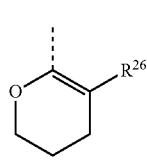

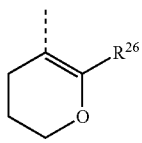 E-9
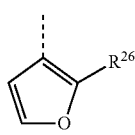 E-10
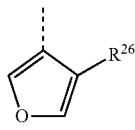 E-11
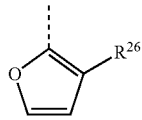 E-12
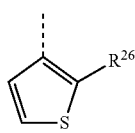 E-13
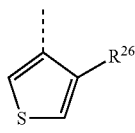 E-14
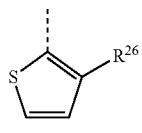 E-15
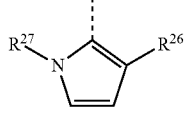 E-16
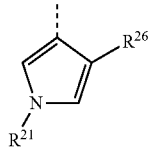 
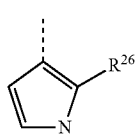 
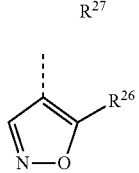 
E-17 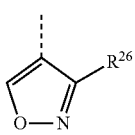
E-18 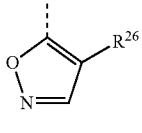
E-19 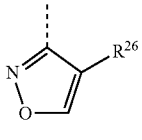
E-20 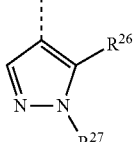
E-21 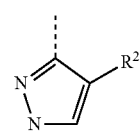
E-22 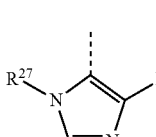
E-23 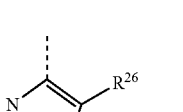
E-24 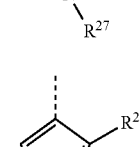
E-25 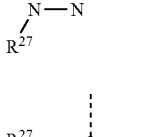
E-26 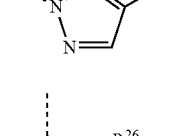
E-27 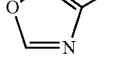

-continued

E-37
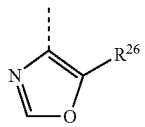

E-38
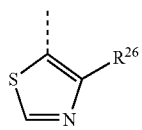

E-39
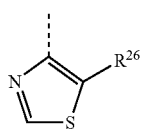

E-40
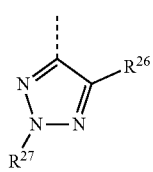

E-41
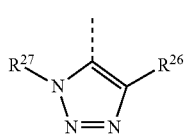

E-42
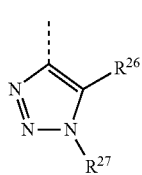

E-43
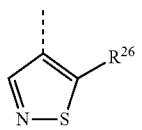

E-44
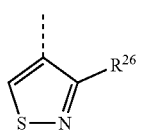

E-45
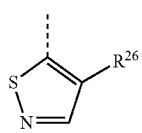

E-46
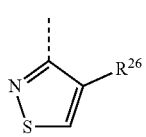

E-47
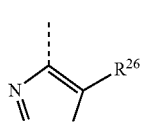

E-48
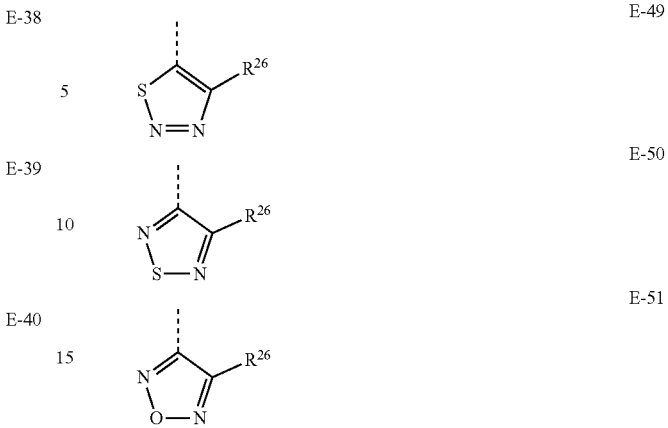

$R^{20}$ represents a radical from the group consisting of hydrogen, halogen, cyano, nitro, amino, hydroxy, $C_1$-$C_6$-alkyl, $C_1$-$C_6$-haloalkyl, cyano-$C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy, $C_1$-$C_6$-haloalkoxy, $C_3$-$C_6$-alkenyloxy, $C_3$-$C_6$-alkynyloxy, $C_3$-$C_6$-cycloalkyloxy, $C_1$-$C_6$-alkylcarbonyloxy, $C_2$-$C_6$-alkenylcarbonyloxy, $C_2$-$C_6$-alkynylcarbonyloxy, $C_3$-$C_6$-cycloalkylcarbonyloxy, $C_1$-$C_6$-alkoxycarbonyloxy, $C_1$-$C_6$-alkylsulphonyloxy, $C_1$-$C_6$-alkylamino, $C_3$-$C_6$-alkenylamino, $C_3$-$C_6$-alkynylamino, $C_3$-$C_6$-cycloalkylamino, $C_1$-$C_6$-alkylthio, $C_1$-$C_6$-haloalkylthio, $C_3$-$C_6$-alkenylthio, $C_3$-$C_6$-alkynylthio, $C_3$-$C_6$-cycloalkylthio, $C_1$-$C_6$-alkylsulphinyl, $C_1$-$C_6$-alkylsulphonyl, $C_1$-$C_6$-alkylcarbonyl, $C_1$-$C_6$-alkoxyimino-$C_1$-$C_6$-alkyl, $C_1$-$C_6$-alkoxycarbonyl, aminocarbonyl, $C_1$-$C_6$-alkylaminocarbonyl, di-($C_1$-$C_6$)-alkylaminocarbonyl, aminothiocarbonyl, $C_1$-$C_6$-alkylaminosulphonyl, $C_1$-$C_6$-alkylsulphonylamino, $C_1$-$C_6$-alkylcarbonylamino, $C_1$-$C_6$-alkylthiocarbonylamino, of phenyl, phenoxy, pyridinyl and pyridinyloxy, each of which is optionally substituted by a radical from the group consisting of halogen, cyano, nitro, amino, hydroxy, $C_1$-$C_6$-alkyl and $C_1$-$C_6$-haloalkyl, $R^{21}$ represents a radical from the group consisting of hydrogen, $C_1$-$C_6$-alkyl, $C_3$-$C_6$-cycloalkyl, $C_1$-$C_6$-haloalkyl, $C_3$-$C_6$-alkenyl, $C_2$-$C_6$-alkynyl, $C_3$-$C_6$-cycloalkyl-$C_1$-$C_6$-alkyl, cyano-$C_1$-$C_6$-alkyl, $C_1$-$C_6$-alkylcarbonyl, $C_2$-$C_6$-alkenylcarbonyl, $C_1$-$C_6$-haloalkylcarbonyl, $C_2$-$C_6$-haloalkenylcarbonyl, $C_1$-$C_6$-alkoxy-$C_1$-$C_6$-alkyl, $C_1$-$C_6$-alkoxycarbonyl, $C_1$-$C_6$-alkylsulphonyl and $C_1$-$C_6$-haloalkylsulphonyl, $R^{23}$ represents a radical from the group consisting of hydrogen, $C_1$-$C_6$-alkyl, $C_2$-$C_4$-alkenyl, $C_2$-$C_4$-alkynyl, $C_3$-$C_6$-cycloalkyl, $C_3$-$C_6$-cycloalkenyl, $C_1$-$C_6$-alkoxy, $C_2$-$C_6$-alkenyloxy, $C_2$-$C_6$-alkynyloxy, $C_3$-$C_6$-cycloalkyloxy, $C_1$-$C_4$-alkylthio-$C_1$-$C_4$-alkyl, $C_2$-$C_4$-alkenylthio-$C_1$-$C_4$-alkyl, cyano-$C_1$-$C_4$-alkyl and $C_1$-$C_4$-alkoxy-$C_1$-$C_4$alkyl, $R^{24}$ represents hydrogen or represents an in each case optionally halogen- or cyano-substituted radical from the group consisting of $C_1$-$C_4$-alkyl, $C_2$-$C_6$-alkenyl, $C_2$-$C_6$-alkynyl, phenyl and phenyl-$C_1$-$C_2$-alkyl, $R^{25}$ represents hydrogen or represents an in each case optionally halogen- or cyano-substituted radical from the group consisting of $C_1$-$C_4$-alkyl, $C_2$-$C_6$-alkenyl, $C_2$-$C_6$-alkynyl, phenyl and phenyl-$C_1$-$C_2$-alkyl, $R^{27}$ represents hydrogen or $C_1$-$C_4$-alkyl and $R^{26}$ represents hydrogen, $C_1$-$C_4$-alkyl, $C_1$-$C_4$-haloalkyl, $C_2$-$C_4$-alkenyl, $C_2$-$C_4$-alkynyl, $C_3$-$C_6$-cycloalkyl, $C_3$-$C_6$- cycloalkyl-$C_1$-$C_4$-alkyl, $C_1$-$C_4$-alkoxy-$C_1$-$C_2$-alkyl, $C_1$-$C_4$-alkylthio-$C_1$-$C_2$-alkyl, $C_1$-$C_4$-alkylsulphinyl-$C_1$-$C_2$-alkyl, $C_1$-$C_4$-alkylsulphonyl-$C_1$-$C_2$-alkyl or cyano-$C_1$-$C_4$-alkyl and compounds of the formula (I) in which
A represents the A radical

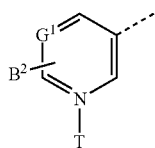
(A-a)

where the broken line represents the bond to the nitrogen atom of the bicycle of the formula (I) and
$G^1$ represents N or C—$B^1$,
$B^1$ represents a radical from the group consisting of hydrogen, halogen, $C_1$-$C_6$-alkyl and $C_1$-$C_4$-haloalkyl,
$B^2$ represents a radical from the group consisting of hydrogen, halogen, $C_1$-$C_6$-alkyl and $C_1$-$C_4$-haloalkyl,
T represents oxygen or an electron pair,
$R^1$ represents a radical from the group consisting of hydrogen, $C_1$-$C_6$-alkyl and $C_1$-$C_6$-alkoxy,
$R^2$ a) represents a B radical from the group consisting of

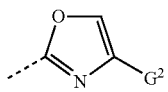 (B-5)

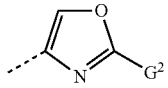 (B-6)

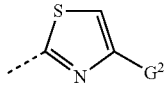 (B-7)

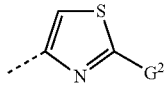 (B-8)

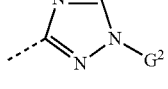 (B-9)

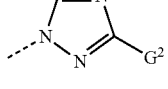 (B-10)

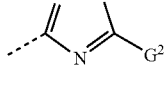 (B-11)

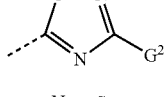 (B-12)

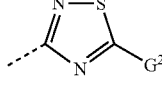 (B-13)

-continued

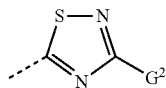 (B-14)

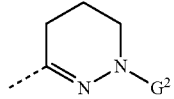 (B-15)

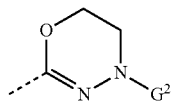 (B-16)

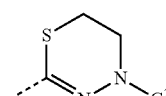 (B-17)

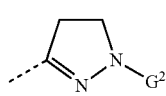 (B-18)

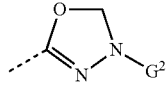 (B-19)

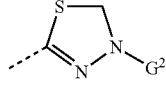 (B-20)

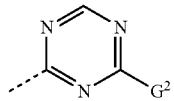 (B-28)

 (B-29)

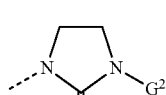 (B-30)

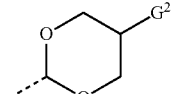 (B-34)

where the broken line represents the bond to the carbon atom of the bicycle of the formula (I),
in which
$G^2$ represents hydrogen or represents a radical from the group consisting of halogen, nitro, amino, cyano, $C_1$-$C_4$-alkylamino, halo-$C_1$-$C_4$-alkylamino, $C_1$-$C_4$-dialkylamino, $C_1$-$C_4$-alkyl, halo-$C_{14}$-alkyl, $C_3$-$C_6$-cycloalkyl, $C_1$-$C_4$-cycloalkenyl, $C_1$-$C_4$-cycloalkyl-$C_1$-$C_4$-alkyl, $C_1$-$C_4$-alkoxy, halo-$C_1$-$C_4$-alkoxy, $C_1$-$C_4$-alkoxy-$C_1$-$C_4$-alkyl, halogenated $C_1$-$C_4$-alkoxy-$C_1$-$C_4$-alkyl, bis($C_1$-$C_4$-alkoxy)-$C_1$-$C_4$-alkyl, bis(halo-$C_1$-$C_4$-alkoxy)-$C_1$-$C_4$-alkyl, $C_1$-$C_4$-alkoxy-($C_1$-$C_4$-alkylsulphanyl)-$C_1$-$C_4$-alkyl, $C_1$-$C_4$-alkoxy-($C_1$-$C_4$-alkylsulphinyl)-$C_1$-$C_4$-alkyl, $C_1$-$C_4$-alkoxy-($C_1$-$C_4$-alkylsulphonyl)-$C_1$-$C_4$-alkyl, bis ($C_1$-$C_4$-alkylsulphanyl)-$C_1$-$C_4$-alkyl, bis(halo-$C_1$-$C_4$-alkylsulphanyl)-$C_1$-$C_4$-alkyl, bis(hydroxy-$C_1$-$C_4$-alkylsulphanyl)-$C_1$-$C_4$-alkyl, $C_1$-$C_4$-alkoxycarbonyl, $C_1$-$C_4$-alkoxycarbonyl-$C_1$-$C_4$-alkyl, alpha-hydroxyimino-$C_1$-$C_4$-alkoxycarbonyl-$C_1$-$C_4$-alkyl, alpha-$C_1$-$C_4$-alkoxyimino-$C_1$-$C_4$-alkoxycarbonyl-$C_1$-$C_4$-alkyl, $C(X^2)$ $NR^3R^4$, $NR^6R^7$, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, the heterocyclyl radicals dioxanyl, dioxolanyl, dioxepanyl, dioxocanyl, oxathianyl, oxathiolanyl, oxathiepanyl, oxathiocanyl, dithianyl, dithiolanyl, dithiepanyl, dithiocanyl, oxathianyl oxide, oxathiolanyl oxide, oxathiepanyl oxide, oxathiocanyl oxide, oxathianyl dioxide, oxathiolanyl dioxide, oxathiepanyl dioxide, oxathiocanyl dioxide, morpholinyl, triazolinonyl, oxazolinyl, dihydrooxadiazinyl, dihydrodioxazinyl, dihydrooxazolyl, dihydrooxazinyl and pyrazolinonyl (which for their part may be substituted by $C_1$-$C_4$-alkyl, halo-$C_1$-$C_4$-alkyl, $C_1$-$C_4$-alkoxy and $C_1$-$C_4$-alkoxy-$C_1$-$C_4$-alkyl), phenyl (which for its part may be substituted by halogen, cyano, nitro, $C_1$-$C_4$-alkyl and halo-$C_1$-$C_4$-alkyl), the heteroaryl radicals pyridyl, pyridyl N-oxide, pyrimidyl, imidazolyl, pyrazolyl, oxazolyl, thiazolyl, furanyl, thienyl, triazolyl, tetrazolyl, oxadiazolyl, thiadiazolyl, pyrazinyl, triazinyl, tetrazinyl and isoquinolinyl (which for their part may be substituted by halogen, nitro, $C_1$-$C_4$-alkyl, halo-$C_1$-$C_4$-alkyl, $C_1$-$C_4$-alkoxy, halo-$C_1$-$C_4$-alkoxy, $C_1$-$C_4$-alkoxy-$C_1$-$C_4$-alkyl, $C_1$-$C_4$-alkylthio, $C_1$-$C_4$-alkylthio-$C_1$-$C_4$-alkyl and $C_3$-$C_6$-cycloalkyl) and the heteroaryl-$C_1$-$C_4$-alkyl radicals triazolyl-$C_1$-$C_4$-alkyl, pyridyl-$C_1$-$C_4$-alkyl, pyrimidyl-$C_1$-$C_4$-alkyl and oxadiazolyl-$C_1$-$C_4$-alkyl (which for their part may be substituted by halogen and $C_1$-$C_4$-alkyl), or $R^2$ aa) represents one of the B radicals below

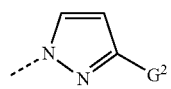
(B-1)

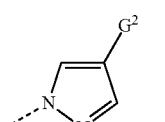
(B-2)

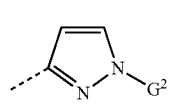
(B-3)

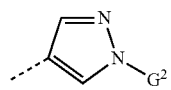
(B-4)

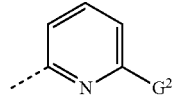
(B-21)

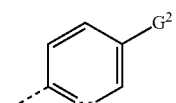
(B-22)

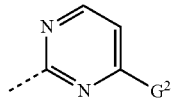
(B-23)

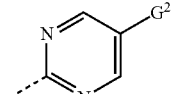
(B-24)

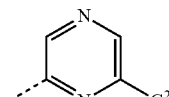
(B-25)

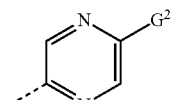
(B-26)

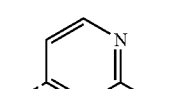
(B-27)

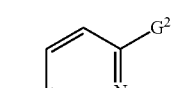
(B-31)

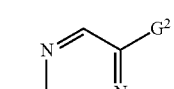
(B-32)

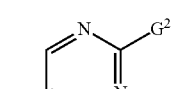
(B-33)

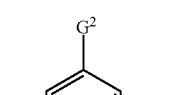
(B-35)

(B-36)

where the broken line represents the bond to the carbon atom of the bicycle of the formula (I), where $G^2$ represents a radical from the group consisting of halogen, nitro, amino, cyano, $C_1$-$C_4$-alkylamino, halo-$C_1$-$C_4$-alkylamino, $C_1$-$C_4$-dialkylamino, $C_3$-$C_6$-cycloalkyl, $C_3$-$C_6$-cycloalkenyl, $C_3$-$C_6$-cycloalkyl-$C_1$-$C_4$-alkyl, halo-$C_1$-$C_4$-alkoxy, $C_1$-$C_4$-alkoxy-$C_1$-$C_4$-alkyl, halogenated $C_1$-$C_4$-alkoxy-$C_1$-$C_4$-alkyl, bis($C_1$-$C_4$-alkoxy)-$C_1$-$C_4$-alkyl, bis(halo-$C_1$-$C_4$-alkoxy)-$C_1$-$C_4$-alkyl, $C_1$-$C_4$-alkoxy-($C_1$-$C_4$-alkylsulphanyl)-$C_1$-$C_4$-alkyl, $C_1$-$C_4$-alkoxy-($C_1$-$C_4$-alkylsulphinyl)-$C_1$-$C_4$-alkyl, $C_1$-$C_4$-alkoxy-($C_1$-$C_4$-alkylsulphonyl)-$C_1$-$C_4$-alkyl, bis($C_1$-$C_4$-alkylsulphanyl)-$C_1$-$C_4$-alkyl, bis(halo-$C_1$-$C_4$-alkylsulphanyl)-$C_1$-$C_4$-alkyl, bis(hydroxy-$C_1$-$C_4$-alkylsulphanyl)-$C_1$-$C_4$-alkyl, $C_1$-$C_4$-alkoxycarbonyl, $C_1$-$C_4$-alkoxycarbonyl-$C_1$-$C_4$- alkyl, alpha-hydroxyimino-$C_1$-$C_4$-alkoxycarbonyl-$C_1$-$C_4$-alkyl, alpha-$C_1$-$C_4$-alkoxyimino-$C_1$-$C_4$-alkoxycarbonyl-$C_1$-$C_4$-alkyl, $C(X^2)NR^3R^4$, $NR^6R^7$, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, the heterocyclyl radicals dioxanyl, dioxolanyl, dioxepanyl, dioxocanyl, oxathianyl, oxathiolanyl, oxathiepanyl, oxathiocanyl, dithianyl, dithiolanyl, dithiepanyl, dithiocanyl, oxathianyl oxide, oxathiolanyl oxide, oxathiepanyl oxide, oxathiocanyl oxide, oxathianyl dioxide, oxathiolanyl dioxide, oxathiepanyl dioxide, oxathiocanyl dioxide, morpholinyl, triazolinonyl, oxazolinyl, dihydrooxadiazinyl, dihydrodioxazinyl, dihydrooxazolyl, dihydrooxazinyl and pyrazolinonyl (which for their part may be substituted by $C_1$-$C_4$-alkyl, halo-$C_1$-$C_4$-alkyl, $C_1$-$C_4$-alkoxy and $C_1$-$C_4$-alkoxy-$C_1$-$C_4$-alkyl), phenyl (which for its part may be substituted by halogen, cyano, nitro, $C_1$-$C_4$-alkyl and halo-$C_1$-$C_4$-alkyl), the heteroaryl radicals imidazolyl, pyrazolyl, oxazolyl, furanyl, thienyl, triazolyl, tetrazolyl, oxadiazolyl, thiadiazolyl, pyrazinyl, triazinyl, tetrazinyl and isoquinolinyl (which for their part may be substituted by halogen, nitro, $C_1$-$C_4$-alkyl, halo-$C_1$-$C_4$-alkyl, $C_1$-$C_4$-alkoxy, halo-$C_1$-$C_4$-alkoxy, $C_1$-$C_4$-alkoxy-$C_1$-$C_4$-alkyl, $C_1$-$C_4$-alkylthio, $C_1$-$C_4$-alkylthio-$C_1$-$C_4$-alkyl and $C_3$-$C_6$-cycloalkyl) and the heteroaryl-$C_1$-$C_4$-alkyl radicals triazolyl-$C_1$-$C_4$-alkyl, pyridyl-$C_1$-$C_4$-alkyl, pyrimidyl-$C_1$-$C_4$-alkyl and oxadiazolyl-$C_1$-$C_4$-alkyl (which for their part may be substituted by halogen and $C_1$-$C_4$-alkyl), or, if $R^2$ represents one of the radicals listed under a) or aa), $G^2$ also represents a C radical from the group consisting of

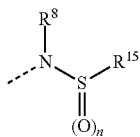
(C-6)

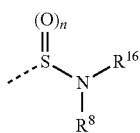
(C-7)

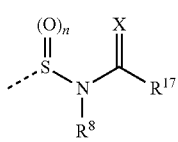
(C-8)

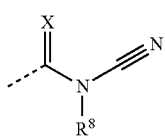
(C-9)

where the broken line represents the bond to the B radicals, or $R^2$ c) represents a radical of the formula

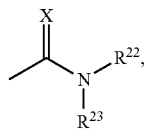

or
$R^2$ d) represents a radical of the formula

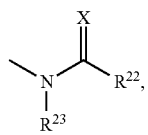

or
$R^2$ e) represents an F radical from the group consisting of

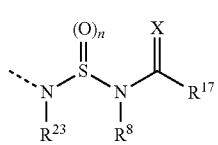
(F-8)

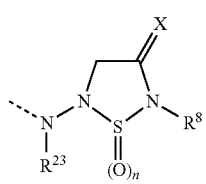
(F-10)

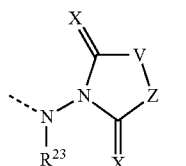
(F-11)

where the broken line represents the bond to the carbon atom in the formula (I) or
$R^2$ f) represents a radical from the group consisting of $C_1$-$C_6$-haloalkyl, carboxyl and amino,
X represents oxygen or sulphur,
$X^2$ represents oxygen, sulphur, $NR^5$ or NOH,
V—Z represents $R^{24}CH$—$CHR^{25}$ or $R^{24}C$=$CR^{25}$,
n represents 1 or 2,
$R^3$ represents hydrogen or $C_1$-$C_6$-alkyl,
$R^4$ represents a radical from the group consisting of hydrogen, $C_1$-$C_4$-alkyl, halo-$C_1$-$C_4$-alkyl, cyano-$C_1$-$C_4$-alkyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_4$-alkyl, $C_1$-$C_4$-alkoxycarbonyl, $C_1$-$C_4$-alkoxycarbonyl-$C_1$-$C_4$-alkyl, $C_1$-$C_4$-alkylthio-$C_1$-$C_4$-alkyl, aryl, aryl-$C_1$-$C_4$-alkyl and hetaryl-$C_1$-$C_4$-alkyl,
$R^5$ represents a radical from the group consisting of hydrogen, $C_1$-$C_4$-alkyl, halo-$C_1$-$C_4$-alkyl, cyano-$C_1$-$C_4$-alkyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_4$-alkyl, $C_1$-$C_4$-alkoxycarbonyl, $C_1$-$C_4$-alkoxycarbonyl-$C_1$-$C_4$-alkyl, $C_1$-$C_4$-alkylthio-$C_1$-$C_4$-alkyl, aryl, aryl-$C_1$-$C_4$-alkyl and hetaryl-$C_1$-$C_4$-alkyl, or R³ and R⁴ together with the nitrogen atom to which they are attached form a 4- to 7-membered ring which may contain one or two further heteroatoms from the group consisting of nitrogen, oxygen and sulphur (where oxygen and sulphur atoms must not be directly adjacent to one another), R⁶ represents hydrogen or $C_1$-$C_4$-alkyl, R⁷ represents a radical from the group consisting of hydrogen, $C_1$-$C_4$-alkyl, halo-$C_1$-$C_4$-alkyl, cyano-$C_1$-$C_4$-alkyl, $C_2$-$C_4$-alkynyl, $C_3$-$C_6$-cycloalkyl, $C_3$-$C_4$-cycloalkyl-$C_1$-$C_4$-alkyl, $C_1$-$C_4$-alkoxy, halo-$C_1$-$C_4$-alkoxy, $C_1$-$C_4$-alkoxy-$C_1$-$C_4$-alkyl, $C_1$-$C_4$-alkoxycarbonyl, $C_1$-$C_4$-alkoxycarbonyl-$C_1$-$C_4$-alkyl, $C_1$-$C_4$-alkylthio-$C_1$-$C_4$-alkyl, aryl, aryl-$C_1$-$C_4$-alkyl and hetaryl-$C_1$-$C_4$-alkyl, or R⁶ and R⁷ together with the nitrogen atom to which they are attached form a 4- to 7-membered ring which may contain one or two further heteroatoms from the group consisting of nitrogen, oxygen and sulphur (where oxygen and sulphur atoms must not be directly adjacent to one another), R⁸ represents a radical from the group consisting of hydrogen, $C_1$-$C_6$-alkyl, $C_1$-$C_6$-haloalkyl, cyano-$C_1$-$C_6$-alkyl, $C_1$-$C_6$-alkoxy, $C_1$-$C_6$-haloalkoxy, $C_2$-$C_6$-alkenyl, $C_1$-$C_6$-alkoxy-$C_1$-$C_6$-alkyl, in each case optionally halogen-substituted $C_1$-$C_6$-alkylcarbonyl and $C_1$-$C_6$-alkylsulphonyl, optionally halogen-substituted $C_1$-$C_6$-alkoxycarbonyl, optionally halogen-, $C_1$-$C_6$-alkyl-, $C_1$-$C_6$-alkoxy-, $C_1$-$C_6$-haloalkyl- and cyano-substituted $C_3$-$C_6$-cycloalkylcarbonyl, or represents a cation or an optionally $C_1$-$C_6$-alkyl- or aryl-$C_1$-$C_6$-alkyl-substituted ammonium ion, R⁹ represents a radical from the group consisting of in each case optionally halogen-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-haloalkylsulphinyl-, $C_1$-$C_6$-alkylsulphonyl- and $C_1$-$C_6$-haloalkylsulphonyl-substituted $C_1$-$C_6$-alkyl, $C_2$-$C_6$-alkenyl and $C_2$-$C_6$-alkynyl, in each case optionally halogen-, $C_1$-$C_6$-alkyl-, $C_1$-$C_6$-haloalkyl-, $C_1$-$C_6$-alkoxy- or $C_1$-$C_6$-haloalkoxy-substituted $C_3$-$C_6$-cycloalkyl, $C_3$-$C_6$-cycloalkyl-$C_1$-$C_6$-alkyl and $C_3$-$C_6$-cycloalkenyl, in which one ring member may be replaced by a heteroatom from the group consisting of sulphur, oxygen (where oxygen atoms must not be directly adjacent to one another) and nitrogen (and here in particular represent

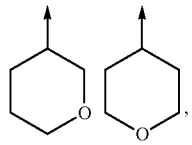

where the arrow in each case denotes the bond to the sulphur atom in the radical (C-1) and in the radical (F-1)), in each case optionally halogen-, cyano- (also in the alkyl moiety), nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-haloalkylsulphinyl-, $C_1$-$C_6$-alkylsulphonyl-, $C_1$-$C_6$-haloalkylsulphonyl-, amino-, $C_1$-$C_6$-alkylamino-, di($C_1$-$C_6$-alkyl)amino-, $C_1$-$C_6$-alkylcarbonylamino-, $C_1$-$C_6$-alkoxycarbonylamino-, $C_1$-$C_6$-alkoxy-$C_1$-$C_6$-alkyl-, $C_1$-$C_6$-haloalkoxy-$C_1$-$C_6$-alkyl-, $C_2$-$C_6$-alkenyl-, $C_2$-$C_6$-alkynyl-, $C_3$-$C_6$-cycloalkyl-$C_1$-$C_6$-alkyl-, $C_1$-$C_6$-alkylcarbonyl-, $C_1$-$C_6$-alkoxycarbonyl- or aminocarbonyl-substituted aryl, heteroaryl, aryl-$C_1$-$C_6$-alkyl, heteroaryl-$C_1$-$C_6$-alkyl or represents NR'R" in which R' and R" independently of one another represent a radical from the group consisting of hydrogen, $C_1$-$C_6$-alkyl, $C_1$-$C_6$-haloalkyl, $C_3$-$C_6$-cycloalkyl, $C_1$-$C_6$-alkoxy, $C_1$-$C_6$-alkylcarbonyl and $C_1$-$C_6$-alkoxylcarbonyl, or R¹⁵ represents a radical from the group consisting of in each case optionally methyl-, cyano-, carbamoyl-substituted $C_1$-$C_6$-alkyl, $C_2$-$C_6$-alkenyl and $C_2$-$C_6$-alkynyl, in each case optionally methyl-, trifluoromethyl-, halogen-, cyano- or carbamoyl-substituted $C_3$-$C_6$-cycloalkyl, $C_3$-$C_6$-cycloalkyl-$C_1$-$C_2$-alkyl and $C_3$-$C_6$-cycloalkenyl, in which the rings may contain at least one heteroatom from the group consisting of sulphur, oxygen (where oxygen atoms must not be directly adjacent to one another) and nitrogen, in each case optionally $C_1$-$C_4$-alkyl-, $C_1$-$C_4$-haloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-haloalkylsulphinyl-, $C_1$-$C_4$-haloalkylsulphonyl-, $C_1$-$C_4$-alkylamino-, di-($C_1$-$C_4$-alkyl)-amino-, halogen-, nitro- or cyano-substituted aryl, heteroaryl, aryl-$C_1$-$C_4$-alkyl and heteroaryl-$C_1$-$C_2$-alkyl and an optionally $C_1$-$C_4$-alkyl-, $C_1$-$C_4$-alkylcarbonyl-, $C_1$-$C_4$-alkyl-$C_1$-$C_4$-alkoxycarbonyl- or $C_1$-$C_4$-alkylsulphonyl-substituted amino group, R⁸ and R¹⁵ in the radical (C-6) may also form, together with the N—S(O)n group to which they are attached, a saturated or unsaturated and optionally substituted 4- to 8-membered ring which may contain one or two further heteroatoms from the group consisting of sulphur, oxygen (where oxygen and sulphur atoms must not be directly adjacent to one another) and nitrogen and/or at least one carbonyl group, R¹⁶ represents a radical from the group consisting of hydrogen, in each case optionally methyl-, cyano-, carbamoyl- or carboxyl-substituted $C_1$-$C_6$-alkyl, $C_1$-$C_6$-alkoxy, $C_2$-$C_4$-alkenyl and $C_2$-$C_4$-alkynyl, in each case optionally halogen-, cyano-, nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-haloalkylsulphinyl-, $C_1$-$C_6$-alkylsulphonyl-, $C_1$-$C_6$-haloalkylsulphonyl-, amino-, $C_1$-$C_6$-alkylamino-, di($C_1$-$C_6$-alkyl)amino-, $C_1$-$C_6$-alkylcarbonylamino-, $C_1$-$C_6$-alkoxycarbonylamino-, $C_2$-$C_6$-alkenyl-, $C_2$-$C_6$-alkynyl- or $C_1$-$C_6$-alkylcarbonyl-substituted $C_3$-$C_6$-cycloalkyl, $C_3$-$C_6$-cycloalkyl-$C_1$-$C_4$-alkyl and $C_3$-$C_6$-cycloalkenyl in which the rings may contain at least one heteroatom from the group consisting of sulphur, oxygen (where oxygen atoms must not be directly adjacent to one another) and nitrogen, in each case optionally halogen-, cyano-, nitro-, $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-haloalkylsulphinyl-, $C_1$-$C_6$-alkylsulphonyl-, $C_1$-$C_6$-haloalkylsulphonyl-, amino-, $C_1$-$C_6$-alkylamino-, di($C_1$-$C_6$-alkyl)amino-, $C_1$-$C_6$-alkylcarbonylamino-, $C_1$-$C_6$-alkoxycarbonylamino-, $C_2$-$C_6$-alkenyl-, $C_2$-$C_6$-alkynyl- or $C_1$-$C_6$-alkylcarbonyl-substituted aryl, heteroaryl, aryl-$C_1$-$C_2$-alkyl and heteroaryl-$C_1$-$C_2$-alkyl and an optionally $C_1$-$C_6$-alkyl-, $C_1$-$C_6$-haloalkyl-, $C_3$-$C_6$-cycloalkyl-, $C_1$-$C_6$-alkoxy-, $C_1$-$C_6$-haloalkoxy-, $C_1$-$C_6$-alkylthio-, $C_1$-$C_6$-haloalkylthio-, $C_1$-$C_6$-alkylsulphinyl-, $C_1$-$C_6$-haloalkylsulphinyl-, $C_1$-$C_6$-alkylsulphonyl-, $C_1$-$C_6$-haloalkylsulphonyl-, $C_2$-$C_6$-alkenyl-, $C_2$-$C_6$-alkynyl- or $C_1$-$C_6$-alkylcarbonyl-substituted amino group, R$^{17}$ represents a radical from the group consisting of in each case optionally halogen-, C$_1$-C$_6$-alkoxy-, C$_1$-C$_6$-haloalkoxy-, C$_1$-C$_6$-alkylthio-, C$_1$-C$_6$-haloalkylthio-, C$_1$-C$_6$-alkylsulphinyl-, C$_1$-C$_6$-haloalkylsulphinyl-, C$_1$-C$_6$-alkylsulphonyl- or C$_1$-C$_6$-haloalkylsulphonyl-substituted C$_1$-C$_6$-alkyl, C$_1$-C$_6$-alkoxy, C$_2$-C$_6$-alkenyl and C$_2$-C$_6$-alkynyl, in each case optionally halogen-, C$_1$-C$_6$-alkyl-, C$_1$-C$_6$-haloalkyl-, C$_1$-C$_6$-alkoxy- or C$_1$-C$_6$-haloalkoxy-substituted C$_3$-C$_6$-cycloalkyl, C$_3$-C$_6$-cycloalkyl-C$_1$-C$_6$-alkyl and C$_3$-C$_6$-cycloalkenyl, N-pyrrolidinyl, N-piperidinyl, N-morpholinyl, N-thiomorpholinyl, N-thiomorpholinyl 1-oxide, N-thiomorpholinyl 1,1-dioxide, N-piperazinyl, N-1-methylpiperazinyl or N-2-oxo-1-methylpiperazinyl, in each case optionally halogen-, cyano- (also in the alkyl moiety), nitro-, C$_1$-C$_6$-alkyl-, C$_1$-C$_6$-haloalkyl-, C$_3$-C$_6$-cycloalkyl-, C$_1$-C$_6$-alkoxy-, C$_1$-C$_6$-haloalkoxy-, C$_1$-C$_6$-alkylthio-, C$_1$-C$_6$-haloalkylthio-, C$_1$-C$_6$-alkylsulphinyl-, C$_1$-C$_6$-haloalkylsulphinyl-, C$_1$-C$_6$-alkylsulphonyl-, C$_1$-C$_6$-haloalkylsulphonyl-, amino-, C$_1$-C$_6$-alkylamino-, di(C$_1$-C$_6$-alkyl)amino-, C$_1$-C$_6$-alkylcarbonylamino-, C$_1$-C$_6$-alkoxycarbonylamino-, C$_1$-C$_6$-alkoxy-C$_1$-C$_6$-alkyl-, C$_1$-C$_6$-haloalkoxy-C$_1$-C$_6$-alkyl-, C$_2$-C$_6$-alkenyl-, C$_2$-C$_6$-alkynyl-, C$_3$-C$_6$-cycloalkyl-C$_1$-C$_6$-alkyl-, C$_1$-C$_6$-alkylcarbonyl-, C$_1$-C$_6$-alkoxycarbonyl- or aminocarbonyl-substituted aryl, heteroaryl, aryl-C$_1$-C$_6$-alkyl, heteroaryl-C$_1$-C$_6$-alkyl or represents NR'R" in which R' and R" independently of one another each represent a radical from the group consisting of hydrogen, C$_1$-C$_6$-alkyl, C$_1$-C$_6$-haloalkyl, C$_3$-C$_6$-cycloalkyl, C$_1$-C$_6$-alkoxy, C$_1$-C$_6$-alkylcarbonyl and C$_1$-C$_6$-alkoxylcarbonyl, R$^8$ and R$^{17}$ in the radical (C-8) and in the radical (F-8) may also form, together with the N—C(X) group to which they are attached, a saturated or unsaturated and optionally halogen-, C$_1$-C$_6$-alkyl-, C$_1$-C$_6$-haloalkyl-, C$_1$-C$_6$-alkoxy-, C$_1$-C$_6$-haloalkoxy-substituted 5- to 7-membered ring which may contain one or two further heteroatoms from the group consisting of sulphur, oxygen (where oxygen atoms must not be directly adjacent to one another) and nitrogen and/or one carbonyl group, in particular, R$^8$ and R$^{17}$ together with the N—C(X) group to which they are attached may represent a radical from the group consisting of

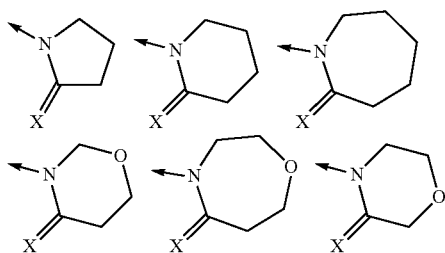

(where the arrow in each case denotes the bond to the sulphur atom in the radical (C-8) and in the radical (F-8)), R$^{18}$ represents a radical from the group consisting of hydrogen, hydroxy, of C$_1$-C$_6$-alkyl, C$_1$-C$_6$-alkoxy, C$_1$-C$_6$-alkoxy-C$_1$-C$_4$-alkyl, C$_1$-C$_6$-alkyl-S—C$_1$-C$_4$-alkyl, C$_1$-C$_6$-alkyl-S(O)—C$_1$-C$_4$-alkyl, C$_1$-C$_6$-alkyl-S(O)$_2$—C$_1$-C$_4$-alkyl, C$_1$-C$_6$-alkylcarbonyl, C$_1$-C$_6$-alkoxycarbonyl, C$_3$-C$_6$-cycloalkyl, C$_3$-C$_6$-cycloalkenyl, C$_3$-C$_6$-cycloalkyl-C$_1$-C$_3$-alkyl, C$_3$-C$_6$-cycloalkenyl-C$_1$-C$_3$-alkyl, heterocyclyl, heterocyclyl-C$_1$-C$_3$-alkyl, each of which is optionally mono- or polysubstituted by halogen or mono- or disubstituted by cyano, and phenyl, phenyl-C$_1$-C$_3$-alkyl, hetaryl and hetaryl-C$_1$-C$_3$-alkyl, each of which is optionally mono- to tetrasubstituted by C$_1$-C$_4$-alkyl, C$_1$-C$_4$-haloalkyl, C$_1$-C$_4$-alkoxy, C$_1$-C$_4$-haloalkoxy, C$_3$-C$_6$-cycloalkyl, halogen or cyano, R$^{19}$ represents hydrogen, an alkali or alkaline earth metal ion, or represents an ammonium ion which is optionally mono- to tetrasubstituted by C$_1$-C$_4$-alkyl, or represents a radical from the group consisting of C$_1$-C$_4$-alkyl, C$_1$-C$_4$-alkoxy, C$_1$-C$_4$-alkoxy-C$_1$-C$_4$-alkyl, C$_1$-C$_4$-alkyl-S—C$_1$-C$_4$-alkyl, C$_1$-C$_4$-alkyl-S(O)—C$_1$-C$_4$-alkyl and C$_1$-C$_4$-alkyl-S(O)$_2$—C$_1$-C$_4$-alkyl, each of which is optionally mono- or polysubstituted by halogen or mono- or disubstituted by cyano, R$^{22}$ represents a radical from the group consisting of (D-1) to (D-3)

(D-1)

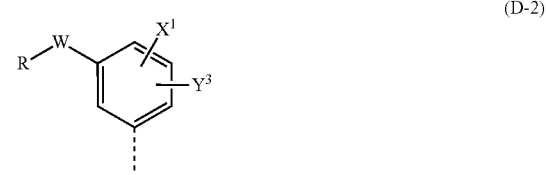

(D-2)

(D-3)

where the broken line represents the bond to the nitrogen atom in the radical c) or to the carbon atom in the radical d), X$^1$ represents a radical from the group consisting of hydrogen, halogen, cyano, nitro, C$_1$-C$_6$-alkyl, C$_1$-C$_6$-haloalkyl, C$_3$-C$_6$-cycloalkyl, C$_1$-C$_6$-alkoxy and C$_1$-C$_6$-haloalkoxy, R represents NR$^{18}$R$^{19}$ or represents C$_1$-C$_6$-alkyl, C$_3$-C$_6$-alkenyl, C$_3$-C$_6$-alkynyl, C$_1$-C$_6$-alkoxy-C$_1$-C$_4$-alkyl, C$_1$-C$_6$-alkyl-S—C$_1$-C$_4$-alkyl, C$_1$-C$_6$-alkyl-S(O)—C$_1$-C$_4$-alkyl, C$_1$-C$_6$-alkyl-S(O)$_2$—C$_1$-C$_4$-alkyl, each of which is optionally substituted by halogen, oxygen (leads to C═O) or cyano, represents R$^{18}$—CO—C$_1$-C$_4$-alkyl, represents NR$^{18}$R$^{19}$—CO—C$_1$-C$_4$-alkyl, represents C$_3$-C$_6$-cycloalkyl which is optionally mono- or disubstituted by oxygen (leads to C═O), C$_1$-C$_4$-alkyl, C$_3$-C$_8$-cycloalkyl, C$_1$-C$_4$-alkoxy and C$_1$-C$_4$-haloalkyl, represents C$_3$-C$_8$-cycloalkenyl which is optionally mono- or disubstituted by oxygen (leads to C═O), C$_1$-C$_4$-alkyl, C$_3$-C$_6$-cycloalkyl, C$_1$-C$_4$-alkoxy and C$_1$-C$_4$-haloalkyl, represents C$_3$-C$_6$-cycloalkyl-C$_1$-C$_4$-alkyl which is optionally mono- or disubstituted by oxygen (leads to C═O), C$_1$-C$_4$-alkyl, C$_3$-C$_6$-cycloalkyl, C$_1$-C$_4$-alkoxy and C$_1$-C$_4$-haloalkyl, represents C$_3$-C$_6$-cycloalkenyl-C$_1$-C$_4$-alkyl which is optionally mono- or disubstituted by oxygen (leads to C═O), $C_1$-$C_4$-alkyl, $C_3$-$C_6$-cycloalkyl, $C_1$-$C_4$-alkoxy and $C_1$-$C_4$-haloalkyl, represents heterocyclyl which is optionally mono- or disubstituted by oxygen (leads to C=O), $C_1$-$C_4$-alkyl, $C_3$-$C_6$-cycloalkyl, $C_1$-$C_4$-alkoxy and $C_1$-$C_4$-haloalkyl, represents heterocyclyl-$C_1$-$C_4$-alkyl which is optionally mono- or disubstituted by oxygen (leads to C=O), $C_1$-$C_4$-alkyl, $C_3$-$C_6$-cycloalkyl, $C_1$-$C_4$-alkoxy and $C_1$-$C_4$-haloalkyl, or represents phenyl, phenyl-$C_1$-$C_4$-alkyl, hetaryl and hetaryl-$C_1$-$C_4$-alkyl, each of which is optionally mono- to trisubstituted by halogen, cyano, $C_1$-$C_4$-alkyl, $C_1$-$C_4$-haloalkyl, $C_3$-$C_6$-cycloalkyl, $C_1$-$C_4$-alkoxy or $C_1$-$C_4$-haloalkoxy, $Y^3$ represents a radical from the group consisting of hydrogen, halogen, cyano, $C_1$-$C_6$-alkyl, $C_1$-$C_6$-haloalkyl, $C_3$-$C_6$-cycloalkyl, $C_1$-$C_6$-alkoxy, $C_1$-$C_6$-haloalkoxy and $NR^{20}R^{21}$, W represents a radical from the group consisting of S, SO and $SO_2$, or $R^{22}$ represents an E radical from the group consisting of

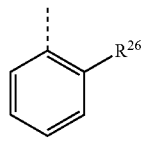
E-1

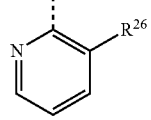
E-2

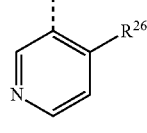
E-3

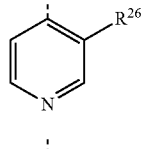
E-4

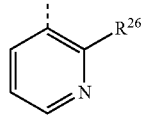
E-5

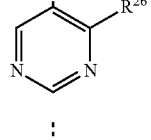
E-6

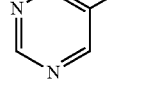
E-7

-continued

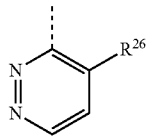
E-8

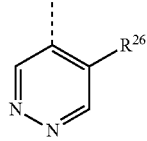
E-9

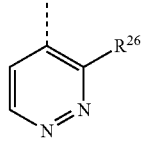
E-10

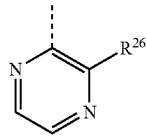
E-11

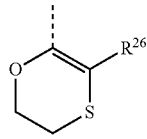
E-12

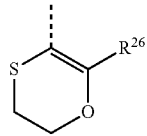
E-13

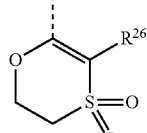
E-14

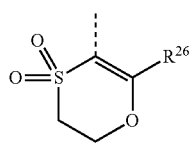
E-15

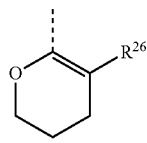
E-16

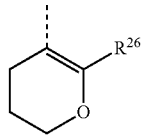
E-17

-continued
E-18 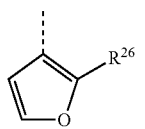
E-19 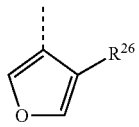
E-20 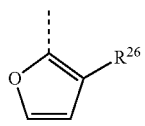
E-21 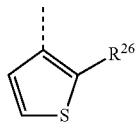
E-22 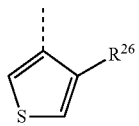
E-23 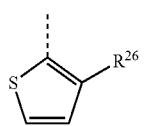
E-24 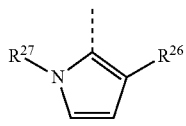
E-25 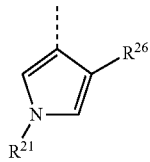
E-26 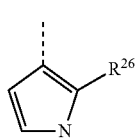
E-27 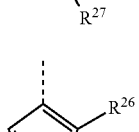
E-28 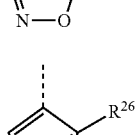
-continued
E-29 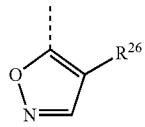
E-30 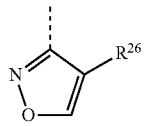
E-31 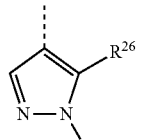
E-32 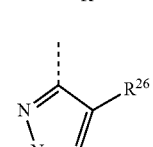
E-33 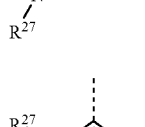
E-34 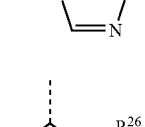
E-35 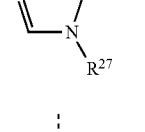
E-36 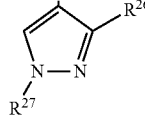
E-37 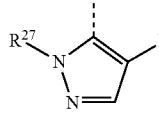
E-38 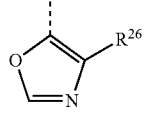
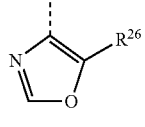

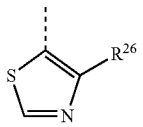 E-39

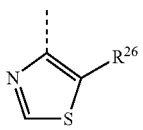 E-40

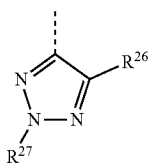 E-41

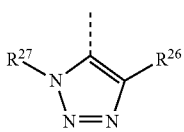 E-42

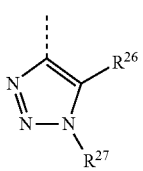 E-43

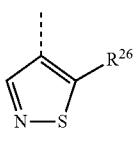 E-44

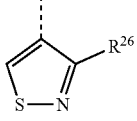 E-45

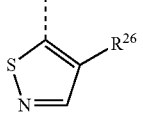 E-46

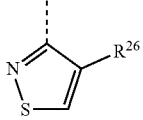 E-47

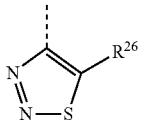 E-48

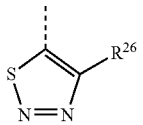 E-49

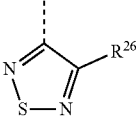 E-50

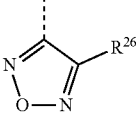 E-51

$R^{20}$ represents a radical from the group consisting of hydrogen, halogen, cyano, nitro, amino, hydroxy, $C_1$-$C_6$-alkyl, $C_1$-$C_6$-haloalkyl, cyano-$C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_6$-alkyl, $C_1$-$C_6$-alkoxy, $C_1$-$C_6$-haloalkoxy, $C_3$-$C_6$-alkenyloxy, $C_3$-$C_6$-alkynyloxy, $C_3$-$C_6$-cycloalkyloxy, $C_1$-$C_6$-alkylcarbonyloxy, $C_2$-$C_6$-alkenylcarbonyloxy, $C_2$-$C_6$-alkynylcarbonyloxy, $C_3$-$C_6$-cycloalkylcarbonyloxy, $C_1$-$C_6$-alkoxycarbonyloxy, $C_1$-$C_6$-alkylsulphonyloxy, $C_1$-$C_6$-alkylamino, $C_3$-$C_6$-alkenylamino, $C_3$-$C_6$-alkynylamino, $C_3$-$C_6$-cycloalkylamino, $C_1$-$C_6$-alkylthio, $C_1$-$C_6$-haloalkylthio, $C_3$-$C_6$-alkenylthio, $C_3$-$C_6$-alkynylthio, $C_3$-$C_6$-cycloalkylthio, $C_1$-$C_6$-alkylsulphinyl, $C_1$-$C_6$-alkylsulphonyl, $C_1$-$C_6$-alkylcarbonyl, $C_1$-$C_6$-alkoxyimino-$C_1$-$C_6$-alkyl, $C_1$-$C_6$-alkoxycarbonyl, aminocarbonyl, $C_1$-$C_6$-alkylaminocarbonyl, di-($C_1$-$C_6$)-alkylaminocarbonyl, aminothiocarbonyl, $C_1$-$C_6$-alkylaminosulphonyl, $C_1$-$C_6$-alkylsulphonylamino, $C_1$-$C_6$-alkylcarbonylamino, $C_1$-$C_6$-alkylthiocarbonylamino, of phenyl, phenoxy, pyridinyl and pyridinyloxy, each of which is optionally substituted by a radical from the group consisting of halogen, cyano, nitro, amino, hydroxy, $C_1$-$C_6$-alkyl and $C_1$-$C_6$-haloalkyl, $R^{21}$ represents a radical from the group consisting of hydrogen, $C_1$-$C_6$-alkyl, $C_3$-$C_6$-cycloalkyl, $C_1$-$C_6$-haloalkyl, $C_3$-$C_6$-alkenyl, $C_2$-$C_6$-alkynyl, $C_3$-$C_6$-cycloalkyl-$C_1$-$C_6$-alkyl, cyano-$C_1$-$C_6$-alkyl, $C_1$-$C_6$-alkylcarbonyl, $C_2$-$C_6$-alkenylcarbonyl, $C_1$-$C_6$-haloalkylcarbonyl, $C_2$-$C_6$-haloalkenylcarbonyl, $C_1$-$C_6$-alkoxy-$C_1$-$C_6$-alkyl, $C_1$-$C_6$-alkoxycarbonyl, $C_1$-$C_6$-alkylsulphonyl and $C_1$-$C_6$-haloalkylsulphonyl, $R^{23}$ represents a radical from the group consisting of hydrogen, $C_1$-$C_6$-alkyl, $C_2$-$C_4$-alkenyl, $C_2$-$C_4$-alkynyl, $C_3$-$C_6$-cycloalkyl, $C_3$-$C_6$-cycloalkenyl, $C_1$-$C_6$-alkoxy, $C_2$-$C_6$-alkenyloxy, $C_2$-$C_6$-alkynyloxy, $C_3$-$C_6$-cycloalkyloxy, $C_1$-$C_4$-alkylthio-$C_1$-$C_4$-alkyl, $C_2$-$C_4$-alkenylthio-$C_1$-$C_4$-alkyl, cyano-$C_1$-$C_4$-alkyl, $C_1$-$C_4$-alkoxy-$C_1$-$C_4$alkyl, $R^{24}$ represents hydrogen or represents an in each case optionally halogen- or cyano-substituted radical from the group consisting of $C_1$-$C_4$-alkyl, $C_2$-$C_6$-alkenyl, $C_2$-$C_6$-alkynyl, phenyl and phenyl-$C_1$-$C_2$-alkyl, $R^{25}$ represents hydrogen or represents an in each case optionally halogen- or cyano-substituted radical from the group consisting of $C_1$-$C_4$-alkyl, $C_2$-$C_6$-alkenyl, $C_2$-$C_6$-alkynyl, phenyl and phenyl-$C_1$-$C_2$-alkyl, $R^{27}$ represents hydrogen or $C_1$-$C_4$-alkyl and $R^{26}$ represents hydrogen, $C_1$-$C_4$-alkyl, $C_1$-$C_4$-haloalkyl, $C_2$-$C_4$-alkenyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_2$-alkyl, $C_1$-$C_4$-alkylthio-$C_1$-$C_2$-alkyl, $C_1$-$C_4$-alkylsulphinyl-$C_1$-$C_2$-alkyl, $C_1$-$C_4$-alkylsulphonyl-$C_1$-$C_2$-alkyl or cyano-$C_1$-$C_4$-alkyl.

Preferred range (2): Particular preference is given to compounds of the formula (I) in which A represents an A radical from the group consisting of

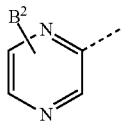
(A-b)

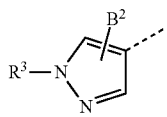
(A-f)

where the broken line represents the bond to the nitrogen atom of the bicycle of the formula (I), B² represents a radical from the group consisting of hydrogen, halogen, C₁-C₆-alkyl and C₁-C₄-haloalkyl, R¹ represents a radical from the group consisting of hydrogen, C₁-C₄-alkyl and C₁-C₄-alkoxy, R² a) represents a B radical from the group consisting of

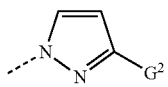
(B-1)

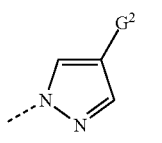
(B-2)

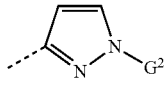
(B-3)

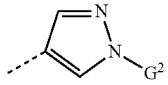
(B-4)

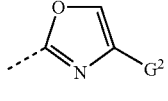
(B-5)

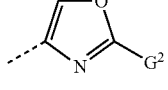
(B-6)

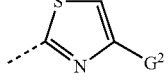
(B-7)

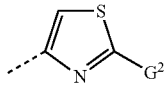
(B-8)

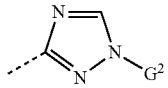
(B-9)

-continued

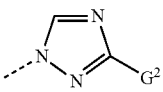
(B-10)

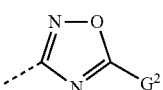
(B-11)

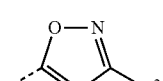
(B-12)

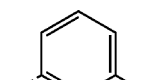
(B-21)

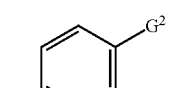
(B-22)

(B-23)

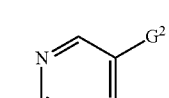
(B-24)

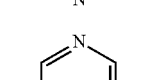
(B-25)

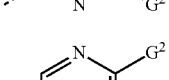
(B-26)

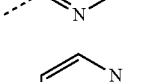
(B-27)

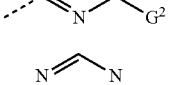
(B-28)

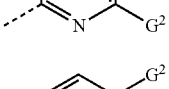
(B-31)

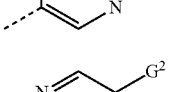
(B-32)

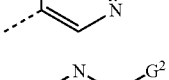
(B-33)

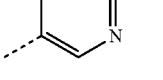

-continued

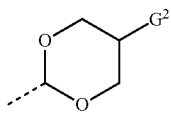
(B-34)

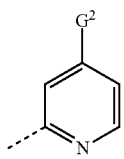
(B-35)

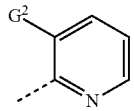
(B-36)

where the broken line represents the bond to the carbon atom of the bicycle of the formula (I) or $R^2$ b) represents a radical from the group consisting of (D-1) to (D-3)

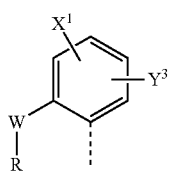
(D-1)

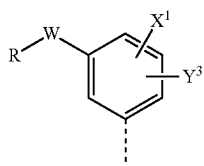
(D-2)

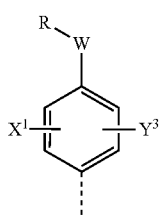
(D-3)

where the broken line represents the bond to the carbon atom of the bicycle of the formula (I) or $R^2$ c) represents a radical of the formula

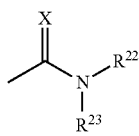

or $R^2$ d) represents a radical of the formula

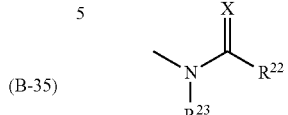

or $R^2$ e) represents an F radical from the group consisting of (F-1), (F-8) and (F-10)

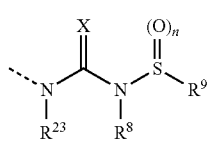
(F-1)

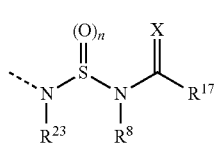
(F-8)

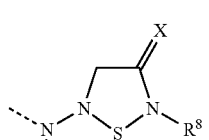
(F-10)

where the broken line represents the bond to the carbon atom in the formula (I) or $R^2$ f) represents a radical from the group consisting of $C_1$-$C_6$-haloalkyl, carboxyl and amino, in which $G^2$ represents hydrogen or a radical from the group consisting of halogen, nitro, amino, cyano, $C_1$-$C_4$-alkylamino, halo-$C_1$-$C_4$-alkylamino, di-($C_1$-$C_4$-alkyl)-amino, $C_1$-$C_4$-alkyl, halo-$C_1$-$C_4$-alkyl, $C_1$-$C_4$-alkoxy, halo-$C_1$-$C_4$-alkoxy, $C_1$-$C_4$-alkoxy-$C_1$-$C_4$-alkyl, halogenated $C_1$-$C_4$-alkoxy-$C_1$-$C_4$-alkyl, bis($C_1$-$C_4$-alkoxy)-$C_1$-$C_4$-alkyl, bis(halo-$C_1$-$C_4$-alkoxy)-$C_1$-$C_4$-alkyl, $C_1$-$C_4$-alkoxy-($C_1$-$C_4$-alkylsulphanyl)-$C_1$-$C_4$-alkyl, $C_1$-$C_4$-alkoxy-($C_1$-$C_4$-alkylsulphinyl)-$C_1$-$C_4$-alkyl, $C_1$-$C_4$-alkoxy-($C_1$-$C_4$-alkylsulphonyl)-$C_1$-$C_4$-alkyl, bis($C_1$-$C_4$-alkylsulphanyl)-$C_1$-$C_4$-alkyl, bis(halo-$C_1$-$C_4$-alkylsulphanyl)-$C_1$-$C_4$-alkyl, bis(hydroxy-$C_1$-$C_4$-alkylsulphanyl)-$C_1$-$C_4$-alkyl, $C_1$-$C_4$-alkoxycarbonyl, $C_1$-$C_4$-alkoxycarbonyl-$C_1$-$C_4$-alkyl, $C(X^2)NR^3R^4$, $NR^6R^7$, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, the heterocyclyl radicals dioxanyl, dioxolanyl, dioxepanyl, dioxocanyl, oxathianyl, oxathiolanyl, oxathiepanyl, oxathiocanyl, dithianyl, dithiolanyl, dithiepanyl, dithiocanyl, oxathianyl oxide, oxathiolanyl oxide, oxathiepanyl oxide, oxathiocanyl oxide, oxathianyl dioxide, oxathiolanyl dioxide, oxathiepanyl dioxide, oxathiocanyl dioxide, morpholinyl, triazolinonyl, oxazolinyl, dihydrooxadiazinyl, dihydrodioxazinyl, dihydrooxazolyl, dihydrooxazinyl and pyrazolinonyl (which for their part may be substituted by $C_1$-$C_4$-alkyl, halo-$C_1$-$C_4$-alkyl, $C_1$-$C_4$-alkoxy and $C_1$-$C_4$-alkoxy-$C_1$-$C_4$-alkyl), phenyl (which for its part may be substituted by halogen, cyano, nitro, $C_1$-$C_4$-alkyl and halo-$C_1$-$C_4$-alkyl), the heteroaryl radicals pyridyl, pyridyl N-oxide, pyrimidyl, imidazolyl, pyrazolyl, oxazolyl, thiazolyl, furanyl, thienyl, triazolyl, tetrazolyl, oxadiazolyl, thiadiazolyl, pyrazinyl, triazinyl, tetrazinyl and isoquinolinyl (which for their part may be substituted by halogen, nitro, $C_1$-$C_4$-alkyl, halo-$C_1$-$C_4$-alkyl, $C_1$-$C_4$-alkoxy, halo-$C_1$-$C_4$-alkoxy, $C_1$-$C_4$-alkoxy-$C_1$-$C_4$-alkyl, $C_1$-$C_4$-alkylthio, $C_1$-$C_4$-alkylthio-$C_1$-$C_4$-alkyl and $C_3$-$C_6$-cyclo-$C_1$-$C_4$-alkyl) and the heteroaryl-$C_1$-$C_4$-alkyl radicals triazolyl-$C_1$-$C_4$-alkyl, pyridyl-$C_1$-$C_4$-alkyl, pyrimidyl-$C_1$-$C_4$-alkyl and oxadiazolyl-$C_1$-$C_4$-alkyl (which for their part may be substituted by halogen and $C_1$-$C_4$-alkyl), or $G^2$ represents a radical from the group consisting of (C-1), (C-6) and (C-9)

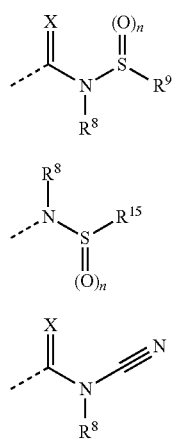

where the broken line represents the bond to the B radicals,

X represents oxygen, $X^1$ represents a radical from the group consisting of hydrogen, fluorine, chlorine, bromine, iodine, cyano, nitro, $C_1$-$C_4$-alkyl, $C_1$-$C_4$-haloalkyl, $C_3$-$C_6$-cycloalkyl, $C_1$-$C_4$-alkoxy and $C_1$-$C_4$-haloalkoxy, $X^2$ represents oxygen, sulphur, $NR^5$ or NOH, n represents 2, R represents $NR^{18}R^{19}$ or represents $C_1$-$C_6$-alkyl, $C_3$-$C_6$-alkenyl, $C_3$-$C_6$-alkynyl, $C_1$-$C_4$-alkoxy-$C_1$-$C_3$-alkyl, $C_1$-$C_4$-alkyl-S—$C_1$-$C_3$-alkyl, $C_1$-$C_4$-alkyl-S(O)—$C_1$-$C_3$-alkyl, $C_1$-$C_4$-alkyl-S(O)$_2$—$C_1$-$C_3$-alkyl, each of which is optionally mono- to heptasubstituted by halogen, mono- or disubstituted by oxygen (leads to C=O) or mono- or disubstituted by cyano, represents $R^{18}$—CO—$C_1$-$C_2$-alkyl, represents $NR^{18}R^{19}$—CO—$C_1$-$C_2$-alkyl, represents $C_3$-$C_6$-cycloalkyl which is optionally mono- or disubstituted by oxygen (leads to C=O), $C_1$-$C_4$-alkyl, $C_3$-$C_6$-cycloalkyl, $C_1$-$C_4$-alkoxy and $C_1$-$C_4$-haloalkyl, represents $C_3$-$C_8$-cycloalkenyl which is optionally mono- or disubstituted by oxygen (leads to C=O), $C_1$-$C_4$-alkyl, $C_3$-$C_6$-cycloalkyl, $C_1$-$C_4$-alkoxy and $C_1$-$C_4$-haloalkyl, represents $C_3$-$C_6$-cycloalkyl-$C_1$-$C_4$-alkyl which is optionally mono- or disubstituted by oxygen (leads to C=O), $C_1$-$C_4$-alkyl, $C_3$-$C_6$-cycloalkyl, $C_1$-$C_4$-alkoxy and $C_1$-$C_4$-haloalkyl, represents $C_3$-$C_6$-cycloalkenyl-$C_1$-$C_4$-alkyl which is optionally mono- or disubstituted by oxygen (leads to C=O), $C_1$-$C_4$-alkyl, $C_3$-$C_6$-cycloalkyl, $C_1$-$C_4$-alkoxy and $C_1$-$C_4$-haloalkyl, represents heterocyclyl which is optionally mono- or disubstituted by oxygen (leads to C=O), $C_1$-$C_4$-alkyl, $C_3$-$C_6$-cycloalkyl, $C_1$-$C_4$-alkoxy and $C_1$-$C_4$-haloalkyl, represents heterocyclyl-$C_1$-$C_4$-alkyl which is optionally mono- or disubstituted by oxygen (leads to C=O), $C_1$-$C_4$-alkyl, $C_3$-$C_6$-cycloalkyl, $C_1$-$C_4$-alkoxy and $C_1$-$C_4$-haloalkyl, or represents phenyl, phenyl-$C_1$-$C_4$-alkyl, hetaryl and hetaryl-$C_1$-$C_4$-alkyl, each of which is optionally mono- to trisubstituted by halogen, cyano, $C_1$-$C_4$-alkyl, $C_1$-$C_4$-haloalkyl, $C_3$-$C_6$-cycloalkyl, $C_1$-$C_4$-alkoxy or $C_1$-$C_4$-haloalkoxy, $R^3$ represents $C_1$-$C_4$-alkyl, $R^4$ represents a radical from the group consisting of hydrogen, $C_1$-$C_4$-alkyl, halo-$C_1$-$C_4$-alkyl, cyano-$C_1$-$C_4$-alkyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_4$-alkyl, $C_1$-$C_4$-alkoxycarbonyl, $C_1$-$C_4$-alkoxycarbonyl-$C_1$-$C_4$-alkyl and $C_1$-$C_4$-alkylthio-$C_1$-$C_4$-alkyl, $R^5$ represents a radical from the group consisting of hydrogen, $C_1$-$C_4$-alkyl, halo-$C_1$-$C_4$-alkyl, cyano-$C_1$-$C_4$-alkyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_4$-alkyl, $C_1$-$C_4$-alkoxycarbonyl, $C_1$-$C_4$-alkoxycarbonyl-$C_1$-$C_4$-alkyl and $C_1$-$C_4$-alkylthio-$C_1$-$C_4$-alkyl, $R^6$ represents hydrogen or $C_1$-$C_4$-alkyl, $R^7$ represents a radical from the group consisting of hydrogen, $C_1$-$C_4$-alkyl, halo-$C_1$-$C_4$-alkyl, cyano-$C_1$-$C_4$-alkyl, $C_2$-$C_4$-alkynyl, $C_1$-$C_4$-alkoxy, halo-$C_1$-$C_4$-alkoxy, $C_1$-$C_4$-alkoxy-$C_1$-$C_4$-alkyl, $C_1$-$C_4$-alkoxycarbonyl, $C_1$-$C_4$-alkoxycarbonyl-$C_1$-$C_4$-alkyl, $C_1$-$C_4$-alkylthio-$C_1$-$C_4$-alkyl, aryl-$C_1$-$C_4$-alkyl or hetaryl-$C_1$-$C_4$-alkyl, or $R^6$ and $R^7$ together with the nitrogen atom to which they are attached form a 4- to 7-membered ring which may contain one or two further heteroatoms from the group consisting of nitrogen, oxygen and sulphur (where oxygen and sulphur atoms must not be directly adjacent to one another), $R^8$ represents a radical from the group consisting of hydrogen, $C_1$-$C_6$-alkyl, $C_1$-$C_6$-haloalkyl, cyano-$C_1$-$C_6$-alkyl, $C_1$-$C_6$-alkoxy, $C_1$-$C_6$-haloalkoxy, $C_2$-$C_6$-alkenyl, $C_1$-$C_6$-alkoxy-$C_1$-$C_6$-alkyl, in each case optionally halogen-substituted $C_1$-$C_6$-alkylcarbonyl and $C_1$-$C_6$-alkylsulphonyl, optionally halogen-substituted $C_1$-$C_6$-alkoxycarbonyl and optionally halogen-, $C_1$-$C_6$-alkyl-, $C_1$-$C_6$-alkoxy-, $C_1$-$C_6$-haloalkyl- and cyano-substituted $C_3$-$C_6$-cycloalkylcarbonyl, or represents a cation or an optionally $C_1$-$C_6$-alkyl- or aryl-$C_1$-$C_6$-alkyl-substituted ammonium ion, $R^9$ represents a radical from the group consisting of in each case optionally halogen-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl- and $C_1$-$C_4$-haloalkylsulphonyl-substituted $C_1$-$C_4$-alkyl, $C_2$-$C_4$-alkenyl and $C_2$-$C_4$-alkynyl, in each case optionally halogen-, $C_1$-$C_4$-alkyl-, $C_1$-$C_4$-haloalkyl-, $C_1$-$C_4$-alkoxy-, $C_1$-$C_4$-haloalkoxy-substituted $C_3$-$C_6$-cycloalkyl, $C_3$-$C_6$-cycloalkyl-$C_1$-$C_4$-alkyl and $C_3$-$C_4$-cycloalkenyl, in which one or two ring members may in each case be replaced by a heteroatom from the group consisting of sulphur, oxygen (where oxygen atoms must not be directly adjacent to one another) and nitrogen (and here in particular represent

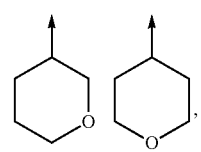

where the arrow in each case denotes the bond to the sulphur atom in the radical (C-1) and in the radical (F-1)), in each case optionally halogen-, cyano- (also in the alkyl moiety), nitro-, $C_1$-$C_4$-alkyl-, $C_1$-$C_4$-haloalkyl-, $C_3$-$C_6$-cycloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl-, $C_1$-$C_4$-haloalkylsulphonyl-, amino-, $C_1$-$C_4$-alkylamino-, di($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted aryl, heteroaryl, aryl-$C_1$-$C_4$-alkyl and heteroaryl-$C_1$-$C_4$-alkyl or represents NR'R" in which R' and R" independently of one another represent a radical from the group consisting of hydrogen and $C_1$-$C_4$-alkyl, or $R^8$ and $R^9$ in the radical (C-1) and in the radical (F-1) may also form, together with the N—S(O)n group to which they are attached, a saturated or unsaturated and optionally halogen-, $C_1$-$C_6$-alkyl-, $C_1$-$C_6$-haloalkyl-, $C_1$-$C_6$-alkoxy-, $C_1$-$C_6$-haloalkoxy-substituted 5- to 7-membered ring which may contain one or two heteroatoms from the group consisting of sulphur, oxygen (where oxygen atoms must not be directly adjacent to one another) and nitrogen and/or at least one and preferably exactly one carbonyl group, in particular, $R^8$ and $R^9$ together with the N—S(O)n group to which they are attached may represent a radical from the group consisting of

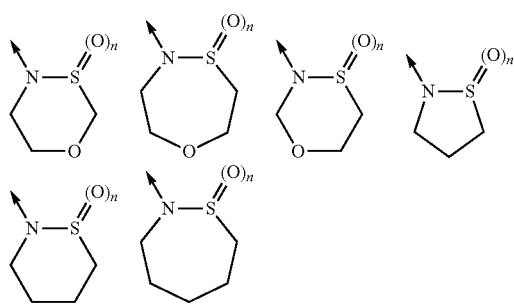

(in which the arrow in each case denotes the bond to the C(X) group), $R^{15}$ represents a radical from the group consisting of in each case optionally methyl-substituted $C_1$-$C_6$-alkyl, $C_2$-$C_6$-alkenyl and $C_2$-$C_6$-alkynyl, in each case optionally methyl-, halogen-, cyano- or carbamoyl-substituted $C_3$-$C_6$-cycloalkyl, $C_3$-$C_6$-cycloalkyl-$C_1$-$C_2$-alkyl and $C_3$-$C_6$-cycloalkenyl, $R^8$ and $R^{15}$ in the radical (C-6) may also form, together with the N—S(O)n group to which they are attached, a saturated or unsaturated and optionally substituted 4- to 8-membered ring which may contain one or two further heteroatoms from the group consisting of sulphur, oxygen (where oxygen and sulphur atoms must not be directly adjacent to one another) and nitrogen and/or at least one carbonyl group, $R^{17}$ represents a radical from the group consisting of in each case optionally halogen-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl- and $C_1$-$C_4$-haloalkylsulphonyl-substituted $C_1$-$C_4$-alkyl, $C_2$-$C_4$-alkenyl and $C_2$-$C_4$-alkynyl, in each case optionally halogen-, $C_1$-$C_4$-alkyl-, $C_1$-$C_4$-haloalkyl-, $C_1$-$C_4$-alkoxy-, $C_1$-$C_4$-haloalkoxy-substituted $C_3$-$C_6$-cycloalkyl, $C_3$-$C_6$-cycloalkyl-$C_1$-$C_4$-alkyl and $C_3$-$C_4$-cycloalkenyl, N-pyrrolidinyl, N-piperidinyl, N-morpholinyl, N-thiomorpholinyl, N-thiomorpholinyl 1-oxide, N-thiomorpholinyl 1,1-dioxide, N-piperazinyl, N-1-methylpiperazinyl and N-2-oxo-1-methylpiperazinyl, in each case optionally halogen-, cyano- (also in the alkyl moiety), nitro-, $C_1$-$C_4$-alkyl-, $C_1$-$C_4$-haloalkyl-, $C_3$-$C_6$-cycloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl-, $C_1$-$C_4$-haloalkylsulphonyl-, amino-, $C_1$-$C_4$-alkylamino-, di($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted aryl, heteroaryl, aryl-$C_1$-$C_4$-alkyl and heteroaryl-$C_1$-$C_4$-alkyl or represents NR'R" in which R' and R" independently of one another represent a radical from the group consisting of hydrogen and $C_1$-$C_4$-alkyl, $R^{18}$ represents a radical from the group consisting of hydrogen, hydroxy, of $C_1$-$C_4$-alkyl, $C_1$-$C_4$-alkoxy, $C_1$-$C_4$-alkoxy-$C_1$-$C_4$-alkyl, $C_1$-$C_4$-alkyl-S—$C_1$-$C_3$-alkyl, $C_1$-$C_4$-alkyl-S(O)—$C_1$-$C_3$-alkyl, $C_1$-$C_4$-alkyl-S(O)$_2$—$C_1$-$C_3$-alkyl, $C_1$-$C_4$-alkylcarbonyl, $C_1$-$C_4$-alkoxycarbonyl, $C_3$-$C_6$-cycloalkyl, $C_3$-$C_6$-cycloalkyl-$C_1$-$C_3$-alkyl, heterocyclyl, heterocyclyl-$C_1$-$C_3$-alkyl, each of which is optionally mono- or polysubstituted by halogen or mono- or disubstituted by cyano, and of phenyl, benzyl, pyridyl, pyrimidyl, thiazolyl, oxazolyl, pyrazolyl, thienyl, furanyl, pyridinylmethyl and thiazolylmethyl, each of which is optionally mono- to trisubstituted by $C_1$-$C_4$-alkyl, $C_1$-$C_3$-haloalkyl, $C_1$-$C_3$-alkoxy, $C_1$-$C_3$-haloalkoxy, cyclopropyl, fluorine, chlorine, bromine or cyano, $R^{19}$ represents hydrogen, represents an alkali or alkaline earth metal ion, or represents an ammonium ion which is optionally mono- to tetrasubstituted by $C_1$-$C_4$-alkyl, or represents a radical from the group consisting of $C_1$-$C_4$-alkyl, $C_1$-$C_4$-alkoxy, $C_1$-$C_4$-alkoxy-$C_1$-$C_2$-alkyl, $C_1$-$C_4$-alkyl-S—$C_1$-$C_2$-alkyl, $C_1$-$C_4$-alkyl-S(O)—$C_1$-$C_2$-alkyl and $C_1$-$C_4$-alkyl-S(O)$_2$—$C_1$-$C_2$-alkyl, each of which is optionally mono- or polysubstituted by halogen or mono- or disubstituted by cyano, $Y^3$ represents a radical from the group consisting of hydrogen, fluorine, chlorine, bromine, iodine, cyano, $C_1$-$C_4$-alkyl, $C_1$-$C_4$-haloalkyl, $C_3$-$C_6$-cycloalkyl, $C_1$-$C_4$-alkoxy and $C_1$-$C_4$-haloalkoxy, W represents a radical from the group consisting of S, SO and SO$_2$, $R^{22}$, if $R^2$ represents the radical c), represents a radical from the group consisting of $C_1$-$C_6$-alkyl, optionally halogen-, carbamoyl-, thiocarbamoyl- or cyano-substituted $C_3$-$C_6$-cycloalkyl, $C_1$-$C_6$-haloalkyl, $C_1$-$C_6$-alkoxy, $C_1$-$C_4$-haloalkoxy, $C_1$-$C_6$-alkoxy-$C_1$-$C_6$-alkyloxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylthio-$C_1$-$C_4$-alkyl, $C_1$-$C_4$-alkylsulphinyl-$C_1$-$C_4$-alkyl, $C_1$-$C_4$-alkylsulphonyl-$C_1$-$C_4$-alkyl, $C_1$-$C_4$-alkylthio-$C_1$-$C_4$-alkyloxy, $C_1$-$C_4$-alkylsulphinyl-$C_1$-$C_4$-alkyloxy, $C_1$-$C_4$-alkylsulphonyl-$C_1$-$C_4$-alkyloxy, $C_1$-$C_4$-haloalkylthio-$C_1$-$C_4$-alkyl, $C_1$-$C_4$-haloalkylsulphinyl-$C_1$-$C_4$-alkyl, $C_1$-$C_4$-haloalkylsulphonyl-$C_1$-$C_4$-alkyl, $C_1$-$C_4$-alkylthio-$C_2$-$C_4$-alkenyl, $C_1$-$C_4$-alkylsulphinyl- $C_2$-$C_4$-alkenyl, $C_1$-$C_4$-alkylsulphonyl-$C_2$-$C_4$-alkenyl, $C_2$-$C_4$-alkenylthio-$C_1$-$C_4$-alkyl, $C_2$-$C_4$-alkenylsulphinyl-$C_1$-$C_4$-alkyl, $C_2$-$C_4$-alkenylsulphonyl-$C_1$-$C_4$-alkyl, $C_1$-$C_4$-alkylcarbonyl-$C_1$-$C_4$-alkyl, $C_1$-$C_4$-haloalkylcarbonyl-$C_1$-$C_4$-alkyl, $C_1$-$C_4$-alkoxy-$C_1$-$C_4$-alkyl, $C_1$-$C_4$-haloalkoxy-$C_1$-$C_4$-alkyl, $C_1$-$C_4$-alkoxycarbonyl-$C_1$-$C_4$-alkyl, $C_1$-$C_4$-haloalkoxycarbonyl-$C_1$-$C_4$-alkyl, $C_1$-$C_4$-alkylaminosulphonyl, di-($C_1$-$C_4$-alkyl)-aminosulphonyl, $R^{23}$, if $R^2$ represents the radical c), represents a radical from the group consisting of hydrogen, $C_1$-$C_6$-alkyl, $C_2$-$C_4$-alkenyl, $C_2$-$C_4$-alkynyl, $C_1$-$C_4$-alkylthio-$C_1$-$C_4$-alkyl, $C_2$-$C_4$-alkenylthio-$C_1$-$C_4$-alkyl, cyano-$C_1$-$C_4$-alkyl, $C_1$-$C_4$-alkoxy-$C_1$-$C_4$-alkyl, $R^{23}$, if $R^2$ represents the radical d), represents a radical from the group consisting of hydrogen, $C_1$-$C_6$-alkyl, $C_2$-$C_4$-alkenyl, $C_2$-$C_4$-alkynyl, $C_3$-$C_6$-cycloalkyl, $C_3$-$C_6$-cycloalkenyl, $C_1$-$C_6$-alkoxy, $C_2$-$C_6$-alkenyloxy, $C_2$-$C_6$-alkynyloxy, $C_3$-$C_6$-cycloalkyloxy, $C_1$-$C_4$-alkylthio-$C_1$-$C_4$-alkyl, $C_2$-$C_4$-alkenylthio-$C_1$-$C_4$-alkyl, cyano-$C_1$-$C_4$-alkyl, $C_1$-$C_4$-alkoxy-$C_1$-$C_4$-alkyl, or, in the case $R^2$=d), $R^{22}$ also represents optionally halogen-, cyano-, nitro-, amino-, hydroxy-, $C_1$-$C_6$-alkyl-, $C_1$-$C_6$-haloalkyl-, $C_3$-$C_6$-cycloalkyl-, $C_1$-$C_6$-alkoxy-, $C_1$-$C_4$-haloalkoxy-, $C_1$-$C_6$-alkoxycarbonyloxy-, $C_1$-$C_6$-alkylamino-, $C_1$-$C_6$-alkylthio-, $C_1$-$C_4$-haloalkylthio-, $C_1$-$C_4$-alkylsulphinyl-, $C_1$-$C_4$-alkylsulphonyl-, $C_1$-$C_6$-alkylcarbonyl-, aminocarbonyl-, $C_1$-$C_6$-alkylaminocarbonyl-, di-($C_1$-$C_6$)-alkylaminocarbonyl-, $C_1$-$C_6$-alkylcarbonylamino-substituted phenyl or represents an E radical from the group consisting of

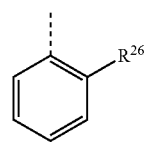
E-1

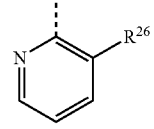
E-2

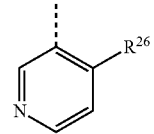
E-3

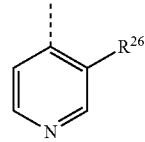
E-4

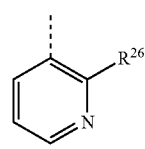
E-5

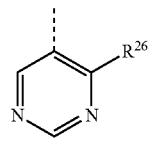
E-6

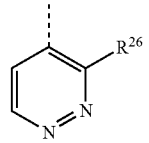
E-10

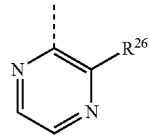
E-11

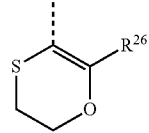
E-13

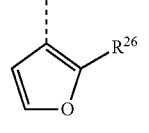
E-18

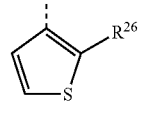
E-21

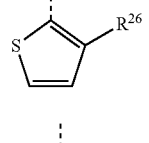
E-23

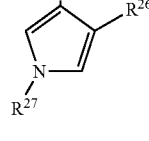
E-25

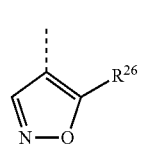
E-27

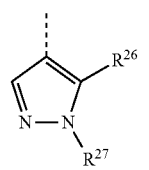
E-31

-continued

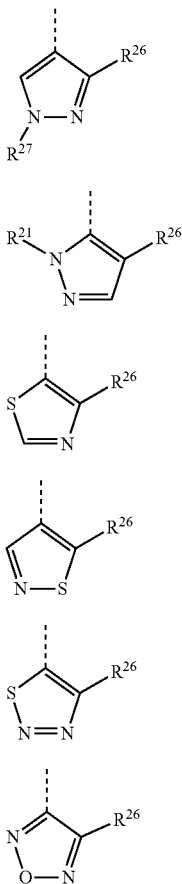

E-35
E-36
E-39
E-44
E-49
E-51

$R^{27}$ represents hydrogen or $C_1$-$C_4$-alkyl and $R^{26}$ represents hydrogen, $C_1$-$C_4$-alkyl, $C_2$-$C_4$-alkenyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_2$-alkyl, $C_1$-$C_4$-alkylthio-$C_1$-$C_2$-alkyl, $C_1$-$C_4$-alkylsulphinyl-$C_1$-$C_2$-alkyl, $C_1$-$C_4$-alkylsulphonyl-$C_1$-$C_2$-alkyl or cyano-$C_1$-$C_4$-alkyl and compounds of the formula (I) in which A represents the A radical

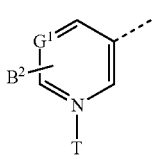

(A-a)

where the broken line represents the bond to the nitrogen atom of the bicycle of the formula (I), $G^1$ represents N or C—$B^1$, $B^1$ represents a radical from the group consisting of hydrogen, halogen, $C_1$-$C_6$-alkyl and $C_1$-$C_4$-haloalkyl, $B^2$ represents a radical from the group consisting of hydrogen, halogen, $C_1$-$C_6$-alkyl and $C_1$-$C_4$-haloalkyl, T represents oxygen or an electron pair, $R^1$ represents a radical from the group consisting of hydrogen, $C_1$-$C_4$-alkyl and $C_1$-$C_4$-alkoxy, $R^2$ a) represents a B radical from the group consisting of

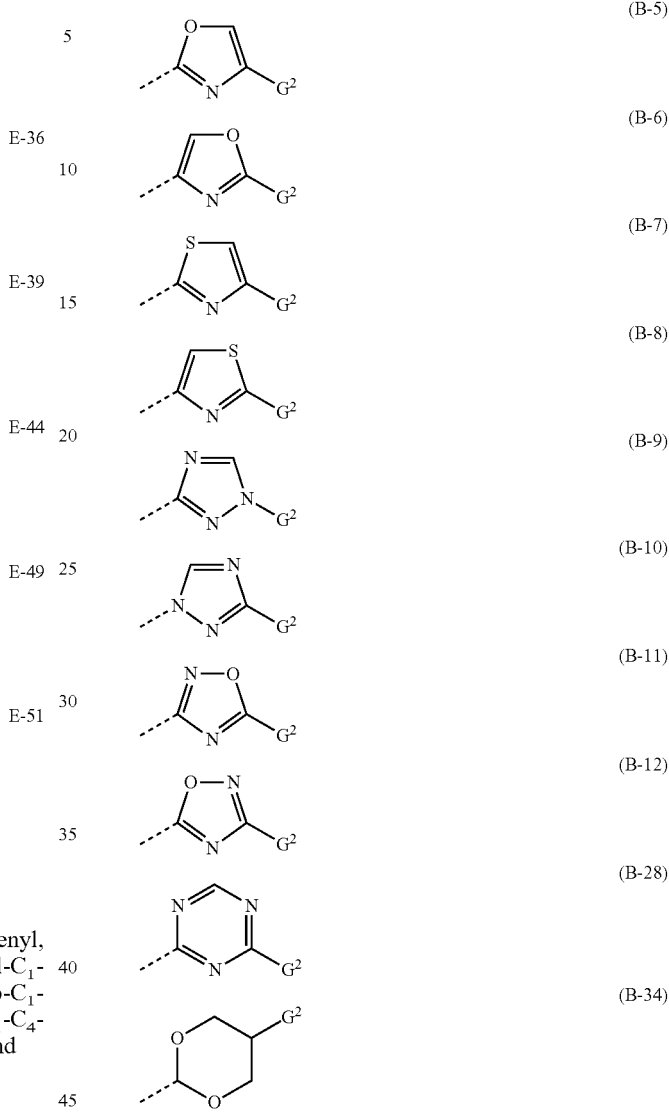

(B-5)
(B-6)
(B-7)
(B-8)
(B-9)
(B-10)
(B-11)
(B-12)
(B-28)
(B-34)

where the broken line represents the bond to the carbon atom of the bicycle of the formula (I), where $G^2$ represents hydrogen or a radical from the group consisting of halogen, nitro, amino, cyano, $C_1$-$C_4$-alkylamino, halo-$C_1$-$C_4$-alkylamino, $C_1$-$C_4$-dialkylamino, $C_1$-$C_4$-alkyl, halo-$C_1$-$C_4$-alkyl, $C_1$-$C_4$-alkoxy, halo-$C_1$-$C_4$-alkoxy, $C_1$-$C_4$-alkoxy-$C_1$-$C_4$-alkyl, halogenated $C_1$-$C_4$-alkoxy-$C_1$-$C_4$-alkyl, bis($C_1$-$C_4$-alkoxy)-$C_1$-$C_4$-alkyl, bis(halo-$C_1$-$C_4$-alkoxy)-$C_1$-$C_4$-alkyl, $C_1$-$C_4$-alkoxy-($C_1$-$C_4$-alkylsulphanyl)-$C_1$-$C_4$-alkyl, $C_1$-$C_4$-alkoxy-($C_1$-$C_4$-alkylsulphinyl)-$C_1$-$C_4$-alkyl, $C_1$-$C_4$-alkoxy-($C_1$-$C_4$-alkylsulphonyl)-$C_1$-$C_4$-alkyl, bis($C_1$-$C_4$-alkylsulphanyl)-$C_1$-$C_4$-alkyl, bis(halo-$C_1$-$C_4$-alkylsulphanyl)-$C_1$-$C_4$-alkyl, bis(hydroxy-$C_1$-$C_4$-alkylsulphanyl)-$C_1$-$C_4$-alkyl, $C_1$-$C_4$-alkoxycarbonyl, $C_1$-$C_4$-alkoxycarbonyl-$C_1$-$C_4$-alkyl, C($X^2$)N$R^3R^4$, N$R^6R^7$, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, the heterocyclyl radicals dioxanyl, dioxolanyl, dioxepanyl, dioxocanyl, oxathianyl, oxathiolanyl, oxathiepanyl, oxathiocanyl, dithianyl, dithiolanyl, dithiepanyl, dithiocanyl, oxathianyl oxide, oxathiolanyl oxide, oxathiepanyl oxide, oxathiocanyl oxide, oxathianyl dioxide, oxathiolanyl dioxide, oxathiepanyl dioxide, oxathiocanyl dioxide, morpholinyl, triazolinonyl, oxazolinyl, dihydrooxadiazinyl, dihydrodioxazinyl, dihydrooxazolyl, dihydrooxazinyl and pyrazolinonyl (which for their part may be substituted by $C_1$-$C_4$-alkyl, halo-$C_1$-$C_4$-alkyl, $C_1$-$C_4$-alkoxy and $C_1$-$C_4$-alkoxy-$C_1$-$C_4$-alkyl), phenyl (which for its part may be substituted by halogen, cyano, nitro, $C_1$-$C_4$-alkyl and halo-$C_1$-$C_4$-alkyl), the heteroaryl radicals pyridyl, pyridyl N-oxide, pyrimidyl, imidazolyl, pyrazolyl, oxazolyl, thiazolyl, furanyl, thienyl, triazolyl, tetrazolyl, oxadiazolyl, thiadiazolyl, pyrazinyl, triazinyl, tetrazinyl and isoquinolinyl (which for their part may be substituted by halogen, nitro, $C_1$-$C_4$-alkyl, halo-$C_1$-$C_4$-alkyl, $C_1$-$C_4$-alkoxy, halo-$C_1$-$C_4$-alkoxy, $C_1$-$C_4$-alkoxy-$C_1$-$C_4$-alkyl, $C_1$-$C_4$-alkylthio, $C_1$-$C_4$-alkylthio-$C_1$-$C_4$-alkyl and $C_3$-$C_6$-cyclo-$C_1$-$C_4$-alkyl) and the heteroaryl-$C_1$-$C_4$-alkyl radicals triazolyl-$C_1$-$C_4$-alkyl, pyridyl-$C_1$-$C_4$-alkyl, pyrimidyl-$C_1$-$C_4$-alkyl and oxadiazolyl-$C_1$-$C_4$-alkyl (which for their part may be substituted by halogen and $C_1$-$C_4$-alkyl), or $R^2$ aa) represents a B radical from the group consisting of

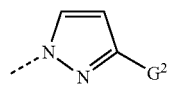

(B-1)

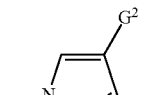

(B-2)

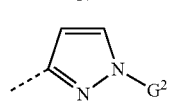

(B-3)

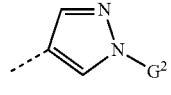

(B-4)

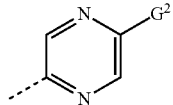

(B-21)

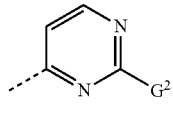

(B-22)

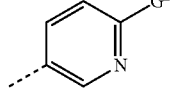

(B-23)

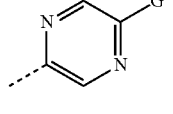

(B-24)

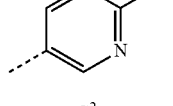

(B-25)

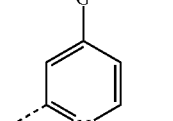

(B-26)

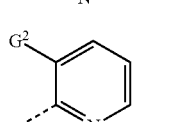

(B-27)

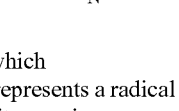

(B-31)

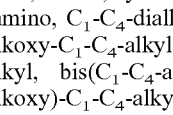

(B-32)

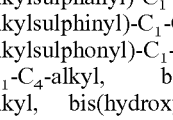

(B-33)

(B-35)

(B-36)

in which $G^2$ represents a radical from the group consisting of halogen, nitro, amino, cyano, $C_1$-$C_4$-alkylamino, halo-$C_1$-$C_4$-alkylamino, $C_1$-$C_4$-dialkylamino, halo-$C_1$-$C_4$-alkoxy, $C_1$-$C_4$-alkoxy-$C_1$-$C_4$-alkyl, halogenated $C_1$-$C_4$-alkoxy-$C_1$-$C_4$-alkyl, bis($C_1$-$C_4$-alkoxy)-$C_1$-$C_4$-alkyl, bis(halo-$C_1$-$C_4$-alkoxy)-$C_1$-$C_4$-alkyl, $C_1$-$C_4$-alkoxy-($C_1$-$C_4$-alkylsulphanyl)-$C_1$-$C_4$-alkyl, $C_1$-$C_4$-alkoxy-($C_1$-$C_4$-alkylsulphinyl)-$C_1$-$C_4$-alkyl, $C_1$-$C_4$-alkoxy-($C_1$-$C_4$-alkylsulphonyl)-$C_1$-$C_4$-alkyl, bis($C_1$-$C_4$-alkylsulphanyl)-$C_1$-$C_4$-alkyl, bis(halo-$C_1$-$C_4$-alkylsulphanyl)-$C_1$-$C_4$-alkyl, bis(hydroxy-$C_1$-$C_4$-alkylsulphanyl)-$C_1$-$C_4$-alkyl, $C_1$-$C_4$-alkoxycarbonyl, $C_1$-$C_4$-alkoxycarbonyl-$C_1$-$C_4$-alkyl, $C(X^2)NR^3R^4$, $NR^6R^7$, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, the heterocyclyl radicals dioxanyl, dioxolanyl, dioxepanyl, dioxocanyl, oxathianyl, oxathiolanyl, oxathiepanyl, oxathiocanyl, dithianyl, dithiolanyl, dithiepanyl, dithiocanyl, oxathianyl oxide, oxathiolanyl oxide, oxathiepanyl oxide, oxathiocanyl oxide, oxathianyl dioxide, oxathiolanyl dioxide, oxathiepanyl dioxide, oxathiocanyl dioxide, morpholinyl, triazolinonyl, oxazolinyl, dihydrooxadiazinyl, dihydrodioxazinyl, dihydrooxazolyl, dihydrooxazinyl and pyrazolinonyl (which for their part may be substituted by $C_1$-$C_4$-alkyl, halo-$C_1$-$C_4$-alkyl, $C_1$-$C_4$-alkoxy and $C_1$-$C_4$-alkoxy-$C_1$-$C_4$-alkyl), phenyl (which for its part may be substituted by halogen, cyano, nitro, $C_1$-$C_4$-alkyl and halo-$C_1$-$C_4$-alkyl), the heteroaryl radicals imidazolyl, pyrazolyl, oxazolyl, furanyl, thienyl, triazolyl, tetrazolyl, oxadiazolyl, thiadiazolyl, pyrazinyl, triazinyl, tetrazinyl and isoquinolinyl (which for their part may be substituted by halogen, nitro, $C_1$-$C_4$-alkyl, halo-$C_1$-$C_4$-alkyl, $C_1$-$C_4$-alkoxy, halo-$C_1$-$C_4$-alkoxy, $C_1$-$C_4$-alkoxy-$C_1$-$C_4$-alkyl, $C_1$-$C_4$-alkylthio, $C_1$-$C_4$-alkylthio-$C_1$-$C_4$-alkyl and $C_3$-$C_6$-cyclo-$C_1$-$C_4$-alkyl) and the heteroaryl-$C_1$-$C_4$-alkyl radicals triazolyl-$C_1$-$C_4$-alkyl, pyridyl-$C_1$-$C_4$-alkyl, pyrimidyl-$C_1$-$C_4$-alkyl and oxadiazolyl-$C_1$-$C_4$-alkyl (which for their part may be substituted by halogen and $C_1$-$C_4$-alkyl), or, if $R^2$ represents one of the radicals listed under a) or aa), $G^2$ also represents a C radical from the group consisting of (C-6) and (C-9)

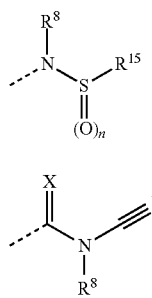

where the broken line represents the bond to the B radicals, or $R^2$ c) represents a radical of the formula

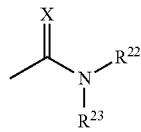

or $R^2$ d) represents a radical of the formula

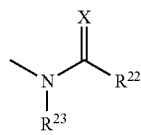

or $R^2$ e) represents an F radical from the group consisting of (F-8) and (F-10)

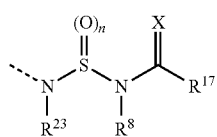

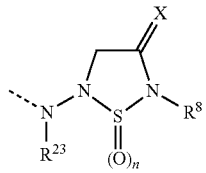

where the broken line represents the bond to the carbon atom in the formula (I) or $R^2$ f) represents a radical from the group consisting of $C_1$-$C_6$-haloalkyl, carboxyl and amino, in which X represents oxygen, $X^2$ represents oxygen, sulphur, $NR^5$ or NOH, n represents 2, $R^3$ represents $C_1$-$C_4$-alkyl, $R^4$ represents a radical from the group consisting of hydrogen, $C_1$-$C_4$-alkyl, halo-$C_1$-$C_4$-alkyl, cyano-$C_1$-$C_4$-alkyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_4$-alkyl, $C_1$-$C_4$-alkoxycarbonyl, $C_1$-$C_4$-alkoxycarbonyl-$C_1$-$C_4$-alkyl and $C_1$-$C_4$-alkylthio-$C_1$-$C_4$-alkyl, $R^5$ represents a radical from the group consisting of hydrogen, $C_1$-$C_4$-alkyl, halo-$C_1$-$C_4$-alkyl, cyano-$C_1$-$C_4$-alkyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_4$-alkyl, $C_1$-$C_4$-alkoxycarbonyl, $C_1$-$C_4$-alkoxycarbonyl-$C_1$-$C_4$-alkyl and $C_1$-$C_4$-alkylthio-$C_1$-$C_4$-alkyl, $R^6$ represents hydrogen or $C_1$-$C_4$-alkyl, $R^7$ represents a radical from the group consisting of hydrogen, $C_1$-$C_4$-alkyl, halo-$C_1$-$C_4$-alkyl, cyano-$C_1$-$C_4$-alkyl, $C_2$-$C_4$-alkynyl, $C_1$-$C_4$-alkoxy, halo-$C_1$-$C_4$-alkoxy, $C_1$-$C_4$-alkoxy-$C_1$-$C_4$-alkyl, $C_1$-$C_4$-alkoxycarbonyl, $C_1$-$C_4$-alkoxycarbonyl-$C_1$-$C_4$-alkyl, $C_1$-$C_4$-alkylthio-$C_1$-$C_4$-alkyl, aryl-$C_1$-$C_4$-alkyl and hetaryl-$C_1$-$C_4$-alkyl, or $R^6$ and $R^7$ together with the nitrogen atom to which they are attached form a 4- to 7-membered ring which may contain one or two further heteroatoms from the group consisting of nitrogen, oxygen and sulphur (where oxygen and sulphur atoms must not be directly adjacent to one another), $R^8$ represents a radical from the group consisting of hydrogen, $C_1$-$C_6$-alkyl, $C_1$-$C_6$-haloalkyl, cyano-$C_1$-$C_6$-alkyl, $C_1$-$C_6$-alkoxy, $C_1$-$C_6$-haloalkoxy, $C_2$-$C_6$-alkenyl, $C_1$-$C_6$-alkoxy-$C_1$-$C_6$-alkyl, in each case optionally halogen-substituted $C_1$-$C_6$-alkylcarbonyl and $C_1$-$C_6$-alkylsulphonyl, optionally halogen-substituted $C_1$-$C_6$-alkoxycarbonyl, optionally halogen-, $C_1$-$C_6$-alkyl-, $C_1$-$C_6$-alkoxy-, $C_1$-$C_6$-haloalkyl- and cyano-substituted $C_3$-$C_6$-cycloalkylcarbonyl, or represents a cation or an optionally $C_1$-$C_6$-alkyl- or aryl-$C_1$-$C_6$-alkyl-substituted ammonium ion, $R^9$ represents a radical from the group consisting of in each case optionally halogen-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl- and $C_1$-$C_4$-haloalkylsulphonyl-substituted $C_1$-$C_4$-alkyl, $C_2$-$C_4$-alkenyl and $C_2$-$C_4$-alkynyl, in each case optionally halogen-, $C_1$-$C_4$-alkyl-, $C_1$-$C_4$-haloalkyl-, $C_1$-$C_4$-alkoxy-, $C_1$-$C_4$-haloalkoxy-substituted $C_3$-$C_6$-cycloalkyl, $C_3$-$C_6$-cycloalkyl-$C_1$-$C_4$-alkyl and $C_3$-$C_4$-cycloalkenyl, in which one or two ring members may in each case be replaced by a heteroatom from the group consisting of sulphur, oxygen (where oxygen atoms must not be directly adjacent to one another) and nitrogen (and here in particular represent

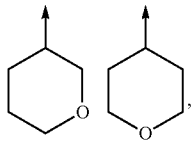

where the arrow in each case marks the bond to the sulphur atom in the radical (C-1)), in each case optionally halogen-, cyano- (also in the alkyl moiety), nitro-, $C_1$-$C_4$-alkyl-, $C_1$-$C_4$-haloalkyl-, $C_3$-$C_6$-cycloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl-, $C_1$-$C_4$-haloalkylsulphonyl-, amino-, $C_1$-$C_4$-alkylamino-, di($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted aryl, heteroaryl, aryl-$C_1$-$C_4$-alkyl and heteroaryl-$C_1$-$C_4$-alkyl or represents NR'R" in which R' and R" independently of one another represent a radical from the group consisting of hydrogen and $C_1$-$C_4$-alkyl, $R^{15}$ represents a radical from the group consisting of in each case optionally methyl-substituted $C_1$-$C_6$-alkyl, $C_2$-$C_6$-alkenyl and $C_2$-$C_6$-alkynyl, in each case optionally methyl-, halogen-, cyano- or carbamoyl-substituted $C_3$-$C_6$-cycloalkyl, $C_3$-$C_6$-cycloalkyl-$C_1$-$C_2$-alkyl and $C_3$-$C_6$-cycloalkenyl, or $R^8$ and $R^{15}$ in the radical (C-6) may also form, together with the N—S(O)n group to which they are attached, a saturated or unsaturated and optionally substituted 4- to 8-membered ring which may contain one or two further heteroatoms from the group consisting of sulphur, oxygen (where oxygen and sulphur atoms must not be directly adjacent to one another) and nitrogen and/or at least one carbonyl group, $R^{17}$ represents a radical from the group consisting of in each case optionally halogen-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl- and $C_1$-$C_4$-haloalkylsulphonyl-substituted $C_1$-$C_4$-alkyl, $C_2$-$C_4$-alkenyl and $C_2$-$C_4$-alkynyl, in each case optionally halogen-, $C_1$-$C_4$-alkyl-, $C_1$-$C_4$-haloalkyl-, $C_1$-$C_4$-alkoxy-, $C_1$-$C_4$-haloalkoxy-substituted $C_3$-$C_6$-cycloalkyl, $C_3$-$C_6$-cycloalkyl-$C_1$-$C_4$-alkyl and $C_3$-$C_4$-cycloalkenyl, N-pyrrolidinyl, N-piperidinyl, N-morpholinyl, N-thiomorpholinyl, N-thiomorpholinyl 1-oxide, N-thiomorpholinyl 1,1-dioxide, N-piperazinyl, N-1-methylpiperazinyl or N-2-oxo-1-methylpiperazinyl, in each case optionally halogen-, cyano- (also in the alkyl moiety), nitro-, $C_1$-$C_4$-alkyl-, $C_1$-$C_4$-haloalkyl-, $C_3$-$C_6$-cycloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl-, $C_1$-$C_4$-haloalkylsulphonyl-, amino-, $C_1$-$C_4$-alkylamino-, di($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted aryl, heteroaryl, aryl-$C_1$-$C_4$-alkyl and heteroaryl-$C_1$-$C_4$-alkyl or represents NR'R" in which R' and R" independently of one another represent a radical from the group consisting of hydrogen and $C_1$-$C_4$-alkyl, $R^{22}$ represents a D radical from the group consisting of (D-1) to (D-3)

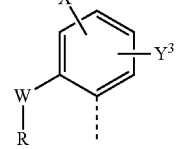

(D-1)

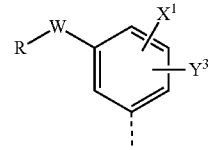

(D-2)

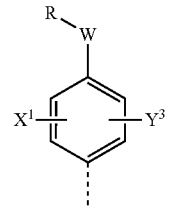

(D-3)

where the broken line represents the bond to the nitrogen atom in the radical c) or to the carbon atom in the radical d), R represents $NR^{18}R^{19}$ or represents $C_1$-$C_6$-alkyl, $C_3$-$C_6$-alkenyl, $C_3$-$C_6$-alkynyl, $C_1$-$C_4$-alkoxy-$C_1$-$C_3$-alkyl, $C_1$-$C_4$-alkyl-S—$C_1$-$C_3$-alkyl, $C_1$-$C_4$-alkyl-S(O)—$C_1$-$C_3$-alkyl, $C_1$-$C_4$-alkyl-S(O)$_2$—$C_1$-$C_3$-alkyl, each of which is optionally mono- to heptasubstituted by halogen, mono- or disubstituted by oxygen (leads to C=O) or mono- or disubstituted by cyano, represents $R^{18}$—CO—$C_1$-$C_2$-alkyl, represents $NR^{18}R^{19}$—CO—$C_1$-$C_2$-alkyl, represents $C_3$-$C_6$-cycloalkyl which is optionally mono- or disubstituted by oxygen (leads to C=O), $C_1$-$C_4$-alkyl, $C_3$-$C_6$-cycloalkyl, $C_1$-$C_4$-alkoxy and $C_1$-$C_4$-haloalkyl, represents $C_3$-$C_8$-cycloalkenyl which is optionally mono- or disubstituted by oxygen (leads to C=O), $C_1$-$C_4$-alkyl, $C_3$-$C_6$-cycloalkyl, $C_1$-$C_4$-alkoxy and $C_1$-$C_4$-haloalkyl, represents $C_3$-$C_6$-cycloalkyl-$C_1$-$C_4$-alkyl which is optionally mono- or disubstituted by oxygen (leads to C=O), $C_1$-$C_4$-alkyl, $C_3$-$C_6$-cycloalkyl, $C_1$-$C_4$-alkoxy and $C_1$-$C_4$-haloalkyl, represents $C_3$-$C_6$-cycloalkenyl-$C_1$-$C_4$-alkyl which is optionally mono- or disubstituted by oxygen (leads to C=O), $C_1$-$C_4$-alkyl, $C_3$-$C_6$-cycloalkyl, $C_1$-$C_4$-alkoxy and $C_1$-$C_4$-haloalkyl, represents heterocyclyl which is optionally mono- or disubstituted by oxygen (leads to C=O), $C_1$-$C_4$-alkyl, $C_3$-$C_6$-cycloalkyl, $C_1$-$C_4$-alkoxy and $C_1$-$C_4$-haloalkyl, represents heterocyclyl-$C_1$-$C_4$-alkyl which is optionally mono- or disubstituted by oxygen (leads to C=O), $C_1$-$C_4$-alkyl, $C_3$-$C_6$-cycloalkyl, $C_1$-$C_4$-alkoxy and $C_1$-$C_4$-haloalkyl, or represents phenyl, phenyl-$C_1$-$C_4$-alkyl, hetaryl and hetaryl-$C_1$-$C_4$-alkyl, each of which is optionally mono- to trisubstituted by halogen, cyano, $C_1$-$C_4$-alkyl, $C_1$-$C_4$-haloalkyl, $C_3$-$C_6$-cycloalkyl, $C_1$-$C_4$-alkoxy or $C_1$-$C_4$-haloalkoxy, $X^1$ represents a radical from the group consisting of hydrogen, fluorine, chlorine, bromine, iodine, cyano, nitro, $C_1$-$C_4$-alkyl, $C_1$-$C_4$-haloalkyl, $C_3$-$C_6$-cycloalkyl, $C_1$-$C_4$-alkoxy and $C_1$-$C_4$-haloalkoxy, $Y^3$ represents a radical from the group consisting of hydrogen, fluorine, chlorine, bromine, iodine, cyano, $C_1$-$C_4$-alkyl, $C_1$-$C_4$-haloalkyl, $C_3$-$C_6$-cycloalkyl, $C_1$-$C_4$-alkoxy and $C_1$-$C_4$-haloalkoxy, W represents a radical from the group consisting of S, SO and $SO_2$, $R^{18}$ represents a radical from the group consisting of hydrogen, hydroxy, of $C_1$-$C_4$-alkyl, $C_1$-$C_4$-alkoxy, $C_1$-$C_4$-alkoxy-$C_1$-$C_4$-alkyl, $C_1$-$C_4$-alkyl-S—$C_1$-$C_3$-alkyl, $C_1$-$C_4$-alkyl-S(O)—$C_1$-$C_3$-alkyl, $C_1$-$C_4$-alkyl-$S(O)_2$—$C_1$-$C_3$-alkyl, $C_1$-$C_4$-alkylcarbonyl, $C_1$-$C_4$-alkoxycarbonyl, $C_3$-$C_6$-cycloalkyl, $C_3$-$C_6$-cycloalkyl-$C_1$-$C_3$-alkyl, heterocyclyl, heterocyclyl-$C_1$-$C_3$-alkyl each of which is optionally mono- or polysubstituted by halogen or mono- or disubstituted by cyano, and of phenyl, benzyl, pyridyl, pyrimidyl, thiazolyl, oxazolyl, pyrazolyl, thienyl, furanyl, pyridinylmethyl and thiazolylmethyl, each of which is optionally mono- to trisubstituted by $C_1$-$C_4$-alkyl, $C_1$-$C_3$-haloalkyl, $C_1$-$C_3$-alkoxy, $C_1$-$C_3$-haloalkoxy, cyclopropyl, fluorine, chlorine, bromine or cyano, $R^{19}$ represents hydrogen, represents an alkali or alkaline earth metal ion, or represents an ammonium ion which is optionally mono- to tetrasubstituted by $C_1$-$C_4$-alkyl, or represents a radical from the group consisting of $C_1$-$C_4$-alkyl, $C_1$-$C_4$-alkoxy, $C_1$-$C_4$-alkoxy-$C_1$-$C_2$-alkyl, $C_1$-$C_4$-alkyl-S—$C_1$-$C_2$-alkyl, $C_1$-$C_4$-alkyl-S(O)—$C_1$-$C_2$-alkyl and $C_1$-$C_4$-alkyl-$S(O)_2$—$C_1$-$C_2$-alkyl, each of which is optionally mono- or polysubstituted by halogen or mono- or disubstituted by cyano, $R^{23}$, if $R^2$ represents the radical c), represents a radical from the group consisting of hydrogen, $C_1$-$C_6$-alkyl, $C_2$-$C_4$-alkenyl, $C_2$-$C_4$-alkynyl, $C_1$-$C_4$-alkylthio-$C_1$-$C_4$-alkyl, $C_2$-$C_4$-alkenylthio-$C_1$-$C_4$-alkyl, cyano-$C_1$-$C_4$-alkyl, $C_1$-$C_4$-alkoxy-$C_1$-$C_4$-alkyl, $R^{23}$, if $R^2$ represents the radical d), represents a radical from the group consisting of hydrogen, $C_1$-$C_6$-alkyl, $C_2$-$C_4$-alkenyl, $C_2$-$C_4$-alkynyl, $C_3$-$C_6$-cycloalkyl, $C_3$-$C_6$-cycloalkenyl, $C_1$-$C_6$-alkoxy, $C_2$-$C_6$-alkenyloxy, $C_2$-$C_6$-alkynyloxy, $C_3$-$C_6$-cycloalkyloxy, $C_1$-$C_4$-alkylthio-$C_1$-$C_4$-alkyl, $C_2$-$C_4$-alkenylthio-$C_1$-$C_4$-alkyl, cyano-$C_1$-$C_4$-alkyl, $C_1$-$C_4$-alkoxy-$C_1$-$C_4$-alkyl, or, in the case $R^2$=d), $R^{22}$ also represents an E radical from the group consisting of

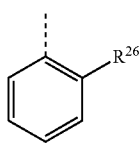
E-1

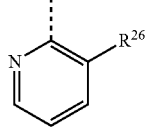
E-2

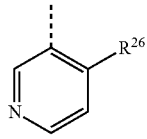
E-3

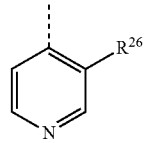
E-4

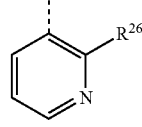
E-5

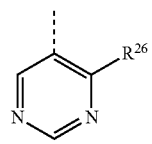
E-6

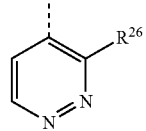
E-10

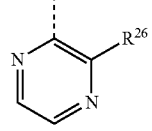
E-11

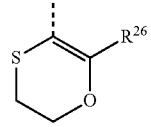
E-13

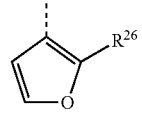
E-18

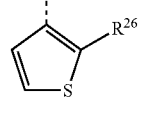
E-21

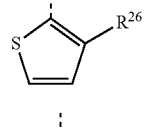
E-23

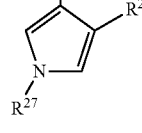
E-25

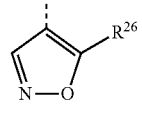
E-27

E-31 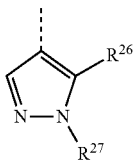

E-35 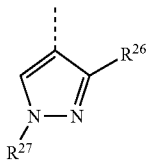

E-36 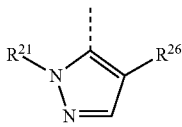

E-39 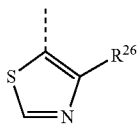

E-44 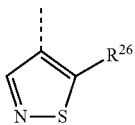

E-49 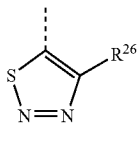

E-51 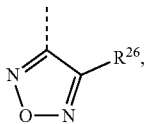

$R^{27}$ represents hydrogen or $C_1$-$C_4$-alkyl and $R^{26}$ represents hydrogen, $C_1$-$C_4$-alkyl, $C_2$-$C_4$-alkenyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_2$-alkyl, $C_1$-$C_4$-alkylthio-$C_1$-$C_2$-alkyl, $C_1$-$C_4$-alkylsulphinyl-$C_1$-$C_2$-alkyl, $C_1$-$C_4$-alkylsulphonyl-$C_1$-$C_2$-alkyl or cyano-$C_1$-$C_4$-alkyl.

Preferred range (3): Very particular preference is given to compounds of the formula (I) in which A represents an A radical from the group consisting of (A-b) and (A-f)

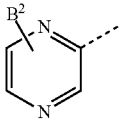 (A-b)

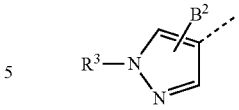 (A-f)

where the broken line represents the bond to the nitrogen atom of the bicycle, $B^2$ represents hydrogen, $R^1$ represents hydrogen, $R^2$ a) represents a B radical from the group consisting of

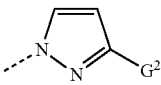 (B-1)

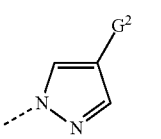 (B-2)

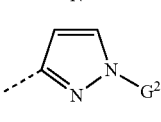 (B-3)

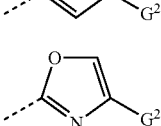 (B-4)

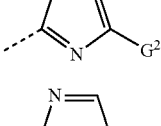 (B-5)

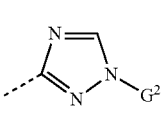 (B-9)

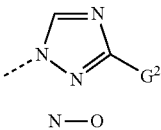 (B-10)

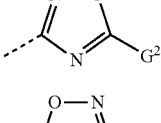 (B-11)

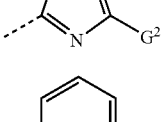 (B-12)

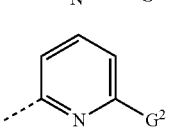 (B-21)

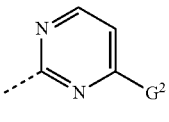 (B-23)

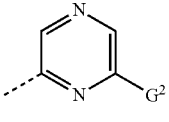 (B-25)

-continued

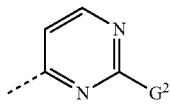
(B-27)

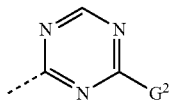
(B-28)

where the broken line represents the bond to the carbon atom of the bicycle of the formula (I) or $R^2$ b) represents a radical from the group consisting of (D-1) to (D-3)

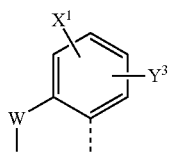
(D-1)

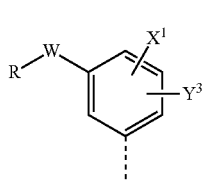
(D-2)

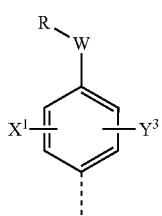
(D-3)

where the broken line represents the bond to the carbon atom of the bicycle of the formula (I) or $R^2$ c) represents a radical of the formula

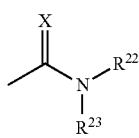

or
$R^2$ d) represents a radical of the formula

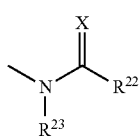

or
$R^2$ e) represents a radical from the group consisting of (F-1), (F-8) and (F-10)

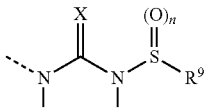
(F-1)

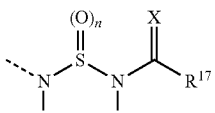
(F-8)

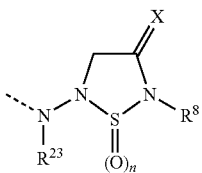
(F-10)

where the broken line represents the bond to the nitrogen atom in the formula (I) or $R^2$ f) represents a radical from the group consisting of $C_1$-$C_6$-haloalkyl, carboxyl and amino, where $G^2$ represents hydrogen or a radical from the group consisting of halogen, nitro, amino, cyano, $C_1$-$C_4$-alkylamino, halo-$C_1$-$C_4$-alkylamino, di-($C_1$-$C_4$-alkyl)-amino, $C_1$-$C_4$-alkyl, halo-$C_1$-$C_4$-alkyl, $C_1$-$C_4$-alkoxy, halo-$C_1$-$C_4$-alkoxy, $C_1$-$C_4$-alkoxy-$C_1$-$C_4$-alkyl, halogenated $C_1$-$C_4$-alkoxy-$C_1$-$C_4$-alkyl, bis($C_1$-$C_4$-alkoxy)-$C_1$-$C_4$-alkyl, bis (halo-$C_1$-$C_4$-alkoxy)-$C_1$-$C_4$-alkyl, $C_1$-$C_4$-alkoxy-($C_1$-$C_4$-alkylsulphanyl)-$C_1$-$C_4$-alkyl, $C_1$-$C_4$-alkoxy-($C_1$-$C_4$-alkylsulphinyl)-$C_1$-$C_4$-alkyl, $C_1$-$C_4$-alkoxy-($C_1$-$C_4$-alkylsulphonyl)-$C_1$-$C_4$-alkyl, bis($C_1$-$C_4$-alkylsulphanyl)-$C_1$-$C_4$-alkyl, bis(halo-$C_1$-$C_4$-alkylsulphanyl)-$C_1$-$C_4$-alkyl, bis(hydroxy-$C_1$-$C_4$-alkylsulphanyl)-$C_1$-$C_4$-alkyl, $C_1$-$C_4$-alkoxycarbonyl, $C_1$-$C_4$-alkoxycarbonyl-$C_1$-$C_4$-alkyl, $C(X^2)NR^3R^4$, $NR^6R^7$, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, or $G^2$ represents a C radical (C-1) or (C-9)

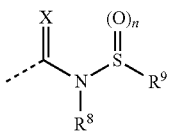
(C-1)

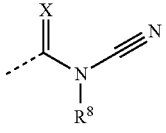
(C-9)

in which the broken line denotes the bond to the B radicals,

X represents oxygen, $X^1$ represents a radical from the group consisting of hydrogen, fluorine, chlorine, bromine, cyano, methyl, ethyl, trifluoromethyl, methoxy, ethoxy, difluoromethoxy and trifluoromethoxy, $X^2$ represents oxygen, sulphur, $NR^5$ or NOH, n represents 2, R represents $NR^{18}R^{19}$ or represents a radical from the group consisting of $C_1$-$C_4$-alkyl, $C_3$-$C_4$-alkenyl, $C_3$-$C_4$-alkynyl, $C_1$-$C_2$-alkoxy-$C_1$-$C_2$-alkyl and $C_1$-$C_2$-alkyl-S—$C_1$-$C_2$-alkyl, $C_1$-$C_2$-alkyl-S(O)—$C_1$-$C_2$-alkyl, $C_1$-$C_2$-alkyl-S(O)$_2$—$C_1$-$C_2$-alkyl, each of which is optionally mono-, di-, tri-, tetra- or pentasubstituted by fluorine, chlorine or mono- or disubstituted by cyano, represents $R^{18}$—CO—$C_1$-$C_2$-alkyl, represents $NR^{18}R^{19}$—CO—$C_1$-$C_2$-alkyl, represents $C_3$-$C_6$-cycloalkyl which is optionally mono- or disubstituted by $C_1$-$C_2$-alkyl, $C_1$-$C_2$-alkoxy or $C_1$-$C_2$-haloalkyl or by an oxygen atom (leads to C=O), represents $C_3$-$C_6$-cycloalkenyl which is optionally mono- or disubstituted by $C_1$-$C_2$-alkyl, $C_1$-$C_2$-alkoxy or $C_1$-$C_2$-haloalkyl or by an oxygen atom (leads to C=O), represents $C_3$-$C_6$-cycloalkyl-$C_1$-$C_2$-alkyl which is optionally mono- or disubstituted by $C_1$-$C_2$-alkyl, $C_1$-$C_2$-alkoxy or $C_1$-$C_2$-haloalkyl, represents $C_3$-$C_6$-cycloalkenyl-$C_1$-$C_2$-alkyl which is optionally mono- or disubstituted by $C_1$-$C_2$-alkyl, $C_1$-$C_2$-alkoxy or $C_1$-$C_2$-haloalkyl, represents heterocyclyl which is optionally mono- or disubstituted by $C_1$-$C_2$-alkyl, $C_1$-$C_2$-alkoxy or $C_1$-$C_2$-haloalkyl, represents heterocyclyl-$C_1$-$C_2$-alkyl which is optionally mono- or disubstituted by $C_1$-$C_2$-alkyl, $C_1$-$C_2$-alkoxy or $C_1$-$C_2$-haloalkyl or represents für phenyl, benzyl, pyridyl, pyrimidyl, thiazolyl, oxazolyl, pyrazolyl, thienyl, furanyl, pyridinylmethyl or thiazolylmethyl, each of which is optionally mono- or disubstituted by fluorine, chlorine, bromine, cyano, methyl, ethyl, difluoromethyl, trifluoromethyl, methoxy, ethoxy, difluoromethoxy or trifluoromethoxy, $R^3$ represents $C_1$-$C_4$-alkyl, $R^4$ represents a radical from the group consisting of hydrogen, $C_1$-$C_4$-alkyl, halo-$C_1$-$C_4$-alkyl, cyano-$C_1$-$C_4$-alkyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_4$-alkyl, $C_1$-$C_4$-alkoxycarbonyl, $C_1$-$C_4$-alkoxycarbonyl-$C_1$-$C_4$-alkyl and $C_1$-$C_4$-alkylthio-$C_1$-$C_4$-alkyl, $R^5$ represents a radical from the group consisting of hydrogen, $C_1$-$C_4$-alkyl, halo-$C_1$-$C_4$-alkyl, cyano-$C_1$-$C_4$-alkyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_4$-alkyl, $C_1$-$C_4$-alkoxycarbonyl, $C_1$-$C_4$-alkoxycarbonyl-$C_1$-$C_4$-alkyl and $C_1$-$C_4$-alkylthio-$C_1$-$C_4$-alkyl, $R^6$ represents hydrogen or $C_1$-$C_4$-alkyl, $R^7$ represents a radical from the group consisting of hydrogen, $C_1$-$C_4$-alkyl, halo-$C_1$-$C_4$-alkyl, cyano-$C_1$-$C_4$-alkyl, $C_2$-$C_4$-alkynyl, $C_1$-$C_4$-alkoxy, halo-$C_1$-$C_4$-alkoxy, $C_1$-$C_4$-alkoxy-$C_1$-$C_4$-alkyl, $C_1$-$C_4$-alkoxycarbonyl, $C_1$-$C_4$-alkoxycarbonyl-$C_1$-$C_4$-alkyl, $C_1$-$C_4$-alkylthio-$C_1$-$C_4$-alkyl, aryl-$C_1$-$C_4$-alkyl and hetaryl-$C_1$-$C_4$-alkyl or $R^6$ and $R^7$ together with the nitrogen atom to which they are attached form a 4- to 7-membered ring which may contain one or two further heteroatoms from the group consisting of nitrogen, oxygen and sulphur (where oxygen and sulphur atoms must not be directly adjacent to one another), $R^8$ represents a radical from the group consisting of hydrogen, $C_1$-$C_6$-alkyl, $C_1$-$C_6$-haloalkyl, cyano-$C_1$-$C_6$-alkyl, $C_1$-$C_6$-alkoxy, $C_1$-$C_6$-haloalkoxy, $C_2$-$C_6$-alkenyl, $C_1$-$C_6$-alkoxy-$C_1$-$C_6$-alkyl, in each case optionally halogen-substituted $C_1$-$C_6$-alkylcarbonyl and $C_1$-$C_6$-alkylsulphonyl, optionally halogen-substituted $C_1$-$C_6$-alkoxycarbonyl, optionally halogen-, $C_1$-$C_6$-alkyl-, $C_1$-$C_6$-alkoxy-, $C_1$-$C_6$-haloalkyl- and cyano-substituted $C_3$-$C_6$-cycloalkylcarbonyl, or represents a cation or an optionally $C_1$-$C_6$-alkyl- or aryl-$C_1$-$C_6$-alkyl-substituted ammonium ion, $R^9$ represents a radical from the group consisting of in each case optionally halogen-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl- and $C_1$-$C_4$-haloalkylsulphonyl-substituted $C_1$-$C_4$-alkyl, $C_2$-$C_4$-alkenyl and $C_2$-$C_4$-alkynyl, in each case optionally halogen-, $C_1$-$C_4$-alkyl-, $C_1$-$C_4$-haloalkyl-, $C_1$-$C_4$-alkoxy-, $C_1$-$C_4$-haloalkoxy-substituted $C_3$-$C_6$-cycloalkyl, $C_3$-$C_6$-cycloalkyl-$C_1$-$C_4$-alkyl and $C_3$-$C_4$-cycloalkenyl, in which one or two ring members may in each case be replaced by a heteroatom from the group consisting of sulphur, oxygen (where oxygen atoms must not be directly adjacent to one another) and nitrogen (and here in particular represent

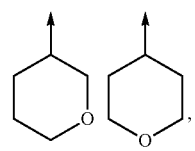

where the arrow in each case marks the bond to the sulphur atom in the radical (C-1) and in the radical (F-1)), in each case optionally halogen-, cyano- (also in the alkyl moiety), nitro-, $C_1$-$C_4$-alkyl-, $C_1$-$C_4$-haloalkyl-, $C_3$-$C_6$-cycloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl-, $C_1$-$C_4$-haloalkylsulphonyl-, amino-, $C_1$-$C_4$-alkylamino-, di-($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted aryl, heteroaryl, aryl-$C_1$-$C_4$-alkyl and heteroaryl-$C_1$-$C_4$-alkyl or represents NR'R'' in which R' and R'' independently of one another represent a radical from the group consisting of hydrogen and $C_1$-$C_4$-alkyl, or $R^8$ and $R^9$ in the radical (C-1) and in the radical (F-1) may also form, together with the N—S(O)n group to which they are attached, a saturated or unsaturated and optionally halogen-, $C_1$-$C_6$-alkyl-, $C_1$-$C_6$-haloalkyl-, $C_1$-$C_6$-alkoxy-, $C_1$-$C_6$-haloalkoxy-substituted 5- to 7-membered ring which may contain one or two heteroatoms from the group consisting of sulphur, oxygen (where oxygen atoms must not be directly adjacent to one another) and nitrogen and/or at least one and preferably one carbonyl group, in particular, $R^8$ and $R^9$ together with the N—S(O)n group to which they are attached may represent a radical from the group consisting of

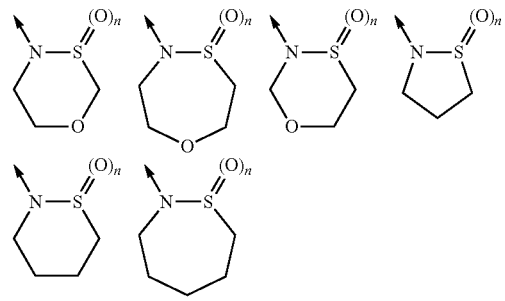

(in which the arrow in each case denotes the bond to the C(X) group).

$R^{17}$ represents a radical from the group consisting of in each case optionally halogen-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl- and $C_1$-$C_4$-haloalkylsulphonyl-substituted $C_1$-$C_4$-alkyl, $C_2$-$C_4$-alkenyl and $C_2$-$C_4$-alkynyl, in each case optionally halogen-, $C_1$-$C_4$-alkyl-, $C_1$-$C_4$-haloalkyl-, $C_1$-$C_4$-alkoxy-, $C_1$-$C_4$-haloalkoxy-substituted $C_3$-$C_6$-cycloalkyl, $C_3$-$C_6$-cycloalkyl-$C_1$-$C_4$-alkyl and $C_3$-$C_4$-cycloalkenyl, N-pyrrolidinyl, N-piperidinyl, N-morpholinyl, N-thiomorpholinyl, N-thiomorpholinyl 1-oxide, N-thiomorpholinyl 1,1-dioxide, N-piperazinyl, N-1-methylpiperazinyl and N-2-oxo-1-methylpiperazinyl, in each case optionally halogen-, cyano- (also in the alkyl moiety), nitro-, $C_1$-$C_4$-alkyl-, $C_1$-$C_4$-haloalkyl-, $C_3$-$C_6$-cycloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl-, $C_1$-$C_4$-haloalkylsulphonyl-, amino-, $C_1$-$C_4$-alkylamino-, di-($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted aryl, heteroaryl, aryl-$C_1$-$C_4$-alkyl, heteroaryl-$C_1$-$C_4$-alkyl or represents NR'R" in which R' and R" independently of one another represent a radical from the group consisting of hydrogen and $C_1$-$C_4$-alkyl, $R^{18}$ represents a radical from the group consisting of hydrogen, hydroxy, represents $C_1$-$C_4$-alkyl, $C_1$-$C_4$-alkoxy, $C_1$-$C_4$-alkoxy-$C_1$-$C_4$-alkyl, $C_1$-$C_4$-alkyl-S—$C_1$-$C_2$-alkyl, $C_1$-$C_4$-alkyl-S(O)—$C_1$-$C_2$-alkyl, $C_1$-$C_4$-alkyl-S(O)$_2$—$C_1$-$C_2$-alkyl, $C_1$-$C_4$-alkylcarbonyl, $C_1$-$C_4$-alkoxycarbonyl, $C_3$-$C_6$-cycloalkyl, $C_3$-$C_6$-cycloalkyl-$C_1$-$C_3$-alkyl, heterocyclyl and heterocyclyl-$C_1$-$C_3$-alkyl, each of which is optionally mono-, di-, tri-, tetra- or pentasubstituted by fluorine, chlorine or mono- or disubstituted by cyano, and of phenyl, benzyl, pyridyl, pyrimidyl, thiazolyl, oxazolyl, pyrazolyl, thienyl, furanyl, pyridinylmethyl and thiazolylmethyl, each of which is optionally mono- to trisubstituted by $C_1$-$C_4$-alkyl, $C_1$-$C_3$-haloalkyl, $C_1$-$C_3$-alkoxy, $C_1$-$C_3$-haloalkoxy, cyclopropyl, fluorine, chlorine, bromine or cyano, $R^{19}$ represents hydrogen, an alkali or alkaline earth metal ion, represents an ammonium ion which is optionally mono- to tetrasubstituted by $C_1$-$C_4$-alkyl or represents a radical from the group consisting of $C_1$-$C_4$-alkyl, $C_1$-$C_4$-alkoxy, $C_1$-$C_4$-alkoxy-$C_1$-$C_2$-alkyl and $C_1$-$C_4$-alkyl-S—$C_1$-$C_2$-alkyl, $C_1$-$C_4$-alkyl-S(O)—$C_1$-$C_2$-alkyl and $C_1$-$C_4$-alkyl-S(O)$_2$—$C_1$-$C_2$-alkyl, each of which is optionally mono-, di-, tri-, tetra- or pentasubstituted by fluorine, chlorine or mono- or disubstituted by cyano, W represents a radical from the group consisting of S, SO and SO$_2$, $Y^3$ represents a radical from the group consisting of hydrogen, fluorine, chlorine, bromine, cyano, methyl, ethyl, trifluoromethyl, methoxy, ethoxy, difluoromethoxy and trifluoromethoxy, $R^{22}$, if $R^2$ represents the radical c), represents a radical from the group consisting of $C_1$-$C_6$-alkyl, optionally cyano-substituted $C_3$-$C_6$-cycloalkyl, $C_1$-$C_6$-haloalkyl, $C_1$-$C_6$-alkoxy, $C_1$-$C_6$-haloalkoxy, $C_1$-$C_6$-alkoxy-$C_1$-$C_6$-alkyloxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylthio-$C_1$-$C_4$-alkyl, $C_1$-$C_4$-alkylsulphinyl-$C_1$-$C_4$-alkyl, $C_1$-$C_4$-alkylsulphonyl-$C_1$-$C_4$-alkyl, $C_1$-$C_4$-alkylthio-$C_1$-$C_4$-alkyloxy, $C_1$-$C_4$-alkylsulphinyl-$C_1$-$C_4$-alkyloxy, $C_1$-$C_4$-alkylsulphonyl-$C_1$-$C_4$-alkyloxy, $C_1$-$C_4$-haloalkylthio-$C_1$-$C_4$-alkyl, $C_1$-$C_4$-haloalkylsulphinyl-$C_1$-$C_4$-alkyl, $C_1$-$C_4$-haloalkylsulphonyl-$C_1$-$C_4$-alkyl, $C_1$-$C_4$-alkylthio-$C_2$-$C_4$-alkenyl, $C_1$-$C_4$-alkylsulphinyl-$C_2$-$C_4$-alkenyl, $C_1$-$C_4$-alkylsulphonyl-$C_2$-$C_4$-alkenyl, $C_2$-$C_4$-alkenylthio-$C_1$-$C_4$-alkyl, $C_2$-$C_4$-alkenylsulphinyl-$C_1$-$C_4$-alkyl, $C_2$-$C_4$-alkenylsulphonyl-$C_1$-$C_4$-alkyl, $C_1$-$C_4$-alkylcarbonyl-$C_1$-$C_4$-alkyl, $C_1$-$C_4$-haloalkylcarbonyl-$C_1$-$C_4$-alkyl, $C_1$-$C_4$-alkoxy-$C_1$-$C_4$-alkyl, $C_1$-$C_4$-haloalkoxy-$C_1$-$C_4$-alkyl, $C_1$-$C_4$-alkoxycarbonyl-$C_1$-$C_4$-alkyl, $C_1$-$C_4$-haloalkoxycarbonyl-$C_1$-$C_4$-alkyl, $C_1$-$C_4$-alkylaminosulphonyl, di-($C_1$-$C_4$-alkyl)-aminosulphonyl, $R^{23}$, if $R^2$ represents the radical c), represents a radical from the group consisting of hydrogen, $C_1$-$C_6$-alkyl, $C_2$-$C_4$-alkenyl, $C_2$-$C_4$-alkynyl, $C_1$-$C_4$-alkylthio-$C_1$-$C_4$-alkyl, $C_2$-$C_4$-alkenylthio-$C_1$-$C_4$-alkyl, cyano-$C_1$-$C_4$-alkyl, $C_1$-$C_4$-alkoxy-$C_1$-$C_4$-alkyl, $R^{22}$, if $R^2$ represents the radical d), represents a radical from the group consisting of $C_1$-$C_4$-alkyl, optionally cyano-substituted $C_3$-$C_6$-cycloalkyl, $C_1$-$C_4$-haloalkyl, $C_1$-$C_4$-alkylthio-$C_1$-$C_4$-alkyl, $C_1$-$C_4$-alkylsulphinyl-$C_1$-$C_4$-alkyl, $C_1$-$C_4$-alkylsulphonyl-$C_1$-$C_4$-alkyl, $C_1$-$C_4$-haloalkylthio-$C_1$-$C_4$-alkyl, $C_1$-$C_4$-haloalkylsulphinyl-$C_1$-$C_4$-alkyl, $C_1$-$C_4$-haloalkylsulphonyl-$C_1$-$C_4$-alkyl, $C_1$-$C_4$-alkylthio-$C_2$-$C_4$-alkenyl, $C_1$-$C_4$-alkylsulphinyl-$C_2$-$C_4$-alkenyl, $C_1$-$C_4$-alkylsulphonyl-$C_2$-$C_4$-alkenyl, $C_2$-$C_4$-alkenylthio-$C_1$-$C_4$-alkyl, $C_2$-$C_4$-alkenylsulphinyl-$C_1$-$C_4$-alkyl, $C_2$-$C_4$-alkenylsulphonyl-$C_1$-$C_4$-alkyl, $C_1$-$C_4$-alkylcarbonyl-$C_1$-$C_4$-alkyl, $C_1$-$C_4$-haloalkylcarbonyl-$C_1$-$C_4$-alkyl, $C_1$-$C_4$-alkoxy-$C_1$-$C_4$-alkyl, $C_1$-$C_4$-haloalkoxy-$C_1$-$C_4$-alkyl, $C_1$-$C_4$-alkoxycarbonyl-$C_1$-$C_4$-alkyl, $C_1$-$C_4$-haloalkoxycarbonyl-$C_1$-$C_4$-alkyl, $C_1$-$C_4$-alkylaminosulphonyl, di-($C_1$-$C_4$-alkyl)-aminosulphonyl, $R^{23}$ if $R^2$ represents the radical d), represents a radical from the group consisting of hydrogen, $C_1$-$C_6$-alkyl, $C_2$-$C_4$-alkenyl, $C_2$-$C_4$-alkynyl, $C_3$-$C_6$-cycloalkyl, $C_3$-$C_6$-cycloalkenyl, $C_1$-$C_6$-alkoxy, $C_2$-$C_6$-alkenyloxy, $C_2$-$C_6$-alkynyloxy, $C_3$-$C_6$-cycloalkyloxy, $C_1$-$C_4$-alkylthio-$C_1$-$C_4$-alkyl, $C_2$-$C_4$-alkenylthio-$C_1$-$C_4$-alkyl, cyano-$C_1$-$C_4$-alkyl, $C_1$-$C_4$-alkoxy-$C_1$-$C_4$-alkyl, and in the case $R^2$=d), $R^{22}$ also represents optionally halogen-, cyano-, nitro-, amino-, hydroxy-, $C_1$-$C_6$-alkyl-, $C_1$-$C_6$-haloalkyl-, $C_2$-$C_6$-alkenyl-, $C_2$-$C_6$-alkynyl-, $C_3$-$C_6$-cycloalkyl-, $C_1$-$C_6$-alkoxy-, $C_1$-$C_6$-haloalkoxy-, $C_3$-$C_6$-alkenyloxy-, $C_3$-$C_6$-alkynyloxy-, $C_1$-$C_6$-alkoxycarbonyloxy-, $C_1$-$C_6$-alkylamino-, $C_3$-$C_6$-alkenylamino-, $C_3$-$C_6$-alkynylamino-, $C_3$-$C_6$-cycloalkylamino-, $C_1$-$C_6$-alkylthio-, $C_1$-$C_6$-haloalkylthio-, $C_3$-$C_6$-alkenylthio-, $C_3$-$C_6$-alkynylthio-, $C_3$-$C_6$-cycloalkylthio-, $C_1$-$C_6$-alkylsulphinyl-, $C_1$-$C_6$-alkylsulphonyl-, $C_1$-$C_6$-alkylcarbonyl-, aminocarbonyl-, $C_1$-$C_6$-alkylaminocarbonyl-, di-($C_1$-$C_6$-alkyl)-aminocarbonyl-, $C_1$-$C_6$-alkylcarbonylamine-substituted phenyl or represents one of the E radicals below

E-1

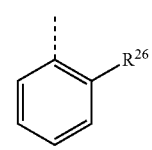

-continued
E-2 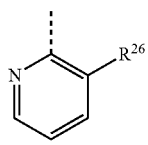
E-3 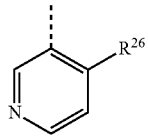
E-4 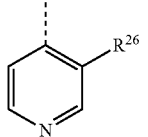
E-5 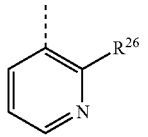
E-6 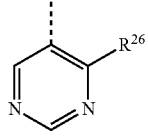
E-10 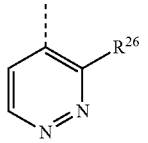
E-11 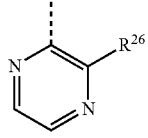
E-13 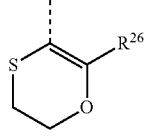
E-18 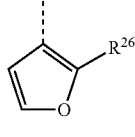
E-21 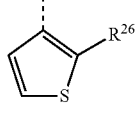
E-23 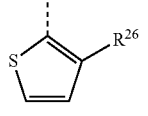
-continued
E-25
E-27
E-31
E-35
E-36
E-39
E-44
E-49
E-51
$R^{27}$ represents hydrogen or methyl and
$R^{26}$ represents hydrogen, methyl, 2,2,2-trifluoroethyl, 2,2-difluoroethyl, propenyl, propargyl, cyclopropyl, cyclopropylmethyl, methoxymethyl, methylthioethyl, methylsulphinylethyl, methylsulphonylethyl or cyanomethyl and compounds of the formula (I) in which
A represents the A radical (A-a)

where the broken line represents the bond to the nitrogen atom of the bicycle of the formula (I),
$G^1$ represents N or C—$B^1$,
$B^1$ represents a radical from the group consisting of hydrogen and fluorine,
T represents oxygen or an electron pair,
$R^1$ represents hydrogen,
$R^2$ a) represents a radical from the group consisting of (B-5)

(B-9)

(B-10)

(B-11)

(B-12)

(B-27)

(B-28)

where the broken line represents the bond to the carbon atom of the bicycle of the formula (I), where
$G^2$ represents hydrogen or a radical from the group consisting of halogen, nitro, amino, cyano, $C_1$-$C_4$-alkylamino, halo-$C_1$-$C_4$-alkylamino, $C_1$-$C_4$-dialkylamino, $C_1$-$C_4$-alkyl, halo-$C_1$-$C_4$-alkyl, $C_1$-$C_4$-alkoxy, halo-$C_1$-$C_4$-alkoxy, $C_1$-$C_4$-alkoxy-$C_1$-$C_4$-alkyl, halogenated $C_1$-$C_4$-alkoxy-$C_1$-$C_4$-alkyl, bis($C_1$-$C_4$-alkoxy)-$C_1$-$C_4$-alkyl, bis(halo-$C_1$-$C_4$-alkoxy)-$C_1$-$C_4$-alkyl, $C_1$-$C_4$-alkoxy-($C_1$-$C_4$-alkylsulphanyl)-$C_1$-$C_4$-alkyl, $C_1$-$C_4$-alkoxy-($C_1$-$C_4$-alkylsulphinyl)-$C_1$-$C_4$-alkyl, $C_1$-$C_4$-alkoxy-($C_1$-$C_4$-alkylsulphonyl)-$C_1$-$C_4$-alkyl, bis($C_1$-$C_4$-alkylsulphanyl)-$C_1$-$C_4$-alkyl, bis(halo-$C_1$-$C_4$-alkylsulphanyl)-$C_1$-$C_4$-alkyl, bis(hydroxy-$C_1$-$C_4$-alkylsulphanyl)-$C_1$-$C_4$-alkyl, $C_1$-$C_4$-alkoxycarbonyl, $C_1$-$C_4$-alkoxycarbonyl-$C_1$-$C_4$-alkyl, C($X^2$)$NR^3R^4$, $NR^6R^7$, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl and $C_1$-$C_4$-haloalkylsulphonyl,
or
$R^2$ aa) represents a radical from the group consisting of (B-1)

(B-2)

(B-3)

(B-4)

(B-21)

(B-23)

(B-25)

(B-27)

in which
$G^2$ represents a radical from the group consisting of halogen, nitro, amino, cyano, $C_1$-$C_4$-alkylamino, halo-$C_1$-$C_4$-alkylamino, $C_1$-$C_4$-dialkylamino, halo-$C_1$-$C_4$-alkoxy, $C_1$-$C_4$-alkoxy-$C_1$-$C_4$-alkyl, halogenated $C_1$-$C_4$-alkoxy-$C_1$-$C_4$-alkyl, bis($C_1$-$C_4$-alkoxy)-$C_1$-$C_4$-alkyl, bis(halo-$C_1$-$C_4$-alkoxy)-$C_1$-$C_4$-alkyl, $C_1$-$C_4$-alkoxy($C_1$-$C_4$-alkylsulphanyl)-$C_1$-$C_4$-alkyl, $C_1$-$C_4$-alkoxy($C_1$-$C_4$-alkylsulphinyl)-$C_1$-$C_4$-alkyl, $C_1$-$C_4$-alkoxy($C_1$-$C_4$-alkylsulphonyl)-$C_1$-$C_4$-alkyl, bis($C_1$-$C_4$-alkylsulphanyl)-$C_1$-$C_4$-alkyl, bis(halo-$C_1$-$C_4$-alkylsulphanyl)-$C_1$-$C_4$-alkyl, bis(hydroxy-$C_1$-$C_4$-alkylsulphanyl)-$C_1$-$C_4$-alkyl, $C_1$-$C_4$-alkoxycarbonyl, $C_1$-$C_4$-alkoxycarbonyl-$C_1$-$C_4$-alkyl, C($X^2$)$NR^3R^4$, $NR^6R^7$, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl and $C_1$-$C_4$-haloalkylsulphonyl, or $R^2$ c) represents a radical of the formula

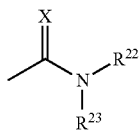

or
$R^2$ d) represents a radical of the formula

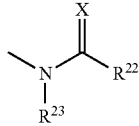

or
$R^2$ e) represents a radical from the group consisting of (F-8) and (F-10)

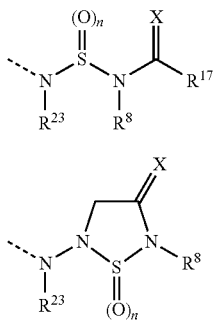

where the broken line represents the bond to the nitrogen atom in the formula (I) or
$R^2$ f) represents a radical from the group consisting of $C_1$-$C_6$-haloalkyl, carboxyl and amino,
or
$G^2$ represents the C radical

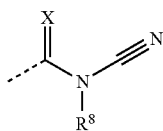

where the broken line represents the bond to the B radicals,
X represents oxygen,
$X^2$ represents oxygen, sulphur, $NR^5$ or NOH;
n represents 2,
$R^3$ represents $C_1$-$C_4$-alkyl,
$R^4$ represents a radical from the group consisting of hydrogen, $C_1$-$C_4$-alkyl, halo-$C_1$-$C_4$-alkyl, cyano-$C_1$-$C_4$-alkyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_4$-alkyl, $C_1$-$C_4$-alkoxycarbonyl, $C_1$-$C_4$-alkoxycarbonyl-$C_1$-$C_4$-alkyl and $C_1$-$C_4$-alkylthio-$C_1$-$C_4$-alkyl,
$R^5$ represents a radical from the group consisting of hydrogen, $C_1$-$C_4$-alkyl, halo-$C_1$-$C_4$-alkyl, cyano-$C_1$-$C_4$-alkyl, $C_2$-$C_4$-alkynyl, $C_3$-$C_6$-cycloalkyl, $C_3$-$C_6$-cycloalkyl-$C_1$-$C_4$-alkyl, $C_1$-$C_4$-alkoxy-$C_1$-$C_4$-alkyl, $C_1$-$C_4$-alkoxycarbonyl, $C_1$-$C_4$-alkoxycarbonyl-$C_1$-$C_4$-alkyl and $C_1$-$C_4$-alkylthio-$C_1$-$C_4$-alkyl,
$R^6$ represents hydrogen or $C_1$-$C_4$-alkyl,
$R^7$ represents a radical from the group consisting of hydrogen, $C_1$-$C_4$-alkyl, halo-$C_1$-$C_4$-alkyl, cyano-$C_1$-$C_4$-alkyl, $C_2$-$C_4$-alkynyl, $C_1$-$C_4$-alkoxy, halo-$C_1$-$C_4$-alkoxy, $C_1$-$C_4$-alkoxy-$C_1$-$C_4$-alkyl, $C_1$-$C_4$-alkoxycarbonyl, $C_1$-$C_4$-alkoxycarbonyl-$C_1$-$C_4$-alkyl, $C_1$-$C_4$-alkylthio-$C_1$-$C_4$-alkyl, aryl-$C_1$-$C_4$-alkyl and hetaryl-$C_1$-$C_4$-alkyl or
$R^6$ and $R^7$ together with the nitrogen atom to which they are attached form a 4- to 7-membered ring which may contain one or two further heteroatoms from the group consisting of nitrogen, oxygen and sulphur (where oxygen and sulphur atoms must not be directly adjacent to one another),
$R^8$ represents a radical from the group consisting of hydrogen, $C_1$-$C_6$-alkyl, $C_1$-$C_6$-haloalkyl, cyano-$C_1$-$C_6$-alkyl, $C_1$-$C_6$-alkoxy, $C_1$-$C_6$-haloalkoxy, $C_2$-$C_6$-alkenyl, $C_1$-$C_6$-alkoxy-$C_1$-$C_6$-alkyl, in each case optionally halogen-substituted $C_1$-$C_6$-alkylcarbonyl and $C_1$-$C_6$-alkylsulphonyl, optionally halogen-substituted $C_1$-$C_6$-alkoxycarbonyl, optionally halogen-, $C_1$-$C_6$-alkyl-, $C_1$-$C_6$-alkoxy-, $C_1$-$C_6$-haloalkyl- and cyano-substituted $C_3$-$C_6$-cycloalkylcarbonyl, or represents a cation or an optionally $C_1$-$C_6$-alkyl- or aryl-$C_1$-$C_6$-alkyl-substituted ammonium ion,
$R^9$ represents a radical from the group consisting of in each case optionally halogen-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl- and $C_1$-$C_4$-haloalkylsulphonyl-substituted $C_1$-$C_4$-alkyl, $C_2$-$C_4$-alkenyl and $C_2$-$C_4$-alkynyl, in each case optionally halogen-, $C_1$-$C_4$-alkyl-, $C_1$-$C_4$-haloalkyl-, $C_1$-$C_4$-alkoxy-, $C_1$-$C_4$-haloalkoxy-substituted $C_3$-$C_6$-cycloalkyl, $C_3$-$C_6$-cycloalkyl-$C_1$-$C_4$-alkyl and $C_3$-$C_4$-cycloalkenyl, in which one or two ring members may in each case be replaced by a heteroatom from the group consisting of sulphur, oxygen (where oxygen atoms must not be directly adjacent to one another) and nitrogen (and here in particular represent

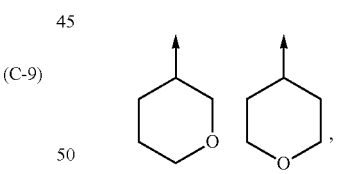

where the arrow in each case marks the bond to the sulphur atom in the radical (C-1)), in each case optionally halogen-, cyano- (also in the alkyl moiety), nitro-, $C_1$-$C_4$-alkyl-, $C_1$-$C_4$-haloalkyl-, $C_3$-$C_6$-cycloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl-, $C_1$-$C_4$-haloalkylsulphonyl-, amino-, $C_1$-$C_4$-alkylamino-, di($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted aryl, heteroaryl, aryl-$C_1$-$C_4$-alkyl and heteroaryl-$C_1$-$C_4$-alkyl or represents NR'R"

in which R' and R" independently of one another represents a radical from the group consisting of hydrogen and $C_1$-$C_4$-alkyl, $R^{17}$ represents a radical from the group consisting of in each case optionally halogen-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl- and $C_1$-$C_4$-haloalkylsulphonyl-substituted $C_1$-$C_4$-alkyl, $C_2$-$C_4$-alkenyl and $C_2$-$C_4$-alkynyl, in each case optionally halogen-, $C_1$-$C_4$-alkyl-, $C_1$-$C_4$-haloalkyl-, $C_1$-$C_4$-alkoxy-, $C_1$-$C_4$-haloalkoxy-substituted $C_3$-$C_6$-cycloalkyl, $C_3$-$C_6$-cycloalkyl-$C_1$-$C_4$-alkyl and $C_3$-$C_4$-cycloalkenyl, N-pyrrolidinyl, N-piperidinyl, N-morpholinyl, N-thiomorpholinyl, N-thiomorpholinyl 1-oxide, N-thiomorpholinyl 1,1-dioxide, N-piperazinyl, N-1-methylpiperazinyl and N-2-oxo-1-methylpiperazinyl, in each case optionally halogen-, cyano- (also in the alkyl moiety), nitro-, $C_1$-$C_4$-alkyl-, $C_1$-$C_4$-haloalkyl-, $C_3$-$C_6$-cycloalkyl-, $C_1$-$C_4$-alkoxy-, $C_1$-$C_4$-haloalkoxy-, $C_1$-$C_4$-alkylthio-, $C_1$-$C_4$-haloalkylthio-, $C_1$-$C_4$-alkylsulphinyl-, $C_1$-$C_4$-haloalkylsulphinyl-, $C_1$-$C_4$-alkylsulphonyl-, $C_1$-$C_4$-haloalkylsulphonyl-, amino-, $C_1$-$C_4$-alkylamino-, di-($C_1$-$C_4$-alkyl)amino-, $C_1$-$C_4$-alkylcarbonylamino-, $C_1$-$C_4$-alkoxycarbonylamino-, $C_1$-$C_4$-alkoxy-$C_1$-$C_4$-alkyl-, $C_1$-$C_4$-haloalkoxy-$C_1$-$C_4$-alkyl-, $C_2$-$C_4$-alkenyl-, $C_2$-$C_4$-alkynyl-, $C_3$-$C_6$-cycloalkyl-$C_1$-$C_4$-alkyl-, $C_1$-$C_4$-alkylcarbonyl-, $C_1$-$C_4$-alkoxycarbonyl- or aminocarbonyl-substituted aryl, heteroaryl, aryl-$C_1$-$C_4$-alkyl and heteroaryl-$C_1$-$C_4$-alkyl or represents NR'R" in which R' and R" independently of one another represent a radical from the group consisting of hydrogen and $C_1$-$C_4$-alkyl, $R^{22}$ represents a radical from the group consisting of (D-1) to (D-3)

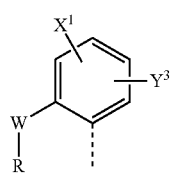

(D-1)

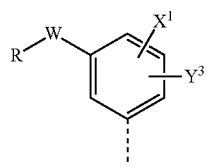

(D-2)

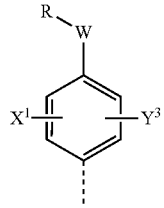

(D-3)

where the broken line represents the bond to the nitrogen atom in the radical c) or to the carbon atom in the radical d), R represents $NR^{18}R^{19}$ or represents a radical from the group consisting of $C_1$-$C_4$-alkyl, $C_3$-$C_4$-alkenyl, $C_3$-$C_4$-alkynyl, $C_1$-$C_2$-alkoxy-$C_1$-$C_2$-alkyl and $C_1$-$C_2$-alkyl-S—$C_1$-$C_2$-alkyl, $C_1$-$C_2$-alkyl-S(O)—$C_1$-$C_2$-alkyl, $C_1$-$C_2$-alkyl-$S(O)_2$—$C_1$-$C_2$-alkyl, each of which is optionally mono-, di-, tri-, tetra- or pentasubstituted by fluorine, chlorine or mono- or disubstituted by cyano, represents $R^{18}$—CO—C1-C2-alkyl, represents $NR^{18}R^{19}$—CO—$C_1$-$C_2$-alkyl, represents $C_3$-$C_6$-cycloalkyl which is optionally mono- or disubstituted by $C_1$-$C_2$-alkyl, $C_1$-$C_2$-alkoxy or $C_1$-$C_2$-haloalkyl or by an oxygen atom (leads to C=O), represents $C_3$-$C_6$-cycloalkenyl which is optionally mono- or disubstituted by $C_1$-$C_2$-alkyl, $C_1$-$C_2$-alkoxy or $C_1$-$C_2$-haloalkyl or by an oxygen atom (leads to C=O), represents $C_3$-$C_6$-cycloalkyl-$C_1$-$C_2$-alkyl which is optionally mono- or disubstituted by $C_1$-$C_2$-alkyl, $C_1$-$C_2$-alkoxy or $C_1$-$C_2$-haloalkyl, represents $C_3$-$C_6$-cycloalkenyl-$C_1$-$C_2$-alkyl which is optionally mono- or disubstituted by $C_1$-$C_2$-alkyl, $C_1$-$C_2$-alkoxy or $C_1$-$C_2$-haloalkyl, represents heterocyclyl which is optionally mono- or disubstituted by $C_1$-$C_2$-alkyl, $C_1$-$C_2$-alkoxy or $C_1$-$C_2$-haloalkyl, represents heterocyclyl-$C_1$-$C_2$-alkyl which is optionally mono- or disubstituted by $C_1$-$C_2$-alkyl, $C_1$-$C_2$-alkoxy or $C_1$-$C_2$-haloalkyl or represents phenyl, benzyl, pyridyl, pyrimidyl, thiazolyl, oxazolyl, pyrazolyl, thienyl, furanyl, pyridinylmethyl or thiazolylmethyl, each of which is optionally mono- or disubstituted by fluorine, chlorine, bromine, cyano, methyl, ethyl, difluoromethyl, trifluoromethyl, methoxy, ethoxy, difluoromethoxy or trifluoromethoxy, $X^1$ represents a radical from the group consisting of hydrogen, fluorine, chlorine, bromine, cyano, methyl, ethyl, trifluoromethyl, methoxy, ethoxy, difluoromethoxy and trifluoromethoxy, W represents a radical from the group consisting of S, SO and $SO_2$, $Y^3$ represents a radical from the group consisting of hydrogen, fluorine, chlorine, bromine, cyano, methyl, ethyl, trifluoromethyl, methoxy, ethoxy, difluoromethoxy and trifluoromethoxy, $R^{18}$ represents a radical from the group consisting of hydrogen, hydroxy, represents $C_1$-$C_4$-alkyl, $C_1$-$C_4$-alkoxy, $C_1$-$C_4$-alkoxy-$C_1$-$C_4$-alkyl, $C_1$-$C_4$-alkyl-S—$C_1$-$C_2$-alkyl, $C_1$-$C_4$-alkyl-S(O)—$C_1$-$C_2$-alkyl, $C_1$-$C_4$-alkyl-$S(O)_2$—$C_1$-$C_2$-alkyl, $C_1$-$C_4$-alkylcarbonyl, $C_1$-$C_4$-alkoxycarbonyl, $C_3$-$C_6$-cycloalkyl, $C_3$-$C_6$-cycloalkyl-$C_1$-$C_3$-alkyl, heterocyclyl and heterocyclyl-$C_1$-$C_3$-alkyl, each of which is optionally mono-, di-, tri-, tetra- or pentasubstituted by fluorine, chlorine or mono- or disubstituted by cyano, and of phenyl, benzyl, pyridyl, pyrimidyl, thiazolyl, oxazolyl, pyrazolyl, thienyl, furanyl, pyridinylmethyl and thiazolylmethyl, each of which is optionally mono- to trisubstituted by $C_1$-$C_4$-alkyl, $C_1$-$C_3$-haloalkyl, $C_1$-$C_3$-alkoxy, $C_1$-$C_3$-haloalkoxy, cyclopropyl, fluorine, chlorine, bromine or cyano, $R^{19}$ represents hydrogen, an alkali or alkaline earth metal ion, represents an ammonium ion which is optionally mono- to tetrasubstituted by $C_1$-$C_4$-alkyl or represents a radical from the group consisting of $C_1$-$C_4$-alkyl, $C_1$-$C_4$-alkoxy, $C_1$-$C_4$-alkoxy-$C_1$-$C_2$-alkyl and $C_1$-$C_4$-alkyl-S—$C_1$-$C_2$-alkyl, $C_1$-$C_4$-alkyl-S(O)—$C_1$-$C_2$-alkyl and $C_1$-$C_4$-alkyl-$S(O)_2$—$C_1$-$C_2$-alkyl, each of which is optionally mono-, di-, tri-, tetra- or pentasubstituted by fluorine, chlorine or mono- or disubstituted by cyano, or $R^{23}$, if $R^2$ represents the radical c), represents a radical from the group consisting of hydrogen, $C_1$-$C_6$-alkyl, $C_2$-$C_4$-alkenyl, $C_2$-$C_4$-alkynyl, $C_1$-$C_4$-alkylthio-$C_1$-$C_4$-alkyl, $C_2$-$C_4$-alkenylthio-$C_1$-$C_4$-alkyl, cyano-$C_1$-$C_4$-alkyl, $C_1$-$C_4$-alkoxy-$C_1$-$C_4$-alkyl, $R^{23}$, if $R^2$ represents the radical d), represents a radical from the group consisting of hydrogen, $C_1$-$C_6$-alkyl, $C_2$-$C_4$- alkenyl, $C_2$-$C_4$-alkynyl, $C_3$-$C_6$-cycloalkyl, $C_3$-$C_6$-cycloalkenyl, $C_1$-$C_6$-alkoxy, $C_2$-$C_6$-alkenyloxy, $C_2$-$C_6$-alkynyloxy, $C_3$-$C_6$-cycloalkyloxy, $C_1$-$C_4$-alkylthio-$C_1$-$C_4$-alkyl, $C_2$-$C_4$-alkenylthio-$C_1$-$C_4$-alkyl, cyano-$C_1$-$C_4$-alkyl, $C_1$-$C_4$-alkoxy-$C_1$-$C_4$-alkyl, and
in the case $R^2$=d),
$R^{22}$ also represents one of the E radicals below
E-1
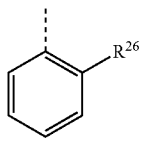
E-2
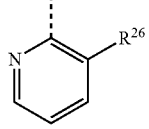
E-3
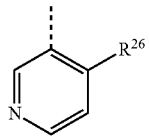
E-4
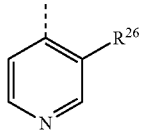
E-5
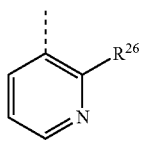
E-6
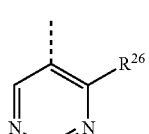
E-10
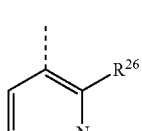
E-11
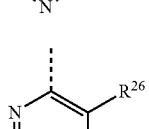
E-13
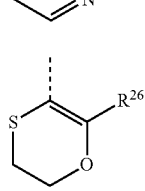
-continued
E-18
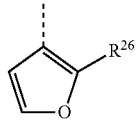
E-21
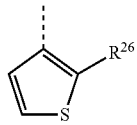
E-23
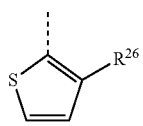
E-25
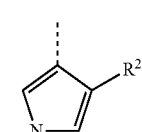
E-27
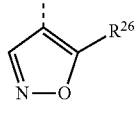
E-31
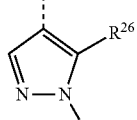
E-35
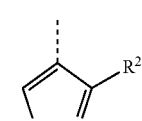
E-36
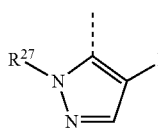
E-39
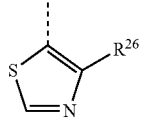
E-44
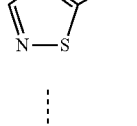
E-49
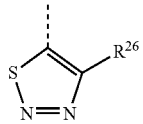

-continued

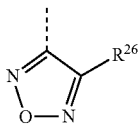
(E-51)

$R^{27}$ represents hydrogen or methyl and
$R^{26}$ represents hydrogen, methyl, 2,2,2-trifluoroethyl, 2,2-difluoroethyl, propenyl, propargyl, cyclopropyl, cyclopropylmethyl, methoxymethyl, methylthioethyl, methylsulphinylethyl, methylsulphonylethyl or cyanomethyl.

Preferred range (4): A particular group of compounds of the formula (I) is that of those in which
A represents a radical from the group consisting of (A-a), (A-b) and (A-f)

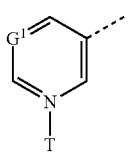
(A-a)

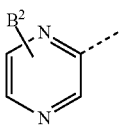
(A-b)

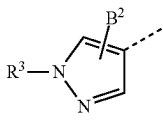
(A-f)

where the broken line represents the bond to the nitrogen atom of the bicycle,
$G^1$ represents N or C—$B^1$,
$B^1$ represents a radical from the group consisting of hydrogen and fluorine,
$B^2$ represents hydrogen,
T represents an electron pair,
$R^1$ represents hydrogen,
$R^2$ a) represents one of the radicals below

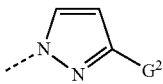
(B-1)

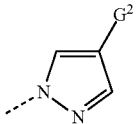
(B-2)

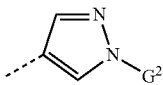
(B-3)

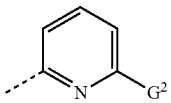
(B-21)

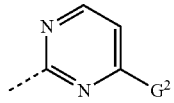
(B-23)

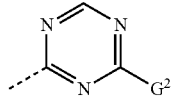
(B-28)

where the broken line represents the bond to the carbon atom of the bicycle of the formula (I) or
$R^2$ b) represents the radical (D-2)

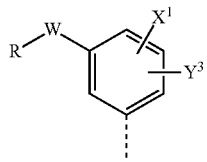
(D-2)

where the broken line represents the bond to the carbon atom of the bicycle of the formula (I),
or
$R^2$ c) represents the radical of the formula

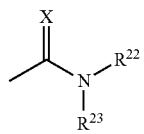

or
$R^2$ f) represents $C_1$-$C_6$-haloalkyl in which
$G^2$ represents a radical from the group consisting of hydrogen, $C_1$-$C_4$-alkyl and halo-$C_1$-$C_4$-alkyl,
X represents oxygen,
$X^1$ represents a radical from the group consisting of hydrogen, fluorine, chlorine and bromine,
R represents $C_1$-$C_4$-alkyl, optionally mono-, di-, tri-, tetra- or pentasubstituted by fluorine, chlorine,
$R^3$ represents $C_1$-$C_4$-alkyl,
W represents a radical from the group consisting of S, SO and $SO_2$,
$Y^3$ represents methyl or ethyl,
$R^{22}$ represents a radical from the group consisting of $C_1$-$C_6$-alkyl, optionally cyano-substituted $C_3$-$C_6$-cycloalkyl, $C_1$-$C_6$-haloalkyl, $C_1$-$C_6$-alkoxy, $C_1$-$C_4$-alkylsulphonyl and di($C_1$-$C_4$-alkylamino)sulphonyl and
$R^{23}$ represents hydrogen or $C_1$-$C_6$-alkyl.

Preferred range (5): A further particular group of compounds of the formula (I) is that of those in which
A represents an A radical from the group consisting of (A-b) and (A-f)

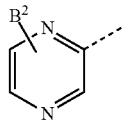
(A-b)

-continued (A-f)

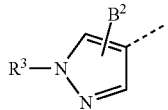

where the broken line represents the bond to the nitrogen atom of the bicycle of the formula (I),
$B^2$ represents hydrogen,
$R^1$ represents hydrogen,
$R^2$ c) represents a radical of the formula

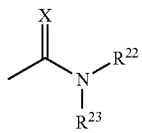

or
$R^2$ d) represents a radical of the formula

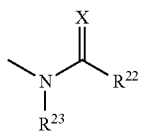

X represents oxygen,
$R^3$ represents $C_1$-$C_4$-alkyl,
$R^{22}$, if $R^2$ represents the radical c), represents a radical from the group consisting of $C_1$-$C_6$-alkyl, optionally cyano-substituted $C_3$-$C_6$-cycloalkyl, $C_1$-$C_6$-haloalkyl, $C_1$-$C_6$-alkoxy, $C_1$-$C_4$-alkylsulphonyl, $C_1$-$C_4$-alkylthio-$C_1$-$C_4$-alkyl, di-($C_1$-$C_4$-alkyl)aminosulphonyl,
$R^{23}$, if $R^2$ represents the radical c), represents a radical from the group consisting of hydrogen and $C_1$-$C_6$-alkyl,
$R^{22}$, if $R^2$ represents the radical d), represents a radical from the group consisting of $C_1$-$C_4$-haloalkyl, $C_1$-$C_4$-alkylthio-$C_1$-$C_4$-alkyl, $C_1$-$C_4$-alkylsulphinyl-$C_1$-$C_4$-alkyl and $C_1$-$C_4$-alkylsulphonyl-$C_1$-$C_4$-alkyl,
$R^{23}$, if $R^2$ represents the radical d), represents a radical from the group consisting of hydrogen and $C_1$-$C_6$-alkyl, and in the case $R^2$=d),
$R^{22}$ also represents optionally halogen-, $C_1$-$C_6$-alkyl- and $C_1$-$C_6$-haloalkylsulphinyl-substituted phenyl and compounds of the formula (I) in which
A represents the A radical (A-a)

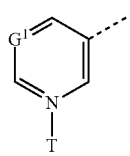

where the broken line represents the bond to the nitrogen atom of the bicycle of the formula (I),
$G^1$ represents N or C—$B^1$,
$B^1$ represents a radical from the group consisting of hydrogen and fluorine, T represents an electron pair,
$R^1$ represents hydrogen,
$R^2$ aa) represents a radical from the group consisting of (B-3)

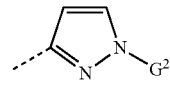

(B-4)

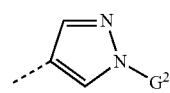

(B-21)

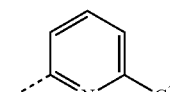

(B-22)

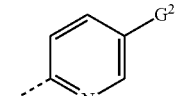

(B-35)

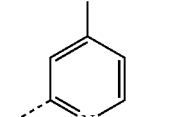

(B-36)

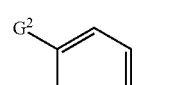

in which
$G^2$ represents a radical from the group consisting of halogen, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylthio-$C_1$-$C_4$-alkyl, $C_1$-$C_4$-alkylsulphinyl-$C_1$-$C_4$-alkyl, $C_1$-$C_4$-alkylsulphonyl-$C_1$-$C_4$-alkyl, or
$R^2$ c) represents a radical of the formula

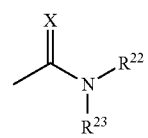

or
$R^2$ d) represents a radical of the formula

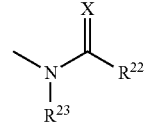

or
$R^2$ f) represents haloalkyl,
X represents oxygen,
$R^{22}$ represents a radical from the group consisting of (D-1) to (D-3)

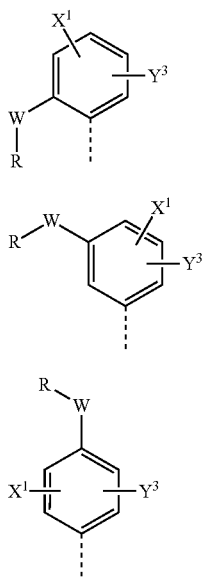

(D-1)

(D-2)

(D-3)

where the broken line represents the bond to the nitrogen atom in the radical c) or to the carbon atom in the radical d), R represents $C_1$-$C_4$-alkyl, in each case optionally mono-, di-, tri-, tetra- or pentasubstituted by fluorine, chlorine, $X^1$ represents a radical from the group consisting of hydrogen, fluorine, chlorine, bromine, methyl and ethyl, W represents a radical from the group consisting of S, SO and $SO_2$, $Y^3$ represents a radical from the group consisting of hydrogen, fluorine, chlorine, bromine, methyl and ethyl.

When sulphur and/or nitrogen occur in rings in the above definitions, for example in expressions such as "in which the rings may contain at least one heteroatom from the group consisting of sulphur, oxygen (where oxygen and sulphur atoms must not be directly adjacent to one another) and nitrogen" or "in which one or two ring members may in each case be replaced by a heteroatom from the group consisting of sulphur, oxygen (where oxygen atoms must not be directly adjacent to one another) and nitrogen", unless stated otherwise, the sulphur may also be present in the form of SO or $SO_2$; the nitrogen, if it is not in the form of —N═, as well as NH, may also be present in the form of N-alkyl (especially N—$C_1$-$C_6$-alkyl).

In the preferred definitions whose combination forms the range of preference (1), unless stated otherwise, cation represents an alkali metal ion selected from the group consisting of lithium, sodium, potassium, rubidium, caesium, preferably from the group consisting of lithium, sodium, potassium, or an alkaline earth metal ion selected from the group consisting of beryllium, magnesium, calcium, strontium, barium, preferably from the group consisting of magnesium and calcium, halogen is selected from the group consisting of fluorine, chlorine, bromine and iodine, preferably in turn from the group consisting of fluorine, chlorine and bromine, aryl (including as part of a larger unit, for example arylalkyl) is selected from the group consisting of phenyl, naphthyl, anthryl, phenanthrenyl, and preferably in turn represents phenyl, hetaryl (synonymous with heteroaryl, including as part of a larger unit, for example hetarylalkyl) is selected from the group consisting of furyl, thienyl, pyrrolyl, pyrazolyl, imidazolyl, 1,2,3-triazolyl, 1,2,4-triazolyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyridyl, pyrimidinyl, pyridazinyl, pyrazinyl, 1,2,3-triazinyl, 1,2,4-triazinyl, 1,3,5-triazinyl, benzofuryl, benzoisofuryl, benzothienyl, benzoisothienyl, indolyl, isoindolyl, indazolyl, benzothiazolyl, benzoisothiazolyl, benzoxazolyl, benzisoxazolyl, benzimidazolyl, 2,1,3-benzoxadiazole, quinolinyl, isoquinolinyl, cinnolinyl, phthalazinyl, quinazolinyl, quinoxalinyl, naphthyridinyl, benzotriazinyl, purinyl, pteridinyl and indolizinyl, heterocyclyl represents a saturated 4-, 5- or 6-membered ring containing 1 or 2 nitrogen atoms and/or one oxygen atom and/or one sulphur atom, for example azetidinyl, azolidinyl, azinanyl, oxetanyl, oxolanyl, oxanyl, dioxanyl, thiethanyl, thiolanyl, thianyl, tetrahydrofuryl, piperazinyl, morpholinyl.

In the particularly preferred definitions whose combination forms the range of preference (2), unless stated otherwise, cation represents an alkali metal ion selected from the group consisting of lithium, sodium, potassium, rubidium, caesium, preferably from the group consisting of lithium, sodium, potassium, or an alkaline earth metal ion selected from the group consisting of beryllium, magnesium, calcium, strontium, barium, preferably from the group consisting of magnesium and calcium, halogen is selected from the group consisting of fluorine, chlorine, bromine and iodine, preferably in turn from the group consisting of fluorine, chlorine and bromine, aryl (including as part of a larger unit, for example arylalkyl) is selected from the group of phenyl, naphthyl, anthryl, phenanthrenyl, and preferably in turn represents phenyl, hetaryl (synonymous with heteroaryl, also as part of a larger unit such as, for example, hetarylalkyl) is selected from the group consisting of pyrazolyl, imidazolyl, 1,2,3-triazolyl, 1,2,4-triazolyl, oxazolyl, isoxazolyl, thiazolyl, isothiazolyl, pyridyl, pyrimidinyl, pyridazinyl, pyrazinyl, 1,2,3-triazinyl, 1,2,4-triazinyl, 1,3,5-triazinyl, heterocyclyl is selected from the group consisting of azetidinyl, azolidinyl, azinanyl, oxetanyl, oxolanyl, oxanyl, dioxanyl, thiethanyl, thiolanyl, thianyl, tetrahydrofuryl, piperazinyl, morpholinyl.

In the very particularly preferred definitions and the especially preferred definitions whose combination forms the range of preference (3), unless stated otherwise, cation represents an alkali metal ion from the group consisting of lithium, sodium, potassium, rubidium, caesium, preferably from the group consisting of lithium, sodium, potassium, or an alkaline earth metal ion from the group consisting of beryllium, magnesium, calcium, strontium, barium, preferably from the group consisting of magnesium and calcium, heterocyclyl represents oxetanyl, thiethanyl, tetrahydrofuryl and morpholinyl.

Aryl represents phenyl, hetaryl (synonymous with heteroaryl, including as part of a larger unit such as, for example, hetarylalkyl) represents a radical from the group consisting of pyridyl, pyrimidyl, pyrazinyl, pyridazinyl, thiazolyl and pyrazolyl.

In the definitions which form the range of preference (4), halogen represents fluorine, chlorine, bromine and iodine, preferably in turn fluorine, chlorine and bromine.

Halogen-substituted radicals, for example haloalkyl, are mono- or polyhalogenated, up to the maximum number of possible substituents. In the case of polyhalogenation, the halogen atoms may be identical or different. In this case, halogen represents fluorine, chlorine, bromine or iodine, in particular fluorine, chlorine or bromine.

Saturated or unsaturated hydrocarbon radicals, such as alkyl or alkenyl, may each be straight-chain or branched if possible, including in combination with heteroatoms, as, for example, in alkoxy.

Unless stated otherwise, optionally substituted radicals may be mono- or polysubstituted, where the substituents in the case of polysubstitutions may be the same or different.

If T in the radical A of the formula (A-a)

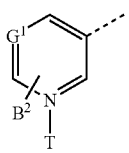
(A-a)

represents an electron pair, the radical is present as a pyridine derivative of the formula

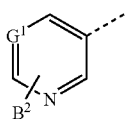

If T in the radical A of the formula (A-a)

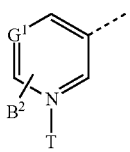
(A-a)

represents oxygen, the radical is present as a pyridine N-oxide derivative of the formula

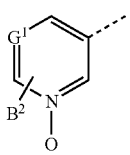

Here, the formal charges (+ at nitrogen and − at oxygen) were omitted from the illustration.

The radical definitions or elucidations given in general terms or listed within ranges of preference apply correspondingly to end products and to starting materials and intermediates. These radical definitions can be combined with one another as desired, i.e. including combinations between the respective ranges of preference.

According to the invention, preference is given to compounds of the formula (I) which contain a combination of the meanings listed above as being preferred (range of preference (1)).

According to the invention, particular preference is given to compounds of the formula (I) which contain a combination of the meanings listed above as being particularly preferred (range of preference (2)).

According to the invention, very particular preference is given to compounds of the formula (I) which contain a combination of the meanings listed above as being very particularly preferred (range of preference (3)).

According to the invention, special preference is given to compounds of the formula (I) which contain a combination of the meanings listed above as being special (range of preference (4)).

According to the invention, special preference is given to compounds of the formula (I) which contain a combination of the meanings listed above as being special (range of preference (5)).

A preferred embodiment of the invention relates to compounds of the formula (I) in which A represents the radical of the formula (A-a)

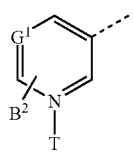
(A-a)

A further preferred embodiment of the invention relates to compounds of the formula (I) in which A represents pyridin-3-yl.

A further preferred embodiment of the invention relates to compounds of the formula (I) in which A represents 5-fluoropyridin-3-yl.

A further preferred embodiment of the invention relates to compounds of the formula (I) in which A represents pyrimidin-5-yl.

A further preferred embodiment of the invention relates to compounds of the formula (I) in which A represents pyridazin-4-yl.

A further preferred embodiment of the invention relates to compounds of the formula (I) in which $R^2$ has the meanings given under a).

A further preferred embodiment of the invention relates to compounds of the formula (I) in which $R^2$ has the meanings given under b).

A further preferred embodiment of the invention relates to compounds of the formula (I) in which $R^2$ has the meanings given under c).

A further preferred embodiment of the invention relates to compounds of the formula (I) in which $R^2$ has the meanings given under d).

A further preferred embodiment of the invention relates to compounds of the formula (I) in which $R^2$ has the meanings given under e).

A further preferred embodiment of the invention relates to compounds of the formula (I) in which $R^2$ has the meanings given under f).

A further preferred embodiment of the invention relates to compounds of the formula (I) in which $R^2$ represents the radical (D-2)

(D-2)

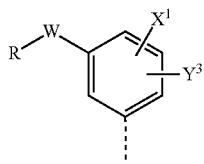

The radical definitions or elucidations given above in general terms or within preferred ranges apply correspondingly to the end products (including the compounds of the formulae (I-A) to (I-N) shown later), and to the starting materials and intermediates. These radical definitions can be combined with one another as desired, i.e. including combinations between the respective ranges of preference.

In a preferred embodiment, the invention relates to compounds of the formula (I-A)

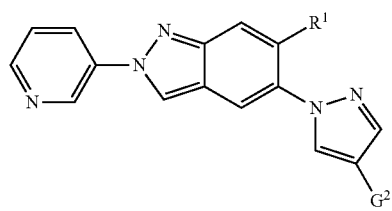

In a further preferred embodiment, the invention relates to compounds of the formula (I-B)

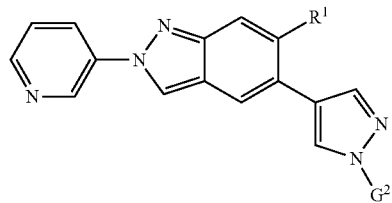

In a further preferred embodiment, the invention relates to compounds of the formula (I-C)

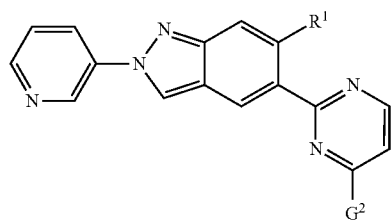

In a further preferred embodiment, the invention relates to compounds of the formula (I-D)

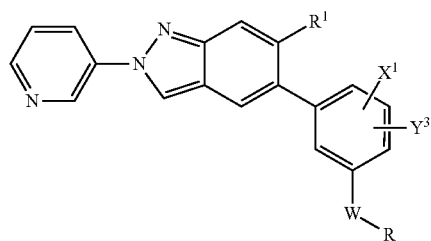

In a further preferred embodiment, the invention relates to compounds of the formula (I-E)

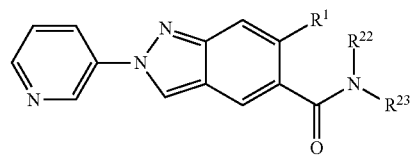

In a further preferred embodiment, the invention relates to compounds of the formula (I-F)

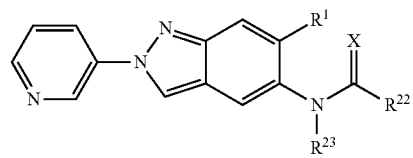

In a further preferred embodiment, the invention relates to compounds of the formula (I-G)

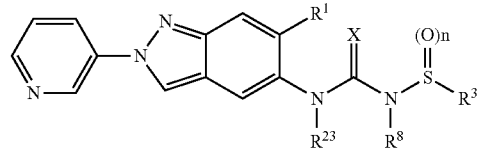

In a preferred embodiment, the invention relates to compounds of the formula (I-H)

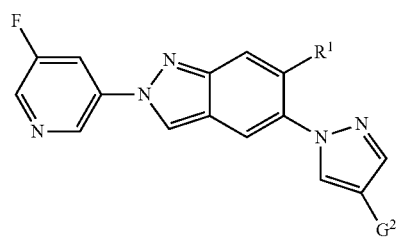

In a further preferred embodiment, the invention relates to compounds of the formula (I-I)

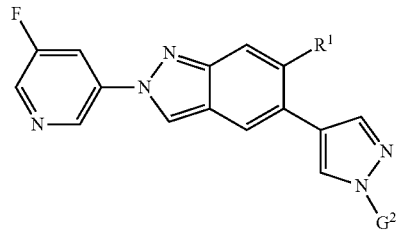

In a further preferred embodiment, the invention relates to compounds of the formula (I-J)

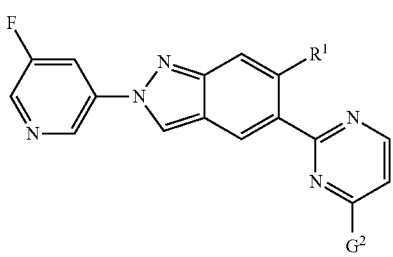

In a further preferred embodiment, the invention relates to compounds of the formula (I-K)

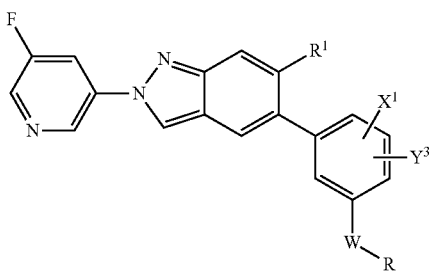

In a further preferred embodiment, the invention relates to compounds of the formula (I-L)

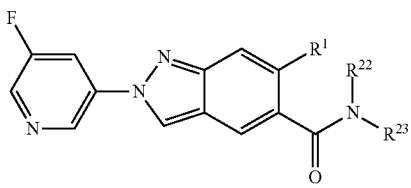

In a further preferred embodiment, the invention relates to compounds of the formula (I-M)

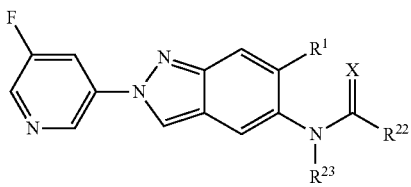

In a further preferred embodiment, the invention relates to compounds of the formula (I-N)

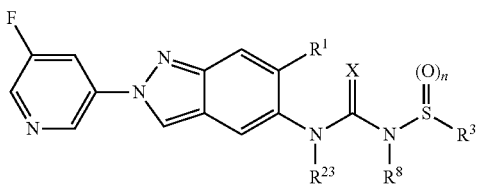

In the formulae (I-A) to (I-N), the variables have the meanings mentioned further above.

The compounds of the formula (I) according to the invention and their acid addition salts and metal salt complexes are highly active, in particular in the control of animal pests including arthropods and in particular insects.

The compounds of the formula (I) may possibly also, depending on the nature of the substituents, be in the form of stereoisomers, i.e. in the form of geometric and/or optical isomers or isomer mixtures of varying composition. This invention provides both the pure stereoisomers and any desired mixtures of these isomers, even though it is generally only compounds of the formula (I) that are discussed here.

The invention therefore relates both to the pure enantiomers and diastereomers and to mixtures thereof for controlling animal pests, including arthropods and particularly insects.

However, preference is given in accordance with the invention to using the optically active, stereoisomeric forms of the compounds of the formula (I) and salts thereof.

Suitable salts of the compounds of the formula (I) which may be mentioned are customary nontoxic salts, i.e. salts with appropriate bases and salts with added acids. Preference is given to salts with inorganic bases, such as alkali metal salts, for example sodium, potassium or caesium salts, alkaline earth metal salts, for example calcium or magnesium salts, ammonium salts, salts with organic bases and with inorganic amines, for example triethylammonium, dicyclohexylammonium, N,N'-dibenzylethylenediammonium, pyridinium, picolinium or ethanolammonium salts, salts with inorganic acids, for example hydrochlorides, hydrobromides, dihydrosulphates, trihydrosulphates, or phosphates, salts with organic carboxylic acids or organic sulfonic acids, for example formates, acetates, trifluoroacetates, maleates, tartrates, methanesulphonates, benzenesulphonates or para-toluenesulphonates, salts with basic amino acids, for example arginates, aspartates or glutamates, and the like.

Furthermore, it has been found that the compounds of the formula (I) and also the compounds in Table 1 not comprised by formula (I) can be prepared by the processes described below.

Compounds of the formula (I) in which the heterocycle A represents optionally $B^2$-substituted pyrimidin-5-yl (A-a; $G^1$=N), pyridin-3-yl (A-a; $G^1$=C—$B^1$), pyrazin-2-yl (A-b), pyridazin-3-yl (A-c), thiazol-5-yl (A-d), isothiazol-4-yl (A-e) and pyrazol-4-yl (A-f) can, for example, be prepared according to Reaction Scheme I in two steps.

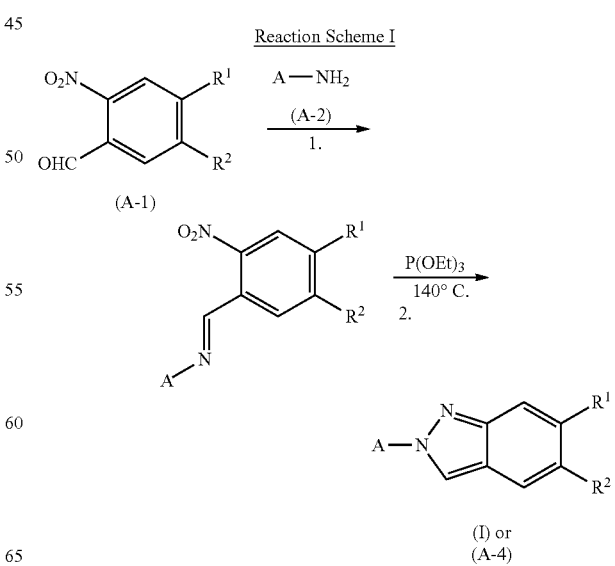

Reaction Scheme I

In Reaction Scheme I, A, $R^1$ and $R^2$ have the meanings mentioned above, unless indicated otherwise.

For example, the substituted 2-nitrobenzaldehydes of the formula (A-1) can be reacted with the corresponding 3-amino-substituted heterocycles of the formula (A-2) in the presence of acidic reaction auxiliaries in a first reaction step to give compounds of the formula (A-3) which are then, in a second reaction step, subjected to reductive cyclization in the presence of a suitable phosphorus(III) reagent, for example triethyl phosphite, with formation of the compounds (A-4).

If, in the process according to the invention for preparing the compound of the formula (I), the compound of the formula (A-1) employed is the 2-nitro-5-(trifluoromethyl)benzaldehyde ($R^1$=H, $R^2$=$CF_3$) and the compound of the formula (A-2) employed is 3-pyridineamine (A=pyridin-3-yl), initially the N-[(2-nitro-5-trifluoromethylphenyl)methylene]-3-pyridineamine (A=pyridin-3-yl, $R^1$=H, $R^2$=$CF_3$) is formed. Subsequent reduction and cyclization then leads to 5-trifluoromethyl-2-(pyridin-3-yl)-2H-indazole (A-4, A=pyridin-3-yl, $R^1$=H, $R^2$=$CF_3$) (cf. Preparation Examples 6 and 16).

Azomethine derivatives or so-called "Schiff bases" of amino-substitutes heterocycles have various applications (they form, for example, metal complexes or are biologically active) and can be obtained by customary processes (cf. also V. Shama, et al., *Intern. J. Univ. Pharm. Bio Science* 2013, 2, 241-57 and the literature cited therein).

Some of the compounds of the formula (A-1) are known and commercially available and/or they can be prepared by preparation processes known in principle (for $R^1$=H, $R^2$=Br; 5-bromo-2-nitrobenzaldehyde (WO 2014/121416 A1); for $R^1$=$OCH_3$, $R^2$=Br; 5-bromo-4-methoxy-2-nitrobenzaldehyde (WO 2008/079988 A2); for $R^1$=H, $R^2$=$COOCH_3$; methyl 3-formyl-4-nitrobenzoate (WO 2007/087129 A2); for $R^1$=$OCH_3$, $R^2$=$NH_2$; 5-amino-4-methoxy-2-nitrobenzaldehyde (X. Han et al., *Chem. Eur. J.* 2007, 13(28), 7957-7964).

For example, 2-nitro-5-trifluoromethylbenzaldehyde ($R^1$=H, $R^2$=$CF_3$) can be synthesized from 2-methyl-1-nitro-4-trifluoromethylbenzene via N,N-dimethylformamide O,O-dimethyl acetal reaction and subsequent sodium periodate oxidation according to Reaction Scheme II (cf. preparation example).

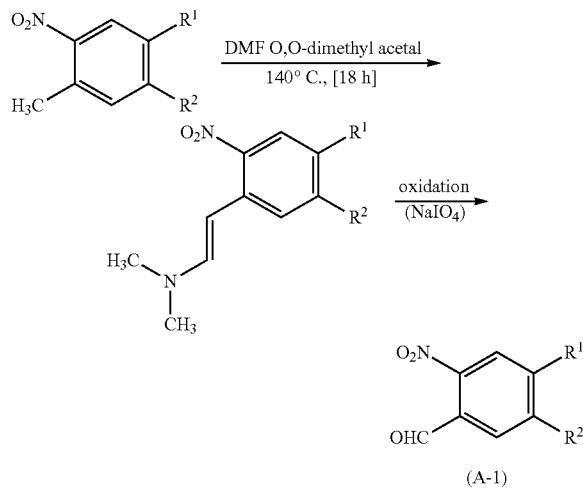

Reaction Scheme II

Some of the compounds of the formula (A-2) are known and commercially available and/or they can be prepared by preparation processes known in principle, cf., for example, for A=5-fluoropyridin-3-yl (A-a; $B^2$=H, $G^1$=C—F; T=electron pair) (WO 2011/123751 A2); pyrazin-2-yl (A-b; $B^2$=H) (WO 2012/151567 A1); pyridazin-4-yl (A-c; $B^2$=H) (WO 2011/038572 A1); thiazol-5-yl (A-d; $B^2$=H) (JP 4600 6049 B4); isothiazol-4-yl (A-e; $B^2$=H) (U.S. Pat. No. 2,839,529) or 1-methyl-1H-pyrazol-4-yl (A-f; $B^2$=H, $R^3$=$CH_3$).

The compounds of the formula (A-3) can be obtained by Step 1 of the preparation process mentioned or by synthesis methods known in principle, cf., for example, for A=pyridin-3-yl (A-a; $B^2$=H, $G^1$=CH; T=electron pair; $R^1$, $R^2$=H) (S. Ostrowski, A. M. Wolniewicz, *Chem. Het. Compd. (New York) (Transl. Khim. Geterotsikl. Soedin.)* 2000, 36(6), 705-713) or for A=pyrimid-2-yl (A-b; $B^2$, $R^1$, $R^2$=H) (A. L. El-Ansary et al., *Egypt. J. Chem.* 1991, 33(2), 129-145).

Finally, the compounds of the formula (I) can be obtained by Step 2 of the preparation process mentioned by reductive cyclization of the ortho-iminonitrobenzenes of the general formula (A-3), for example by the Candogan indazole synthesis in the presence of triethyl phosphite (cf. J. I. G. Candogan et al., *J. Chem. Soc.* 1965, 4831).

Alternatively, it is also possible to utilize modified Candogan et al. reductive cyclization reaction conditions or to employ alternative reaction conditions, for example the transition metal-catalysed reductive cyclization of iminonitroaromatics and the thermal transition metal-catalysed cyclization of 2-azidoimines (cf. N. E. Genung et al., *Org. Lett.* 2014, 16, 3114-3117 and the literature cited therein).

In addition, a number of other methods such as, for example, reductive cyclizations of ortho-nitrobenzylamines (F. Sun et al. *Tetrahedron* 2012, 68, 3851), intramolecular amination reactions (J. J. Song, N. K. Yee, *Org. Lett.* 2000, 2, 519) or acylated azobenzene cyclizations (H. Li, et al., *Chem. Commun.* 2013, 49, 9170) have also become known. However, these methods are of limited use at elevated temperatures with respect to the width, the use of transition metal catalysts and intermediates, some of which are high-energy.

In the presence of the phosphorus(III) reagent, initially the nitro group in substrate (A-3) is reduced with formation of a nitro group which subsequently forms a nitrene or a nitrene-like intermediate which then causes intramolecular cyclization (cf. N. E. Genung et al., *Org. Lett.* 2014, 16, 3114-3117). Further studies confirmed that, besides triethyl phosphite, it is also possible to use tricyclohexylphosphine, tri-(n-butyl)phosphine or tri-(tert-butyl)phosphine (M.-A. Armour et al., *J. Chem. Soc., Perkin Trans. 2* 1975, 1185-1189; N. E. Genung et al., *Org. Lett.* 2014, 16, 3114-3117) as alternative phosphorus(III) reagents.

Compounds of the formula (I) in which A, $R^1$ have the meaning mentioned further above and $R^2$ represents a radical from the group consisting of (B-1) to (B-34) can be prepared, for example, from compounds of the formula (I) in which $R^2$ preferably represents halogen from the group consisting of bromine and iodine, by generally known methods (Method A: cf. J. C. Antilla et al., *J. Org. Chem.*, 2004, 69, 5578-5587 and Method B: cf. H. Dong et al., *Org. Lett.*, 2011, 13, 2726-2729; Ch. O. Ndubaku et al., *J. Med. Chem.*, 2013, 56, 4597-4610; T. Furuya et al., *J. Am. Chem. Soc.*, 2010, 132, 3793-3807).

Compounds of the formula (I) in which $R^2$ represents halogen, for example bromine or iodine, can be obtained according to Reaction Scheme I from correspondingly halogenated 2-nitrobenzaldehydes (A-1).

For example, the compounds of the formula (I) in which $R^2$ represents a radical (B-2), (B-21) or (B-23) can be obtained according to Reaction Scheme III (cf. also preparation examples for (I-B-2)/Method A: A=pyridin-3-yl; $R^1$=H, $G^2$=$CF_3$, Example 55 and (I-B-21)/Method B: A=pyridin-3-yl; $R^1$, $G^2$=H; Example 59).

(B-31) to (B-33) can take place similar to the Methods B and C shown in Reaction Scheme III.

For example, the compounds (B-3) to (B-9), (B-11) to (B-28) and (B-31) to (B-33) having a suitable leaving group (LG=B(OH)$_2$) or (hetero)arylboronic ester (LG=B(OR)$_2$) can be reacted with the appropriate compounds of the

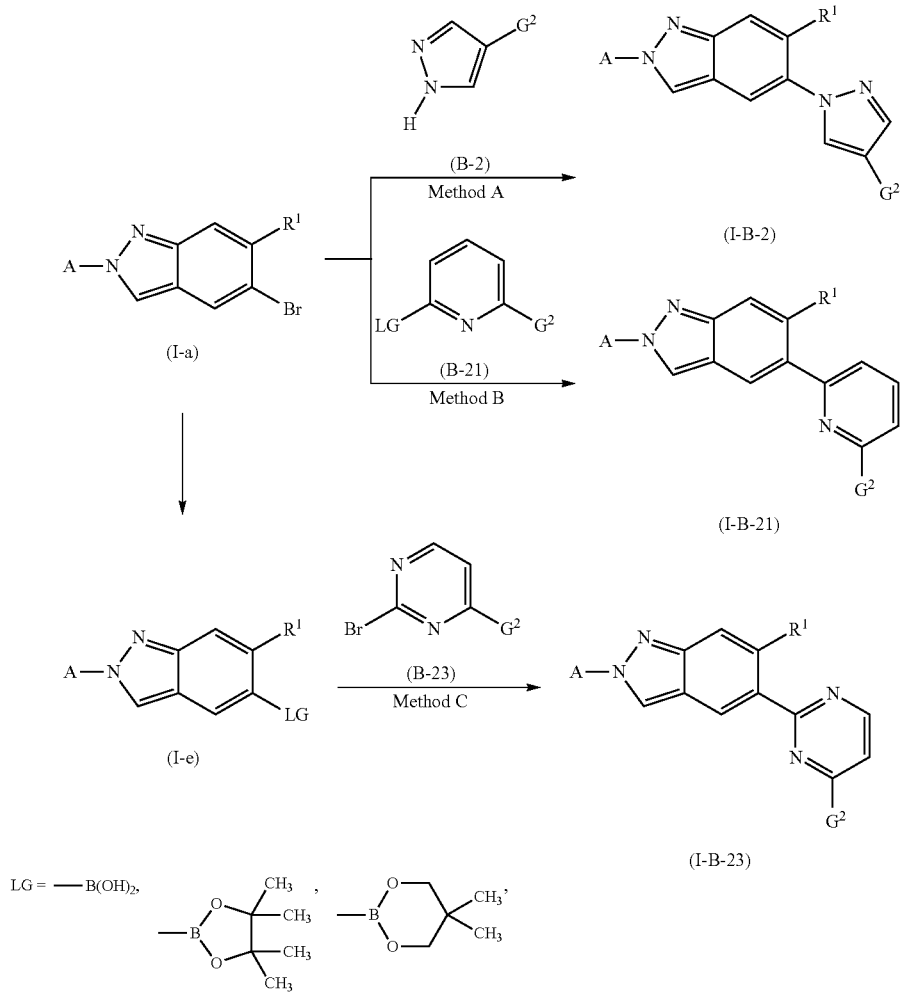

In Reaction Scheme III, the compounds (I-e) and (B-21) in which $G^2$ has the meaning mentioned further above have a nucleofugic leaving group LG, which is optionally generated in situ.

The preparation of compounds of the formula (I) in which $R^2$ represents a radical (B-1), (B-2), (B-10), (B-29) or (B-30) can be carried out analogously to Method A, which is known from the literature, preferably in the presence of copper(I) iodide and basic reaction auxiliaries, for example trans-N,N'-dimethylcyclohexane-1,2-diamine and potassium carbonate, in a suitable solvent or diluent. Useful solvents or diluents include all inert organic solvents, for example aliphatic or aromatic hydrocarbons.

Preference is given to using aromatic hydrocarbons such as, for example, toluene.

The preparation of compounds of the formula (I) in which $R^2$ represents a radical (B-3) to (B-9), (B-11) to (B-28) and formula (I-a) according to known methods (cf. *Chem. Rev.* 1995, 95, 2457-2483; *Tetrahedron* 2002, 58, 9633-9695; *Metal-Catalyzed Cross-Coupling Reactions* (Eds.: A. de Meijere, F. Diederich), 2nd ed., Wiley-VCH, Weinheim, 2004) in the presence of suitable catalysts from the group of the transition metal salts to give compounds of the formula (I-B-3) to (I-B-9), (I-B-11) to (I-B-28) and (I-B-31) to (I-B-33).

Some of the compounds (B-3) to (B-9), (B-11) to (B-13) and (B-21) to (B-33) having a suitable leaving group (LG=B(OH)$_2$) or (hetero)arylboronic ester (LG=B(OR)$_2$) are known, and/or they can be prepared by known methods: e.g. 1-(methyl-1H-pyrazol-4-yl)boronic acid [(B-3), LG=B(OH)$_2$, $G^2$=hydrogen, WO 2009/155527], 2-phenyl-4-(4,4,5,5-tetramethyl-1,3,2-dioxaborolan-2-yl)oxazole [(B-6), LG=B(OCMe$_2$)$_2$, $G^2$=phenyl, WO 2010/094755]; thiazol-2-ylboronic acid [(B-7), LG=B(OH)$_2$, $G^2$=hydrogen, U.S. Pat.

No. 6,310,095 B1]; 5-phenyl-1,2,4-thiadiazol-3-ylboronic acid [(B-13), LG=B(OH)$_2$, G$^2$=phenyl, DE 19710614 A1], pyridin-3-ylboronic acid [(B-21) vs (B-22), LG=B(OH)$_2$, G$^2$=hydrogen, WO 2013/186089]; 1,3,5-triazin-2-ylboronic acid [(B-28), LG=B(OH)$_2$, G$^2$=hydrogen, Korean Kongkae Taeho Kongbo (2011), KR 2011/079401].

Alternatively, the compounds of the formula (I-a) can initially be converted by methods known from the literature into compounds of the formula (I-e) which are then reacted further with halogen-activated heterocycles according to Reaction Scheme III by Method C (cf. T. Ishiyama et al., J. Org. Chem., 1995, 60, 7508-7510; WO 2010/151601); (cf. preparation examples for (I-B-23)/Method C: A=pyridin-3-yl; R$^2$=pyrimidin-2-yl; R$^1$, G$^2$=H; Example 60).

Some halogen-activated compounds (B-3) to (B-9), (B-11) to (B-13) and (B-21) to (B-33) are known, and/or they can be prepared by generally known methods: e.g. 3-bromo-4,5-dihydro-1-phenyl-1H-pyrazole [(B-18), LG=Br, G$^2$=phenyl, J. Elguero et al., Bull. Soc. Chim. France 1996, 5, 1683-1686].

The preparation of compounds of the formula (I) in which R$^2$ represents a radical (B-21) or (B-23) can be carried out similar to Methods B and C, which are known from the literature and shown in Reaction Scheme III, preferably in the presence of suitable coupling catalysts, basic reaction auxiliaries and in a suitable solvent or diluent. Useful solvents or diluents include all inert organic solvents, for example aliphatic or aromatic hydrocarbons.

Preference is given to using aromatic hydrocarbons such as, for example, toluene.

The preparation of compounds of the formula (I) in which R$^2$ represents a radical (B-3) to (B-9), (B-11) to (B-28) and (B-31) to (B-33) can be carried out similar to Methods B and C, which are shown in Reaction Scheme III, preferably in the presence of suitable coupling catalysts, basic reaction auxiliaries and in a suitable solvent or diluent.

Examples of preferred coupling catalysts include palladium catalysts such as [1,1'-bis(diphenylphosphino)ferrocene]dichloropalladium (II) or tetrakis(triphenylphosphine) palladium.

Suitable basic reaction auxiliaries used for carrying out the processes according to Reaction Scheme III are preferably carbonates of sodium or potassium.

Preferably, the diluents used are nitriles such as acetonitrile, benzonitrile, in particular acetonitrile, or ethers such as diethyl ether, dioxane, tetrahydrofuran, 1,2-dimethoxyethane, in particular 1,2-dimethoxyethane in combination with water.

Compounds of the formula (I) in which R$^2$ represents a radical from the group consisting of (C-1) to (C-9) or represents C(X)NR$^{22}$R$^{23}$ can be prepared, for example, from compounds of the formula (I) in which R$^2$ represents a carboxyl group, following suitable activation (i.e. LG represents a nucleofugic leaving group optionally generated in situ) by known methods.

For example, the compounds of the formula (I) in which R$^2$ represents a radical (C-1) or represents C(X)NR$^{22}$R$^{23}$ can be obtained according to Reaction Scheme IV (cf. also preparation examples for (I-C-1): A=pyridin-3-yl or N-methylpyrazol-4-yl; R$^1$, R$^8$=H, R$^9$=N(CH$_3$)$_2$, n=2; Examples 5 and 42; (Id): A=pyridin-3-yl or pyrimidin-5-yl; R$^1$=H, R$^{22}$, R$^{23}$=CH$_3$, Examples 1, and 27).

Reaction Scheme IV

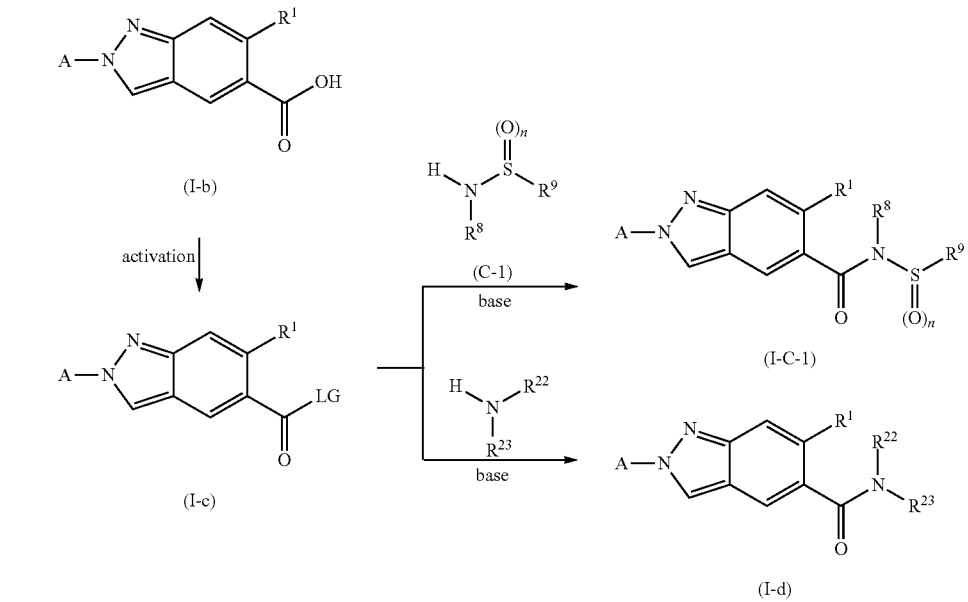

LG = leaving group, e.g. halogen,
O—CO—R (R = aryl, alkyl)
N-imidazol-1-yl, etc.

Compounds of the formula (I) in which R$^2$ represents carboxyl can be obtained according to Reaction Scheme I from corresponding alkyl 3-formyl-4-nitrobenzoates (A-1; R$^2$=COOR). Subsequent ester hydrolysis by customary methods then leads to the compounds of the formula (I-b).

Suitable condensing agents for activating the carboxylic acids of the formula (I-b) are all condensing agents customarily used for such amidation reactions. Examples include acid halide formers such as phosgene, phosgene derivatives such as carbonyldiimidazole (CDI), phosphorus trichloride, oxalyl chloride or thionyl chloride; carbodiimides such as N,N'-dicyclohexylcarbodiimide (DCC) and 1-(3-dimethylaminopropyl)-3-ethylcarbodiimide (EDCI), or other customary condensing agents such as phosphorus pentoxide, polyphosphoric acid, N,N'-carbonyldiimidazole, 2-chloropyridine 1-methoiodide (Mukaiyama's reagent), 2-ethoxy-N-ethoxycarbonyl-1,2-dihydroquinoline (EEDQ), triphenylphosphine/carbon tetrachloride, bromotripyrrolidinophosphonium hexafluorophosphate (BROP), O-(1H-benzotriazol-1-yloxy)tris(dimethylamino)phosphonium hexafluorophosphate (BOP), bis(2-oxo-3-oxazolidinyl)phosphinic chloride (BOP-Cl), N,N,N',N'-bis(tetramethylene)chlorouronium tetrafluoroborate, O-(1H-benzotriazol-1-yl)-N,N,N',N'-tetramethyluronium hexafluorophosphate (HBTU), O-(1H-benzotriazol-1-yl)-N,N,N',N'-bis(tetramethylene)uronium hexafluorophosphate, O-(1H-benzotriazol-1-yl)-N,N,N',N'-tetramethyluronium tetrafluoroborate (TBTU), O-(1H-benzotriazol-1-yl)-N,N,N',N'-bis(tetramethylene)uronium tetrafluoroborate, O-(7-azabenzotriazol-1-yl)-N,N,N',N'-tetramethyluronium hexafluorophosphate (HATU), 1-hydroxybenzotriazole (HOBt) and 4-(4,6-dimethoxy-1,3,5-triazin-2-yl)-4-methylmorpholinium salt (DMT.MM), usually available as chloride. These reagents can be used separately or, if appropriate, in combination.

However, for the targeted activation of the compounds of the formula (I-b) it is also possible to use mixed anhydrides (LG=COOR), which lead to the preparation of compounds of the formula (I-C-1) and (I-d) (cf. G. W. Anderson et al. *J. Am. Chem. Soc.* 1967, 89, 5012-5017). Various chloroformic esters can be employed in this process, such as, for example, isobutyl chloroformate (LG=COOR where R=isobutyl) and isopropyl chloroformate (LG=COOR where R=isopropyl). It is likewise possible to use diethylacetyl chloride, trimethylacetyl chloride and the like for this purpose.

Subsequent reactions of the activated compounds of the formula (I-c) with the respective amine components according to Reaction Scheme IV are optionally carried out in the presence of a suitable reaction auxiliary and in the presence of a suitable solvent or diluent.

Suitable reaction auxiliaries for carrying out the processes according to Reaction Scheme IV are basic reaction auxiliaries.

Examples which may be mentioned are the hydroxides, hydrides, oxides and carbonates of lithium, sodium, potassium, magnesium, calcium and barium, furthermore further basic compounds such as amidine bases or guanidine bases, such as 7-methyl-1,5,7-triazabicyclo[4.4.0]dec-5-ene (MTBD); diazabicyclo[4.3.0]nonene (DBN), diazabicyclo[2.2.2]octane (DABCO), 1,8-diazabicyclo[5.4.0]undecene (DBU), cyclohexyltetrabutylguanidine (CyTBG), cyclohexyltetramethylguanidine (CyTMG), N,N,N,N-tetramethyl-1,8-naphthalenediamine, pentamethylpiperidine, tertiary amines, such as triethylamine, trimethylamine, tribenzylamine, triisopropylamine, tributylamine, tricyclohexylamine, triamylamine, trihexylamine, N,N-dimethylaniline, N,N-dimethyltoluidine, N,N-dimethyl-p-aminopyridine, N-methylpyrrolidine, N-methylpiperidine, N-methylimidazole, N-methylpyrazole, N-methylmorpholine, N-methylhexamethylenediamine, pyridine, 4-pyrrolidinopyridine, 4-dimethylaminopyridine, quinoline, α-picoline, β-picoline, isoquinoline, pyrimidine, acridine, N,N,N',N'-tetramethylenediamine, N,N',N'-tetraethylenediamine, quinoxaline, N-propyldiisopropylamine, N-ethyldiisopropylamine ("Hünig's Base"), N,N'-dimethylcyclohexylamine, 2,6-lutidine, 2,4-lutidine or triethyldiamine.

Suitable for use as basic reaction auxiliaries for carrying out the processes according to Reaction Scheme IV are all suitable acid binders, for example amines, in particular tertiary amines, and alkali metal and alkaline earth metal compounds.

For preparing compounds of the formula (I-C-1) or (I-d), use is preferably made of tertiary amines such as N-propyldiisopropylamine or N-ethyldiisopropylamine (DIEA; Hünig's base).

Suitable solvents or diluents include all inert organic solvents, for example aliphatic or aromatic hydrocarbons (such as petroleum ether, toluene), halogenated hydrocarbons (such as chlorotoluene, dichloromethane, chloroform, 1,2-dichloroethane), ethers (such as diethyl ether, dioxane, tetrahydrofuran, 1,2-dimethoxyethane), esters (such as ethyl or methyl acetate), nitrohydrocarbons (such as nitromethane, nitroethane, nitrobenzene), nitriles (such as acetonitrile, benzonitrile), amides (such as N,N-dimethylformamide, N,N-dimethylacetamide, N-methylformanilide, N-methylpyrrolidone, hexamethylphosphoramide), and also dimethyl sulphoxide or water or mixtures of the solvents mentioned.

Preference is given to using amides as solvents, for example N,N-dimethylformamide.

Compounds of the formula (I) in which $R^2$ represents a radical from the group consisting of (D-1) to (D-3) can be prepared, for example, from compounds of the formula (I) in which $R^2$ represents halogen from the group consisting of bromine and iodine, by known methods.

For example, the compounds of the formula (I) in which $R^2$ represents a radical from the group consisting of (D-1) to (D-3) can be obtained according to Reaction Scheme V by methods known from the literature (cf. US2013/0267493; T. Furuya et al., *J. Am. Chem. Soc.*, 2010, 132, 3793-3807) (cf. also preparation examples for (I-D-2): A=pyridin-3-yl; R=$CH_2CF_3$, $R^1$=H, W=S, $X^1$=2-F, $Y^3$=4-$CH_3$).

Reaction Scheme V

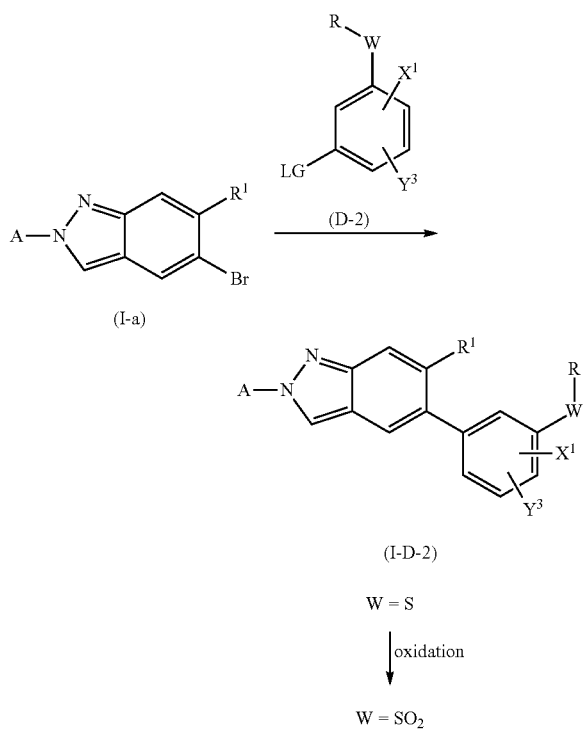

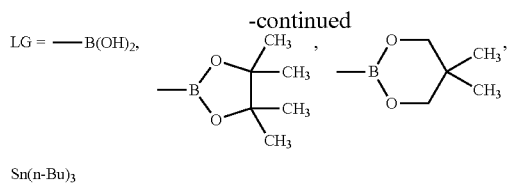

LG = —B(OH)$_2$,

Sn(n-Bu)$_3$

In Reaction Scheme V, the compounds (D-2) in which R, X$^1$, Y$^3$ have the meaning mentioned above and W represents S, SO or SO$_2$ have a nucleofugic leaving group LG, which is optionally generated in situ.

For example, the compounds (D-1) to (D-3) having a suitable leaving group (LG=B(OH)$_2$) or (hetero)arylboronic ester (LG=B(OR)$_2$) can be reacted with the appropriate compounds of the formula (I-a) according to known methods (cf. *Chem. Rev.* 1995, 95, 2457-2483; *Tetrahedron* 2002, 58, 9633-9695; *Metal-Catalyzed Cross-Coupling Reactions* (Eds.: A. de Meijere, F. Diederich), 2nd ed., Wiley-VCH, Weinheim, 2004) in the presence of suitable catalysts from the group of the transition metal salts to give compounds of the formula (I-D-1) to (I-D-3).

The preparation of compounds of the formula (I) in which R$^2$ represents a radical (D-1) to (D-3) can be carried out similar to Reaction Scheme V, preferably in the presence of suitable coupling catalysts, basic reaction auxiliaries and in a suitable solvent or diluent.

Examples of preferred coupling catalysts include palladium catalysts such as [1,1'-bis(diphenylphosphino)ferrocene]dichloropalladium (II) or tetrakis(triphenylphosphine)palladium.

Suitable basic reaction auxiliaries used for carrying out the processes according to Reaction Scheme III are preferably carbonates of sodium or potassium.

Preference is given to using nitriles such as acetonitrile, benzonitrile, in particular acetonitrile, or ethers such as diethyl ether, dioxane, tetrahydrofuran, 1,2-dimethoxyethane, in particular 1,2-dimethoxyethane in combination with water.

Subsequent oxidation of the sulphur in the compounds of the formula (I-D-2) in which A, R, R$^1$, X$^1$, Y$^3$ have the meaning mentioned above and W represents sulphur leads to compounds of the formula (I-D-2) in which A, R, R$^1$, X$^1$, Y$^3$ have the meaning mentioned above and W represents SO or SO$_2$ (cf. Reaction Scheme V; see preparation examples for (I-D-2): A=pyridin-3-yl; R=CH$_2$CF$_3$, R$^1$=H, W=SO, X$^1$=2-F, Y$^3$=4-CH$_3$; cf. Example 52 or A=pyridin-3-yl; R=CH$_2$CF$_3$, R$^1$, X$^1$=H, W=SO, Y$^3$=4-CH$_3$; cf. Example 53).

Compounds of the formula (I) in which W represents SO (sulphoxides) or W represents SO$_2$ (sulphones) can be prepared by oxidation by processes known from the literature from compounds of the formula (I) in which W represents S (thioethers), for example by an oxidizing agent in a suitable solvent or diluent. Suitable oxidizing agents are, for example, diluted nitric acid, hydrogen peroxide, Oxone® and peroxycarboxylic acids, for example meta-chloroperbenzoic acid. Suitable solvents or diluents are inert organic solvents, typically acetonitrile and halogenated solvents such as dichloromethane, chloroform or dichloroethane, and water and alcohols such as methanol for the reaction with Oxone®.

A variety of methods are suitable for producing enantiomerically enriched sulphoxides, as described by G. E. O'Mahony et al., in *ARKIVOC* (Gainesville, Fla., United states), 2011, 1, 1-110: metal-catalysed asymmetric oxidations of thioethers, for example with titanium or vanadium as the most frequently employed catalyst sources, in the form of Ti(O$^i$Pr$_4$) or VO(acac)$_2$, together with a chiral ligand and an oxidizing agent such as tert-butyl hydroperoxide (TBHP), 2-phenylpropan-2-yl hydroperoxide (CHP) or hydrogen peroxide; non-metal-catalysed asymmetric oxidations employing chiral oxidizing agents or chiral catalysts; electrochemical or biological asymmetric oxidations and also kinetic resolution of sulphoxides and nucleophilic shift (according to Andersen's method).

Compounds of the formula (I) in which A, R$^1$ have the meaning mentioned above and R$^2$ represents —NR$^{23}$—C(X)—R$^{22}$ can be obtained, for example, from compounds of the formula (I) in which R$^2$ represents —NHR$^{23}$ via an N-acylation reaction using activated compounds of the formula LG-CX—R$^{22}$ in which LG represents a nucleofugic leaving group, which is optionally generated in situ.

These compounds of the formula (I) in which R$^2$ represents —NHR$^{23}$ can be prepared from compounds of the formula (I) in which R$^2$ represents a carboxyl group according to Reaction Scheme VI, by known methods.

Reaction Scheme VI

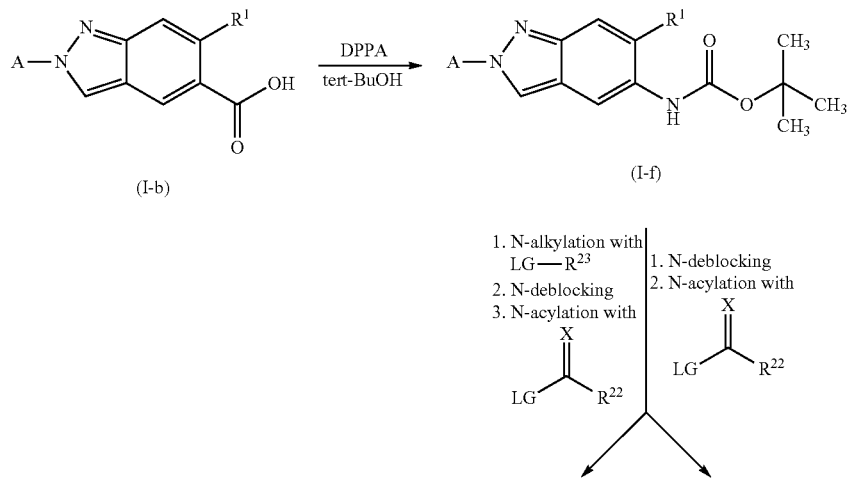

-continued

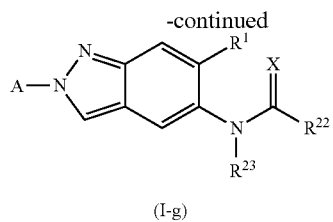

(I-g)

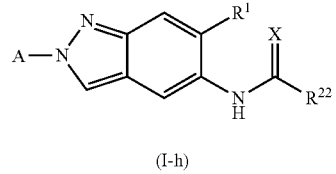

(I-h)

LG = leaving group, e.g. halogen
DPPA = diphenylphosphorylazide

For example, compounds of the formula (I-f) can be obtained by Curtius degradation as described, for example, in Houben-Weyl, *Methoden der Organischen Chemie* [Methods of Organic Chemistry], Volume XI/1 (Georg Thieme Verlag Stuttgart), p. 865.

Here, the compounds of the formula (I-b) can, for example, be reacted directly with diphenylphosphoryl azide (DPPA) in the presence of tert-butanol to give compounds of the formula (I-f).

From the compounds of the formula (I-f), it is possible to obtain the compounds of the formula (I-g) by N-alkylation in a first reaction step, N-deblocking (i.e. cleavage of the Boc group) in a second reaction step and subsequent N-acylation in a third reaction step.

The compounds of the formula (I-h) can be prepared by N-deblocking (i.e. cleavage of the Boc group) in a first reaction step and subsequent N-acylation in a second reaction step (cf. Examples 105 to 130).

In general, for removing the protective group, it is possible to use acidic or basic reaction auxiliaries, according to procedures known from the literature. When protective groups of the carbamate type are used, preference is given to using acidic reaction auxiliaries. When the tert-butylcarbamate protective group (Boc group) is employed, for example, mixtures of mineral acids such as hydrochloric acid, hydrobromic acid, nitric acid, sulphuric acid, phosphoric acid or of organic acids such as benzoic acid, formic acid, acetic acid, trifluoroacetic acid, methanesulphonic acid, benzenesulphonic acid or toluenesulphonic acid in a suitable diluent such as water and/or an organic solvent such as tetrahydrofuran, dioxane, dichloromethane, chloroform, ethyl acetate, ethanol or methanol are used. Preference is given to mixtures of hydrochloric acid or acetic acid with water and/or an organic solvent such as ethyl acetate.

If compounds of the formula (I) are referred to hereinbelow, this also includes those compounds in Table 1 which are not embraced by formula (I).

Isomers

Depending on the nature of the substituents, the compounds of the formula (I) may be in the form of geometric and/or optically active isomers or corresponding isomer mixtures in different compositions. These stereoisomers are, for example, enantiomers, diastereomers, atropisomers or geometric isomers. Accordingly, the invention encompasses both pure stereoisomers and any mixtures of these isomers.

Methods and Uses

The invention also relates to methods for controlling animal pests, in which compounds of the formula (I) are allowed to act on animal pests and/or their habitat. The control of the animal pests is preferably conducted in agriculture and forestry, and in material protection. This preferably excludes methods for surgical or therapeutic treatment of the human or animal body and diagnostic methods carried out on the human or animal body.

The invention further relates to the use of the compounds of the formula (I) as pesticides, especially crop protection agents.

In the context of the present application, the term "pesticide" also always encompasses the term "crop protection agent".

The compounds of the formula (I), given good plant tolerance, favourable homeotherm toxicity and good environmental compatibility, are suitable for protecting plants and plant organs against biotic and abiotic stress factors, for increasing harvest yields, for improving the quality of the harvested material and for controlling animal pests, especially insects, arachnids, helminths, nematodes and molluscs, which are encountered in agriculture, in horticulture, in animal husbandry, in aquatic cultures, in forests, in gardens and leisure facilities, in the protection of stored products and of materials, and in the hygiene sector. They can preferably be used as pesticides. They are active against normally sensitive and resistant species and also against all or specific stages of development. The abovementioned pests include:

pests from the phylum of the Arthropoda, especially from the class of the Arachnida, for example *Acarus* spp., for example *Acarus siro, Aceria kuko, Aceria sheldoni, Aculops* spp., *Aculus* spp., for example *Aculus fockeui, Aculus schlechtendali, Amblyomma* spp., *Amphitetranychus viennensis, Argas* spp., *Boophilus* spp., *Brevipalpus* spp., for example *Brevipalpus phoenicis, Bryobia graminum, Bryobia praetiosa, Centruroides* spp., *Chorioptes* spp., *Dermanyssus gallinae, Dermatophagoides pteronyssinus, Dermatophagoides farinae, Dermacentor* spp., *Eotetranychus* spp., for example *Eotetranychus hicoriae, Epitrimerus pyri, Eutetranychus* spp., for example *Eutetranychus banksi, Eriophyes* spp., for example *Eriophyes pyri, Glycyphagus domesticus, Halotydeus destructor, Hemitarsonemus* spp., for example *Hemitarsonemus latus (=Polyphagotarsonemus latus), Hyalomma* spp., *Ixodes* spp., *Latrodectus* spp., *Loxosceles* spp., *Neutrombicula autumnalis, Nuphersa* spp., *Oligonychus* spp., for example *Oligonychus coffeae, Oligonychus coniferarum, Oligonychus ilicis, Oligonychus indicus, Oligonychus mangiferus, Oligonychus pratensis, Oligonychus punicae, Oligonychus yothersi, Ornithodorus* spp., *Ornithonyssus* spp., *Panonychus* spp., for example *Panonychus citri (=Metatetranychus citri), Panonychus ulmi (=Metatetranychus ulmi), Phyllocoptruta oleivora, Platytetranychus multidigituli, Polyphagotarsonemus latus, Psoroptes* spp., *Rhipicephalus* spp., *Rhizoglyphus* spp., *Sarcoptes* spp., *Scorpio maurus, Steneotarsonemus* spp., *Steneotarsonemus spinki, Tarsonemus* spp., for example *Tarsonemus confusus, Tarsonemus pallidus, Tetranychus* spp., for example *Tetranychus canadensis, Tetranychus cinnabarinus, Tetranychus turkestani, Tetranychus urticae, Trombicula alfreddugesi, Vaejovis* spp., *Vasates lycopersici;* from the class of the Chilopoda, for example *Geophilus* spp., *Scutigera* spp.;

from the order or the class of the Collembola, for example *Onychiurus armatus; Sminthurus viridis;* from the class of the Diplopoda, for example *Blaniulus guttulatus;* from the class of the Insecta, for example from the order of the Blattodea, for example *Blatta orientalis, Blattella asahinai, Blattella germanica, Leucophaea maderae, Loboptera decipiens, Neostylopyga rhombifolia, Panchlora* spp., *Parcoblatta* spp., *Periplaneta* spp., for example *Periplaneta americana, Periplaneta australasiae, Pycnoscelus surinamensis, Supella longipalpa;* from the order of the Coleoptera, for example *Acalymma vittatum, Acanthoscelides obtectus, Adoretus* spp., *Aethina tumida, Agelastica alni, Agriotes* spp., for example *Agriotes linneatus, Agriotes mancus, Alphitobius diaperinus, Amphimallon solstitialis, Anobium punctatum, Anoplophora* spp., *Anthonomus* spp., for example *Anthonomus grandis, Anthrenus* spp., *Apion* spp., *Apogonia* spp., *Atomaria* spp., for example *Atomaria linearis, Attagenus* spp., *Baris caerulescens, Bruchidius obtectus, Bruchus* spp., for example *Bruchus pisorum, Bruchus rufimanus, Cassida* spp., *Cerotoma trifurcata, Ceutorrhynchus* spp., for example *Ceutorrhynchus assimilis, Ceutorrhynchus quadridens, Ceutorrhynchus rapae, Chaetocnema* spp., for example *Chaetocnema confinis, Chaetocnema denticulata, Chaetocnema ectypa, Cleonus mendicus, Conoderus* spp., *Cosmopolites* spp., for example *Cosmopolites sordidus, Costelytra zealandica, Ctenicera* spp., *Curculio* spp., for example *Curculio caryae, Curculio caryatrypes, Curculio obtusus, Curculio sayi, Cryptolestes ferrugineus, Cryptolestes pusillus, Cryptorhynchus lapathi, Cryptorhynchus mangiferae, Cylindrocopturus* spp., *Cylindrocopturus adspersus, Cylindrocopturus furnissi, Dermestes* spp., *Diabrotica* spp., for example *Diabrotica balteata, Diabrotica barberi, Diabrotica undecimpunctata howardi, Diabrotica undecimpunctata undecimpunctata, Diabrotica virgifera virgifera, Diabrotica virgifera zeae, Dichocrocis* spp., *Dicladispa armigera, Diloboderus* spp., *Epicaerus* spp., *Epilachna* spp., for example *Epilachna borealis, Epilachna varivestis, Epitrix* spp., for example *Epitrix cucumeris, Epitrix fuscula, Epitrix hirtipennis, Epitrix subcrinita, Epitrix tuberis, Faustinus* spp., *Gibbium psylloides, Gnathocerus cornutus, Hellula undalis, Heteronychus arator, Heteronyx* spp., *Hylamorpha elegans, Hylotrupes bajulus, Hypera postica, Hypomeces squamosus, Hypothenemus* spp., for example *Hypothenemus hampei, Hypothenemus obscurus, Hypothenemus pubescens, Lachnosterna consanguinea, Lasioderma serricorne, Latheticus oryzae, Lathridius* spp., *Lema* spp., *Leptinotarsa decemlineata, Leucoptera* spp., for example *Leucoptera coffeella, Lissorhoptrus oryzophilus, Listronotus (=Hyperodes)* spp., *Lixus* spp., *Luperomorpha xanthodera, Luperodes* spp., *Lyctus* spp., *Megascelis* spp., *Melanotus* spp., for example *Melanotus longulus oregonensis, Meligethes aeneus, Melolontha* spp., for example *Melolontha melolontha, Migdolus* spp., *Monochamus* spp., *Naupactus xanthographus, Necrobia* spp., *Neogalerucella* spp., *Niptus hololeucus, Oryctes rhinoceros, Oryzaephilus surinamensis, Oryzaphagus oryzae, Otiorhynchus* spp., for example *Otiorhynchus cribricollis, Otiorhynchus ligustici, Otiorhynchus ovatus, Otiorhynchus rugosostriarus, Otiorhynchus sulcatus, Oulema* spp., z.B. *Oulema melanopus, Oulema oryzae, Oxycetonia jucunda, Phaedon cochleariae, Phyllophaga* spp., *Phyllophaga helleri, Phyllotreta* spp., for example *Phyllotreta armoraciae, Phyllotreta pusilla, Phyllotreta ramosa, Phyllotreta striolata, Popillia japonica, Premnotrypes* spp., *Prostephanus truncatus, Psylliodes* spp., for example *Psylliodes affinis, Psylliodes chrysocephala, Psylliodes punctulata, Ptinus* spp., *Rhizobius ventralis, Rhizopertha dominica, Rhynchophorus* spp., *Rhynchophorus ferrugineus, Rhynchophorus palmarum, Sinoxylon perforans, Sitophilus* spp., for example *Sitophilus granarius, Sitophilus linearis, Sitophilus oryzae, Sitophilus zeamais, Sphenophorus* spp., *Stegobium paniceum, Sternechus* spp., for example *Sternechus paludatus, Symphyletes* spp., *Tanymecus* spp., for example *Tanymecus dilaticollis, Tanymecus indicus, Tanymecus palliatus, Tenebrio molitor, Tenebrioides mauretanicus, Tribolium* spp., for example *Tribolium audax, Tribolium castaneum, Tribolium confusum, Trogoderma* spp., *Tychius* spp., *Xylotrechus* spp., *Zabrus* spp., for example *Zabrus tenebrioides;* from the order of the Dermaptera, for example *Anisolabis maritime, Forficula auricularia, Labidura riparia;* from the order of the Diptera, for example *Aedes* spp., for example *Aedes aegypti, Aedes albopictus, Aedes sticticus, Aedes vexans, Agromyza* spp., for example *Agromyza frontella, Agromyza parvicornis, Anastrepha* spp., *Anopheles* spp., for example *Anopheles quadrimaculatus, Anopheles gambiae, Asphondylia* spp., *Bactrocera* spp., for example *Bactrocera cucurbitae, Bactrocera dorsalis, Bactrocera oleae, Bibio hortulanus, Calliphora erythrocephala, Calliphora vicina, Ceratitis capitata, Chironomus* spp., *Chrysomya* spp., *Chrysops* spp., *Chrysozona pluvialis, Cochliomya* spp., *Contarinia* spp., for example *Contarinia johnsoni, Contarinia nasturtii, Contarinia pyrivora, Contarinia schulzi, Contarinia sorghicola, Contarinia tritici, Cordylobia anthropophaga, Cricotopus sylvestris, Culex* spp., for example *Culex pipiens, Culex quinquefasciatus, Culicoides* spp., *Culiseta* spp., *Cuterebra* spp., *Dacus oleae, Dasineura* spp., for example *Dasineura brassicae, Delia* spp., for example *Delia antiqua, Delia coarctata, Delia florilega, Delia platura, Delia radicum, Dermatobia hominis, Drosophila* spp., for example *Drosphila melanogaster, Drosophila suzukii, Echinocnemus* spp., *Euleia heraclei, Fannia* spp., *Gasterophilus* spp., *Glossina* spp., *Haematopota* spp., *Hydrellia* spp., *Hydrellia griseola, Hylemya* spp., *Hippobosca* spp., *Hypoderma* spp., *Liriomyza* spp., for example *Liriomyza brassicae, Liriomyza huidobrensis, Liriomyza sativae, Lucilia* spp., for example *Lucilia cuprina, Lutzomyia* spp., *Mansonia* spp., *Musca* spp., for example *Musca domestica, Musca domestica vicina, Oestrus* spp., *Oscinella frit, Paratanytarsus* spp., *Paralauterborniella subcincta, Pegomya* spp., for example *Pegomya betae, Pegomya hyoscyami, Pegomya rubivora, Phlebotomus* spp., *Phorbia* spp., *Phormia* spp., *Piophila casei, Platyparea poeciloptera, Prodiplosis* spp., *Psila rosae, Rhagoletis* spp., for example *Rhagoletis cingulata, Rhagoletis completa, Rhagoletis fausta, Rhagoletis indifferens, Rhagoletis mendax, Rhagoletis pomonella, Sarcophaga* spp., *Simulium* spp., for example *Simulium meridionale, Stomoxys* spp., *Tabanus* spp., *Tetanops* spp., *Tipula* spp., for example *Tipula paludosa, Tipula simplex, Toxotrypana curvicauda;* from the order of the Hemiptera for example *Acizzia acaciaebaileyanae, Acizzia dodonaeae, Acizzia uncatoides, Acrida turrita, Acyrthosipon* spp., for example *Acyrthosiphon pisum, Acrogonia* spp., *Aeneolamia* spp., *Agonoscena* spp., *Aleurocanthus* spp., *Aleyrodes proletella, Aleurolobus barodensis, Aleurothrixus floccosus, Allocaridara malayensis, Amrasca* spp., for example *Amrasca bigutulla, Amrasca devastans, Anuraphis cardui, Aonidiella* spp., for example *Aonidiella aurantii, Aonidiella citrina, Aonidiella inornata, Aphanostigma piri, Aphis* spp., for example *Aphis citricola, Aphis craccivora, Aphis fabae, Aphis forbesi, Aphis gly-*

*cines, Aphis gossypii, Aphis hederae, Aphis illinoisensis, Aphis middletoni, Aphis nasturtii, Aphis nerii, Aphis pomi, Aphis spiraecola, Aphis viburniphila, Arboridia apicalis, Arytainilla* spp., *Aspidiella* spp., *Aspidiotus* spp., for example *Aspidiotus nerii, Atanus* spp., *Aulacorthum solani, Bemisia tabaci, Blastopsylla occidentalis, Boreioglycaspis melaleucae, Brachycaudus helichrysi, Brachycolus* spp., *Brevicoryne brassicae, Cacopsylla* spp., for example *Cacopsylla pyricola, Calligypona marginata, Capulinia* spp., *Carneocephala fulgida, Ceratovacuna lanigera, Cercopidae, Ceroplastes* spp., *Chaetosiphon fragaefolii, Chionaspis tegalensis, Chlorita onukii, Chondracris rosea, Chromaphis juglandicola, Chrysomphalus aonidum, Chrysomphalus ficus, Cicadulina mbila, Coccomytilus halli, Coccus* spp., for example *Coccus hesperidum, Coccus longulus, Coccus pseudomagnoliarum, Coccus viridis, Cryptomyzus ribis, Cryptoneossa* spp., *Ctenaytaina* spp., *Dalbulus* spp., *Dialeurodes chittendeni, Dialeurodes citri, Diaphorina citri, Diaspis* spp., *Diuraphis* spp., *Doralis* spp., *Drosicha* spp., *Dysaphis* spp., for example *Dysaphis apiifolia, Dysaphis plantaginea, Dysaphis tulipae, Dysmicoccus* spp., *Empoasca* spp., for example *Empoasca abrupta, Empoasca fabae, Empoasca maligna, Empoasca solana, Empoasca stevensi, Eriosoma* spp., for example *Eriosoma americanum, Eriosoma lanigerum, Eriosoma pyricola, Erythroneura* spp., *Eucalyptolyma* spp., *Euphyllura* spp., *Euscelis bilobatus, Ferrisia* spp., *Fiorinia* spp., *Furcaspis oceanica, Geococcus coffeae, Glycaspis* spp., *Heteropsylla cubana, Heteropsylla spinulosa, Homalodisca coagulata, Hyalopterus arundinis, Hyalopterus pruni, Icerya* spp., for example *Icerya purchasi, Idiocerus* spp., *Idioscopus* spp., *Laodelphax striatellus, Lecanium* spp., for example *Lecanium corni (=Parthenolecanium corni), Lepidosaphes* spp., for example *Lepidosaphes ulmi, Lipaphis erysimi, Lopholeucaspis japonica, Lycorma delicatula, Macrosiphum* spp., for example *Macrosiphum euphorbiae, Macrosiphum lilii, Macrosiphum rosae, Macrosteles facifrons, Mahanarva* spp., *Melanaphis sacchari, Metcalfiella* spp., *Metcalfa pruinosa, Metopolophium dirhodum, Monellia costalis, Monelliopsis pecanis, Myzus* spp., for example *Myzus ascalonicus, Myzus cerasi, Myzus ligustri, Myzus ornatus, Myzus persicae, Myzus nicotianae, Nasonovia ribisnigri, Neomaskellia* spp., *Nephotettix* spp., for example *Nephotettix cincticeps, Nephotettix nigropictus, Nettigonicla spectra, Nilaparvata lugens, Oncometopia* spp., *Orthezia praelonga, Oxya chinensis, Pachypsylla* spp., *Parabemisia myricae, Paratrioza* spp., for example *Paratrioza cockerelli, Parlatoria* spp., *Pemphigus* spp., for example *Pemphigus bursarius, Pemphigus populivenae, Peregrinus maidis, Perkinsiella* spp., *Phenacoccus* spp., for example *Phenacoccus madeirensis, Phloeomyzus passerinii, Phorodon humuli, Phylloxera* spp., for example *Phylloxera devastatrix, Phylloxera notabilis, Pinnaspis aspidistrae, Planococcus* spp., for example *Planococcus citri, Prosopidopsylla flava, Protopulvinaria pyriformis, Pseudaulacaspis pentagona, Pseudococcus* spp., for example *Pseudococcus calceolariae, Pseudococcus comstocki, Pseudococcus longispinus, Pseudococcus maritimus, Pseudococcus viburni, Psyllopsis* spp., *Psylla* spp., for example *Psylla buxi, Psylla mali, Psylla pyri, Pteromalus* spp., *Pulvinaria* spp., *Pyrilla* spp., *Quadraspidiotus* spp., for example *Quadraspidiotus juglansregiae, Quadraspidiotus ostreaeformis, Quadraspidiotus perniciosus, Quesada gigas, Rastrococcus* spp., *Rhopalosiphum* spp., for example *Rhopalosiphum maidis, Rhopalosiphum oxyacanthae, Rhopalosiphum padi, Rhopalosiphum rufiabdominale, Saissetia* spp., for example *Saissetia coffeae, Saissetia miranda, Saissetia neglecta, Saissetia oleae, Scaphoideus titanus, Schizaphis graminum, Selenaspidus articulatus, Sipha flava, Sitobion avenae, Sogata* spp., *Sogatella furcifera, Sogatodes* spp., *Stictocephala festina, Siphoninus phillyreae, Tenalaphara malayensis, Tetragonocephela* spp., *Tinocallis caryaefoliae, Tomaspis* spp., *Toxoptera* spp., for example *Toxoptera aurantii, Toxoptera citricidus, Trialeurodes vaporariorum, Trioza* spp., for example *Trioza diospyri, Typhlocyba* spp., *Unaspis* spp., *Viteus vitifolii, Zygina* spp.; from the suborder of the Heteroptera, for example *Aelia* spp., *Anasa tristis, Antestiopsis* spp., *Boisea* spp., *Blissus* spp., *Calocoris* spp., *Campylomma livida, Caveleríus* spp., *Cimex* spp., for example *Cimex adjunctus, Cimex hemipterus, Cimex lectularius, Cimex pilosellus, Collaria* spp., *Creontiades dilutus, Dasynus piperis, Dichelops furcatus, Diconocoris hewetti, Dysdercus* spp., *Euschistus* spp., for example *Euschistus heros, Euschistus servus, Euschistus tristigmus, Euschistus variolarius, Eurydema* spp., *Eurygaster* spp., *Halyomorpha halys, Heliopeltis* spp., *Horcias nobilellus, Leptocorisa* spp., *Leptocorisa varicornis, Leptoglossus occidentalis, Leptoglossus phyllopus, Lygocoris* spp., for example *Lygocoris pabulinus, Lygus* spp., for example *Lygus elisus, Lygus hesperus, Lygus lineolaris, Macropes excavatus, Megacopta cribraria, Miridae, Monalonion atratum, Nezara* spp., for example *Nezara viridula, Nysius* spp., *Oebalus* spp., *Pentomidae, Piesma quadrata, Piezodorus* spp., for example *Piezodorus guildinii, Psallus* spp., *Pseudacysta persea, Rhodnius* spp., *Sahlbergella singularis, Scaptocoris castanea, Scotinophora* spp., *Stephanitis nashi, Tibraca* spp., *Triatoma* spp.;

from the order of the Hymenoptera, for example *Acromyrmex* spp., *Athalia* spp., for example *Athalia rosae, Atta* spp., *Camponotus* spp., *Dolichovespula* spp., *Diprion* spp., for example *Diprion similis, Hoplocampa* spp., for example *Hoplocampa cookei, Hoplocampa testudinea, Lasius* spp., *Linepithema (Iridiomyrmex) humile, Monomorium pharaonis, Paratrechina* spp., *Paravespula* spp., *Plagiolepis* spp., *Sirex* spp., *Solenopsis invicta, Tapinoma* spp., *Technomyrmex albipes, Urocerus* spp., *Vespa* spp., for example *Vespa crabro, Wasmannia auropunctata, Xeris* spp.;

from the order of the Isopoda, for example *Armadillidium vulgare, Oniscus asellus, Porcellio scaber;* from the order of the Isoptera, for example *Coptotermes* spp., for example *Coptotermes formosanus, Cornitermes cumulans, Cryptotermes* spp., *Incisitermes* spp., *Kalotermes* spp., *Microtermes obesi, Nasutitermes* spp., *Odontotermes* spp., *Reticulitermes* spp., for example *Reticulitermes flavipes, Reticulitermes hesperus;* from the order of the Lepidoptera, for example *Achroia grisella, Acronicta major, Adoxophyes* spp., for example *Adoxophyes orana, Aedia leucomelas, Agrotis* spp., for example *Agrotis segetum, Agrotis ipsilon, Alabama* spp., for example *Alabama argillacea, Amyelois transitella, Anarsia* spp., *Anticarsia* spp., for example *Anticarsia gemmatalis, Argyroploce* spp., *Autographa* spp., *Barathra brassicae, Blastodacna atra, Borbo cinnara, Bucculatrix thurberiella, Bupalus piniarius, Busseola* spp., *Cacoecia* spp., *Caloptilia theivora, Capua reticulana, Carpocapsa pomonella, Carposina niponensis, Cheimatobia brumata, Chilo* spp., for example *Chilo plejadellus, Chilo suppressalis, Choreutis pariana, Choristoneura* spp., *Chrysodeixis chalcites, Clysia ambiguella, Cnaphalocerus* spp., *Cnaphalocrocis medinalis, Cnephasia* spp., *Conopomorpha* spp., *Conotrachelus* spp., *Copitarsia* spp., *Cydia* spp., for example *Cydia nigricana, Cydia pomonella, Dalaca noctuides, Diaphania* spp., *Diparopsis* spp., *Diatraea saccharalis, Earias* spp., *Ecdytolopha aurantium, Elasmopalpus lignosellus, Eldana saccharina, Ephestia* spp., for example *Ephestia elutella,*

*Ephestia kuehniella, Epinotia* spp., *Epiphyas postvittana, Erannis* spp., *Erschoviella musculana, Etiella* spp., *Eudocima* spp., *Eulia* spp., *Eupoecilia ambiguella, Euproctis* spp., for example *Euproctis chrysorrhoea, Euxoa* spp., *Feltia* spp., *Galleria mellonella, Gracillaria* spp., *Grapholitha* spp., for example *Grapholita molesta, Grapholita prunivora, Hedylepta* spp., *Helicoverpa* spp., for example *Helicoverpa armigera, Helicoverpa zea, Heliothis* spp., for example *Heliothis virescens, Hofmannophila pseudospretella, Homoeosoma* spp., *Homona* spp., *Hyponomeuta padella, Kakivoria flavofasciata, Lampides* spp., *Laphygma* spp., *Laspeyresia molesta, Leucinodes orbonalis, Leucoptera* spp., for example *Leucoptera coffeella, Lithocolletis* spp., for example *Lithocolletis blancardella, Lithophane antennata, Lobesia* spp., for example *Lobesia botrana, Loxagrotis albicosta, Lymantria* spp., for example *Lymantria dispar, Lyonetia* spp., for example *Lyonetia clerkella, Malacosoma neustria, Maruca testulalis, Mamestra brassicae, Melanitis leda, Mocis* spp., *Monopis obviella, Mythimna separata, Nemapogon cloacellus, Nymphula* spp., *Oiketicus* spp., *Omphisa* spp., *Operophtera* spp., *Oria* spp., *Orthaga* spp., *Ostrinia* spp., for example *Ostrinia nubilalis, Panolis flammea, Parnara* spp., *Pectinophora* spp., for example *Pectinophora gossypiella, Perileucoptera* spp., *Phthorimaea* spp., for example *Phthorimaea operculella, Phyllocnistis citrella, Phyllonorycter* spp., for example *Phyllonorycter blancardella, Phyllonorycter crataegella, Pieris* spp., for example *Pieris rapae, Platynota stultana, Plodia interpunctella, Plusia* spp., *Plutella xylostella* (=*Plutella maculipennis*), *Prays* spp., *Prodenia* spp., *Protoparce* spp., *Pseudaletia* spp., for example *Pseudaletia unipuncta, Pseudoplusia includens, Pyrausta nubilalis, Rachiplusia nu, Schoenobius* spp., for example *Schoenobius bipunctifer, Scirpophaga* spp., for example *Scirpophaga innotata, Scotia segetum, Sesamia* spp., for example *Sesamia inferens, Sparganothis* spp., *Spodoptera* spp., for example *Spodoptera eradiana, Spodoptera exigua, Spodoptera frugiperda, Spodoptera praefica, Stathmopoda* spp., *Stenoma* spp., *Stomopteryx subsecivella, Synanthedon* spp., *Tecia solanivora, Thaumetopoea* spp., *Thermesia gemmatalis, Tinea cloacella, Tinea pellionella, Tineola bisselliella, Tortrix* spp., *Trichophaga tapetzella, Trichoplusia* spp., for example *Trichoplusia ni, Tryporyza incertulas, Tuta absoluta, Virachola* spp.;

from the order of the Orthoptera or Saltatoria, for example *Acheta domesticus, Dichroplus* spp., *Gryllotalpa* spp., for example *Gryllotalpa gryllotalpa, Hieroglyphus* spp., *Locusta* spp., for example *Locusta migratoria, Melanoplus* spp., for example *Melanoplus devastator, Paratlanticus ussuriensis, Schistocerca gregaria;* from the order of the Phthiraptera, for example *Damalinia* spp., *Haematopinus* spp., *Linognathus* spp., *Pediculus* spp., *Phylloxera vastatrix, Phthirus pubis, Trichodectes* spp.;

from the order of the Psocoptera, for example *Lepinotus* spp., *Liposcelis* spp.;

from the order of the Siphonaptera, for example *Ceratophyllus* spp., *Ctenocephalides* spp., for example *Ctenocephalides canis, Ctenocephalides felis, Pulex irritans, Tunga penetrans, Xenopsylla cheopis;* from the order of the Thysanoptera, for example *Anaphothrips obscurus, Baliothrips biformis, Chaetanaphothrips leeuweni, Drepanothrips reuteri, Enneothrips flavens, Frankliniella* spp., for example *Frankliniella fusca, Frankliniella occidentalis, Frankliniella schultzei, Frankliniella tritici, Frankliniella vaccinii, Frankliniella williamsi, Haplothrips* spp., *Heliothrips* spp., *Hercinothrips femoralis, Kakothrips* spp., *Rhipiphorothrips cruentatus, Scirtothrips* spp., *Taeniothrips cardamomi, Thrips* spp., for example *Thrips palmi, Thrips tabaci;* from the order of the Zygentoma (=Thysanura), for example *Ctenolepisma* spp., *Lepisma saccharina, Lepismodes inquilinus, Thermobia domestica;* from the class of the Symphyla, for example *Scutigerella* spp., for example *Scutigerella immaculata;* pests from the phylum of the Mollusca, in particular from the class of the Bivalvia, for example *Dreissena* spp.;

and also from the class of the Gastropoda, for example *Arion* spp., for example *Arion ater rufus, Biomphalaria* spp., *Bulinus* spp., *Deroceras* spp., for example *Deroceras laeve, Galba* spp., *Lymnaea* spp., *Oncomelania* spp., *Pomacea* spp., *Succinea* spp.;

animal and human parasites from the phyla of the Platyhelminthes and Nematoda, for example *Aelurostrongylus* spp., *Amidostomum* spp., *Ancylostoma* spp, for example *Ancylostoma duodenale, Ancylostoma ceylanicum, Acylostoma braziliensis, Angiostrongylus* spp., *Anisakis* spp., *Anoplocephala* spp., *Ascaris* spp., *Ascaridia* spp., *Baylisascaris* spp., *Brugia* spp., for example *Brugia malayi, Brugia timori, Bunostomum* spp., *Capillaria* spp., *Chabertia* spp., *Clonorchis* spp., *Cooperia* spp., *Crenosoma* spp., *Cyathostoma* spp., *Dicrocoelium* spp., *Dictyocaulus* spp., for example *Dictyocaulus filaria, Diphyllobothrium* spp., for example *Diphyllobothrium latum, Dipylidium* spp., *Dirofilaria* spp., *Dracunculus* spp., for example *Dracunculus medinensis, Echinococcus* spp., for example *Echinococcus granulosus, Echinococcus multilocularis, Echinostoma* spp., *Enterobius* spp., for example *Enterobius vermicularis, Eucoleus* spp., *Fasciola* spp., *Fascioloides* spp., *Fasciolopsis* spp., *Filaroides* spp., *Gongylonema* spp., *Gyrodactylus* spp., *Habronema* spp., *Haemonchus* spp., *Heligmosomoides* spp., *Heterakis* spp., *Hymenolepis* spp., for example *Hymenolepis nana, Hyostrongylus* spp., *Litomosoides* spp., *Loa* spp., for example *Loa Loa, Metastrongylus* spp., *Metorchis* spp., *Mesocestoides* spp., *Moniezia* spp., *Muellerius* spp., *Necator* spp., *Nematodirus* spp., *Nippostrongylus* spp., *Oesophagostomum* spp., *Ollulanus* spp., *Onchocerca* spp, for example *Onchocerca volvulus, Opisthorchis* spp., *Oslerus* spp., *Ostertagia* spp., *Oxyuris* spp., *Paracapillaria* spp., *Parafilaria* spp., *Paragonimus* spp., *Paramphistomum* spp., *Paranoplocephala* spp., *Parascaris* spp., *Passalurus* spp., *Protostrongylus* spp., *Schistosoma* spp., *Setaria* spp., *Spirocerca* spp., *Stephanofilaria* spp., *Stephanurus* spp., *Strongyloides* spp., for example *Strongyloides fuelleborni, Strongyloides stercoralis, Strongylus* spp., *Syngamus* spp., *Taenia* spp., for example *Taenia saginata, Taenia solium, Teladorsagia* spp., *Thelazia* spp., *Toxascaris* spp., *Toxocara* spp., *Trichinella* spp., for example *Trichinella spiralis, Trichinella nativa, Trichinella britovi, Trichinella nelsoni, Trichinella pseudopsiralis, Trichobilharzia* spp., *Trichostrongylus* spp., *Trichuris* spp., for example *Trichuris trichiura, Uncinaria* spp., *Wuchereria* spp., for example *Wuchereria bancrofti;* plant pests from the phylum of the Nematoda, i.e. *phytoparasitic nematodes*, especially *Aglenchus* spp., for example *Aglenchus agricola, Anguina* spp., for example *Anguina tritici, Aphelenchoides* spp., for example *Aphelenchoides arachidis, Aphelenchoides fragariae, Belonolaimus* spp., for example *Belonolaimus gracilis, Belonolaimus longicaudatus, Belonolaimus nortoni, Bursaphelenchus* spp., for example *Bursaphelenchus cocophilus, Bursaphelenchus eremus, Bursaphelenchus xylophilus, Cacopaurus* spp., for example *Cacopaurus pestis, Criconemella* spp., for example *Criconemella curvata, Criconemella onoensis, Criconemella ornata, Criconemella rusium, Criconemella* xenoplax (=*Mesocriconema xenoplax*), *Criconemoides* spp., for example *Criconemoides ferniae, Criconemoides onoense, Criconemoides ornatum, Ditylenchus* spp., for example *Ditylenchus dipsaci, Dolichodorus* spp., *Globodera* spp., for example *Globodera pallida, Globodera rostochiensis, Helicotylenchus* spp., for example *Helicotylenchus dihystera, Hemicriconemoides* spp., *Hemicycliophora* spp., *Heterodera* spp., for example *Heterodera avenae, Heterodera glycines, Heterodera schachtii, Hirschmaniella* spp., *Hoplolaimus* spp., *Longidorus* spp., for example *Longidorus africanus, Meloidogyne* spp., for example *Meloidogyne chitwoodi, Meloidogyne fallax, Meloidogyne hapla, Meloidogyne incognita, Meloinema* spp., *Nacobbus* spp., *Neotylenchus* spp., *Paralongidorus* spp., *Paraphelenchus* spp., *Paratrichodorus* spp., for example *Paratrichodorus minor, Paratylenchus* spp., *Pratylenchus* spp., for example *Pratylenchus penetrans, Pseudohalenchus* spp., *Psilenchus* spp., *Punctodera* spp., *Quinisulcius* spp., *Radopholus* spp., for example *Radopholus citrophilus, Radopholus similis, Rotylenchulus* spp., *Rotylenchus* spp., *Scutellonema* spp., *Subanguina* spp., *Trichodorus* spp., for example *Trichodorus obtusus, Trichodorus primitivus, Tylenchorhynchus* spp., for example *Tylenchorhynchus annulatus, Tylenchulus* spp., for example *Tylenchulus semipenetrans, Xiphinema* spp., for example *Xiphinema index*.

In addition, it is possible to control, from the sub-kingdom of the Protozoa, the order of the Coccidia, for example *Eimeria* spp.

The compounds of the formula (I) can optionally, at certain concentrations or application rates, also be used as herbicides, safeners, growth regulators or agents to improve plant properties, as microbicides or gametocides, for example as fungicides, antimycotics, bactericides, virucides (including agents against viroids) or as agents against MLO (mycoplasma-like organisms) and RLO (rickettsia-like organisms). They can, as the case may be, also be used as intermediates or precursors for the synthesis of other active compounds.

Formulations

The present invention further relates to formulations and use forms prepared therefrom as pesticides, for example drench, drip and spray liquors, comprising at least one compound of the formula (I). Optionally, the use forms comprise further pesticides and/or adjuvants which improve action, such as penetrants, e.g. vegetable oils, for example rapeseed oil, sunflower oil, mineral oils, for example paraffin oils, alkyl esters of vegetable fatty acids, for example rapeseed oil methyl ester or soya oil methyl ester, or alkanol alkoxylates and/or spreaders, for example alkylsiloxanes and/or salts, for example organic or inorganic ammonium or phosphonium salts, for example ammonium sulphate or diammonium hydrogenphosphate and/or retention promoters, for example dioctyl sulphosuccinate or hydroxypropylguar polymers and/or humectants, for example glycerol and/or fertilizers, for example ammonium-, potassium- or phosphorus-containing fertilizers.

Customary formulations are, for example, water-soluble liquids (SL), emulsion concentrates (EC), emulsions in water (EW), suspension concentrates (SC, SE, FS, OD), water-dispersible granules (WG), granules (GR) and capsule concentrates (CS); these and further possible formulation types are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations, in addition to one or more compounds of the formula (I), optionally comprise further agrochemically active compounds.

Preference is given to formulations or use forms comprising auxiliaries, for example extenders, solvents, spontaneity promoters, carriers, emulsifiers, dispersants, frost protection agents, biocides, thickeners and/or further auxiliaries, for example adjuvants. An adjuvant in this context is a component which enhances the biological effect of the formulation, without the component itself having any biological effect. Examples of adjuvants are agents which promote retention, spreading, attachment to the leaf surface or penetration.

These formulations are prepared in a known way, for example by mixing the compounds of the formula (I) with auxiliaries such as, for example, extenders, solvents and/or solid carriers and/or other auxiliaries such as, for example, surfactants. The formulations are produced either in suitable facilities or else before or during application.

The auxiliaries used may be substances suitable for imparting special properties, such as certain physical, technical and/or biological properties, to the formulation of the compounds of the formula (I), or to the use forms prepared from these formulations (for example ready-to-use pesticides such as spray liquors or seed dressing products).

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the simple and substituted amines, amides, lactams (such as N-alkylpyrrolidones) and lactones, the sulphones and sulphoxides (such as dimethyl sulphoxide).

If the extender utilized is water, it is also possible to use, for example, organic solvents as auxiliary solvents. Useful liquid solvents are essentially: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and water.

In principle, it is possible to use all suitable solvents. Examples of suitable solvents are aromatic hydrocarbons, such as xylene, toluene or alkylnaphthalenes, chlorinated aromatic or aliphatic hydrocarbons, such as chlorobenzene, chloroethylene or methylene chloride, aliphatic hydrocarbons, such as cyclohexane, paraffins, mineral oil fractions, mineral and vegetable oils, alcohols, such as methanol, ethanol, isopropanol, butanol or glycol and their ethers and esters, ketones such as acetone, methyl ethyl ketone, methyl isobutyl ketone or cyclohexanone, strongly polar solvents, such as dimethyl sulphoxide, and also water.

In principle, it is possible to use all suitable carriers. Useful carriers especially include: for example ammonium salts and ground natural minerals such as kaolins, clays, talc, chalk, quartz, attapulgite, montmorillonite or diatomaceous earth, and ground synthetic minerals such as finely divided silica, alumina and natural or synthetic silicates, resins, waxes and/or solid fertilizers. It is likewise possible to use mixtures of such carriers. Useful carriers for granules include: for example crushed and fractionated natural rocks such as calcite, marble, pumice, sepiolite, dolomite, and synthetic granules of inorganic and organic flours, and also granules of organic material such as sawdust, paper, coconut shells, maize cobs and tobacco stalks.

It is also possible to use liquefied gaseous extenders or solvents. Especially suitable are those extenders or carriers which are gaseous at standard temperature and under atmospheric pressure, for example aerosol propellants such as halogenated hydrocarbons, and also butane, propane, nitrogen and carbon dioxide.

Examples of emulsifiers and/or foam formers, dispersants or wetting agents having ionic or nonionic properties or mixtures of these surface-active substances are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyl taurates), phosphoric esters of polyethoxylated alcohols or phenols, fatty acid esters of polyols, and derivatives of the compounds containing sulphates, sulphonates and phosphates, for example alkylaryl polyglycol ethers, alkylsulphonates, alkyl sulphates, arylsulphonates, protein hydrolysates, lignosulphite waste liquors and methylcellulose. The presence of a surfactant is advantageous if one of the compounds of the formula (I) and/or one of the inert carriers is insoluble in water and if the application takes place in water.

Further auxiliaries which may be present in the formulations and the use forms derived therefrom are dyes such as inorganic pigments, for example iron oxide, titanium oxide and Prussian Blue, and organic dyes such as alizarin dyes, azo dyes and metal phthalocyanine dyes, and nutrients and trace nutrients such as salts of iron, manganese, boron, copper, cobalt, molybdenum and zinc.

Additional components which may be present are stabilizers, such as cold stabilizers, preservatives, antioxidants, light stabilizers, or other agents which improve chemical and/or physical stability. Foam generators or antifoams may also be present.

In addition, the formulations and the use forms derived therefrom may also comprise, as additional auxiliaries, stickers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids. Further auxiliaries may be mineral and vegetable oils.

It is possible if appropriate for still further auxiliaries to be present in the formulations and the use forms derived therefrom. Examples of such additives are fragrances, protective colloids, binders, adhesives, thickeners, thixotropic agents, penetrants, retention promoters, stabilizers, sequestrants, complexing agents, humectants, spreaders. In general, the compounds of the formula (I) can be combined with any solid or liquid additive commonly used for formulation purposes.

Useful retention promoters include all those substances which reduce dynamic surface tension, for example dioctyl sulphosuccinate, or increase viscoelasticity, for example hydroxypropylguar polymers.

Useful penetrants in the present context are all those substances which are typically used to improve the penetration of active agrochemical ingredients into plants. Penetrants are defined in this context by their ability to penetrate from the (generally aqueous) application liquor and/or from the spray coating into the cuticle of the plant and hence increase the mobility of the active compounds in the cuticle. The method described in the literature (Baur et al., 1997, Pesticide Science 51, 131-152) can be used for determining this property. Examples include alcohol alkoxylates such as coconut fatty ethoxylate (10) or isotridecyl ethoxylate (12), fatty acid esters, for example rapeseed oil methyl ester or soya oil methyl ester, fatty amine alkoxylates, for example tallowamine ethoxylate (15), or ammonium and/or phosphonium salts, for example ammonium sulphate or diammonium hydrogenphosphate.

The formulations preferably comprise between 0.00000001% and 98% by weight of the compound of the formula (I), more preferably between 0.01% and 95% by weight of the compound of the formula (I), most preferably between 0.5% and 90% by weight of the compound of the formula (I), based on the weight of the formulation.

The content of the compound of the formula (I) in the use forms prepared from the formulations (in particular pesticides) may vary within wide ranges. The concentration of the compound of the formula (I) in the use forms may typically be between 0.00000001% and 95% by weight of the compound of the formula (I), preferably between 0.00001% and 1% by weight, based on the weight of the use form. Application is accomplished in a customary manner appropriate for the use forms.

Mixtures

The compounds of the formula (I) can also be used in a mixture with one or more suitable fungicides, bactericides, acaricides, molluscicides, nematicides, insecticides, microbiological agents, beneficial organisms, herbicides, fertilizers, bird repellents, phytotonics, sterilants, safeners, semiochemicals and/or plant growth regulators, in order thus, for example, to broaden the spectrum of action, prolong the period of action, enhance the rate of action, prevent repellency or prevent evolution of resistance. In addition, active compound combinations of this kind can improve plant growth and/or tolerance to abiotic factors, for example high or low temperatures, to drought or to elevated water content or soil salinity. It is also possible to improve flowering and fruiting performance, optimize germination capacity and root development, facilitate harvesting and improve yields, influence maturation, improve the quality and/or the nutritional value of the harvested products, prolong storage life and/or improve the processability of the harvested products.

In addition, the compounds of the formula (I) may be present in a mixture with other active compounds or semiochemicals such as attractants and/or bird repellents and/or plant activators and/or growth regulators and/or fertilizers. Likewise, the compounds of the formula (I) can be used in mixtures with agents to improve plant properties, for example growth, yield and quality of the harvested material.

In a particular embodiment according to the invention, the compounds of the formula (I) are present in formulations or in the use forms prepared from these formulations in a mixture with further compounds, preferably those as described below.

If one of the compounds mentioned below can occur in different tautomeric forms, these forms are also included even if not explicitly mentioned in each case.

Insecticides/Acaricides/Nematicides

The active ingredients specified here with their common names are known and are described for example in "The Pesticide Manual", 16th ed., British Crop Protection Council 2012, or can be searched for on the Internet (e.g. http://www.alanwood.net/pesticides).

(1) Acetylcholinesterase (AChE) inhibitors, for example carbamates, e.g. alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC and xylylcarb; or organophosphates, e.g. acephate, azamethiphos, azinphos-ethyl, azinphos-methyl, cadusafos, chlorethoxyfos, chlorfenvinphos, chlormephos, chloropyrifos, chloropyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothiophosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, triclorfon and vamidothion.

(2) GABA-gated chloride channel antagonists, for example cyclodiene-organochlorines, e.g. chlordane and endosulphan or phenylpyrazoles (fiproles), e.g. ethiprole and fipronil.

(3) Sodium channel modulators/voltage-gated sodium channel blockers, for example pyrethroids, e.g. acrinathrin, allethrin, d-cis-trans allethrin, d-trans allethrin, bifenthrin, bioallethrin, bioallethrin S-cyclopentenyl isomer, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin [(1R)-trans isomers], deltamethrin, empenthrin [(EZ)-(1R) isomers], esfenvalerate, etofenprox, fenpropathrin, fenvalerate, flucythrinate, flumethrin, tau-fluvalinate, halfenprox, imiprothrin, kadethrin, momfluorothrin, permethrin, phenothrin [(1R)-trans isomer], prallethrin, pyrethrins (pyrethrum), resmethrin, silafluofen, tefluthrin, tetramethrin, tetramethrin [(1R) isomers)], tralomethrin and transfluthrin or DDT or methoxychlor.

(4) Nicotinergic acetylcholine receptor (nAChR) agonists, for example neonicotinoids, e.g. acetamiprid, clothianidin, dinotefuran, imidacloprid, nitenpyram, thiacloprid and thiamethoxam or nicotine or sulphoxaflor or flupyradifurone.

(5) Allosteric activators of the nicotinergic acetylcholine receptor (nAChR), for example spinosyns, e.g. spinetoram and spinosad.

(6) Chloride channel activators, for example avermectins/milbemycins, e.g. abamectin, emamectin benzoate, lepimectin and milbemectin.

(7) Juvenile hormone imitators, for example, juvenile hormone analogues, e.g. hydroprene, kinoprene and methoprene or fenoxycarb or pyriproxyfen.

(8) Active compounds having unknown or nonspecific mechanisms of action, for example
alkyl halides, e.g. methyl bromide and other alkyl halides; or chloropicrine or sulphuryl fluoride or borax or tartar emetic.

(9) Selective antifeedants, e.g. pymetrozine or flonicamid.

(10) Mite growth inhibitors, e.g. clofentezine, hexythiazox and diflovidazin or etoxazole.

(11) Microbial disruptors of the insect gut membrane, e.g. Bacillus thuringiensis subspecies *israelensis*, *Bacillus sphaericus*, *Bacillus thuringiensis* subspecies *aizawai*, *Bacillus thuringiensis* subspecies *kurstaki*, *Bacillus thuringiensis* subspecies *tenebrionis*, and BT plant proteins: Cry1Ab, Cry1Ac, Cry1Fa, Cry2Ab, mCry3A, Cry3Ab, Cry3Bb, Cry34/35Ab1.

(12) Oxidative phosphorylation inhibitors, ATP disruptors, for example diafenthiuron or organotin compounds, e.g. azocyclotin, cyhexatin and fenbutatin oxide or propargite or tetradifon.

(13) Oxidative phosphorylation decouplers that interrupt the H proton gradient, for example chlorfenapyr, DNOC and sulphluramid.

(14) Nicotinergic acetylcholine receptor antagonists, for example bensultap, cartap hydrochloride, thiocyclam, and thiosultap-sodium.

(15) Inhibitors of chitin biosynthesis, type 0, for example bistrifluron, chlorfluazuron, diflubenzuron, flucycloxuron, flufenoxuron, hexaflumuron, lufenuron, novaluron, noviflumuron, teflubenzuron and triflumuron.

(16) Inhibitors of chitin biosynthesis, type 1, for example buprofezin.

(17) Moulting inhibitors (especially for Diptera, i.e. dipterans), for example cyromazine.

(18) Ecdysone receptor agonists, for example chromafenozide, halofenozide, methoxyfenozide and tebufenozide.

(19) Octopaminergic agonists, for example amitraz.

(20) Complex-III electron transport inhibitors, for example hydramethylnon or acequinocyl or fluacrypyrim.

(21) Complex-I electron transport inhibitors, for example METI acaricides, e.g. fenazaquin, fenpyroximate, pyrimidifen, pyridaben, tebufenpyrad and tolfenpyrad or rotenone (Derris).

(22) Voltage-gated sodium channel blockers, for example indoxacarb or metaflumizone.

(23) Inhibitors of acetyl-CoA carboxylase, for example tetronic and tetramic acid derivatives, e.g. spirodiclofen, spiromesifen and spirotetramat.

(24) Complex-IV electron transport inhibitors, for example phosphines, e.g. aluminium phosphide, calcium phosphide, phosphine and zinc phosphide or cyanide.

(25) Complex-II electron transport inhibitors, for example cyenopyrafen and cyflumetofen.

(28) Ryanodine receptor effectors, for example diamides, e.g. chlorantraniliprole, cyantraniliprole and flubendiamide.

Further active compounds having an unknown or unclear mechanism of action, for example afidopyropen, afoxolaner, azadirachtin, benclothiaz, benzoximate, bifenazate, bromopropylate, chinomethionat, cryolite, cyclaniliprole, cycloxaprid, cyhalodiamide, dicloromezotiaz, dicofol, diflovidazin, flometoquin, fluensulfone, flufenerim, flufenoxystrobin, flufiprole, fluhexafon, fluopyram, fluralaner, fufenozide, guadipyr, heptafluthrin, imidaclothiz, iprodione, meperfluthrin, paichongding, pyflubumide, pyridalyl, pyrifluquinazon, pyriminostrobin, tetramethylfluthrin, tetraniliprole, tetrachlorantraniliprole, tioxazafen, triflumezopyrim and iodomethane; and additionally preparations based on *Bacillus firmus* (I-1582, BioNeem, Votivo), and the following known active compounds: 1-{2-fluoro-4-methyl-5-[(2,2,2-trifluoroethyl)sulphinyl]phenyl}-3-(trifluoromethyl)-1H-1,2,4-triazole-5-amine (known from WO2006/043635), {1'-[(2E)-3-(4-chlorophenyl)prop-2-en-1-yl]-5-fluorospiro[indol-3,4'-piperidin]-1(2H)-yl}(2-chloropyridin-4-yl)methanone (known from WO2003/106457), 2-chloro-N-[2-{1-[(2E)-3-(4-chlorophenyl)prop-2-en-1-yl]piperidin-4-yl}-4-(trifluoromethyl)phenyl]isonicotinamide (known from WO2006/003494), 3-(2,5-dimethylphenyl)-4-hydroxy-8-methoxy-1,8-diazaspiro[4.5]dec-3-en-2-one (known from WO2009/049851), 3-(2,5-dimethylphenyl)-8-methoxy-2-oxo-1,8-diazaspiro[4.5]dec-3-en-4-ylethyl carbonate (known from WO2009/049851), 4-(but-2-yn-1-yloxy)-6-(3,5-dimethylpiperidin-1-yl)-5-fluoropyrimidine (known from WO2004/099160), 4-(but-2-yn-1-yloxy)-6-(3-chlorophenyl)pyrimidine (known from WO2003/076415), PF1364 (CAS Reg. No. 1204776-60-2), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-2-ethylhydrazinecarboxylate (known from WO2005/085216), N-[2-(5-amino-1,3,4-thiadiazol-2-yl)-4-chloro-6-methylphenyl]-3-bromo-1-(3-chloropyridin-2-yl)-1H-pyrazole-5-carboxamide (known from CN102057925), 8-chloro-N-[(2-chloro-5-methoxyphenyl)sulfonyl]-6-(trifluoromethyl)imidazo[1,2-a]pyridine-2-carboxamide (known from WO2010/129500), 4-[5-(3,5-dichlorophenyl)-5-(trifluoromethyl)-4,5-dihydro-1,2-oxazol-3-yl]-2-methyl-N-(1-oxidothietan-3-yl)benzamide (known from WO2009/080250), N-[(2E)-1-[(6-chloropyridin-3-yl)methyl]pyridin-2(1H)-ylidene]-2,2,-3-trifluoroacetamide (known from WO2012/029672), 1-[(2-chloro-1,3-thiazol-5-yl)methyl]-4-oxo-3-phenyl-4H-pyrido[1,2-a]pyrimidin-1-ium-2-olate (known from WO2009/099929), 1-[(6-chloropyridin-3-yl)methyl]-4-oxo-3-phenyl-4H-pyrido[1,2-a]pyrimidin-1-ium-2-olate (known from WO2009/099929), 4-(3-{2,6-dichloro-4-[(3,3-dichloroprop-2-en-1-yl)oxy]phenoxy}propoxy)-2-methoxy-6-(trifluoromethyl)pyrimidine (known from CN101337940), N-[2-(tert-butylcarbamoyl)-4-chloro-6-methylphenyl]-1-(3-chloropyridin-2-yl)-3-(fluoromethoxy)-1H-pyrazole-5-carboxamide (known from WO2008/134969, 3-[benzoyl(methyl)amino]-N-[2-bromo-4-[1,2,2,2-tetrafluoro-1-(trifluoromethyl)ethyl]-6-(trifluoromethyl)phenyl]-2-fluorobenzamide (known from WO 2010018714), butyl [2-(2,4-dichlorophenyl)-3-oxo-4-oxaspiro[4.5]dec-1-en-1-yl]carbonate (known from CN 102060818), 4-[5-(3,5-dichlorophenyl)-5-(trifluoromethyl)-4H-isoxazol-3-yl]-N-[(Z)-methoxyiminomethyl]-2-methylbenzamide (known from WO2007/026965), 3E)-3-[1-[(6-chloro-3-pyridyl)methyl]-2-pyridylidene]-1,1,1-trifluoropropan-2-one (known from WO2013/144213, N-(methylsulphonyl)-6-[2-(pyridin-3-yl)-1,3-thiazol-5-yl]pyridine-2-carboxamide (known from WO2012/000896), N-[3-(benzylcarbamoyl)-4-chlorophenyl]-1-methyl-3-(pentafluoroethyl)-4-(trifluoromethyl)-1H-pyrazole-5-carboxamide (known from WO2010/051926).

Fungicides

The active ingredients specified herein by their common name are known and described, for example, in "Pesticide Manual" or on the Internet (for example: http://www.alanwood.net/pesticides).

All the fungicidal mixing components listed in classes (1) to (15) may optionally form salts with corresponding bases or acids if suitable functional groups are present. In addition, the fungicidal mixing components listed in classes (1) to (15) also include tautomeric forms if tautomerism is possible.

1) inhibitors of the ergosterol biosynthesis, for example (1.01) aldimorph, (1.02) azaconazole, (1.03) bitertanol, (1.04) bromuconazole, (1.05) cyproconazole, (1.06) diclobutrazole, (1.07) difenoconazole, (1.08) diniconazole, (1.09) diniconazole-M, (1.10) dodemorph, (1.11) dodemorph acetate, (1.12) epoxiconazole, (1.13) etaconazole, (1.14) fenarimol, (1.15) fenbuconazole, (1.16) fenhexamide, (1.17) fenpropidin, (1.18) fenpropimorph, (1.19) fluquinconazole, (1.20) flurprimidol, (1.21) flusilazole, (1.22) flutriafol, (1.23) furconazole, (1.24) furconazole-cis, (1.25) hexaconazole, (1.26) imazalil, (1.27) imazalil sulphate, (1.28) imibenconazole, (1.29) ipconazole, (1.30) metconazole, (1.31) myclobutanil, (1.32) naftifine, (1.33) nuarimol, (1.34) oxpoconazole, (1.35) paclobutrazole, (1.36) pefurazoate, (1.37) penconazole, (1.38) piperalin, (1.39) prochloraz, (1.40) propiconazole, (1.41) prothioconazole, (1.42) pyributicarb, (1.43) pyrifenox, (1.44) quinconazole, (1.45) simeconazole, (1.46) spiroxamine, (1.47) tebuconazole, (1.48) terbinafin, (1.49) tetraconazole, (1.50) triadimefon, (1.51) triadimenol, (1.52) tridemorph, (1.53) triflumizole, (1.54) triforin, (1.55) triticonazole, (1.56) uniconazole, (1.57) uniconazole-p, (1.58) viniconazole, (1.59) voriconazole, (1.60) 1-(4-chlorophenyl)-2-(1H-1,2,4-triazol-1-yl)cycloheptanol, (1.61) 1-(2,2-dimethyl-2,3-dihydro-1H-inden-1-yl)-1H-imidazole-5-carboxylic acid methyl ester, (1.62) N'-{5-(difluoromethyl)-2-methyl-4-[3-(trimethylsilyl)propoxy]phenyl}-N-ethyl-N-methylimidoformamide, (1.63) N-ethyl-N-methyl-N'-{2-methyl-5-(trifluoromethyl)-4-[3-(trimethylsilyl)propoxy]phenyl}imidoformamide, (1.64) O-[1-(4-methoxyphenoxy)-3,3-dimethylbutan-2-yl]-1H-imidazole-1-carbothioate, (1.65) pyrisoxazole, (1.66) 2-{[3-(2-chlorophenyl)-2-(2,4-difluorophenyl)oxiran-2-yl]methyl}-2,4-dihydro-3H-1,2,4-triazole-3-thione, (1.67) 1-{[3-(2-chlorophenyl)-2-(2,4-difluorophenyl)oxiran-2-yl]methyl}-1H-1,2,4-triazol-5-ylthiocyanate, (1.68) 5-(allylsulphanyl)-1-{[3-(2-chlorophenyl)-2-(2,4-difluorophenyl)oxiran-2-yl]methyl}-1H-1,2,4-triazole, (1.69) 2-[1-(2,4-dichlorophenyl)-5-hydroxy-2,6,6-trimethylheptan-4-yl]-2,4-dihydro-3H-1,2,4-triazole-3-thione, (1.70) 2-{[rel(2R,3S)-3-(2-chlorophenyl)-2-(2,4-difluorophenyl)oxiran-2-yl]methyl}-2,4-dihydro-3H-1,2,4-triazole-3-thione, (1.71) 2-{[rel(2R,3R)-3-(2-chlorophenyl)-2-(2,4-difluorophenyl)oxiran-2-yl]methyl}-2,4-dihydro-3H-1,2,4-triazole-3-thione, (1.72) 1-{[rel(2R,3S)-3-(2-chlorophenyl)-2-(2,4-difluorophenyl)oxiran-2-yl]methyl}-1H-1,2,4-triazol-5-ylthiocyanate, (1.73) 1-{[rel(2R,3R)-3-(2-chlorophenyl)-2-(2,4-difluorophenyl)oxiran-2-yl]methyl}-1H-1,2,4-triazol-5-ylthiocyanate, (1.74) 5-(allylsulphanyl)-1-{[rel(2R,3S)-3-(2-chlorophenyl)-2-(2,4-difluorophenyl)oxiran-2-yl]methyl}-1H-1,2,4-triazole, (1.75) 5-(allylsulphanyl)-1-{[rel(2R,3R)-3-(2-chlorophenyl)-2-(2,4-difluorophenyl)oxiran-2-yl]methyl}-1H-1,2,4-triazole, (1.76) 2-[(2S,4S,5S)-1-(2,4-dichlorophenyl)-5-hydroxy-2,6,6-trimethylheptan-4-yl]-2,4-dihydro-3H-1,2,4-triazole-3-thione, (1.77) 2-[(2R,4S,5S)-1-(2,4-dichlorophenyl)-5-hydroxy-2,6,6-trimethylheptan-4-yl]-2,4-dihydro-3H-1,2,4-triazole-3-thione, (1.78) 2-[(2R,4R,5R)-1-(2,4-dichlorophenyl)-5-hydroxy-2,6,6-trimethylheptan-4-yl]-2,4-dihydro-3H-1,2,4-triazole-3-thione, (1.79) 2-[(2S,4R,5R)-1-(2,4-dichlorophenyl)-5-hydroxy-2,6,6-trimethylheptan-4-yl]-2,4-dihydro-3H-1,2,4-triazole-3-thione, (1.80) 2-[(2S,4S,5R)-1-(2,4-dichlorophenyl)-5-hydroxy-2,6,6-trimethylheptan-4-yl]-2,4-dihydro-3H-1,2,4-triazole-3-thione, (1.81) 2-[(2R,4S,5R)-1-(2,4-dichlorophenyl)-5-hydroxy-2,6,6-trimethylheptan-4-yl]-2,4-dihydro-3H-1,2,4-triazole-3-thione, (1.82) 2-[(2R,4R,5S)-1-(2,4-dichlorophenyl)-5-hydroxy-2,6,6-trimethylheptan-4-yl]-2,4-dihydro-3H-1,2,4-triazole-3-thione, (1.83) 2-[(2S,4R,5S)-1-(2,4-dichlorophenyl)-5-hydroxy-2,6,6-trimethylheptan-4-yl]-2,4-dihydro-3H-1,2,4-triazole-3-thione, (1.84) 2-[4-(4-chlorophenoxy)-2-(trifluoromethyl)phenyl]-1-(1H-1,2,4- triazol-1-yl)propan-2-ol, (1.85) 2-[4-(4-chlorophenoxy)-2-(trifluoromethyl)phenyl]-1-(1H-1,2,4-triazol-1-yl)butan-2-ol, (1.86) 2-[4-(4-chlorophenoxy)-2-(trifluoromethyl)phenyl]-1-(1H-1,2,4-triazol-1-yl)pentan-2-ol, (1.87) 2-[2-chloro-4-(4-chlorophenoxy)phenyl]-1-(1H-1,2,4-triazol-1-yl)butan-2-ol, (1.88) 2-[2-chloro-4-(2,4-dichlorophenoxy)phenyl]-1-(1H-1,2,4-triazol-1-yl)propan-2-ol, (1.89) (2R)-2-(1-chlorocyclopropyl)-4-[(1R)-2,2-dichlorocyclopropyl]-1-(1H-1,2,4-triazol-1-yl)butan-2-ol, (1.90) (2R)-2-(1-chlorocyclopropyl)-4-[(1S)-2,2-dichlorocyclopropyl]-1-(1H-1,2,4-triazol-1-yl)butan-2-ol, (1.91) (2S)-2-(1-chlorocyclopropyl)-4-[(1S)-2,2-dichlorocyclopropyl]-1-(1H-1,2,4-triazol-1-yl)butan-2-ol, (1.92) (2S)-2-(1-chlorocyclopropyl)-4-[(1R)-2,2-dichlorocyclopropyl]-1-(1H-1,2,4-triazol-1-yl)butan-2-ol, (1.93) (1S,2R,5R)-5-(4-chlorobenzyl)-2-(chloromethyl)-2-methyl-1-(1H-1,2,4-triazol-1-ylmethyl)cyclopentanol, (1.94) (1R,2S,5S)-5-(4-chlorobenzyl)-2-(chloromethyl)-2-methyl-1-(1H-1,2,4-triazol-1-ylmethyl)cyclopentanol, (1.95) 5-(4-chlorobenzyl)-2-(chloromethyl)-2-methyl-1-(1H-1,2,4-triazol-1-ylmethyl)cyclopentanol.

2) Inhibitors of the respiratory chain on complex I or II, for example (2.01) bixafen, (2.02) boscalid, (2.03) carboxin, (2.04) diflumetorim, (2.05) fenfuram, (2.06) fluopyram, (2.07) flutolanil, (2.08) fluxapyroxad, (2.09) furametpyr, (2.10) furmecyclox, (2.11) isopyrazam (mixture of syn-epimeric racemate 1RS,4SR,9RS and anti-epimeric racemate 1RS,4SR,9SR), (2.12) isopyrazam (anti-epimeric racemate 1RS,4SR,9SR), (2.13) isopyrazam (anti-epimeric enantiomer 1R,4S,9S), (2.14) isopyrazam (anti-epimeric enantiomer 1S,4R,9R), (2.15) isopyrazam (syn-epimeric racemate 1RS,4SR,9RS), (2.16) isopyrazam (syn-epimeric enantiomer 1R,4S,9R), (2.17) isopyrazam (syn-epimeric enantiomer 1S,4R,9S), (2.18) mepronil, (2.19) oxycarboxin, (2.20) penflufen, (2.21) penthiopyrad, (2.22) sedaxane, (2.23) thifluzamide, (2.24) 1-methyl-N-[2-(1,1,2,2-tetrafluoroethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide, (2.28) 5,8-difluoro-N-[2-(2-fluoro-4-{[4-(trifluoromethyl)pyridin-2-yl]oxy}phenyl)ethyl]quinazolin-4-amin, (2.29) benzovindiflupyr, (2.30) N-[(1S,4R)-9-(dichloromethylene)-1,2,3,4-tetrahydro-1,4-methanonaphthalin-5-yl]-3-(difluoromethyl)-1-methyl-1H-pyrazole-4-carboxamide, (2.31) N-[(1R,4S)-9-(dichloromethylene)-1,2,3,4-tetrahydro-1,4-methanonaphthalin-5-yl]-3-(difluoromethyl)-1-methyl-1H-pyrazole-4-carboxamide, (2.32) 3-(difluoromethyl)-1-methyl-N-(1,1,3-trimethyl-2,3-dihydro-1H-inden-4-yl)-1H-pyrazole-4-carboxamide, (2.33) 1,3,5-trimethyl-N-(1,1,3-trimethyl-2,3-dihydro-1H-inden-4-yl)-1H-pyrazole-4-carboxamide, (2.34) 1-methyl-3-(trifluoromethyl)-N-(1,1,3-trimethyl-2,3-dihydro-1H-inden-4-yl)-1H-pyrazole-4-carboxamide, (2.35) 1-methyl-3-(trifluoromethyl)-N-[(3R)-1,1,3-trimethyl-2,3-dihydro-1H-inden-4-yl]-1H-pyrazole-4-carboxamide, (2.36) 1-methyl-3-(trifluoromethyl)-N-[(3S)-1,1,3-trimethyl-2,3-dihydro-1H-inden-4-yl]-1H-pyrazole-4-carboxamide, (2.37) 3-(difluoromethyl)-1-methyl-N-[(3S)-1,1,3-trimethyl-2,3-dihydro-1H-inden-4-yl]-1H-pyrazole-4-carboxamide, (2.38) 3-(difluoromethyl)-1-methyl-N-[(3R)-1,1,3-trimethyl-2,3-dihydro-1H-inden-4-yl]-1H-pyrazole-4-carboxamide, (2.39) 1,3,5-trimethyl-N-[(3R)-1,1,3-trimethyl-2,3-dihydro-1H-inden-4-yl]-1H-pyrazole-4-carboxamide, (2.40) 1,3,5-trimethyl-N-[(3S)-1,1,3-trimethyl-2,3-dihydro-1H-inden-4-yl]-1H-pyrazole-4-carboxamide, (2.41) benodanil, (2.42) 2-chloro-N-(1,1,3-trimethyl-2,3-dihydro-1H-inden-4-yl)pyridine-3-carboxamide, (2.43) isofetamid, (2.44) 1-methyl-3-(trifluoromethyl)-N-[2'-(trifluoromethyl)biphenyl-2-yl]-1H-pyrazole-4-carboxamide, (2.45) N-(4'-chlorobiphenyl-2-yl)-3-(difluoromethyl)-1-methyl-1H-pyrazole-4-carboxamide, (2.46) N-(2',4'-dichlorobiphenyl-2-yl)-3-(difluoromethyl)-1-methyl-1H-pyrazole-4-carboxamide, (2.47) 3-(difluoromethyl)-1-methyl-N-[4'-(trifluoromethyl)biphenyl-2-yl]-1H-pyrazole-4-carboxamide, (2.48) N-(2',5'-difluorobiphenyl-2-yl)-1-methyl-3-(trifluoromethyl)-1H-pyrazole-4-carboxamide, (2.49) 3-(difluoromethyl)-1-methyl-N-[4'-(prop-1-yn-1-yl)biphenyl-2-yl]-1H-pyrazole-4-carboxamide, (2.50) 5-fluoro-1,3-dimethyl-N-[4'-(prop-1-yn-1-yl)biphenyl-2-yl]-1H-pyrazole-4-carboxamide, (2.51) 2-chloro-N-[4'-(prop-1-yn-1-yl)biphenyl-2-yl]nicotinamide, (2.52) 3-(difluoromethyl)-N-[4'-(3,3-dimethylbut-1-yn-1-yl)biphenyl-2-yl]-1-methyl-1H-pyrazole-4-carboxamide, (2.53) N-[4'-(3,3-dimethylbut-1-yn-1-yl)biphenyl-2-yl]-5-fluoro-1,3-dimethyl-1H-pyrazole-4-carboxamide, (2.54) 3-(difluoromethyl)-N-(4'-ethynylbiphenyl-2-yl)-1-methyl-1H-pyrazole-4-carboxamide, (2.55) N-(4'-ethynylbiphenyl-2-yl)-5-fluoro-1,3-dimethyl-1H-pyrazole-4-carboxamide, (2.56) 2-chloro-N-(4'-ethynylbiphenyl-2-yl)nicotinamide, (2.57) 2-chloro-N-[4'-(3,3-dimethylbut-1-yn-1-yl)biphenyl-2-yl]nicotinamide, (2.58) 4-(difluoromethyl)-2-methyl-N-[4'-(trifluoromethyl)biphenyl-2-yl]-1,3-thiazole-5-carboxamide, (2.59) 5-fluoro-N-[4'-(3-hydroxy-3-methylbut-1-yn-1-yl)biphenyl-2-yl]-1,3-dimethyl-1H-pyrazole-4-carboxamide, (2.60) 2-chloro-N-[4'-(3-hydroxy-3-methylbut-1-yn-1-yl)biphenyl-2-yl]nicotinamide, (2.61) 3-(difluoromethyl)-N-[4'-(3-methoxy-3-methylbut-1-yn-1-yl)biphenyl-2-yl]-1-methyl-1H-pyrazole-4-carboxamide, (2.62) 5-fluoro-N-[4'-(3-methoxy-3-methylbut-1-yn-1-yl)biphenyl-2-yl]-1,3-dimethyl-1H-pyrazole-4-carboxamide, (2.63) 2-chloro-N-[4'-(3-methoxy-3-methylbut-1-yn-1-yl)biphenyl-2-yl]nicotinamide, (2.64) 1,3-dimethyl-N-(1,1,3-trimethyl-2,3-dihydro-1H-inden-4-yl)-1H-pyrazole-4-carboxamide, (2.65) 1,3-dimethyl-N-[(3R)-1,1,3-trimethyl-2,3-dihydro-1H-inden-4-yl]-1H-pyrazole-4-carboxamide, (2.66) 1,3-dimethyl-N-[(3S)-1,1,3-trimethyl-2,3-dihydro-1H-inden-4-yl]-1H-pyrazole-4-carboxamide, (2.67) 3-(difluoromethyl)-N-methoxy-1-methyl-N-[1-(2,4,6-trichlorophenyl)propan-2-yl]-1H-pyrazole-4-carboxamide, (2.68) 3-(difluoromethyl)-N-(7-fluoro-1,1,3-trimethyl-2,3-dihydro-1H-inden-4-yl)-1-methyl-1H-pyrazole-4-carboxamide, (2.69) 3-(difluoromethyl)-N-[(3R)-7-fluoro-1,1,3-trimethyl-2,3-dihydro-1H-inden-4-yl]-1-methyl-1H-pyrazole-4-carboxamide, (2.70) 3-(difluoromethyl)-N-[(3S)-7-fluoro-1,1,3-trimethyl-2,3-dihydro-1H-inden-4-yl]-1-methyl-1H-pyrazole-4-carboxamide.

3) Inhibitors of the respiratory chain on complex III, for example (3.01) ametoctradin, (3.02) amisulbrom, (3.03) azoxystrobin, (3.04) cyazofamid, (3.05) coumethoxystrobin, (3.06) coumoxystrobin, (3.07) dimoxystrobin, (3.08) enoxastrobin, (3.09) famoxadon, (3.10) fenamidon, (3.11) flufenoxystrobin, (3.12) fluoxastrobin, (3.13) kresoxim-methyl, (3.14) metominostrobin, (3.15) orysastrobin, (3.16) picoxystrobin, (3.17) pyraclostrobin, (3.18) pyrametostrobin, (3.19) pyraoxystrobin, (3.20) pyribencarb, (3.21) triclopyricarb, (3.22) trifloxystrobin, (3.23) (2E)-2-(2-{[6-(3-chloro-2-methylphenoxy)-5-fluoropyrimidin-4-yl]oxy}phenyl)-2-(methoxyimino)-N-methylacetamide, (3.24) (2E)-2-(methoxyimino)-N-methyl-2-(2-{[({(1E)-1-[3-(trifluoromethyl)phenyl]ethyliden}amino)oxy]methyl}phenyl)

acetamide, (3.25) (2E)-2-(methoxyimino)-N-methyl-2-{2-[(E)-({1-[3-(trifluoromethyl)phenyl]ethoxy}imino)methyl] phenyl}acetamide, (3.26) (2E)-2-{2-[({[(1E)-1-(3-{[(E)-1-fluoro-2-phenylvinyl]oxy}phenyl)ethyliden]amino}oxy) methyl]phenyl}-2-(methoxyimino)-N-methylacetamide, (3.27) fenaminostrobin, (3.28) 5-methoxy-2-methyl-4-(2-{[({(1E)-1-[3-(trifluoromethyl)phenyl]ethyliden}amino) oxy]methyl}phenyl)-2,4-dihydro-3H-1,2,4-triazol-3-one, (3.29) (2E)-2-{2-[({cyclopropyl[(4-methoxyphenyl)imino] methyl}sulphanyl)methyl]phenyl}-3-methoxyacrylic acid methyl ester, (3.30) N-(3-ethyl-3,5,5-trimethylcyclohexyl)-3-formamido-2-hydroxybenzamide, (3.31) 2-{2-[(2,5-dimethylphenoxy)methyl]phenyl}-2-methoxy-N-methylacetamide, (3.32) 2-{2-[(2,5-dimethylphenoxy)methyl]phenyl}-2-methoxy-N-methylacetamide, (3.33) (2E,3Z)-5-{[1-(4-chlorophenyl)-1H-pyrazol-3-yl]oxy}-2-(methoxyimino)-N,3-dimethylpent-3-enamide.

4) Inhibitors of mitosis and cell division, for example (4.01) benomyl, (4.02) carbendazim, (4.03) chlorfenazole, (4.04) diethofencarb, (4.05) ethaboxam, (4.06) fluopicolide, (4.07) fuberidazole, (4.08) pencycuron, (4.09) thiabendazole, (4.10) thiophanate-methyl, (4.11) thiophanate, (4.12) zoxamide, (4.13) 5-chloro-7-(4-methylpiperidin-1-yl)-6-(2,4,6-trifluorophenyl)[1,2,4]triazolo[1,5-a]pyrimidine, (4.14) 3-chloro-5-(6-chloropyridin-3-yl)-6-methyl-4-(2,4,6-trifluorophenyl)pyridazine.

5) Compounds capable of having multisite action, for example (5.01) Bordeaux mixture, (5.02) captafol, (5.03) captan, (5.04) chlorothalonil, (5.05) copper hydroxide, (5.06) copper naphthenate, (5.07) copper oxide, (5.08) copper oxychloride, (5.09) copper(2+) sulphate, (5.10) dichlofluanid, (5.11) dithianon, (5.12) dodine, (5.13) dodine free base, (5.14) ferbam, (5.15) fluorofolpet, (5.16) folpet, (5.17) guazatine, (5.18) guazatine acetate, (5.19) iminoctadine, (5.20) iminoctadine albesilate, (5.21) iminoctadine triacetate, (5.22) mancopper, (5.23) mancozeb, (5.24) maneb, (5.25) metiram, (5.26) metiram zinc, (5.27) oxine-copper, (5.28) propamidine, (5.29) propineb, (5.30) sulphur and sulphur preparations including calcium polysulphide, (5.31) thiram, (5.32) tolylfluanid, (5.33) zineb, (5.34) ziram, (5.35) anilazine.

6) Compounds capable of inducing host defense, for example (6.01) acibenzolar-S-methyl, (6.02) isotianil, (6.03) probenazole, (6.04) tiadinil, (6.05) laminarin.

7) Inhibitors of the amino acid and/or protein biosynthesis, for example (7.01) andoprim, (7.02) blasticidin-S, (7.03) cyprodinil, (7.04) kasugamycin, (7.05) kasugamycin hydrochloride hydrate, (7.06) mepanipyrim, (7.07) pyrimethanil, (7.08) 3-(5-fluoro-3,3,4,4-tetramethyl-3,4-dihydroisoquinolin-1-yl)quinoline, (7.09) oxytetracycline, (7.10) streptomycin.

8) Inhibitors of ATP production, for example (8.01) fentin acetate, (8.02) fentin chloride, (8.03) fentin hydroxide, (8.04) silthiofam.

9) Inhibitors of cell wall synthesis, for example (9.01) benthiavalicarb, (9.02) dimethomorph, (9.03) flumorph, (9.04) iprovalicarb, (9.05) mandipropamid, (9.06) polyoxins, (9.07) polyoxorim, (9.08) validamycin A, (9.09) valifenalate, (9.10) polyoxin B, (9.11) (2E)-3-(4-tert-butylphenyl)-3-(2-chloropyridin-4-yl)-1-(morpholin-4-yl)prop-2-en-1-one, (9.12) (2Z)-3-(4-tert-butylphenyl)-3-(2-chloropyridin-4-yl)-1-(morpholin-4-yl)prop-2-en-1-one.

10) Inhibitors of lipid and membrane synthesis, for example (10.01) biphenyl, (10.02) chloroneb, (10.03) dicloran, (10.04) edifenphos, (10.05) etridiazole, (10.06) iodocarb, (10.07) iprobenfos, (10.08) isoprothiolane, (10.09) propamocarb, (10.10) propamocarb hydrochloride, (10.11) prothiocarb, (10.12) pyrazophos, (10.13) quintozene, (10.14) tecnazene, (10.15) tolclofos-methyl.

11) Inhibitors of melanin biosynthesis, for example (11.01) carpropamid, (11.02) diclocymet, (11.03) fenoxanil, (11.04) phthalide, (11.05) pyroquilon, (11.06) tricyclazole, (11.07) 2,2,2-trifluoroethyl {3-methyl-1-[(4-methylbenzoyl)amino]butan-2-yl}carbamate.

12) Inhibitors of nucleic acid synthesis, for example (12.01) benalaxyl, (12.02) benalaxyl-M (kiralaxyl), (12.03) bupirimate, (12.04) clozylacon, (12.05) dimethirimol, (12.06) ethirimol, (12.07) furalaxyl, (12.08) hymexazole, (12.09) metalaxyl, (12.10) metalaxyl-M (mefenoxam), (12.11) ofurace, (12.12) oxadixyl, (12.13) oxolinic acid, (12.14) octhilinone.

13) Inhibitors of signal transduction, for example (13.01) chlozolinate, (13.02) fenpiclonil, (13.03) fludioxonil, (13.04) iprodione, (13.05) procymidone, (13.06) quinoxyfen, (13.07) vinclozolin, (13.08) proquinazid.

14) Compounds capable of acting as uncouplers, for example (14.01) binapacryl, (14.02) dinocap, (14.03) ferimzone, (14.04) fluazinam, (14.05) meptyldinocap.

15) Further compounds, for example (15.001) benthiazole, (15.002) bethoxazin, (15.003) capsimycin, (15.004) carvone, (15.005) quinomethionate, (15.006) pyriofenone (chlazafenone), (15.007) cufraneb, (15.008) cyflufenamid, (15.009) cymoxanil, (15.010) cyprosulphamide, (15.011) dazomet, (15.012) debacarb, (15.013) dichlorophen, (15.014) diclomezin, (15.015) difenzoquat, (15.016) difenzoquat metilsulphate, (15.017) diphenylamine, (15.018) Ecomate, (15.019) fenpyrazamine, (15.020) flumetover, (15.021) fluoroimide, (15.022) flusulphamide, (15.023) flutianil, (15.024) fosetyl-aluminium, (15.025) fosetyl-calcium, (15.026) fosetyl-sodium, (15.027) hexachlorobenzene, (15.028) irumamycin, (15.029) methasulphocarb, (15.030) methyl isothiocyanate, (15.031) metrafenone, (15.032) mildiomycin, (15.033) natamycin, (15.034) nickel dimethyldithiocarbamate, (15.035) nitrothal-isopropyl, (15.036) oxamocarb, (15.037) oxyfenthiin, (15.038) pentachlorophenol and salts, (15.039) phenothrin, (15.040) phosphorous acid and salts thereof, (15.041) propamocarb-fosetylate, (15.042) propanosin-sodium, (15.043) pyrimorph, (15.044) pyrrolnitrin, (15.045) tebufloquin, (15.046) tecloftalam, (15.047) tolnifanid, (15.048) triazoxide, (15.049) trichlamid, (15.050) zarilamid, (15.051) 2-methyl-propanoic acid (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl ester, (15.052) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.053) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.054) oxathiapiproline, (15.055) 1H-imidazole-1-carboxylic acid 1-(4-methoxyphenoxy)-3,3-dimethylbutan-2-yl ester, (15.056) 2,3,5,6-tetrachloro-4-(methylsulphonyl)pyridine, (15.057) 2,3-dibutyl-6-chlorothieno[2,3-d]pyrimidin-4(3H)-one, (15.058) 2,6-dimethyl-1H,5H-[1,4]dithiino[2,3-c:5,6-c']dipyrrole-1,3,5,7(2H,6H)-tetrone, (15.059) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, (15.060) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, (15.061) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, (15.062)

2-butoxy-6-iodo-3-propyl-4H-chromen-4-one, (15.063) 2-chloro-5-[2-chloro-1-(2,6-difluoro-4-methoxyphenyl)-4-methyl-1H-imidazol-5-yl]pyridine, (15.064) 2-phenylphenol and salts, (15.065) 3-(4,4,5-trifluoro-3,3-dimethyl-3,4-dihydroisoquinolin-1-yl)quinoline, (15.066) 3,4,5-trichloropyridine-2,6-dicarboxylic acid nitrile, (15.067) 3-chloro-5-(4-chlorophenyl)-4-(2,6-difluorophenyl)-6-methylpyridazine, (15.068) 4-(4-chlorophenyl)-5-(2,6-difluorophenyl)-3,6-dimethylpyridazine, (15.069) 5-amino-1,3,4-thiadiazole-2-thiol, (15.070) 5-chloro-N'-phenyl-N'-(prop-2-yn-1-yl)thiophene-2-sulphonohydrazide, (15.071) 5-fluoro-2-[(4-fluorobenzyl)oxy]pyrimidin-4-amine, (15.072) 5-fluoro-2-[(4-methylbenzyl)oxy]pyrimidin-4-amine, (15.073) 5-methyl-6-octyl[1,2,4]triazolo[1,5-a]pyrimidin-7-amine, (15.074) (2Z)-3-amino-2-cyano-3-phenylacrylic acid ethyl ester, (15.075) N'-(4-{[3-(4-chlorobenzyl)-1,2,4-thiadiazol-5-yl]oxy}-2,5-dimethylphenyl)-N-ethyl-N-methylimidoformamide, (15.076) N-(4-chlorobenzyl)-3-[3-methoxy-4-(prop-2-yn-1-yloxy)phenyl]propanamide, (15.077) N-[(4-chlorophenyl)(cyano)methyl]-3-[3-methoxy-4-(prop-2-yn-1-yloxy)phenyl]propanamide, (15.078) N-[(5-bromo-3-chloropyridin-2-yl)methyl]-2,4-dichloronicotinamide, (15.079) N-[1-(5-bromo-3-chloropyridin-2-yl)ethyl]-2,4-dichloronicotinamide, (15.080) N-[1-(5-bromo-3-chloropyridin-2-yl)ethyl]-2-fluoro-4-iodonicotinamide, (15.081) N—{(E)-[(cyclopropylmethoxy)imino][6-(difluoromethoxy)-2,3-difluorophenyl]methyl}-2-phenylacetamide, (15.082) N—{(Z)-[(cyclopropylmethoxy)imino][6-(difluoromethoxy)-2,3-difluorophenyl]methyl}-2-phenylacetamide, (15.083) N'-{4-[(3-tert-butyl-4-cyano-1,2-thiazol-5-yl)oxy]-2-chloro-5-methylphenyl}-N-ethyl-N-methylimidoformamide, (15.084) N-methyl-2-(1-{[5-methyl-3-(trifluoromethyl)-1H-pyrazol-1-yl]acetyl}piperidin-4-yl)-N-(1,2,3,4-tetrahydronaphthalin-1-yl)-1,3-thiazole-4-carboxamide, (15.085) N-methyl-2-(1-{[5-methyl-3-(trifluoromethyl)-1H-pyrazol-1-yl]acetyl}piperidin-4-yl)-N-[(1R)-1,2,3,4-tetrahydronaphthalin-1-yl]-1,3-thiazole-4-carboxamide, (15.086) N-methyl-2-(1-{[5-methyl-3-(trifluoromethyl)-1H-pyrazol-1-yl]acetyl}piperidin-4-yl)-N-[(1S)-1,2,3,4-tetrahydronaphthalin-1-yl]-1,3-thiazole-4-carboxamide, (15.087) {6-[({[(1-methyl-1H-tetrazol-5-yl)(phenyl)methylene]amino}oxy)methyl]pyridin-2-yl}carbamic acid pentyl ester, (15.088) phenazine-1-carboxylic acid, (15.089) quinolin-8-ol, (15.090) quinolin-8-ol sulphate (2:1), (15.091) {6-[({[(1-methyl-1H-tetrazol-5-yl)(phenyl)methylene]amino}oxy)methyl]pyridin-2-yl}carbamic acid tert-butyl ester, (15.092) (5-bromo-2-methoxy-4-methylpyridin-3-yl)(2,3,4-trimethoxy-6-methylphenyl)methanone, (15.093) N-[2-(4-{[3-(4-chlorophenyl)prop-2-yn-1-yl]oxy}-3-methoxyphenyl)ethyl]-N2-(methylsulphonyl)valinamide, (15.094) 4-oxo-4-[(2-phenylethyl)amino]butanoic acid, (15.095) {6-[({1 [(Z)-(1-methyl-1H-tetrazol-5-yl)(phenyl)methylene]amino}oxy)methyl]pyridin-2-yl}carbamic acid but-3-yn-1-yl ester, (15.096) 4-amino-5-fluoropyrimidin-2-ol (tautomeric form: 4-amino-5-fluoropyrimidin-2(1H)-one), (15.097) 3,4,5-trihydroxybenzoic acid propyl ester, (15.098) [3-(4-chloro-2-fluorophenyl)-5-(2,4-difluorophenyl)-1,2-oxazol-4-yl](pyridin-3-yl)methanol, (15.099) (S)-[3-(4-chloro-2-fluorophenyl)-5-(2,4-difluorophenyl)-1,2-oxazol-4-yl](pyridin-3-yl)methanol, (15.100) (R)-[3-(4-chloro-2-fluorophenyl)-5-(2,4-difluorophenyl)-1,2-oxazol-4-yl](pyridin-3-yl)methanol, (15.101) 2-fluoro-6-(trifluoromethyl)-N-(1,1,3-trimethyl-2,3-dihydro-1H-inden-4-yl)benzamide, (15.102) 2-(6-benzylpyridin-2-yl)quinazoline, (15.103) 2-[6-(3-fluoro-4-methoxyphenyl)-5-methylpyridin-2-yl]quinazoline, (15.104) 3-(4,4-difluoro-3,3-dimethyl-3,4-dihydroisoquinolin-1-yl)quinoline, (15.105) abscisic acid, (15.106) N'-[5-bromo-6-(2,3-dihydro-1H-inden-2-yloxy)-2-methylpyridin-3-yl]-N-ethyl-N-methylimidoformamide, (15.107) N'-{5-bromo-6-[1-(3,5-difluorophenyl)ethoxy]-2-methylpyridin-3-yl}-N-ethyl-N-etthylimidoformamide, (15.108) N'-{5-bromo-6-[(1R)-1-(3,5-difluorophenyl)ethoxy]-2-methylpyridin-3-yl}-N-ethyl-N-methylimidoformamide, (15.109) N'-{5-bromo-6-[(1S)-1-(3,5-difluorophenyl)ethoxy]-2-methylpyridin-3-yl}-N-ethyl-N-methylimidoformamide, (15.110) N'-{5-bromo-6-[(cis-4-isopropylcyclohexyl)oxy]-2-methylpyridin-3-yl}-N-ethyl-N-methylimidoformamide, (15.111) N'-{5-bromo-6-[(trans-4-isopropylcyclohexyl)oxy]-2-methylpyridin-3-yl}-N-ethyl-N-methylimidoformamide, (15.112) N-cyclopropyl-3-(difluoromethyl)-5-fluoro-N-(2-isopropylbenzyl)-1-methyl-1H-pyrazole-4-carboxamide, (15.113) N-cyclopropyl-N-(2-cyclopropylbenzyl)-3-(difluoromethyl)-5-fluoro-1-methyl-1H-pyrazole-4-carboxamide, (15.114) N-(2-tert-butylbenzyl)-N-cyclopropyl-3-(difluoromethyl)-5-fluoro-1-methyl-1H-pyrazole-4-carboxamide, (15.115) N-(5-chloro-2-ethylbenzyl)-N-cyclopropyl-3-(difluoromethyl)-5-fluoro-1-methyl-1H-pyrazole-4-carboxamide, (15.116) N-(5-chloro-2-isopropylbenzyl)-N-cyclopropyl-3-(difluoromethyl)-5-fluoro-1-methyl-1H-pyrazole-4-carboxamide, (15.117) N-cyclopropyl-3-(difluoromethyl)-N-(2-ethyl-5-fluorobenzyl)-5-fluoro-1-methyl-1H-pyrazole-4-carboxamide, (15.118) N-cyclopropyl-3-(difluoromethyl)-5-fluoro-N-(5-fluoro-2-isopropylbenzyl)-1-methyl-1H-pyrazole-4-carboxamide, (15.119) N-cyclopropyl-N-(2-cyclopropyl-5-fluorobenzyl)-3-(difluoromethyl)-5-fluoro-1-methyl-1H-pyrazole-4-carboxamide, (15.120) N-(2-cyclopentyl-5-fluorobenzyl)-N-cyclopropyl-3-(difluoromethyl)-5-fluoro-1-methyl-1H-pyrazole-4-carboxamide, (15.121) N-cyclopropyl-3-(difluoromethyl)-5-fluoro-N-(2-fluoro-6-isopropylbenzyl)-1-methyl-1H-pyrazole-4-carboxamide, (15.122) N-cyclopropyl-3-(difluoromethyl)-N-(2-ethyl-5-methylbenzyl)-5-fluoro-1-methyl-1H-pyrazole-4-carboxamide, (15.123) N-cyclopropyl-3-(difluoromethyl)-5-fluoro-N-(2-isopropyl-5-methylbenzyl)-1-methyl-1H-pyrazole-4-carboxamide, (15.124) N-cyclopropyl-N-(2-cyclopropyl-5-methylbenzyl)-3-(difluoromethyl)-5-fluoro-1-methyl-1H-pyrazole-4-carboxamide, (15.125) N-(2-tert-butyl-5-methylbenzyl)-N-cyclopropyl-3-(difluoromethyl)-5-fluoro-1-methyl-1H-pyrazole-4-carboxamide, (15.126) N-[5-chloro-2-(trifluoromethyl)benzyl]-N-cyclopropyl-3-(difluoromethyl)-5-fluoro-1-methyl-1H-pyrazole-4-carboxamide, (15.127) N-cyclopropyl-3-(difluoromethyl)-5-fluoro-1-methyl-N-[5-methyl-2-(trifluoromethyl)benzyl]-1H-pyrazole-4-carboxamide, (15.128) N-[2-chloro-6-(trifluoromethyl)benzyl]-N-cyclopropyl-3-(difluoromethyl)-5-fluoro-1-methyl-1H-pyrazole-4-carboxamide, (15.129) N-[3-chloro-2-fluoro-6-(trifluoromethyl)benzyl]-N-cyclopropyl-3-(difluoromethyl)-5-fluoro-1-methyl-1H-pyrazole-4-carboxamide, (15.130) N-cyclopropyl-3-(difluoromethyl)-N-(2-ethyl-4,5-dimethylbenzyl)-5-fluoro-1-methyl-1H-pyrazole-4-carboxamide, (15.131) N-cyclopropyl-3-(difluoromethyl)-5-fluoro-N-(2-isopropylbenzyl)-1-methyl-1H-pyrazole-4-carbothioamide, (15.132) N'-(2,5-dimethyl-4-phenoxyphenyl)-N-ethyl-N-methylimidoformamide, (15.133) N'-{4-[(4,5-dichloro-1,3-thiazol-2-yl)oxy]-2,5-dimethylphenyl}-N-ethyl-N-methylimidoformamide, (15.134) N-(4-chloro-2,6-difluorophenyl)-4-(2-chloro-4-fluorophenyl)-1,3-dimethyl-1H-pyrazol-5-amine, (15.135) 9-fluoro-2,2-dimethyl-5-(quinolin-3-yl)-2,3-dihydro-1,4- benzoxazepine, (15.136) 2-{2-fluoro-6-[(8-fluoro-2-methylquinolin-3-yl)oxy]phenyl}propan-2-ol, (15.137) 2-{2-[(7,8-difluoro-2-methylquinolin-3-yl)oxy]-6-fluorophenyl}propan-2-ol, (15.138) 4-(2-chloro-4-fluorophenyl)-N-(2-fluorophenyl)-1,3-dimethyl-1H-pyrazol-5-amine, (15.139) 4-(2-chloro-4-fluorophenyl)-N-(2,6-difluorophenyl)-1,3-dimethyl-1H-pyrazol-5-amine, (15.140) 4-(2-chloro-4-fluorophenyl)-N-(2-chloro-6-fluorophenyl)-1,3-dimethyl-1H-pyrazol-5-amine, (15.141) 4-(2-bromo-4-fluorophenyl)-N-(2-chloro-6-fluorophenyl)-1,3-dimethyl-1H-pyrazol-5-amine, (15.142) N-(2-bromo-6-fluorophenyl)-4-(2-chloro-4-fluorophenyl)-1,3-dimethyl-1H-pyrazol-5-amine, (15.143) 4-(2-bromo-4-fluorophenyl)-N-(2-bromophenyl)-1,3-dimethyl-1H-pyrazol-5-amine, (15.144) 4-(2-bromo-4-fluorophenyl)-N-(2-bromo-6-fluorophenyl)-1,3-dimethyl-1H-pyrazol-5-amine, (15.145) 4-(2-bromo-4-fluorophenyl)-N-(2-chlorophenyl)-1,3-dimethyl-1H-pyrazol-5-amine, (15.146) N-(2-bromophenyl)-4-(2-chloro-4-fluorophenyl)-1,3-dimethyl-1H-pyrazol-5-amine, (15.147) 4-(2-chloro-4-fluorophenyl)-N-(2-chlorophenyl)-1,3-dimethyl-1H-pyrazol-5-amine, (15.148) 4-(2-bromo-4-fluorophenyl)-N-(2,6-difluorophenyl)-1,3-dimethyl-1H-pyrazol-5-amine, (15.149) 4-(2-bromo-4-fluorophenyl)-N-(2-fluorophenyl)-1,3-dimethyl-1H-pyrazol-5-amine, (15.150) N'-(4-{3-[(difluoromethyl)sulphanyl]phenoxy}-2,5-dimethylphenyl)-N-ethyl-N-methylimidoformamide, (15.151) N'-(2,5-dimethyl-4-{3-[(1,1,2,2-tetrafluoroethyl)sulphanyl]phenoxy}phenyl)-N-ethyl-N-methylimidoformamide, (15.152) N'-(2,5-dimethyl-4-{3-[(2,2,2-trifluoroethyl)sulphanyl]phenoxy}phenyl)-N-ethyl-N-methylimidoformamide, (15.153) N'-(2,5-dimethyl-4-{3-[(2,2,3,3-tetrafluoropropyl)sulphanyl]phenoxy}phenyl)-N-ethyl-N-methylimidoformamide, (15.154) N'-(2,5-dimethyl-4-{3-[(pentafluoroethyl)sulphanyl]phenoxy}phenyl)-N-ethyl-N-methylimidoformamide, (15.155) N'-(4-{[3-(difluoromethoxy)phenyl]sulphanyl}-2,5-dimethylphenyl)-N-ethyl-N-methylimidoformamide, (15.156) N'-(2,5-dimethyl-4-{[3-(1,1,2,2-tetrafluoroethoxy)phenyl]sulphanyl}phenyl)-N-ethyl-N-methylimidoformamide, (15.157) N'-(2,5-dimethyl-4-{[3-(2,2,2-trifluoroethoxy)phenyl]sulphanyl}phenyl)-N-ethyl-N-methylimidoformamide, (15.158) N'-(2,5-dimethyl-4-{[3-(2,2,3,3-tetrafluoropropoxy)phenyl]sulphanyl}phenyl)-N-ethyl-N-methylimidoformamide, (15.159) N'-(2,5-dimethyl-4-{[3-(pentafluoroethoxy)phenyl]sulphanyl}phenyl)-N-ethyl-N-methylimidoformamide, (15.160) 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone, (15.161) 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.162) 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone, (15.163) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenylmethanesulphonate, (15.164) 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethanesulphonate, (15.165) 2-[3,5-bis(difluoromethyl)-1H-pyrazol-1-yl]-1-[4-(4-{(5S)-5-[2-(prop-2-yn-1-yloxy)phenyl]-4,5-dihydro-1,2-oxazol-3-yl}-1,3-thiazol-2-yl)piperidin-1-yl]ethanone, (15.166) 2-[3,5-bis(difluoromethyl)-1H-pyrazol-1-yl]-1-[4-(4-{(5R)-5-[2-(prop-2-yn-1-yloxy)phenyl]-4,5-dihydro-1,2-oxazol-3-yl}-1,3-thiazol-2-yl)piperidin-1-yl]ethanone, (15.167) 2-[3,5-bis(difluoromethyl)-1H-pyrazol-1-yl]-1-[4-(4-{(5S)-5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.168) 2-[3,5-bis(difluoromethyl)-1H-pyrazol-1-yl]-1-[4-(4-{(5R)-5-[2-fluoro-6-(prop-2-yn-1-yloxy)phenyl]-4,5-dihydro-1,2-oxazol-3-yl}-1,3-thiazol-2-yl)piperidin-1-yl]ethanone, (15.169) 2-[3,5-bis(difluoromethyl)-1H-pyrazol-1-yl]-1-[4-(4-{(5S)-5-[2-chloro-6-(prop-2-yn-1-yloxy)phenyl]-4,5-dihydro-1,2-oxazol-3-yl}-1,3-thiazol-2-yl)piperidin-1-yl]ethanone, (15.170) 2-[3,5-bis(difluoromethyl)-1H-pyrazol-1-yl]-1-[4-(4-{(5R)-5-[2-chloro-6-(prop-2-yn-1-yloxy)phenyl]-4,5-dihydro-1,2-oxazol-3-yl}-1,3-thiazol-2-yl)piperidin-1-yl]ethanone, (15.171) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenylmethanesulphonate, (15.172) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}phenylmethanesulphonate, (15.173) 2-{(5S)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethanesulphonate, (15.174) 2-{(5R)-3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenylmethanesulphonate.

Biological Pesticides as Mixing Components

The compounds of the formula (I) can be combined with biological pesticides.

Biological pesticides include especially bacteria, fungi, yeasts, plant extracts and products formed by microorganisms, including proteins and secondary metabolites.

Biological pesticides include bacteria such as spore-forming bacteria, root-colonizing bacteria and bacteria which act as biological insecticides, fungicides or nematicides.

Examples of such bacteria which are used or can be used as biological pesticides are:

*Bacillus amyloliquefaciens*, strain FZB42 (DSM 231179), or *Bacillus cereus*, especially *B. cereus* strain CNCM I-1562 or *Bacillus firmus*, strain I-1582 (Accession number CNCM I-1582) or *Bacillus pumilus*, especially strain GB34 (Accession No. ATCC 700814) and strain QST2808 (Accession No. NRRL B-30087), or *Bacillus subtilis*, especially strain GB03 (Accession No. ATCC SD-1397), or *Bacillus subtilis* strain QST713 (Accession No. NRRL B-21661) or *Bacillus subtilis* strain OST 30002 (Accession No. NRRL B-50421) *Bacillus thuringiensis*, especially *B. thuringiensis* subspecies *israelensis* (serotype H-14), strain AM65-52 (Accession No. ATCC 1276), or *B. thuringiensis* subsp. *aizawai*, especially strain ABTS-1857 (SD-1372), or *B. thuringiensis* subsp. *kurstaki* strain HD-1, or *B. thuringiensis* subsp. *tenebrionis* strain NB 176 (SD-5428), *Pasteuria penetrans, Pasteuria* spp. (*Rotylenchulus reniformis* nematode)-PR3 (Accession Number ATCC SD-5834), *Streptomyces microflavus* strain AQ6121 (=QRD 31.013, NRRL B-50550), *Streptomyces galbus* strain AQ 6047 (Accession Number NRRL 30232).

Examples of fungi and yeasts which are used or can be used as biological pesticides are:

*Beauveria bassiana*, in particular strain ATCC 74040, *Coniothyrium minitans*, in particular strain CON/M/91-8 (Accession No. DSM-9660), *Lecanicillium* spp., in particular strain HRO LEC 12, *Lecanicillium lecanii*, (formerly known as *Verticillium lecanii*), in particular strain KV01, *Metarhizium anisopliae*, in particular strain F52 (DSM3884/ATCC 90448), *Metschnikowia fructicola*, in particular strain NRRL Y-30752, *Paecilomyces fumosoroseus* (new: *Isaria fumosorosea*), in particular strain IFPC 200613, or strain Apopka 97 (Accession No. ATCC 20874), *Paecilomyces lilacinus*, in particular *P. lilacinus* strain 251 (AGAL 89/030550), *Talaromyces flavus*, in particular strain V117b, *Trichoderma atroviride*, in particular strain SC1 (Accession Number CBS 122089), *Trichoderma harzianum*, in particular *T. harzianum* rifai T39 (Accession Number CNCM I-952).

Examples of viruses which are used or can be used as biological pesticides are:

*Adoxophyes orana* (summer fruit *tortrix*) granulosis virus (GV), *Cydia pomonella* (codling moth) granulosis virus (GV), *Helicoverpa armigera* (cotton bollworm) nuclear polyhedrosis virus (NPV), *Spodoptera exigua* (beet armyworm) mNPV, *Spodoptera frugiperda* (fall armyworm) mNPV, *Spodoptera littoralis* (African cotton leafworm) NPV.

Also included are bacteria and fungi which are added as 'inoculant' to plants or plant parts or plant organs and which, by virtue of their particular properties, promote plant growth and plant health. Examples include:

*Agrobacterium* spp., *Azorhizobium caulinodans*, *Azospirillum* spp., *Azotobacter* spp., *Bradyrhizobium* spp., *Burkholderia* spp., especially *Burkholderia cepacia* (formerly known as *Pseudomonas cepacia*), *Gigaspora* spp., or *Gigaspora monosporum*, *Glomus* spp., *Laccaria* spp., *Lactobacillus buchneri*, *Paraglomus* spp., *Pisolithus tinctorus*, *Pseudomonas* spp., *Rhizobium* spp., especially *Rhizobium trifolii*, *Rhizopogon* spp., *Scleroderma* spp., *Suillus* spp., *Streptomyces* spp.

Examples of plant extracts and products formed by microorganisms, including proteins and secondary metabolites, which are used or can be used as biological pesticides are:

*Allium sativum*, *Artemisia absinthium*, azadirachtin, Biokeeper WP, *Cassia nigricans*, *Celastrus angulatus*, *Chenopodium anthelminticum*, chitin, Armour-Zen, Dryopteris filix-mas, *Equisetum arvense*, Fortune Aza, Fungastop, Heads Up (*Chenopodium quinoa* saponin extract), Pyrethrum/Pyrethrins, *Quassia amara*, *Quercus*, *Quillaja*, Regalia, "Requiem™ Insecticide", rotenone, ryania/ryanodine, *Symphytum officinale*, *Tanacetum vulgare*, thymol, Triact 70, TriCon, *Tropaeulum majus*, *Urtica dioica*, Veratrin, *Viscum album*, Brassicaceae extract, especially oilseed rape powder or mustard powder.

Safeners as Mixing Components

The compounds of the formula (I) can be combined with safeners, for example benoxacor, cloquintocet (-mexyl), cyometrinil, cyprosulphamide, dichlormid, fenchlorazole (-ethyl), fenclorim, flurazole, fluxofenim, furilazole, isoxadifen (-ethyl), mefenpyr (-diethyl), naphthalic anhydride, oxabetrinil, 2-methoxy-N-({4-[(methylcarbamoyl)amino]phenyl}sulphonyl)benzamide (CAS 129531-12-0), 4-(dichloroacetyl)-1-oxa-4-azaspiro[4.5]decane (CAS 71526-07-3), 2,2,5-trimethyl-3-(dichloroacetyl)-1,3-oxazolidine (CAS 52836-31-4).

Plants and Plant Parts

All plants and plant parts can be treated in accordance with the invention. Plants are understood here to mean all plants and populations of plants, such as desirable and undesirable wild plants or crop plants (including naturally occurring crop plants), for example cereals (wheat, rice, triticale, barley, rye, oats), maize, soya bean, potato, sugar beet, sugar cane, tomatoes, bell peppers and chili peppers, cucumbers, melons, carrots, water melons, onions, lettuce, spinach, leeks, beans, *Brassica oleracea* (e.g. cabbage), peas and other vegetable species, cotton, tobacco, oilseed rape and also fruit plants (with the fruits apples, pears, citrus fruits and grapes). Crop plants may be plants which can be obtained by conventional breeding and optimization methods or by biotechnological and genetic engineering methods or combinations of these methods, including the transgenic plants and including the plant cultivars which are protectable or non-protectable by plant breeders' rights. Plants shall be understood to mean all developmental stages of the plants, for example seeds, cuttings and young (immature) plants up to mature plants. Plant parts shall be understood to mean all parts and organs of the plants above and below ground, such as shoot, leaf, flower and root, examples given being leaves, needles, stalks, stems, flowers, fruit bodies, fruits and seeds, and also roots, tubers and rhizomes. Plant parts also include harvested material (harvested plants or plant parts) and vegetative and generative propagation material, for example cuttings, tubers, rhizomes, slips and seeds.

The inventive treatment of the plants and parts of plants with the compounds of the formula (I) is effected directly or by allowing them to act on the surroundings, habitat or storage space thereof by the customary treatment methods, for example by dipping, spraying, evaporating, fogging, scattering, painting on, injecting, and, in the case of propagation material, especially in the case of seeds, also by applying one or more coats.

As already mentioned above, it is possible to treat all plants and parts thereof in accordance with the invention. In a preferred embodiment, wild plant species and plant cultivars, or those obtained by conventional biological breeding methods, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. Particular preference is given in accordance with the invention to treating plants of the respective commercially customary plant cultivars or those that are in use. Plant cultivars are understood to mean plants having new properties ("traits") and which have been grown by conventional breeding, by mutagenesis or by recombinant DNA techniques. They may be cultivars, varieties, biotypes or genotypes.

Transgenic Plants, Seed Treatment and Integration Events

The preferred transgenic plants or plant cultivars (those obtained by genetic engineering) which are to be treated in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher harvest yields, higher quality and/or higher nutritional value of the harvested products, better capability for storage and/or processability of the harvested products. Further and particularly emphasized examples of such properties are increased resistance of the plants against animal and microbial pests, such as insects, arachnids, nematodes, mites, slugs and snails, owing, for example, to toxins formed in the plants, in particular those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF and also combinations thereof), and also increased resistance of the plants against phytopathogenic fungi, bacteria and/or viruses caused, for example, by systemic acquired resistance (SAR), systemin, phytoalexins, elicitors and resistance genes and correspondingly expressed proteins and toxins, and also increased tolerance of the plants to certain herbicidally active compounds, for example imidazolinones, sulphonylureas, glyphosates or phosphinothricin (for example the "PAT" gene). The genes which impart the desired properties ("traits") in question may also be present in combinations with one another in the transgenic plants. Examples of transgenic plants include the important crop plants, such as cereals (wheat, rice, triticale, barley, rye, oats), maize, soya beans, potatoes, sugar beet, sugar cane, tomatoes, peas and other types of vegetable, cotton, tobacco, oilseed rape and also fruit plants (with the fruits apples, pears, citrus fruits and grapes), particular emphasis being given to maize, soya beans, wheat, rice, potatoes, cotton, sugar cane, tobacco and oilseed rape. Properties ("traits") which are particularly emphasized are the increased resistance of the plants to insects, arachnids, nematodes and slugs and snails.

Crop Protection—Types of Treatment

The plants and plant parts are treated with the compounds of the formula (I) directly or by action on their surroundings, habitat or storage space using customary treatment methods, for example by dipping, spraying, atomizing, irrigating, evaporating, dusting, fogging, broadcasting, foaming, painting, spreading-on, injecting, watering (drenching), drip irrigating and, in the case of propagation material, in particular in the case of seed, additionally by dry seed treatment, liquid seed treatment, slurry treatment, by incrusting, by coating with one or more coats, etc. It is furthermore possible to apply the compounds of the formula (I) by the ultra-low volume method or to inject the application form or the compound of the formula (I) itself into the soil.

A preferred direct treatment of the plants is foliar application, i.e. compounds of the formula (I) are applied to the foliage, where treatment frequency and the application rate should be adjusted according to the level of infestation with the pest in question.

In the case of systemically active compounds, the compounds of the formula (I) also access the plants via the root system. The plants are then treated by the action of the compounds of the formula (I) on the habitat of the plant. This can be accomplished, for example, by drenching, or by mixing into the soil or the nutrient solution, meaning that the locus of the plant (e.g. soil or hydroponic systems) is impregnated with a liquid form of the compounds of the formula (I), or by soil application, meaning that the compounds of the formula (I) are introduced in solid form (e.g. in the form of granules) into the locus of the plants. In the case of paddy rice crops, this can also be accomplished by metering the compound of the formula (I) in a solid application form (for example as granules) into a flooded paddy field.

Seed Treatment

The control of animal pests by the treatment of the seed of plants has long been known and is the subject of constant improvements. Nevertheless, the treatment of seed entails a series of problems which cannot always be solved in a satisfactory manner. Thus, it is desirable to develop methods for protecting the seed and the germinating plant which dispense with, or at least reduce considerably, the additional application of pesticides during storage, after sowing or after emergence of the plants. It is additionally desirable to optimize the amount of active ingredient used so as to provide optimum protection for the seed and the germinating plant from attack by animal pests, but without damage to the plant itself by the active ingredient used. In particular, methods for the treatment of seed should also take account of the intrinsic insecticidal or nematicidal properties of pest-resistant or -tolerant transgenic plants in order to achieve optimal protection of the seed and the germinating plant with a minimum expenditure on pesticides.

The present invention therefore in particular also relates to a method for the protection of seed and germinating plants from attack by pests, by treating the seed with one of the compounds of the formula (I). The method according to the invention for protecting seed and germinating plants against attack by pests further comprises a method in which the seed is treated simultaneously in one operation or sequentially with a compound of the formula (I) and a mixing component. It further also comprises a method where the seed is treated at different times with a compound of the formula (I) and a mixing component.

The invention likewise relates to the use of the compounds of the formula (I) for the treatment of seed for protecting the seed and the resulting plant from animal pests.

The invention further relates to seed which has been treated with a compound of the formula (I) for protection from animal pests. The invention also relates to seed which has been treated simultaneously with a compound of the formula (I) and a mixing component. The invention further relates to seed which has been treated at different times with a compound of the formula (I) and a mixing component. In the case of seed which has been treated at different times with a compound of the formula (I) and a mixing component, the individual substances may be present on the seed in different layers. In this case, the layers comprising a compound of the formula (I) and a mixing component may optionally be separated by an intermediate layer. The invention also relates to seed in which a compound of the formula (I) and a mixing component have been applied as part of a coating or as a further layer or further layers in addition to a coating.

The invention further relates to seed which, after the treatment with a compound of the formula (I), is subjected to a film-coating process to prevent dust abrasion on the seed.

One of the advantages encountered with a systemically acting compound of the formula (I) is the fact that, by treating the seed, not only the seed itself but also the plants resulting therefrom are, after emergence, protected against animal pests. In this way, the immediate treatment of the crop at the time of sowing or shortly thereafter can be dispensed with.

A further advantage is that the treatment of the seed with a compound of the formula (I) can enhance germination and emergence of the treated seed.

It is likewise considered to be advantageous that compounds of the formula (I) can especially also be used for transgenic seed.

Furthermore, compounds of the formula (I) can be employed in combination with compositions of signalling technology, leading to better colonization by symbionts such as, for example, rhizobia, mycorrhizae and/or endophytic bacteria or fungi, and/or to optimized nitrogen fixation.

The compounds of the formula (I) are suitable for protection of seed of any plant variety which is used in agriculture, in the greenhouse, in forests or in horticulture. More particularly, this includes seed of cereals (for example wheat, barley, rye, millet and oats), maize, cotton, soya beans, rice, potatoes, sunflowers, coffee, tobacco, canola, oilseed rape, beet (for example sugar beet and fodder beet), peanuts, vegetables (for example tomatoes, cucumbers, beans, cruciferous vegetables, onions and lettuce), fruit plants, lawns and ornamental plants. Of particular significance is the treatment of the seed of cereals (such as wheat, barley, rye and oats), maize, soya beans, cotton, canola, oilseed rape and rice.

As already mentioned above, the treatment of transgenic seed with a compound of the formula (I) is also of particular importance. This involves the seed of plants which generally contain at least one heterologous gene which controls the expression of a polypeptide having insecticidal and/or nematicidal properties in particular. The heterologous genes in transgenic seed may originate in this case from microorganisms such as *Bacillus, Rhizobium, Pseudomonas, Serratia, Trichoderma, Clavibacter, Glomus* or *Gliocladium*. The present invention is particularly suitable for the treatment of transgenic seed containing at least one heterologous gene originating from *Bacillus* sp. The heterologous gene is more preferably derived from *Bacillus thuringiensis*.

In the context of the present invention, the compound of the formula (I) is applied to the seed. The seed is preferably treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content which allows storage. Alternatively, it is also possible to use seed which, after drying, has been treated with, for example, water and then dried again, for example priming. In the case of rice seed, it is also possible to use seed which has been pre-swollen in water up to a certain stage (pigeon breast stage) for example, which leads to improved germination and more uniform emergence.

When treating the seed, care must generally be taken that the amount of the compound of the formula (I) applied to the seed and/or the amount of further additives is chosen in such a way that the germination of the seed is not adversely affected, or that the resulting plant is not damaged. This has to be ensured particularly in the case of active compounds which can exhibit phytotoxic effects at certain application rates.

In general, the compounds of the formula (I) are applied to the seed in the form of a suitable formulation. Suitable formulations and processes for seed treatment are known to the person skilled in the art.

The compounds of the formula (I) can be converted to the customary seed-dressing formulations, such as solutions, emulsions, suspensions, powders, foams, slurries or other coating compositions for seed, and also ULV formulations.

These formulations are prepared in a known manner, by mixing compounds of the formula (I) with customary additives such as, for example, customary extenders and also solvents or diluents, dyes, wetting agents, dispersants, emulsifiers, antifoams, preservatives, secondary thickeners, adhesives, gibberellins and also water.

Dyes which may be present in the seed-dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed-dressing formulations usable in accordance with the invention are all substances which promote wetting and which are customary for the formulation of active agrochemical ingredients. Alkyl naphthalenesulphonates, such as diisopropyl or diisobutyl naphthalenesulphonates, can be used with preference.

Suitable dispersants and/or emulsifiers which may be present in the seed-dressing formulations usable in accordance with the invention are all nonionic, anionic and cationic dispersants customary for the formulation of active agrochemical ingredients. Nonionic or anionic dispersants or mixtures of nonionic or anionic dispersants can be used with preference. Suitable nonionic dispersants include in particular ethylene oxide/propylene oxide block polymers, alkylphenol polyglycol ethers and tristyrylphenol polyglycol ethers, and the phosphated or sulphated derivatives thereof. Suitable anionic dispersants are especially lignosulphonates, polyacrylic acid salts and arylsulphonate-formaldehyde condensates.

Antifoams which may be present in the seed-dressing formulations usable in accordance with the invention are all foam-inhibiting substances customary for the formulation of active agrochemical ingredients. Silicone antifoams and magnesium stearate can be used with preference.

Preservatives which may be present in the seed-dressing formulations usable in accordance with the invention are all substances usable for such purposes in agrochemical compositions. Examples include dichlorophene and benzyl alcohol hemiformal.

Secondary thickeners which may be present in the seed-dressing formulations usable in accordance with the invention are all substances which can be used for such purposes in agrochemical compositions. Preferred examples include cellulose derivatives, acrylic acid derivatives, xanthan, modified clays and finely divided silica.

Useful stickers which may be present in the seed-dressing formulations usable in accordance with the invention are all customary binders usable in seed-dressing products. Preferred examples include polyvinylpyrrolidone, polyvinyl acetate, polyvinyl alcohol and tylose.

Gibberellins which may be present in the seed-dressing formulations usable in accordance with the invention are preferably the gibberellins A1, A3 (=gibberellic acid), A4 and A7; particular preference is given to using gibberellic acid. The gibberellins are known (cf. R. Wegler "Chemie der Pflanzenschutz-und Schädlingsbekämpfungsmittel", vol. 2, Springer Verlag, 1970, pp. 401-412).

The seed-dressing formulations usable in accordance with the invention can be used to treat a wide variety of different kinds of seed, either directly or after prior dilution with water. For instance, the concentrates or the preparations obtainable therefrom by dilution with water can be used to dress the seed of cereals, such as wheat, barley, rye, oats and triticale, and also the seed of maize, rice, oilseed rape, peas, beans, cotton, sunflowers, soya beans and beets, or else a wide variety of different vegetable seed. The seed-dressing formulations usable in accordance with the invention, or the dilute use forms thereof, can also be used to dress seed of transgenic plants.

For the treatment of seed with the seed-dressing formulations usable in accordance with the invention, or use forms prepared therefrom, all mixing units usable customarily for the seed dressing are useful. Specifically, the procedure in seed dressing is to place the seed into a mixer in batchwise or continuous operation, to add the particular desired amount of seed-dressing formulations, either as such or after prior dilution with water, and to mix until the formulation is distributed homogeneously on the seed. If appropriate, this is followed by a drying operation.

The application rate of the seed-dressing formulations usable in accordance with the invention can be varied within a relatively wide range. It is guided by the particular content of the compounds of the formula (I) in the formulations and by the seed. The application rates of the compound of the formula (I) are generally between 0.001 and 50 g per kilogram of seed, preferably between 0.01 and 15 g per kilogram of seed.

Animal Health

In the animal health field, i.e. the field of veterinary medicine, the compounds of the formula (I) are active against animal parasites, in particular ectoparasites or endoparasites. The term "endoparasites" includes especially helminths and protozoa, such as coccidia. Ectoparasites are typically and preferably arthropods, especially insects and acarids.

In the field of veterinary medicine, the compounds of the formula (I) having favourable endotherm toxicity are suitable for controlling parasites which occur in animal breeding and animal husbandry in livestock, breeding animals, zoo animals, laboratory animals, experimental animals and domestic animals. They are active against all or specific stages of development of the parasites.

Agricultural livestock include, for example, mammals such as sheep, goats, horses, donkeys, camels, buffalo, rabbits, reindeer, fallow deer, and particularly cattle and pigs; poultry such as turkeys, ducks, geese, and particularly chickens; fish and crustaceans, for example in aquaculture, and also insects such as bees.

Domestic animals include, for example, mammals, such as hamsters, guinea pigs, rats, mice, chinchillas, ferrets, and particularly dogs, cats, caged birds, reptiles, amphibians and aquarium fish.

In a preferred embodiment, the compounds of the formula (I) are administered to mammals.

In another preferred embodiment, the compounds of the formula (I) are administered to birds, namely caged birds and particularly poultry.

Use of the compounds of the formula (I) for the control of animal parasites is intended to reduce or prevent illness, cases of death and reductions in performance (in the case of meat, milk, wool, hides, eggs, honey and the like), such that more economical and simpler animal husbandry is enabled and better animal well-being is achievable.

In relation to the field of animal health, the term "control" or "controlling" means that the compounds of the formula (I) are effective in reducing the incidence of the particular parasite in an animal infected with such parasites to an innocuous degree. More specifically, "controlling" in the present context means that the compound of the formula (I) can kill the respective parasite, inhibit its growth, or inhibit its proliferation.

Arthropods include:

from the order Anoplurida, for example *Haematopinus* spp., *Linognathus* spp., *Pediculus* spp., *Phtirus* spp., *Solenopotes* spp.; from the order Mallophagida and the suborders Amblycerina and Ischnocerina, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; from the order Diptera and the suborders Nematocerina and Brachycerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; from the order Siphonapterida, for example *Pulex* spp., *Ctenocephalides* spp., *Tunga* spp., *Xenopsylla* spp., *Ceratophyllus* spp.;

from the order Heteropterida, for example *Cimex* spp., *Triatoma* spp., *Rhodnius* spp., *Panstrongylus* spp.; and also nuisance and hygiene pests from the order Blattarida.

Arthropods further include:

from the subclass Acari (Acarina) and the order Metastigmata, for example from the family Argasidae like *Argas* spp., *Ornithodorus* spp., *Otobius* spp., from the family Ixodidae like *Ixodes* spp., *Amblyomma* spp., *Rhipicephalus* (*Boophilus*) spp., *Dermacentor* spp., *Haemophysalis* spp., *Hyalomma* spp., *Rhipicephalus* spp. (the original genus of multi-host ticks); from the order Mesostigmata like *Dermanyssus* spp., *Ornithonyssus* spp., *Pneumonyssus* spp., *Raillietia* spp., *Pneumonyssus* spp., *Sternostoma* spp., *Varroa* spp., *Acarapis* spp.; from the order Actinedida (Prostigmata), for example *Acarapis* spp., *Cheyletiella* spp., *Ornithocheyletia* spp., *Myobia* spp., *Psorergates* spp., *Demodex* spp., *Trombicula* spp., *Neotrombiculla* spp., *Listrophorus* spp.; and from the order Acaridida (Astigmata), for example *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

Parasitic protozoa include:

Mastigophora (*Flagellata*), for example Trypanosomatidae, for example *Trypanosoma b. brucei*, *T.b. gambiense*, *T.b. rhodesiense*, *T. congolense*, *T. cruzi*, *T. evansi*, *T. equinum*, *T. lewisi*, *T. percae*, *T. simiae*, *T. vivax*, *Leishmania brasiliensis*, *L. donovani*, *L. tropica*, for example Trichomonadidae, for example *Giardia lamblia*, *G. canis*;

Sarcomastigophora (Rhizopoda) such as Entamoebidae, for example *Entamoeba histolytica*, Hartmanellidae, for example *Acanthamoeba* sp., *Harmanella* sp.;

Apicomplexa (Sporozoa) such as Eimeridae, for example *Eimeria acervulina*, *E. adenoides*, *E. alabamensis*, *E. anatis*, *E. anserina*, *E. arloingi*, *E. ashata*, *E. auburnensis*, *E. bovis*, *E. brunetti*, *E. canis*, *E. chinchillae*, *E. clupearum*, *E. columbae*, *E. contorta*, *E. crandalis*, *E. debliecki*, *E. dispersa*, *E. ellipsoidales*, *E. falciformis*, *E. faurei*, *E. flavescens*, *E. gallopavonis*, *E. hagani*, *E. intestinalis*, *E. iroquoina*, *E. irresidua*, *E. labbeana*, *E. leucarti*, *E. magna*, *E. maxima*, *E. media*, *E. meleagridis*, *E. meleagrimitis*, *E. mitis*, *E. necatrix*, *E. ninakohlyakimovae*, *E. ovis*, *E. parva*, *E. pavonis*, *E. perforans*, *E. phasani*, *E. piriformis*, *E. praecox*, *E. residua*, *E. scabra*, *E. spec.*, *E. stiedai*, *E. suis*, *E. tenella*, *E. truncata*, *E. truttae*, *E. zuernii*, *Globidium spec.*, *Isospora belli*, *I. canis*, *I. felis*, *I. ohioensis*, *I. rivolta*, *I. spec.*, *I. suis*, *Cystisospora spec.*, *Cryptosporidium spec.*, in particular *C. parvum*; such as Toxoplasmadidae, for example *Toxoplasma gondii*, *Hammondia heydornii*, *Neospora caninum*, *Besnoitia besnoitii*; such as Sarcocystidae, for example *Sarcocystis bovicanis*, *S. bovihominis*, *S. ovicanis*, *S. ovifelis*, *S. neurona*, *S. spec.*, *S. suihominis*, such as Leucozoidae, for example *Leucozytozoon simondi*, such as Plasmodiidae, for example *Plasmodium berghei*, *P. falciparum*, *P. malariae*, *P. ovale*, *P. vivax*, *P. spec.*, such as Piroplasmea, for example *Babesia argentina*, *B. bovis*, *B. canis*, *B. spec.*, *Theileria parva*, *Theileria spec.*, such as Adeleina, for example *Hepatozoon canis*, *H. spec*.

Pathogenic endoparasites which are helminths include Platyhelmintha (e.g. *Monogenea, cestodes* and *trematodes*), nematodes, Acanthocephala, and Pentastoma. These include:

Monogenea: for example: *Gyrodactylus* spp., *Dactylogyrus* spp., *Polystoma* spp.;

Cestodes: from the order of Pseudophyllidea, for example: *Diphyllobothrium* spp., *Spirometra* spp., *Schistocephalus* spp., *Ligula* spp., *Bothridium* spp., *Diphlogonoporus* spp.; from the order Cyclophyllida, for example: *Mesocestoides* spp., *Anoplocephala* spp., *Paranoplocephala* spp., *Moniezia* spp., *Thysanosoma* spp., *Thysaniezia* spp., *Avitellina* spp., *Stilesia* spp., *Cittotaenia* spp., *Andyra* spp., *Bertiella* spp., *Taenia* spp., *Echinococcus* spp., *Hydatigera* spp., *Davainea* spp., *Raillietina* spp., *Hymenolepis* spp., *Echinolepis* spp., *Echinocotyle* spp., *Diorchis* spp., *Dipylidium* spp., *Joyeuxiella* spp., *Diplopylidium* spp.;

Trematodes: from the class of Digenea, for example: *Diplostomum* spp., *Posthodiplostomum* spp., *Schistosoma* spp., *Trichobilharzia* spp., *Ornithobilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hypoderaeum* spp., *Fasciola* spp., *Fascioloides* spp., *Fasciolopsis* spp., *Cyclocoelum* spp., *Typhlocoelum* spp., *Paramphistomum* spp., *Calicophoron* spp., *Cotylophoron* spp., *Gigantocotyle* spp., *Fischoederius* spp., *Gastrothylacus* spp., *Notocotylus* spp., *Catatropis* spp., *Plagiorchis* spp., *Prosthogonimus* spp., *Dicrocoelium* spp., *Eurytrema* spp., *Troglotrema* spp., *Paragonimus* spp., *Collyriclum* spp., *Nanophyetus* spp., *Opisthorchis* spp., *Clonorchis* spp., *Metorchis* spp., *Heterophyes* spp., *Metagonimus* spp.;

Nematodes: Trichinellida, for example: *Trichuris* spp., *Capillaria* spp., *Paracapillaria* spp., *Eucoleus* spp., *Trichomosoides* spp., *Trichinella* spp., from the order Tylenchida, for example: *Micronema* spp., *Strongyloides* spp.;

from the order Rhabditida, for example: *Strongylus* spp., *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp., *Chabertia* spp., *Stephanurus* spp., *Ancylostoma* spp., *Uncinaria* spp., *Necator* spp., *Bunostomum* spp., *Globocephalus* spp., *Syngamus* spp., *Cyathostoma* spp., *Metastrongylus* spp., *Dictyocaulus* spp., *Muellerius* spp., *Protostrongylus* spp., *Neostrongylus* spp., *Cystocaulus* spp., *Pneumostrongylus* spp., *Spicocaulus* spp., *Elaphostrongylus* spp., *Parelaphostrongylus* spp., *Crenosoma* spp., *Paracrenosoma* spp., *Oslerus* spp., *Angiostrongylus* spp., *Aelurostrongylus* spp., *Filaroides* spp., *Parafilaroides* spp., *Trichostrongylus* spp., *Haemonchus* spp., *Ostertagia* spp., *Teladorsagia* spp., *Marshallagia* spp., *Cooperia* spp., *Nippostrongylus* spp., *Heligmosomoides* spp., *Nematodirus* spp., *Hyostrongylus* spp., *Obeliscoides* spp., *Amidostomum* spp., *Ollulanus* spp;

from the order Spirurida, for example: *Oxyuris* spp., *Enterobius* spp., *Passalurus* spp., *Syphacia* spp., *Aspiculuris* spp., *Heterakis* spp.; *Ascaris* spp., *Toxascaris* spp., *Toxocara* spp., *Baylisascaris* spp., *Parascaris* spp., *Anisakis* spp., *Ascaridia* spp.; *Gnathostoma* spp., *Physaloptera* spp., *Thelazia* spp., *Gongylonema* spp., *Habronema* spp., *Parabronema* spp., *Draschia* spp., *Dracunculus* spp.; *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp., *Spirocerca* spp.;

Acanthocephala: from the order of Oligacanthorhynchida, for example: *Macracanthorhynchus* spp., *Prosthenorchis* spp.; from the order Polymorphida for example: *Filicollis* spp.; from the order Moniliformida for example: *Moniliformis* spp.;

from the order Echinorhynchida, for example *Acanthocephalus* spp., *Echinorhynchus* spp., *Leptorhynchoides* spp.;

Pentastoma: from the order Porocephalida, for example *Linguatula* spp.

In the veterinary field and in animal husbandry, the compounds of the formula (I) are administered by methods generally known in the art, such as via the enteral, parenteral, dermal or nasal route in the form of suitable preparations. Administration may be prophylactic or therapeutic.

Thus, one embodiment of the present invention refers to the use of a compound of the formula (I) as a medicament.

A further aspect refers to the use of a compound of the formula (I) as an antiendoparasitic agent, in particular a helminthicidal agent or antiprotozoic agent. Compounds of the formula (I) are suitable for use as an antiendoparasitic agent, especially as a helminthicidal agent or antiprotozoic agent, for example in animal breeding, in animal husbandry, in animal houses and in the hygiene sector.

A further aspect in turn relates to the use of a compound of the formula (I) as an antiectoparasitic agent, in particular an arthropodicide such as an insecticide or an acaricide. A further aspect relates to the use of a compound of the formula (I) as an antiectoparasitic agent, in particular an arthropodicide such as an insecticide or an acaricide, for example in animal husbandry, in animal breeding, in animal houses or in the hygiene sector.

Vector Control

The compounds of the formula (I) can also be used in vector control. In the context of the present invention, a vector is an arthropod, especially an insect or arachnid, capable of transmitting pathogens, for example viruses, worms, single-cell organisms and bacteria, from a reservoir (plant, animal, human, etc.) to a host. The pathogens can be transmitted either mechanically (for example trachoma by non-stinging flies) to a host or after injection (for example malaria parasites by mosquitoes) into a host.

Examples of vectors and the diseases or pathogens they transmit are:

1) mosquitoes
   *Anopheles*: malaria, filariasis;
   *Culex*: Japanese encephalitis, filariasis, other viral diseases, transmission of worms;
   *Aedes*: yellow fever, dengue fever, filariasis, other viral diseases;
   Simuliidae: transmission of worms, in particular *Onchocerca volvulus;*
2) Lice: skin infections, epidemic typhus;
3) Fleas: plague, endemic typhus;
4) Flies: sleeping sickness (trypanosomiasis); cholera, other bacterial diseases;
5) Mites: acariosis, epidemic typhus, rickettsialpox, tularaemia, Saint Louis encephalitis, tick-borne encephalitis (TBE), Crimean-Congo haemorrhagic fever, borreliosis;
6) Ticks: borellioses such as *Borrelia duttoni*, tick-borne encephalitis, Q fever (*Coxiella burnetii*), babesioses (*Babesia canis canis*).

Examples of vectors in the context of the present invention are insects, such as aphids, flies, leafhoppers or thrips, which can transmit plant viruses to plants. Other vectors capable of transmitting plant viruses are spider mites, lice, beetles and nematodes.

Further examples of vectors in the context of the present invention are insects and arachnids such as mosquitoes, especially of the genera *Aedes, Anopheles*, for example *A. gambiae, A. arabiensis, A. funestus, A. dirus* (malaria) and *Culex*, lice, fleas, flies, mites and ticks, which can transmit pathogens to animals and/or humans.

Vector control is also possible if the compounds of the formula (I) are resistance-breaking.

Compounds of the formula (I) are suitable for use in the prevention of diseases and/or pathogens transmitted by vectors. Thus, a further aspect of the present invention is the use of compounds of the formula (I) for vector control, for example in agriculture, in horticulture, in forests, in gardens and in leisure facilities, and also in the protection of materials and stored products.

Protection of Industrial Materials

The compounds of the formula (I) are suitable for protecting industrial materials against attack or destruction by insects, for example from the orders Coleoptera, Hymenoptera, Isoptera, Lepidoptera, Psocoptera and Zygentoma.

Industrial materials in the present context are understood to mean inanimate materials, such as preferably plastics, adhesives, sizes, papers and cards, leather, wood, processed wood products and coating compositions. The use of the invention for protection of wood is particularly preferred.

In a further embodiment, the compounds of the formula (I) are used together with at least one further insecticide and/or at least one fungicide.

In a further embodiment, the compounds of the formula (I) are present as a ready-to-use pesticide, i.e. it can be applied to the material in question without further modifications. Suitable further insecticides or fungicides are in particular those mentioned above.

Surprisingly, it has also been found that the compounds of the formula (I) can be employed for protecting objects which come into contact with saltwater or brackish water, in particular hulls, screens, nets, buildings, moorings and signalling systems, against fouling. It is equally possible to use the compounds of the formula (I), alone or in combinations with other active compounds, as antifouling agents.

Control of Animal Pests in the Hygiene Sector

The compounds of the formula (I) are suitable for controlling animal pests in the hygiene sector. More particularly, the invention can be used in the domestic protection sector, in the hygiene protection sector and in the protection of stored products, particularly for control of insects, arachnids and mites encountered in enclosed spaces, for example dwellings, factory halls, offices, vehicle cabins. For controlling animal pests, the compounds of the formula (I) are used alone or in combination with other active compounds and/or auxiliaries. They are preferably used in domestic insecticide products. The compounds of the formula (I) are effective against sensitive and resistant species, and against all developmental stages.

These pests include, for example, pests from the class Arachnida, from the orders Scorpiones, Araneae and Opiliones, from the classes Chilopoda and Diplopoda, from the class Insecta the order Blattodea, from the orders Coleoptera, Dermaptera, Diptera, Heteroptera, Hymenoptera, Isoptera, Lepidoptera, Phthiraptera, Psocoptera, Saltatoria or Orthoptera, Siphonaptera and Zygentoma and from the class Malacostraca the order Isopoda.

Application is effected, for example, in aerosols, unpressurized spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or bait stations.

Description of the Processes and Intermediates

The preparation and use examples which follow illustrate the invention without limiting it. The products were characterized by $^1$H NMR spectroscopy and/or LC-MS (Liquid Chromatography Mass Spectrometry).

The log P values were determined in accordance with OECD Guideline 117 (EC Directive 92/69/EEC) by HPLC (high-performance liquid chromatography) using reversed-phase (RP) columns (C18), by the following methods:

[a] The LC-MS determination in the acidic range is carried out at pH 2.7 with 0.1% aqueous formic acid and acetonitrile (contains 0.1% formic acid) as eluents; linear gradient from 10% acetonitrile to 95% acetonitrile.

[b] LC-MS determination in the neutral range is effected at pH 7.8 with 0.001 molar aqueous ammonium hydrogencarbonate solution and acetonitrile as eluents; linear gradient from 10% acetonitrile to 95% acetonitrile.

Calibration is carried out using unbranched alkan-2-ones (having 3 to 16 carbon atoms) with known log P values (log P values determined on the basis of the retention times by linear interpolation between two successive alkanones).

The NMR spectra were determined using a Bruker Avance 400 fitted with a flow probe head (60 µl volume). In individual cases, the NMR spectra were measured with a Bruker Avance II 600.

The $^1$H NMR data of selected examples are noted in the form of 1H-NMR peak lists. For each signal peak, first the δ value in ppm and then the signal intensity in round brackets are listed. The δ value-signal intensity number pairs for different signal peaks are listed with separation from one another by semicolons.

The peak list for one example therefore has the form:
$\delta_1$ (intensity 1); $\delta_2$ (intensity 2); . . . ; $\delta_i$ (intensity i); . . . ; $\delta_n$ (intensity n)

The intensity of sharp signals correlates with the height of the signals in a printed example of an NMR spectrum in cm and shows the true ratios of the signal intensities. In the case of broad signals, several peaks or the middle of the signal and the relative intensity thereof may be shown in comparison to the most intense signal in the spectrum.

Calibration of the chemical shift of $^1$H NMR spectra is accomplished using tetramethylsilane and/or the chemical shift of the solvent, particularly in the case of spectra which are measured in DMSO. Therefore, the tetramethylsilane peak may but need not occur in NMR peak lists.

The lists of the $^1$H NMR peaks are similar to the conventional $^1$H NMR printouts and thus usually contain all peaks listed in a conventional NMR interpretation.

In addition, like conventional $^1$H NMR printouts, they may show solvent signals, signals of stereoisomers of the target compounds which are likewise provided by the invention, and/or peaks of impurities.

In the reporting of compound signals within the delta range of solvents and/or water, our lists of $^1$H NMR peaks show the standard solvent peaks, for example peaks of DMSO in DMSO-$D_6$ and the peak of water, which usually have a high intensity on average.

The peaks of stereoisomers of the target compounds and/or peaks of impurities usually have a lower intensity on average than the peaks of the target compounds (for example with a purity of >90%).

Such stereoisomers and/or impurities may be typical of the particular preparation process. Their peaks can thus help in this case to identify the reproduction of our preparation process with reference to "by-product fingerprints".

An expert calculating the peaks of the target compounds by known methods (MestreC, ACD simulation, but also with empirically evaluated expected values) can, if required, isolate the peaks of the target compounds, optionally using additional intensity filters. This isolation would be similar to the peak picking in question in conventional $^1$H NMR interpretation.

Further details of $^1$H NMR peak lists can be found in the Research Disclosure Database Number 564025.

General Synthesis of 4,5-Disubstituted 2-(hetaryl)indazoles of the Formula (I); Examples 1 to 52

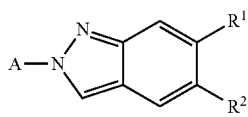

Step 1: Synthesis of Compounds of the Formula (A-3)

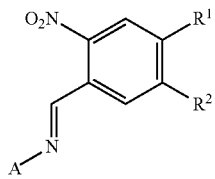

19.6 mmol of a heterocyclic amino compound (A-2), 1.0 mmol of para-toluenesulphonic acid (PTSA), 5.9 mmol of 4A molecular sieve and magnesium sulphate were added to a solution of 119.6 mmol of ortho-nitrobenzaldehyde of the formula (A-1) in 75 mmol of toluene. The reaction mixture was then stirred at reflux temperature for 18 hours. Thin-layer chromatogram (mobile phase: ethyl acetate) showed that the reaction had ended. The reaction mixture was filtered and the filtrate gave, after concentration, the crude products (A-3), which were reacted further without further purification.

Step 2: Synthesis of 4,5-disubstituted 2-(hetaryl)indazoles of the Formula (I)

At room temperature, 58.8 mmol of triethyl phosphite were added to 19.6 mmol of the compounds of the formula (A-3). The reaction mixture was then stirred at 140° C. for about 18 hours. Thin-layer chromatogram (mobile phase: petroleum ether:ethyl acetate=1:1) showed that the reaction had ended. After concentration of the reaction mixture under reduced pressure, the residue that remained was purified by CombiFlash chromatography (mobile phase gradient: 100% petroleum ether to 70% ethyl acetate/petroleum ether).

General Synthesis of 4-Substituted 2-(hetaryl)indazole-5-carboxylic Acids of the Formula (I, $R^2$=COOH)

Method A:

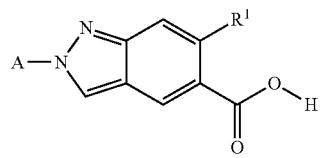

At room temperature, 21.1 mmol of aqueous sodium hydroxide solution were added to 7.03 mmol of the compounds of the formula (I; $R^2$=COOCH$_3$) in a mixture of 10 ml of tetrahydrofuran and 10 ml of water. The reaction mixture was then stirred at 70° C. for about 18 hours. Thin-layer chromatogram (mobile phase: petroleum ether: ethyl acetate=1:1) showed that the reaction had ended. After concentration of the reaction mixture under reduced pressure, the residue that remained was adjusted with 12N hydrochloric acid to pH=3. Thereafter, the precipitated solid was filtered off, washed with water and dried.

Method B:

1 equiv. of the compounds of the formula (I; $R^2$=COOCH$_3$) were dissolved in methanol (3 ml/mmol), and 1.5 equiv. of 1M lithium hydroxide solution were added at room temperature. The reaction mixture was then stirred at 50° C. for 2 hours. Subsequently, the reaction mixture was adjusted to pH=3 by addition of 1M hydrochloric acid. If a solid had formed, this was filtered off and dried. Otherwise, the reaction solution was extracted with dichloromethane (3×3 ml/mmol). The combined organic phases were dried over magnesium sulphate and concentrated under reduced pressure.

2-(1-Methyl-1H-pyrazol-4-yl)-2H-indazole-5-carboxylic acid (I, A=1-methyl-1H-pyrazol-4-yl; $R^1$=H, $R^2$=COOH)

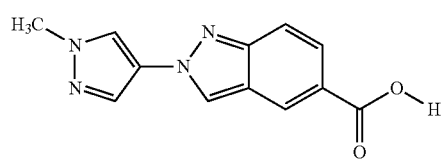 [SMILES: Cn1cc(-n2cc3cc(C(=O)O)ccc3n2)cn1]

This compound was prepared from 3.46 g (13.5 mmol) of methyl 2-(1-methyl-1H-pyrazol-4-yl)-2H-indazole-5-carboxylate in accordance with the general synthesis mentioned. This gave 2.87 g (88% yield) of the title compound.
APCI MS, m/z=243 [M+H]$^+$ General Synthesis of 4-substituted 2-(hetaryl)indazole-5-carboxamides of the Formula (I, $R^2$=CONHR)

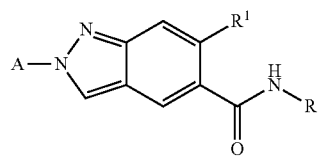

a) Carbonyldiimidazole (CDI) Method

In a first reaction step, at room temperature, 134 mg (0.84 mmol) of carbonyldiimidazole (CDI) were added to a solution of 0.84 mmol of 2-(hetaryl)indazole-5-carboxylic acid in 8 ml of N,N-dimethylformamide, and the reaction mixture was then stirred for 2 hours. In a second reaction step, 1.04 mmol of 60% pure sodium hydride were added at room temperature to 1.04 mmol of the reactive component prepared in this manner in 8 ml of N,N-dimethylformamide. After one hour, 0.84 mmol of the respective amine were added and the mixture was stirred at room temperature for a further 18 hours. For work-up, water was added, the reaction was concentrated under reduced pressure and the residue that remained was purified by column chromatography on silica gel (mobile phase gradient: dichloromethane:methanol=50:1 to 5:1).

b) Phosgene Method

In a first reaction step, at 0° C., 5 drops of N,N-dimethylformamide and 3 mmol of phosgene were added to a solution of 1.0 mmol of 2-(hetaryl)indazole-5-carboxylic acid in 12 ml of dichloromethane. The reaction mixture was then stirred at room temperature for 3 hours. Concentration of the reaction mixture under reduced pressure gave 2-(hetaryl)indazole-5-carbonyl chloride.

In a second reaction step, 1.0 mmol of the 2-(hetaryl)indazole-5-carbonyl chloride in 15 ml of dichloromethane was stirred at room temperature, and 3.0 mmol of the respective amine and 4 mmol of N,N-diisopropylethylamine (DIPEA) were added. The reaction mixture was then stirred at room temperature for 18 hours. For work-up, the reaction mixture was concentrated under reduced pressure and the residue that remained was purified by CombiFlash (mobile phase gradient: dichloromethane to 4% methanol in dichloromethane).

General Synthesis of 4-Substituted 2-(hetaryl)-5-trifluoromethylindazoles of the Formula (I, R²=CF₃)

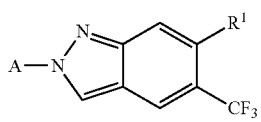

Step 1: Synthesis of 2-nitro-5-(trifluoromethyl)benzaldehyde (A-1)

At room temperature, 63.7 mmol of N,N-dimethylformamide O,O-dimethyl acetal were added dropwise to a solution of 4.9 mmol of 2-methyl-1-nitro-4-(trifluoromethyl)benzene in 15 ml of N,N-dimethylformamide. The reaction mixture was then stirred at 140° C. for 18 hours. The reaction mixture was then concentrated under reduced pressure and 15 ml of tetrahydrofuran and 15 ml of water were added to the residue that remained. 147 mmol of sodium periodate (NaIO₄) were then added, and the reaction mixture was stirred at room temperature for a further 18 hours. The reaction mixture was then extracted with dichloromethane and the organic phase was concentrated under reduced pressure. The residue that remained was chromatographed by ISCO (mobile phase gradient: 100% petroleum ether to 10% ethyl acetate in petroleum ether).

Step 2: Synthesis of Compounds of the Formula (A-3; R¹=H; R²=CF₃)

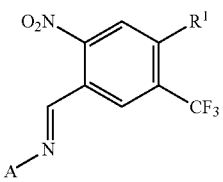

1.095 mmol of a heterocyclic amino compound (A-2), 0.046 mmol PTSA, 0.27 mmol 4A molecular sieve and magnesium sulphate were added to a solution of 0.913 mmol of 2-nitro-5-trifluoromethylbenzaldehyde (A-1, R¹=H) in 75 ml of toluene. The reaction mixture was then stirred at reflux temperature for 18 hours. The reaction mixture was filtered and the filtrate gave, after concentration, the crude products (A-3), which were reacted further without further purification.

Step 3: Synthesis of 4-substituted 2-(hetaryl)-5-trifluoromethylindazoles of the Formula (I; R¹=H; R²=CF₃)

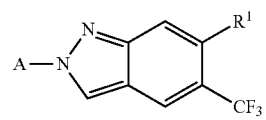

At room temperature, 2.739 mmol of triethyl phosphite were added to 0.913 mmol of the compounds of the formula (A-3). The reaction mixture was then stirred at 140° C. for about 18 hours. Thin-layer chromatogram (mobile phase: petroleum ether:ethyl acetate=1:1) showed that the reaction had ended. After concentration of the reaction mixture under reduced pressure, the residue that remained was chromatographed by ISCO (mobile phase gradient: 100% petroleum ether to 20% ethyl acetate/petroleum ether).

Example 49: 5-[2-Fluoro-4-methyl-5-(2,2,2-trifluoroethylsuphanyl)phenyl]-2-(3-pyridyl)indazole

Step 1

Synthesis of (E/Z)-N-[(5-bromo-2-nitrophenyl)methylidene]pyridine-3-amine

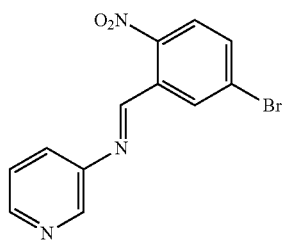 [SMILES: O=[N+]([O-])c1ccc(Br)cc1/C=N/c1cccnc1]

35.75 g (155.42 mmol) of 5-bromo-2-nitrobenzaldehyde, 15.04 g (159.81 mmol) of pyridine-3-amine and 200 ml of ethanol were added to a 500 ml round-bottom flask. The reaction mixture was then stirred on an oil bath at 80° C. for about 18 hours. The course of the reaction was monitored by LCMS. Thereafter, the reaction mixture was concentrated under reduced pressure. This gave 45 g of crude (Z/E)-N-[(5-bromo-2-nitrophenyl)methylidene]pyridine-3-amine as a brown solid.

LC-MS (ES, m/z): 305.9 [M+H]

Step 2

Synthesis of 5-bromo-2-(3-pyridyl)-2H-indazole

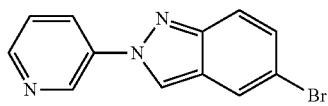 [SMILES: Brc1ccc2nn(-c3cccnc3)cc2c1]

45 g (147.00 mmol) of (Z/E)-N-[(5-bromo-2-nitrophenyl)methylidene]pyridine-3-amine and 75 g (451.38 mmol) of triethyl phosphite were stirred in a 500 ml round-bottom flask. The solution was then stirred in an oil bath at 90° C. for about 18 hours. The course of the reaction was monitored by LCMS. The reaction mixture was then washed with sodium hydroxide. The solution formed was extracted three times with 50 ml of ethyl acetate and the organic phases were combined. The organic phase was then washed three times with 50 ml of water and, after drying, concentrated under reduced pressure. The residue that remained was purified by column chromatography using the gradient ethyl acetate:petroleum ether=(25:75). This gave 12.3 g (yield: 30% of theory) of 5-bromo-2-(3-pyridyl)-2H-indazole as a yellow solid.

LC-MS (ES, m/z): 274.0 [M+H] and 276.0[M+H]

$^1$H-NMR (400.0 MHz, CDCl$_3$): δ=9.21 (s, 1H), 8.71 (d, J=4.0 Hz, 1H), 8.44 (s, 1H), 8.32 (d, J=7.2 Hz, 1H), 7.92 (s, 1H), 7.70 (d, J=9.2 Hz, 1H), 7.54-7.57 (m, 1H), 7.43 (d, J=9.2 Hz, 1H) ppm.

Step 3

5-[2-Fluoro-4-methyl-5-(2,2,2-trifluoroethylsulphanyl)phenyl]-2-(3-pyridyl)indazole

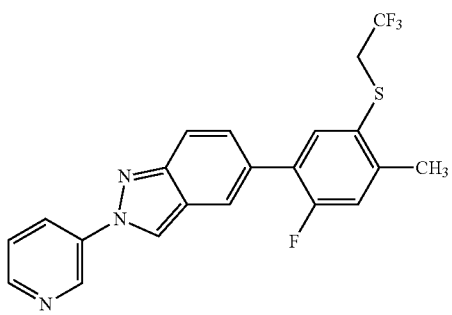 [SMILES: Cc1cc(F)c(-c2ccc3nn(-c4cccnc4)cc3c2)cc1SCC(F)(F)F]

Similar to the reaction procedure from US 2013/0267493, a solution of 77 mg (0.73 mmol) of sodium carbonate in 375 µl of water and 1.5 ml of 1,4-dioxane were added to a mixture of 100 mg (365 µmol) of 5-bromo-2-(3-pyridyl) indazole (cf. Example 49, step 2) and 105 mg (392 µmol) of [2-fluoro-4-methyl-5-(2,2,2-trifluoroethylsulphanyl)phenyl] boronic acid. The reaction mixture was repeatedly flushed with a stream of argon, 15 mg (19 µmol) of [1,1'-bis(diphenylphosphino)ferrocene]dichloropalladium(II) were added and the vessel was closed. The mixture was heated in a CEM Discover microwave reactor at 90° C. for 40 min and, after cooling to room temperature, filtered through a depth filter which was rinsed with ethyl acetate. The reaction was carried out three times in total and the batches were combined prior to purification. After the solvent has been removed under reduced pressure, the residue is separated chromatographically by MPLC on silica gel (gradient: ethyl acetate/cyclohexane 0:100→50:50). This gave 392 mg (93% pure, 86% yield) of 5-[2-fluoro-4-methyl-5-(2,2,2-trifluoroethylsulphanyl)phenyl]-2-(3-pyridyl)indazole.

$^1$H-NMR (400.0 MHz, d$_6$-DMSO): δ=9.374 (3.5); 9.367 (3.5); 9.306 (5.9); 9.305 (5.9); 8.686 (2.4); 8.682 (2.6); 8.674 (2.5); 8.671 (2.6); 8.541 (1.3); 8.537 (1.5); 8.534 (1.5); 8.531 (1.3); 8.520 (1.5); 8.516 (1.5); 8.513 (1.7); 8.510 (1.4); 8.228 (0.3); 7.975 (3.7); 7.860 (2.7); 7.837 (3.1); 7.774 (3.1); 7.754 (3.2); 7.687 (1.9); 7.675 (1.9); 7.666 (1.9); 7.655 (1.9); 7.558 (1.3); 7.553 (2.2); 7.549 (1.3); 7.535 (1.1); 7.531 (2.0); 7.527 (1.1); 7.338 (2.8); 7.309 (2.7); 4.066 (1.3); 4.040 (4.2); 4.014 (4.4); 3.988 (1.5); 3.335 (28.4); 2.893 (0.4); 2.528 (0.5); 2.514 (12.2); 2.510 (24.6); 2.505 (32.5); 2.501 (24.0); 2.496 (11.9); 2.453 (16.0); 2.406 (0.4); 1.397 (1.7).

Example 50: 5-[4-Methyl-3-(2,2,2-trifluoroethylsulphanyl)phenyl]-2-(3-pyridyl)indazole

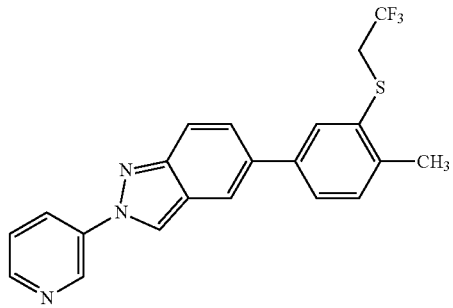 [SMILES: Cc1ccc(-c2ccc3nn(-c4cccnc4)cc3c2)cc1SCC(F)(F)F]

The preparation of 5-[4-methyl-3-(2,2,2-trifluoroethylsulphanyl)phenyl]-2-(3-pyridyl)indazole was carried out analogously to the synthesis of 5-[2-fluoro-4-methyl-5-(2,2,2-trifluoroethylsulphanyl) phenyl]-2-(3-pyridyl)indazole. Here, 100 mg (365 µmol) of 5-bromo-2-(3-pyridyl)indazole (cf. Example 49, step 2) and 98 mg (0.39 mmol) of [4-methyl-3-(2,2,2-trifluoroethylsulphanyl)phenyl]boronic acid were employed. The reaction was carried out twice and the batches were combined prior to purification. This gave 149 mg of 5-[4-methyl-3-(2,2,2-trifluoroethylsulphanyl) phenyl]-2-(3-pyridyl)indazole (97% pure, 50% yield).

$^1$H-NMR (400.0 MHz, d$_6$-DMSO): δ=9.377 (3.4); 9.371 (3.5); 9.274 (5.9); 9.272 (6.2); 8.678 (2.3); 8.675 (2.6); 8.666 (2.5); 8.663 (2.7); 8.542 (1.4); 8.539 (1.6); 8.536 (1.6); 8.532 (1.4); 8.522 (1.5); 8.518 (1.6); 8.515 (1.7); 8.511 (1.5); 8.072 (4.1); 7.858 (2.7); 7.855 (2.3); 7.851 (3.7); 7.847 (3.9); 7.835 (3.6); 7.731 (2.9); 7.727 (2.9); 7.708 (2.1); 7.704 (2.1); 7.681 (1.9); 7.669 (1.9); 7.660 (1.9); 7.648 (1.9); 7.587 (1.9); 7.583 (1.9); 7.568 (2.3); 7.563 (2.3); 7.380 (3.2); 7.360 (2.6); 4.171 (1.3); 4.145 (4.3); 4.119 (4.4); 4.093 (1.5); 3.349 (0.4); 3.334 (63.3); 2.673 (0.3); 2.526 (0.8); 2.513 (18.3); 2.509 (37.9); 2.504 (50.6); 2.499 (37.8); 2.495 (19.1); 2.416 (16.0); 2.331 (0.3); 1.397 (0.4).

Example 51: 5-[2,4-Dimethyl-5-(2,2,2-trifluoroethylsulphanyl)phenyl]-2-(3-pyridyl)indazole

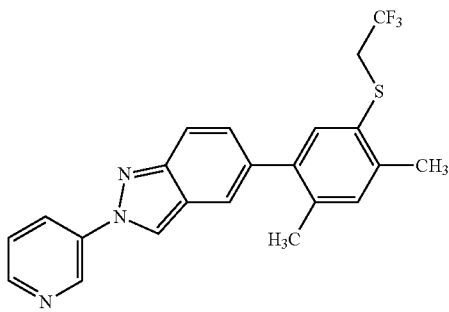 [SMILES: Cc1cc(C)c(-c2ccc3nn(-c4cccnc4)cc3c2)cc1SCC(F)(F)F]

Similar to the reaction procedure from T. Furuya et al., *J. Am. Chem. Soc.*, 2010, 132, 3793-3807, under argon, 60 mg (0.43 mmol) of potassium carbonate, 100 mg (289 μmol) of 2-[2,4-dimethyl-5-(2,2,2-trifluoroethylsulphanyl)phenyl]-4,4,5,5-tetramethyl-1,3,2-dioxaborolane and 17 mg (15 μmol) of tetrakis(triphenylphosphine)palladium were added to a solution of 79 mg (0.28 mmol) of 5-bromo-2-(3-pyridyl)indazole (cf. Example 49, step 2) in 1.0 ml of 1,2-dimethoxyethane and 1.0 ml of water. The reaction mixture was stirred at 100° C. for 3 hours and, after cooling to room temperature, water was added. The phases were separated and the aqueous phase was extracted with ethyl acetate. The combined organic phases were washed with saturated sodium chloride solution and dried with sodium sulphate, and the solvent was removed under reduced pressure. The residue was separated chromatographically by MPLC on silica gel (gradient: ethyl acetate/cyclohexane 0:100→60:40) and then once more by HPLC (gradient: H₂O/acetonitrile 90:10→0:100). This gave 37 mg (98% pure, 30% yield) of 5-[2,4-dimethyl-5-(2,2,2-trifluoroethylsulphanyl)phenyl]-2-(3-pyridyl)indazole.

¹H-NMR (400.0 MHz, d₆-DMSO): δ=9.366 (3.2); 9.359 (3.2); 9.247 (5.6); 9.245 (5.6); 8.679 (2.2); 8.676 (2.4); 8.667 (2.3); 8.664 (2.4); 8.533 (1.3); 8.529 (1.5); 8.526 (1.5); 8.523 (1.3); 8.512 (1.4); 8.508 (1.5); 8.505 (1.6); 8.502 (1.4); 7.810 (2.7); 7.788 (3.0); 7.706 (4.1); 7.681 (1.8); 7.670 (1.7); 7.661 (1.7); 7.649 (1.7); 7.441 (5.8); 7.352 (2.5); 7.348 (2.5); 7.329 (2.3); 7.325 (2.4); 7.236 (4.8); 3.979 (1.3); 3.953 (4.0); 3.927 (4.2); 3.901 (1.4); 3.335 (13.6); 2.528 (0.4); 2.524 (0.6); 2.515 (8.4); 2.510 (17.5); 2.506 (23.5); 2.501 (17.5); 2.497 (8.7); 2.409 (14.6); 2.242 (16.0); 0.000 (1.1).

Example 52: 5-[2-Fluoro-4-methyl-5-(2,2,2-trifluoroethylsulphinyl)phenyl]-2-(3-pyridyl)indazole

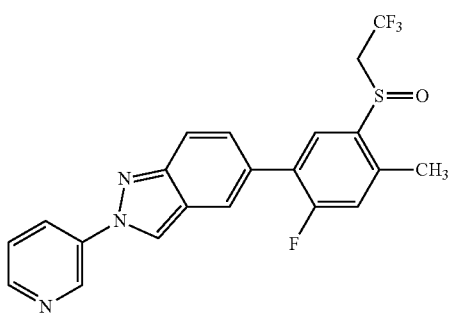 [SMILES: Cc1cc(F)c(-c2ccc3nn(-c4cccnc4)cc3c2)cc1S(=O)CC(F)(F)F]

At 0° C., 56 mg (0.23 mmol) of meta-chloroperbenzoic acid (70% pure) were added to a solution of 56 mg (0.23 mmol) of 5-[2-fluoro-4-methyl-5-(2,2,2-trifluoroethylsulphanyl)phenyl]-2-(3-pyridyl)indazole (Example 49) in 5 ml of methylene chloride. The reaction mixture was stirred at room temperature for 2 hours, and saturated sodium carbonate solution was then added. After 15 minutes, the phases were separated, the aqueous phase was extracted with methylene chloride and the combined organic phases were dried over sodium sulphate. The solvent was removed under reduced pressure and the residue was separated chromatographically by MPLC on silica gel (gradient: ethyl acetate/cyclohexane 0:100→50:50). This gave 60 mg (100% pure, 62% yield) of 5-[2-fluoro-4-methyl-5-(2,2,2-trifluoroethylsulphinyl)phenyl]-2-(3-pyridyl)indazole.

¹H-NMR (400.0 MHz, d₆-DMSO): δ=9.377 (3.5); 9.371 (3.5); 9.323 (6.1); 9.321 (5.9); 8.692 (2.5); 8.688 (2.7); 8.680 (2.6); 8.677 (2.7); 8.545 (1.4); 8.541 (1.6); 8.538 (1.5); 8.535 (1.4); 8.524 (1.6); 8.521 (1.6); 8.518 (1.7); 8.514 (1.4); 8.059 (7.0); 8.039 (3.4); 7.900 (2.8); 7.878 (3.3); 7.693 (1.9); 7.692 (1.9); 7.681 (1.8); 7.673 (1.8); 7.661 (1.8); 7.660 (1.8); 7.613 (1.3); 7.609 (2.3); 7.605 (1.3); 7.591 (1.2); 7.587 (2.0); 7.582 (1.1); 7.447 (2.6); 7.418 (2.5); 4.298 (0.5); 4.288 (0.5); 4.271 (0.7); 4.261 (1.7); 4.243 (0.4); 4.233 (2.1); 4.203 (1.8); 4.193 (0.6); 4.175 (0.6); 4.166 (0.6); 3.329 (42.3); 2.677 (0.4); 2.672 (0.5); 2.668 (0.4); 2.525 (1.4); 2.512 (28.8); 2.508 (57.1); 2.503 (74.6); 2.499 (54.0); 2.494 (25.9); 2.451 (16.0); 2.334 (0.4); 2.330 (0.5); 2.325 (0.4); 1.990 (0.7); 1.176 (0.4); 0.008 (1.4); 0.000 (41.3); -0.009 (1.3).

In an analogous manner, the compound 74 listed in Tables 1 and 3 was obtained from compound 63 by oxidation of the sulphur.

Example 53: 5-[4-Methyl-3-(2,2,2-trifluoroethylsulphinyl)phenyl]-2-(3-pyridyl)indazole

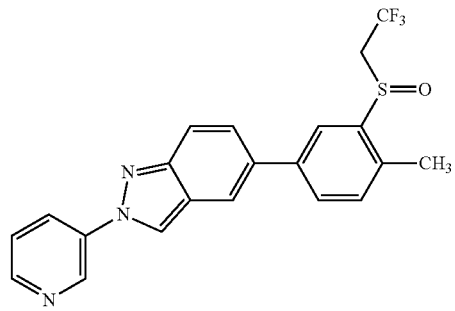 [SMILES: Cc1ccc(-c2ccc3nn(-c4cccnc4)cc3c2)cc1S(=O)CC(F)(F)F]

The preparation of 5-[4-methyl-3-(2,2,2-trifluoroethylsulphinyl)phenyl]-2-(3-pyridyl)indazole was carried out analogously to the synthesis of Example 52. Here, 104 mg (217 μmol) of 5-[4-methyl-3-(2,2,2-trifluoroethylsulphanyl)phenyl]-2-(3-pyridyl)indazole and 54 mg (0.22 mmol) of meta-chloroperbenzoic acid (70% pure) were employed. This gave 64 mg (100% pure, 71% yield) of 5-[4-methyl-3-(2,2,2-trifluoroethylsulphinyl)phenyl]-2-(3-pyridyl)indazole.

¹H-NMR (400.0 MHz, d₆-DMSO): δ=9.379 (3.6); 9.373 (3.7); 9.294 (6.2); 9.293 (6.0); 8.686 (2.5); 8.683 (2.7); 8.674 (2.7); 8.671 (2.7); 8.546 (1.4); 8.542 (1.7); 8.539 (1.6); 8.536 (1.4); 8.525 (1.6); 8.521 (1.7); 8.518 (1.8); 8.515 (1.5); 8.196 (4.0); 8.191 (4.2); 8.144 (4.2); 7.910 (2.1); 7.900 (2.9); 7.890 (2.4); 7.885 (2.4); 7.877 (3.7); 7.778 (2.9); 7.774 (2.8); 7.755 (2.0); 7.751 (2.0); 7.689

(1.9); 7.677 (1.9); 7.669 (1.9); 7.657 (1.8); 7.485 (3.0); 7.465 (2.7); 4.257 (0.4); 4.247 (0.6); 4.230 (0.8); 4.220 (1.9); 4.206 (1.8); 4.193 (2.0); 4.178 (2.0); 4.166 (0.8); 4.151 (0.7); 4.142 (0.4); 3.331 (136.6); 2.676 (0.5); 2.672 (0.7); 2.667 (0.5); 2.525 (1.9); 2.512 (38.7); 2.507 (77.7); 2.503 (102.1); 2.498 (75.9); 2.494 (38.6); 2.437 (16.0); 2.334 (0.5); 2.330 (0.7); 2.325 (0.5); 1.989 (0.6); 0.008 (0.5); 0.000 (14.6); −0.008 (0.7).

Example 54: 5-[2,4-Dimethyl-5-(2,2,2-trifluoroethylsulphinyl)phenyl]-2-(3-pyridyl)indazole

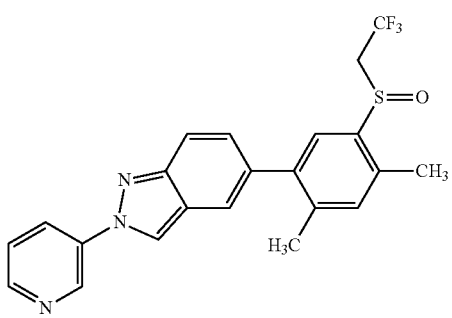 [SMILES: Cc1cc(C)c(S(=O)CC(F)(F)F)cc1-c1ccc2nn(-c3cccnc3)cc2c1]

The preparation of 5-[2,4-dimethyl-5-(2,2,2-trifluoroethylsulphinyl)phenyl]-2-(3-pyridyl)indazole was carried out analogously to the synthesis of Example 52. Here, 117 mg of 5-[2,4-dimethyl-5-(2,2,2-trifluoroethylsulphanyl)phenyl]-2-(3-pyridyl)indazole (purity <70%) and 71 mg (0.28 mmol) of meta-chloroperbenzoic acid (70% pure) were employed. This gave 54 mg (100% pure) of 5-[2,4-dimethyl-5-(2,2,2-trifluoroethylsulphinyl)phenyl]-2-(3-pyridyl)indazole.

$^1$H-NMR (400.0 MHz, $d_6$-DMSO): δ=9.371 (3.3); 9.365 (3.5); 9.263 (5.7); 8.681 (2.5); 8.672 (2.5); 8.669 (2.6); 8.536 (1.6); 8.534 (1.6); 8.515 (1.7); 8.513 (1.7); 8.510 (1.4); 7.847 (2.6); 7.825 (2.9); 7.788 (4.4); 7.753 (6.3); 7.687 (1.8); 7.675 (1.8); 7.666 (1.8); 7.654 (1.7); 7.404 (2.3); 7.400 (2.4); 7.381 (2.2); 7.378 (2.2); 7.331 (4.8); 4.173 (1.1); 4.146 (3.4); 4.118 (3.5); 4.091 (1.2); 3.329 (83.0); 2.672 (0.9); 2.562 (0.3); 2.507 (107.3); 2.503 (138.4); 2.498 (111.3); 2.403 (14.9); 2.341 (16.0); 1.989 (0.6); 0.146 (0.9); 0.000 (175.9); −0.150 (0.9).

Example 55: 2-(3-Pyridyl)-5-[4-(trifluoromethyl) pyrazol-1-yl]indazole

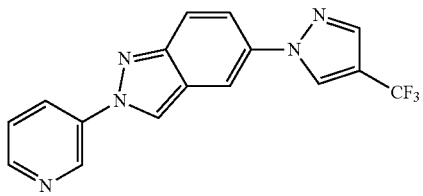 [SMILES: FC(F)(F)c1cnn(-c2ccc3nn(-c4cccnc4)cc3c2)c1]

Similar to the reaction procedure from J. C. Antilla et al., J. Org. Chem., 2004, 69, 5578-5587, under argon, 100 mg (365 µmol) of 5-bromo-2-(3-pyridyl)indazole (cf. Example 49, step 2) and 20 µl (0.12 mmol) of trans-N,N'-dimethylcyclohexane-1,2-diamine in 1.0 ml of degassed toluene were added to a mixture of 12 mg (63 µmol) copper(I) iodide, 41 mg (0.30 mmol) of 4-(trifluoromethyl)-1H-pyrazole and 88 mg (0.64 mmol) of potassium carbonate. The vessel was closed and the reaction mixture was heated in a CEM Discover microwave reactor to 120° C. for 18 hours. After cooling to room temperature, the mixture was filtered though a depth filter which was subsequently rinsed with ethyl acetate. After the solvent has been removed under reduced pressure, the residue is separated chromatographically by MPLC on silica gel (gradient: ethyl acetate/cyclohexane 0:100→50:50). This gave 17 mg (94% pure, 16% yield) of 2-(3-pyridyl)-5-[4-(trifluoromethyl)pyrazol-1-yl]indazole.

$^1$H-NMR (400.0 MHz, $d_6$-DMSO): δ=9.379 (2.7); 9.361 (13.4); 9.259 (7.9); 9.210 (0.4); 8.695 (2.3); 8.686 (2.4); 8.550 (2.2); 8.547 (2.6); 8.544 (2.5); 8.541 (2.1); 8.529 (2.4); 8.526 (2.6); 8.523 (2.7); 8.520 (2.2); 8.285 (8.4); 8.237 (9.1); 7.947 (16.0); 7.943 (15.7); 7.693 (2.6); 7.681 (2.6); 7.672 (2.6); 7.660 (2.5); 5.759 (0.7); 3.333 (56.9); 2.678 (0.5); 2.673 (0.7); 2.527 (2.0); 2.513 (40.5); 2.509 (79.4); 2.505 (102.3); 2.500 (75.1); 2.336 (0.5); 2.331 (0.6); 1.245 (0.5); 1.230 (0.5); 0.146 (0.9); 0.022 (0.5); 0.008 (8.3); 0.000 (189.5); −0.009 (7.9); −0.150 (1.0).

Example 56: 2-(3-Pyridyl)-5-[3-(trifluoromethyl) pyrazol-1-yl]indazole

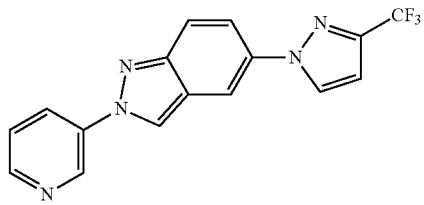 [SMILES: FC(F)(F)c1ccn(-c2ccc3nn(-c4cccnc4)cc3c2)n1]

The preparation of 2-(3-pyridyl)-5-[3-(trifluoromethyl) pyrazol-1-yl]indazole was carried out analogously to the synthesis of Example 55. Here, 100 mg (735 µmol) of 3-(trifluoromethyl)-1H-pyrazole, 242 mg (882 µmol) of 5-bromo-2-(3-pyridyl)indazole (cf. Example 49, step 2), 7.1 mg (37 µmol) of copper(I) iodide, 213 mg (1.54 mmol) of potassium carbonate and 24 µl (0.15 mmol) of trans-N,N'-dimethylcyclohexane-1,2-diamine were employed. The reaction was carried out in degassed toluene (1 ml) and the reaction time was 6 hours. This gave 167 mg (100% pure, 69% yield) of 2-(3-pyridyl)-5-[3-(trifluoromethyl)pyrazol-1-yl]indazole.

$^1$H-NMR (400.0 MHz, $d_6$-DMSO): δ=9.375 (8.8); 9.368 (8.8); 9.346 (16.0); 8.809 (7.3); 8.806 (7.4); 8.699 (5.9); 8.696 (6.4); 8.688 (6.1); 8.684 (6.3); 8.547 (3.4); 8.543 (3.9); 8.540 (3.8); 8.537 (3.4); 8.526 (3.7); 8.522 (3.9); 8.519 (4.1); 8.516 (3.4); 8.318 (0.5); 8.277 (9.1); 8.274 (8.8); 7.968 (3.2); 7.944 (11.9); 7.930 (9.9); 7.925 (9.3); 7.907 (2.6); 7.902 (2.8); 7.695 (4.7); 7.683 (4.6); 7.674 (4.6); 7.662 (4.4); 7.076 (8.5); 7.070 (8.5); 3.332 (215.6); 2.677 (0.9); 2.673 (1.2); 2.669 (0.9); 2.526 (3.4); 2.513 (66.6); 2.508 (131.4); 2.504 (171.9); 2.499 (127.4); 2.335 (0.8); 2.331 (1.2); 2.326 (0.8); 1.990 (0.6); 0.000 (0.7).

Example 57: 2,5-Bis(3-pyridyl)indazole

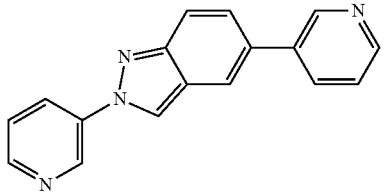 [SMILES: c1cncc(-c2ccc3nn(-c4cccnc4)cc3c2)c1]

Similar to the reaction procedure from H. Dong et al., *Org. Lett.*, 2011, 13, 2726-2729, under argon [1,1'-bis(diphenylphosphino)ferrocene]dichloropalladium(II), 4.0 ml of 1,4-dioxane, 1.0 ml of water and 100 mg (365 µmol) of 5-bromo-2-(3-pyridyl)indazole (cf. Example 49, step 2) were added to a mixture of 58 mg (0.47 mmol) of 3-pyridylboronic acid, 155 mg (1.46 mmol) of sodium carbonate and 13.0 mg (18 µmol). The reaction mixture was heated at 80° C. for 2.5 hours and, after cooling to room temperature, filtered through cotton and then made basic with 1 M aqueous sodium hydroxide solution. The phases were separated and the aqueous phase was extracted repeatedly with methylene chloride. The combined organic phases were dried with sodium sulphate and the solvent was removed under reduced pressure. The residue was separated chromatographically by MPLC on silica gel (gradient: ethyl acetate/cyclohexane 0:100→100:0). This gave 80 mg (100% pure, 81% yield) of 2,5-bis(3-pyridyl)indazole.

$^1$H-NMR (400.0 MHz, $d_6$-DMSO): δ=9.384 (9.1); 9.377 (9.3); 9.309 (16.0); 8.988 (8.7); 8.983 (8.9); 8.685 (5.7); 8.682 (6.6); 8.673 (6.1); 8.670 (6.6); 8.591 (5.6); 8.587 (6.3); 8.579 (6.0); 8.575 (6.2); 8.554 (3.3); 8.550 (3.9); 8.547 (4.0); 8.544 (3.5); 8.533 (3.6); 8.529 (4.0); 8.527 (4.3); 8.523 (3.6); 8.318 (0.3); 8.179 (3.3); 8.173 (4.8); 8.169 (3.6); 8.154 (15.7); 7.898 (6.3); 7.876 (8.7); 7.754 (7.1); 7.750 (7.3); 7.732 (5.3); 7.727 (5.5); 7.686 (5.1); 7.674 (5.0); 7.665 (5.0); 7.653 (4.8); 7.528 (4.8); 7.516 (4.7); 7.508 (4.6); 7.496 (4.4); 3.332 (103.5); 2.677 (0.7); 2.673 (0.9); 2.669 (0.7); 2.526 (2.4); 2.508 (102.3); 2.504 (136.8); 2.499 (104.3); 2.335 (0.6); 2.331 (0.9); 2.326 (0.7); 1.990 (0.4); 1.259 (0.4); 1.250 (0.3); 1.230 (0.5); 0.000 (5.7).

Example 58: 5-(1-Methylpyrazol-4-yl)-2-(3-pyridyl) indazole

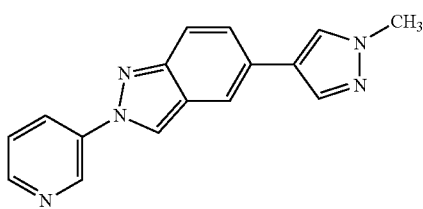 [SMILES: Cn1cc(-c2ccc3nn(-c4cccnc4)cc3c2)cn1]

Similar to the reaction procedure from Ch. O. Ndubaku et al., *J. Med. Chem.*, 2013, 56, 4597-4610, 1.2 ml of water and 0.6 ml of acetonitrile were added to a mixture of 100 mg (365 µmol) of 5-bromo-2-(3-pyridyl)indazole (cf. Example 49, step 2) and 107 mg (1.09 mmol) of potassium acetate. The reaction mixture was repeatedly flushed with a stream of argon, and 114 mg (547 µmol) of 1-methyl-4-(4,4,5,5-tetramethyl-1,3,2-dioxaborolan-2-yl)-1H-pyrazole as a solution in 0.6 ml of acetonitrile followed by 42 mg (36 µmol) of tetrakis(triphenylphosphine)palladium were then added. The vessel was closed and the reaction mixture was heated in a CEM Discover microwave reactor to 120° C. for 60 min. The reaction mixture was filtered through a depth filter which was rinsed with ethyl acetate. The filtrate was washed with water, the phases were separated and the aqueous phase was extracted with ethyl acetate. The combined organic phases were dried with sodium sulphate and the solvent was removed under reduced pressure. The residue was separated chromatographically by MPLC on silica gel (gradient: ethyl acetate/cyclohexane 0:100→100:0). This gave 26 mg (100% pure, 26% yield) of 5-(1-methylpyrazol-4-yl)-2-(3-pyridyl) indazole.

$^1$H-NMR (400.0 MHz, $d_6$-DMSO): δ=9.349 (2.4); 9.343 (2.4); 9.149 (4.2); 9.147 (4.1); 8.656 (1.7); 8.653 (1.8); 8.645 (1.8); 8.641 (1.8); 8.511 (1.0); 8.507 (1.2); 8.504 (1.1); 8.501 (1.0); 8.490 (1.1); 8.486 (1.2); 8.483 (1.2); 8.480 (1.0); 8.199 (4.4); 7.943 (4.6); 7.942 (4.5); 7.913 (3.2); 7.757 (1.8); 7.735 (2.5); 7.664 (1.3); 7.663 (1.3); 7.652 (1.3); 7.643 (1.3); 7.631 (1.3); 7.630 (1.3); 7.618 (2.1); 7.614 (2.1); 7.596 (1.6); 7.592 (1.6); 3.885 (16.0); 3.334 (44.0); 2.526 (0.9); 2.512 (17.3); 2.508 (34.2); 2.504 (44.4); 2.499 (32.6); 2.495 (16.2); 1.232 (0.8); 0.000 (7.6).

Example 59: 5-(2-Pyridyl)-2-(3-pyridyl)indazole

Step 1: 2-(3-Pyridyl)-5-(4,4,5,5-tetramethyl-1,3,2-dioxaborolan-2-yl)indazole (59a)

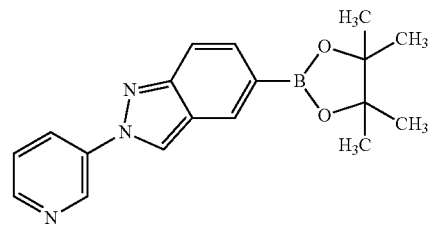 [SMILES: CC1(C)OB(c2ccc3nn(-c4cccnc4)cc3c2)OC1(C)C]

Similar to the reaction procedure from T. Ishiyama et al., *J. Org. Chem.*, 1995, 60, 7508-7510, under argon, degassed 1,4-dioxane (6.0 ml) was added to a mixture of 500 mg (1.82 mmol) of 5-bromo-2-(3-pyridyl)indazole (cf. Example 49, step 2), 486 mg (1.92 mmol) of bis(pinacolato)diboron, 537 mg (5.47 mmol) of potassium acetate, 45 mg (55 µmol) of [1,1'-bis(diphenylphosphino)ferrocene]dichlorpalladium(II) (1:1 adduct with methylene chloride) and 30 mg (55 µmol) of 1,1'-bis(diphenylphosphino)ferrocene. The reaction mixture was heated under reflux for 6 hours and, after cooling to room temperature, filtered through a depth filter which was rinsed with ethyl acetate. Water and methylene chloride were added to the filtrate, the phases were separated and the aqueous phase was extracted with methylene chloride. The combined organic phases were dried with sodium sulphate and the solvent was removed under reduced pressure. The residue was separated chromatographically by MPLC on silica gel (gradient: ethyl acetate/cyclohexane 0:100→50:50). This gave 343 mg (70% pure, 42% yield) of 2-(3-pyridyl)-5-(4,4,5,5-tetramethyl-1,3,2-dioxaborolan-2-yl)indazole as a mixture with 2-(3-pyridyl)indazole. Without further purification, this mixture was used for subsequent reactions.

$^1$H-NMR (400.0 MHz, $d_6$-DMSO): δ=9.349 (1.4); 9.342 (1.4); 9.287 (1.4); 9.285 (1.4); 9.216 (1.2); 9.214 (1.2);

8.678 (0.6); 8.674 (0.6); 8.666 (1.1); 8.663 (1.1); 8.655 (0.5); 8.651 (0.5); 8.523 (0.3); 8.520 (0.4); 8.517 (0.4); 8.513 (0.6); 8.510 (0.4); 8.506 (0.4); 8.503 (0.6); 8.499 (0.5); 8.496 (0.5); 8.492 (0.7); 8.489 (0.4); 8.486 (0.4); 8.217 (1.3); 7.810 (0.6); 7.789 (0.6); 7.754 (0.5); 7.752 (0.5); 7.732 (0.6); 7.730 (0.6); 7.716 (0.6); 7.694 (0.8); 7.673 (0.5); 7.669 (0.5); 7.668 (0.5); 7.661 (0.5); 7.655 (0.6); 7.654 (0.6); 7.648 (0.5); 7.640 (0.5); 7.636 (0.4); 7.559 (0.8); 7.557 (0.8); 7.537 (0.6); 7.535 (0.6); 7.354 (0.4); 7.352 (0.4); 7.349 (0.3); 7.332 (0.3); 7.330 (0.3); 7.157 (0.4); 7.155 (0.4); 7.140 (0.4); 7.139 (0.4); 7.136 (0.4); 7.134 (0.4); 3.939 (0.4); 3.336 (6.5); 2.510 (8.3); 2.505 (10.7); 2.501 (7.9); 1.397 (1.3); 1.328 (16.0); 1.072 (2.3).

Step 2: 5-(2-Pyridyl)-2-(3-pyridyl)indazole

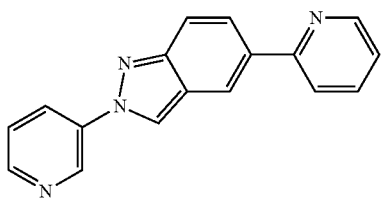 [SMILES: c1ccc(-c2ccc3nn(-c4cccnc4)cc3c2)nc1]

Similar to the reaction procedure from T. Furuya et al., *J. Am. Chem. Soc.*, 2010, 132, 3793-3807, under argon, 39 mg (0.28 mmol) of potassium carbonate, 100 mg (218 μmol) of 2-(3-pyridyl)-5-(4,4,5,5-tetramethyl-1,3,2-dioxaborolan-2-yl)indazole (70% pure) and 11 mg (9.6 μmol) of tetrakis(triphenylphosphine)palladium were added to a solution of 18 μl (0.19 mmol) of 2-bromopyridine in 1.0 ml of 1,2-dimethoxyethane. The reaction mixture was heated at 100° C. for 3 hours and, after cooling to room temperature, water was added. The phases were separated and the aqueous phase was extracted with ethyl acetate. The combined organic phases were dried with sodium sulphate and the solvent was removed under reduced pressure. The residue was separated chromatographically by MPLC on silica gel (gradient: ethyl acetate/cyclohexane 0:100→100:0). This gave 25 mg (100% pure, 41% yield) of 5-(2-pyridyl)-2-(3-pyridyl)indazole.

$^1$H-NMR (400.0 MHz, $d_6$-DMSO): δ=9.378 (9.5); 9.371 (9.4); 9.330 (15.8); 9.329 (16.0); 8.697 (5.2); 8.695 (5.4); 8.684 (11.3); 8.681 (10.9); 8.672 (6.8); 8.669 (6.8); 8.548 (3.8); 8.544 (4.4); 8.541 (4.4); 8.537 (4.3); 8.527 (14.6); 8.520 (5.2); 8.517 (3.9); 8.318 (0.6); 8.167 (6.3); 8.163 (6.1); 8.144 (7.2); 8.140 (7.2); 8.078 (6.7); 8.058 (8.6); 7.926 (3.6); 7.921 (3.6); 7.906 (5.6); 7.902 (5.5); 7.887 (3.1); 7.883 (3.1); 7.856 (8.5); 7.833 (7.4); 7.686 (5.2); 7.675 (5.0); 7.666 (5.0); 7.654 (4.8); 7.373 (4.1); 7.371 (4.3); 7.359 (4.5); 7.355 (4.3); 7.353 (4.0); 7.342 (3.8); 7.340 (3.8); 3.336 (231.2); 2.677 (1.2); 2.672 (1.6); 2.668 (1.2); 2.526 (4.3); 2.512 (90.3); 2.508 (177.5); 2.503 (229.6); 2.499 (167.1); 2.495 (82.5); 2.335 (1.1); 2.330 (1.5); 2.326 (1.1); 2.237 (0.6); 0.008 (2.4); 0.000 (66.9); −0.008 (2.5).

The compounds 61 to 73, 101 and 104 listed in Tables 1 and 3 were prepared in an analogous manner.

Example 60:
2-(3-Pyridyl)-5-pyrimidin-2-yl-indazole

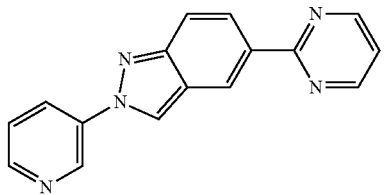 [SMILES: c1cnc(-c2ccc3nn(-c4cccnc4)cc3c2)nc1]

Similar to the reaction procedure from WO 2010/151601, under argon, degassed acetonitrile (1.0 ml) and a solution of 86 mg (0.81 mmol) of sodium carbonate in degassed water (1.0 ml) were added to a mixture of 32 mg (0.20 mmol) of 2-bromopyrimidine, 109 mg (238 μmol) of 2-(3-pyridyl)-5-(4,4,5,5-tetramethyl-1,3,2-dioxaborolan-2-yl)indazole (70% pure) and 7 mg (6 μmol) of tetrakis(triphenylphosphine)palladium. The reaction mixture was heated at 73° C. for 24 hours and, after cooling to room temperature, water and ethyl acetate were added. The phases were separated and the aqueous phase was extracted with ethyl acetate. The combined organic phases were dried with magnesium sulphate and the solvent was removed under reduced pressure. The residue was separated chromatographically by MPLC on silica gel (gradient: ethyl acetate/cyclohexane 50:50→75:2). This gave 60 mg (96% pure, yield 88%) of 2-(3-pyridyl)-5-pyrimidin-2-ylindazole.

$^1$H-NMR (400.0 MHz, $d_6$-DMSO): δ=9.408 (7.7); 9.406 (7.6); 9.373 (4.0); 9.367 (4.0); 8.934 (14.4); 8.922 (16.0); 8.918 (6.0); 8.915 (4.4); 8.695 (2.8); 8.691 (3.0); 8.683 (2.9); 8.679 (3.0); 8.544 (1.8); 8.541 (2.1); 8.538 (2.0); 8.534 (1.8); 8.524 (2.0); 8.520 (2.1); 8.517 (2.2); 8.513 (1.9); 8.418 (3.6); 8.414 (3.5); 8.395 (3.9); 8.391 (3.9); 7.871 (4.3); 7.848 (4.0); 7.694 (2.3); 7.693 (2.3); 7.682 (2.3); 7.681 (2.3); 7.673 (2.3); 7.672 (2.3); 7.661 (2.2); 7.660 (2.2); 7.456 (3.9); 7.443 (7.3); 7.431 (3.8); 5.761 (0.7); 3.340 (50.8); 2.529 (0.6); 2.524 (0.9); 2.516 (14.0); 2.511 (28.9); 2.507 (38.4); 2.502 (27.9); 2.498 (13.6); 0.000 (5.9).

Example 75: N-Cyclopropyl-N-methyl-2-(pyridin-3-yl)-2H-indazole-5-carboxamide

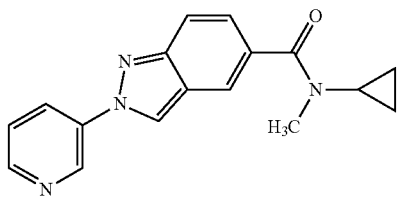 [SMILES: CN(C(=O)c1ccc2nn(-c3cccnc3)cc2c1)C1CC1]

A solution of 57 mg (0.24 mmol) of 2-(pyridin-3-yl)-2H-indazole-5-carboxylic acid, 17 mg (0.24 mmol) of N-methylcyclopropanamine, 55 mg (0.29 mmol) of 1-ethyl-3-(3-dimethylaminopropyl)carbodiimide and 3.2 mg (24 μmol) of 1-hydroxy-1H-benzotriazole in 3 ml of pyridine was stirred at room temperature for 4 hours. The reaction mixture was diluted with water and ethyl acetate. The phases were separated and the aqueous phase was then extracted three times with ethyl acetate. The combined organic phases were dried with sodium sulphate and filtered and the solvent was removed under reduced pressure. The residue was separated chromatographically by MPLC on silica gel (gradient: ethyl acetate/cyclohexane 0:100→100:0). This gave 30 mg (100% pure, 43% yield) of N-cyclopropyl-N-methyl-2-(pyridin-3-yl)-2H-indazole-5-carboxamide.

$^1$H-NMR (400.0 MHz, $d_6$-DMSO): $^1$H-NMR (400.0 MHz, $d_6$-DMSO): δ=9.350 (3.2); 9.343 (3.3); 9.287 (5.6); 9.285 (5.5); 8.681 (2.1); 8.677 (2.3); 8.669 (2.3); 8.666 (2.3); 8.522 (1.2); 8.518 (1.4); 8.515 (1.4); 8.512 (1.3); 8.501 (1.3); 8.497 (1.4); 8.495 (1.5); 8.491 (1.3); 7.978 (3.7); 7.761 (2.5); 7.738 (2.9); 7.677 (1.8); 7.665 (1.7); 7.656 (1.7); 7.644 (1.7); 7.468 (2.0); 7.465 (2.0); 7.446 (1.7); 7.442 (1.8); 5.755 (3.4); 3.319 (22.1); 3.008 (16.0); 2.987 (1.3); 2.978 (0.9); 2.970 (0.7); 2.960 (0.4); 2.672 (0.4); 2.525 (0.7); 2.511 (19.0); 2.507 (38.5); 2.503 (51.1); 2.498 (37.7); 2.494 (18.9); 0.561 (1.8); 0.547 (1.8); 0.458 (2.1); 0.008 (0.8); 0.000 (23.7); −0.008 (1.0) ppm.

Example 76: 5-[4-(Ethylsulphanyl)pyridin-2-yl]-2-(pyridin-3-yl)-2H-indazole

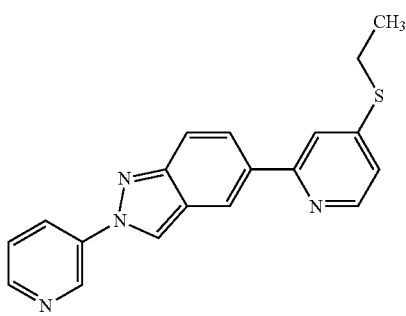 [SMILES: CCSc1ccnc(-c2ccc3nn(-c4cccnc4)cc3c2)c1]

93 mg (0.89 mmol) of sodium ethanethiolate were added to a solution of 27 mg (89 μmol) of 5-(4-chloropyridin-2-yl)-2-(pyridin-3-yl)-2H-indazole in 4 ml of absolute dimethylformamide. The reaction mixture was stirred at room temperature overnight, and then the solvent was removed under reduced pressure. The residue was taken up in ethyl acetate and water, the phases were separated and the aqueous phase was extracted three times with ethyl acetate. The combined organic phases were dried with sodium sulphate and filtered and the solvent was removed under reduced pressure. The residue was separated chromatographically by MPLC on silica gel (gradient: ethyl acetate/cyclohexane 0:100→50:0). This gave 11 mg (100% pure, 38% yield) of 5-[4-(ethylsulphanyl)pyridin-2-yl]-2-(pyridin-3-yl)-2H-indazole.

$^1$H-NMR (400.0 MHz, $d_6$-DMSO): $^1$H-NMR (400.0 MHz, $d_6$-DMSO): δ=9.375 (4.2); 9.369 (4.3); 9.309 (7.2); 8.683 (2.9); 8.680 (3.1); 8.672 (3.1); 8.669 (3.1); 8.545 (6.4); 8.534 (1.8); 8.523 (1.9); 8.519 (2.0); 8.516 (2.1); 8.513 (1.7); 8.486 (4.3); 8.473 (4.4); 8.150 (2.8); 8.146 (2.7); 8.127 (3.2); 8.123 (3.1); 7.852 (5.0); 7.850 (5.1); 7.837 (4.0); 7.814 (3.4); 7.685 (2.3); 7.673 (2.2); 7.664 (2.2); 7.652 (2.1); 7.236 (3.1); 7.232 (3.1); 7.223 (3.1); 7.219 (3.0); 3.318 (62.4); 3.232 (2.2); 3.214 (6.9); 3.195 (7.1); 3.177 (2.3); 2.676 (0.6); 2.671 (0.8); 2.667 (0.6); 2.507 (87.7); 2.502 (113.3); 2.498 (84.3); 2.333 (0.6); 2.329 (0.7); 2.325 (0.5); 1.363 (7.6); 1.345 (16.0); 1.327 (7.4); 1.259 (0.4); 1.250 (0.7); 1.230 (0.6); 0.000 (2.0) ppm.

The compounds 77 to 80 listed in Tables 1 and 3 were prepared in an analogous manner.

Example 81: N-{2,4-Dimethyl-5-[(2,2,2-trifluoroethyl)sulphanyl]phenyl}-2-(pyridin-3-yl)-2H-indazole-5-carboxamide

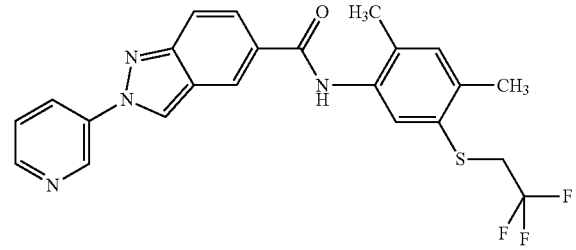 [SMILES: Cc1cc(C)c(SCC(F)(F)F)cc1NC(=O)c1ccc2nn(-c3cccnc3)cc2c1]

Under an atmosphere of argon, 0.53 ml (1.07 mmol) of a 2M solution of trimethylaluminium in toluene was slowly added dropwise to a solution of 251 mg (1.07 mmol) of 2,4-dimethyl-5-[(2,2,2-trifluoroethyl)sulphanyl]aniline in 5 ml of 1,2-dichloroethane. The solution was stirred at room temperature for 30 minutes, 200 mg (0.71 mmol) of methyl 2-(pyridin-3-yl)-2H-indazole-5-carboxylate were added and the mixture was then stirred at 100° C. overnight. After cooling to room temperature, a saturated potassium sodium tartrate solution was added to the reaction mixture carefully, and the mixture was then extracted repeatedly with dichloromethane. The combined organic phases were dried with sodium sulphate and filtered and the solvent was removed under reduced pressure. The residue was separated chromatographically by MPLC on silica gel (gradient: ethyl acetate/cyclohexane 0:100→100:0). This gave 102 mg (90% pure, 28% yield) of N-{2,4-dimethyl-5-[(2,2,2-trifluoroethyl) sulphanyl]phenyl}-2-(pyridin-3-yl)-2H-indazole-5-carboxamide.

$^1$H-NMR (400.0 MHz, $d_6$-DMSO): $^1$H-NMR (400.0 MHz, $d_6$-DMSO): δ=9.967 (3.6); 9.462 (5.6); 9.448 (0.4); 9.390 (3.2); 9.384 (3.3); 8.702 (2.3); 8.699 (2.5); 8.690 (2.4); 8.687 (2.5); 8.557 (5.0); 8.539 (1.5); 8.536 (1.8); 8.533 (1.9); 8.529 (1.5); 7.921 (1.4); 7.918 (1.3); 7.899 (2.6); 7.895 (2.6); 7.851 (3.5); 7.828 (1.8); 7.698 (1.8); 7.686 (1.8); 7.678 (1.8); 7.666 (1.7); 7.571 (5.2); 7.208 (4.7); 4.038 (0.4); 4.021 (0.4); 3.892 (1.1); 3.866 (3.5); 3.840 (3.6); 3.814 (1.2); 3.317 (32.3); 2.675 (0.4); 2.671 (0.5); 2.666 (0.4); 2.524 (1.5); 2.510 (31.3); 2.506 (61.7); 2.502 (81.3); 2.497 (60.7); 2.493 (30.4); 2.385 (14.2); 2.333 (0.5); 2.329 (0.6); 2.324 (0.5); 2.226 (16.0); 2.204 (1.4); 2.185 (0.9); 1.988 (1.9); 1.193 (0.5); 1.175 (1.0); 1.158 (0.5); 0.008 (1.4); 0.000 (38.9); −0.008 (1.4) ppm.

The compounds 82 to 93 listed in Tables 1 and 3 were prepared in an analogous manner.

Example 94: N-{4-Methyl-3-[(2,2,2-trifluoroethyl) sulphinyl]phenyl}-2-(pyridin-3-yl)-2H-indazole-5-carboxamide

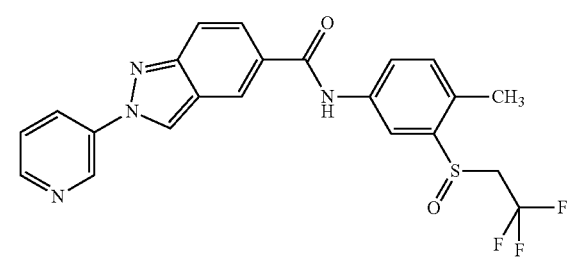 [SMILES: Cc1ccc(NC(=O)c2ccc3nn(-c4cccnc4)cc3c2)cc1S(=O)CC(F)(F)F]

A catalytic amount of sodium tungstate was added to a solution of 50 mg (0.11 mmol) of N-{4-methyl-3-[(2,2,2-trifluoroethyl)sulphanyl]phenyl}-2-(pyridin-3-yl)-2H-indazole-5-carboxamide in 2.5 ml of acetic acid, and 98 µl (0.11 mmol) of 3.5% strength hydrogen peroxide solution were added at 0° C. The reaction mixture was stirred at 0° C. for one hour and overnight at room temperature. 4 µl (44 µmol) of 35% strength hydrogen peroxide solution were then added, and the mixture was stirred at room temperature for a further night. The reaction mixture was diluted with water and dichloromethane. The organic phase was separated off and washed successively with water and concentrated sodium bisulphite solution. The organic phase was then dried with sodium sulphate and filtered and the solvent was removed under reduced pressure. The residue was separated chromatographically by MPLC on silica gel (gradient: ethyl acetate/cyclohexane 20:80→100:0). This gave 19.8 mg (95% pure, 37% yield) of N-{4-methyl-3-[(2,2,2-trifluoroethyl)sulphinyl]phenyl}-2-(pyridin-3-yl)-2H-indazole-5-carboxamide.

$^1$H-NMR (400.0 MHz, d$_6$-DMSO): $^1$H-NMR (400.0 MHz, d$_6$-DMSO): δ=10.618 (4.2); 9.478 (6.2); 9.394 (3.7); 9.387 (3.8); 8.706 (2.5); 8.703 (2.8); 8.695 (2.7); 8.691 (2.9); 8.600 (4.5); 8.563 (1.4); 8.560 (1.7); 8.557 (1.6); 8.553 (1.5); 8.543 (1.6); 8.539 (1.7); 8.536 (1.8); 8.532 (1.5); 8.373 (3.9); 8.368 (4.2); 8.314 (0.3); 8.000 (1.9); 7.995 (1.9); 7.980 (2.1); 7.974 (2.1); 7.940 (1.7); 7.936 (1.8); 7.917 (3.3); 7.913 (3.5); 7.869 (4.0); 7.847 (2.1); 7.703 (2.0); 7.691 (1.9); 7.682 (1.9); 7.670 (1.9); 7.367 (3.0); 7.346 (2.8); 4.181 (1.0); 4.171 (0.5); 4.153 (1.1); 4.143 (1.3); 4.126 (0.5); 4.116 (1.3); 4.089 (0.4); 3.949 (0.3); 3.922 (1.2); 3.913 (0.4); 3.895 (1.4); 3.885 (1.1); 3.868 (0.5); 3.858 (1.0); 3.832 (0.3); 3.318 (50.7); 2.791 (0.6); 2.676 (0.6); 2.671 (0.8); 2.667 (0.6); 2.635 (0.5); 2.524 (2.4); 2.511 (44.9); 2.507 (91.6); 2.502 (122.3); 2.497 (92.4); 2.493 (47.8); 2.351 (16.0); 2.333 (0.9); 2.329 (1.0); 2.324 (0.8); 1.336 (0.7); 1.299 (0.5); 1.259 (0.8); 1.250 (1.0); 1.234 (0.5); 0.146 (0.6); 0.008 (5.1); 0.000 (138.3); −0.008 (6.3); −0.150 (0.6) ppm.

The compounds 95 to 97 listed in Tables 1 and 3 were prepared in an analogous manner.

Example 98: 5-(1H-Pyrazol-4-yl)-2-(pyridin-3-yl)-2H-indazole

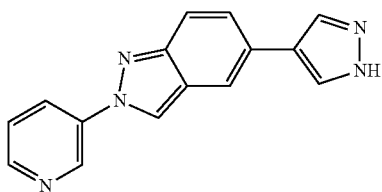 [SMILES: c1cncc(-n2cc3cc(-c4cn[nH]c4)ccc3n2)c1]

1.06 g (5.47 mmol) of 5-(4,4,5,5-tetramethyl-1,3,2-dioxaborolan-2-yl)-1H-pyrazole in 15 ml of N,N-dimethylformamide and 8.25 ml of water were initially charged in a 50 ml round-bottom flask. The flask was flushed with argon and kept under a stream of argon while 1.74 g (16.42 mmol) of sodium carbonate, 1.50 g (5.47 mmol) of 5-bromo-2-(3-pyridyl)indazole and 0.31 g (0.27 mmol) of tetrakis(triphenylphosphine)palladium were added. The reaction mixture was then stirred on an oil bath at 120° C. for about 18 hours. After cooling, the reaction mixture was filtered and the filter was rinsed with ethyl acetate. The filtrate was washed repeatedly with water. The organic phase was separated off and washed with water. The combined organic phases were dried over dried sodium sulphate, filtered and freed of the solvent under reduced pressure. For further purification, the residue was subjected to incipient dissolution in dichloromethane and separated from insoluble constituents by filtration. The filtrate was stirred with water and the insoluble fraction was filtered off and dried under reduced pressure. This gave 505 mg (100% pure by LC/MS, 35% yield) of the title compound.

$^1$H-NMR (400.0 MHz, d$_6$-DMSO): δ=12.941 (2.9); 9.350 (9.6); 9.344 (9.6); 9.136 (16.0); 8.655 (6.5); 8.652 (7.1); 8.643 (6.8); 8.640 (7.0); 8.510 (3.7); 8.507 (4.5); 8.505 (4.5); 8.501 (3.8); 8.490 (4.0); 8.486 (4.6); 8.484 (4.8); 8.480 (3.8); 8.314 (0.7); 8.257 (4.7); 8.007 (4.6); 7.951 (12.7); 7.755 (5.7); 7.732 (9.9); 7.676 (8.2); 7.673 (8.3); 7.662 (5.6); 7.650 (9.7); 7.641 (5.2); 7.629 (4.7); 3.321 (105.7); 2.891 (0.4); 2.732 (0.4); 2.672 (1.3); 2.507 (159.7); 2.503 (205.5); 2.498 (160.5); 2.329 (1.3); 0.000 (5.4) ppm.

Example 99: 2-(Pyridin-3-yl)-5-[1-(2,2,2-trifluoroethyl)-1H-pyrazol-4-yl]-2H-indazole

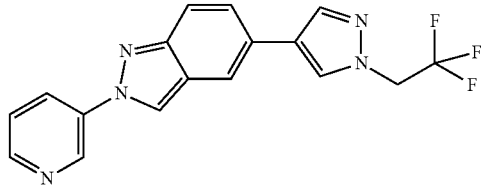 [SMILES: FC(F)(F)Cn1cc(-c2ccc3nn(-c4cccnc4)cc3c2)cn1]

100 mg (0.38 mmol) of 5-(1H-pyrazol-4-yl)-2-(pyridin-3-yl)-2H-indazole were initially charged in 2 ml of dried N,N-dimethylformamide. 79 mg (0.57 mmol) of potassium carbonate were added, the flask was kept under a stream of argon and 83 µl (133 mg, 0.57 mmol) of 2,2,2-trifluoroethyl trifluoromethanesulphonate were added. The reaction mixture was then stirred at room temperature overnight. The progress of the reaction was monitored by thin-layer chromatography and LC/MS. After addition of 28 µl (0.11 mmol) of trifluoroethyl trifluoromethanesulphonate, the reaction mixture was stirred at room temperature over the weekend. The filtrate was washed repeatedly with water and the combined organic phases were dried over dried sodium sulphate, filtered and freed of the solvent under reduced pressure. For further purification, the residue was subjected to incipient dissolution in dichloromethane and separated from insoluble constituents by filtration. The filtrate was stirred with water and the resulting solid was isolated by filtration. This gave 505 mg (100% pure by LC/MS, 35% yield) of the title compound.

$^1$H-NMR (400.0 MHz, d$_6$-DMSO): δ=9.356 (8.4); 9.350 (8.8); 9.175 (14.9); 8.661 (6.6); 8.649 (6.7); 8.513 (4.1); 8.492 (4.4); 8.349 (15.0); 8.139 (16.0); 7.998 (11.7); 7.786 (6.0); 7.763 (8.2); 7.667 (4.5); 7.655 (4.9); 7.646 (11.1); 7.635 (4.8); 7.623 (5.3); 5.206 (2.9); 5.183 (9.2); 5.160 (9.6); 5.137 (3.3); 3.323 (45.8); 2.673 (0.7); 2.504 (114.3); 2.330 (0.7); 1.990 (0.9); 1.176 (0.5); 0.146 (0.6); 0.000 (109.6); −0.150 (0.6) ppm.

General Synthesis of 2-(hetaryl)-2H-indazole-5-amines of the Formula (I, R²=NH₂)

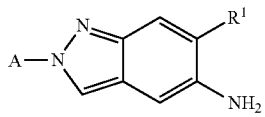

Under an atmosphere of protective gas (argon), the 4-substituted 2-(hetaryl)indazole-5-carboxylic acids of the formula (I; R²=COOH) were dissolved in dried 1,4-dioxane (4 ml/mmol), and 1.5 equiv. of diphenylphosporyl azide (DPPA) and 1.5 equiv. of triethylamine were then added. The reaction mixture was then stirred at room temperature for 3 hours. After addition of 1M hydrochloric acid (4 ml/mmol), the reaction mixture was stirred at 100° C. for 30 minutes. After cooling to room temperature, the pH was adjusted to 7 by addition of a sodium carbonate solution and the reaction mixture was extracted with dichloromethane (3×4 ml/mmol). The organic phase was dried over magnesium sulphate and concentrated under reduced pressure. The crude product that remained was purified on a silica gel column; the mobile phase used was a gradient from 0% to 5% methanol in dichloromethane.

2-(1-Methyl-1H-pyrazol-4-yl)-2H-indazole-5-amines of the Formula (I, A=1-methyl-1H-pyrazol-4-yl; R¹=H, R²=NH₂)

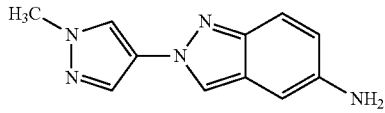 [SMILES: Cn1cc(-n2cc3cc(N)ccc3n2)cn1]

This compound was prepared, for example, from 2.87 g (11.8 mmol) of 2-(1-methyl-1H-pyrazol-4-yl)-2H-indazole-5-carboxylic acid in accordance with the general synthesis mentioned. This gave 2.06 g (81% yield of theory; purity according to HPLC-MS 98%) of the title compound.
APCI MS, m/z=214 [M+H]⁺

General Synthesis of N-methyl-2-(hetaryl)-2H-indazole-5-amines of the Formula (I, R²=NHCH₃)

Method A:

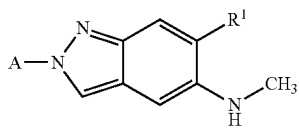

A sodium methoxide solution which had been prepared from 5 equiv. of sodium and methanol (5 ml/mmol) was added to a suspension consisting of the corresponding 2-(hetaryl)-2H-indazole-5-amines of the formula (I, R²=NH₂) and 5 equiv. of paraformaldehyde in methanol (50 ml/mmol). The reaction mixture was then stirred at reflux temperature for one hour, and 5 equiv. of sodium borohydride were added. The reaction mixture was then stirred for a further 30 minutes and cooled to room temperature. 1M sodium hydroxide solution (50 ml/mmol) was added and the reaction mixture was extracted with dichloromethane (3×50 ml/mmol). The combined organic phase was dried over magnesium sulphate, filtered and concentrated under reduced pressure.

N-Methyl-2-(1-methyl-1H-pyrazol-4-yl)-2H-indazole-5-amines of the formula (I, A=1-methyl-1H-pyrazol-4-yl; R¹=H, R²=NH₂)

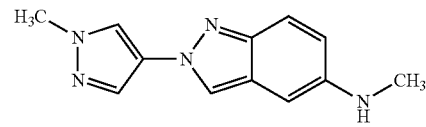

This compound was prepared, for example, from 9.90 g (4.6 mmol) of 2-(1-methyl-1H-pyrazol-4-yl)-2H-indazole-5-amine in accordance with the general synthesis mentioned. This gave 1.20 g (100% yield of theory; purity according to HPLC-MS 99%) of the title compound.
APCI MS, m/z=228 [M+H]⁺
Method B:

Step 1

Under an atmosphere of protective gas (argon), the 5-bromo-2-(hetaryl)-2H-indazoles (cf. compound 49, step 2) were dissolved in dried 1,4-dioxane (3 ml/mmol), and 1.2 equiv. of tert-butyl carbamate, 2 equiv. of caesium carbonate, 0.05 equiv. of tris(dibenzylideneacetone)dipalladium and 0.1 equiv. of Xantphos were then added. The reaction mixture was stirred at reflux temperature for 6 hours and then cooled to room temperature. Water (3 ml/mmol) was then added, and the reaction mixture was extracted with ethyl acetate (3×3 ml/mmol). The organic phase was dried over magnesium sulphate, filtered and concentrated under reduced pressure. The crude product that remained was purified on a silica gel column; the mobile phase used was a gradient from 0% to 7% methanol in dichloromethane.

tert-Butyl (2-(2-pyridin-3-yl)-2H-indazol-5-yl)carbamates of the formula (I-f, A=pyridin-3-yl-; R¹=H, R²=NH—CO—C(CH₃)₃

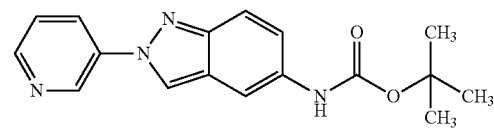 [SMILES: CC(C)(C)OC(=O)Nc1ccc2nn(-c3cccnc3)cc2c1]

This compound was prepared, for example, from 2.47 g (9 mmol) of 5-bromo-2-(pyridin-3-yl)-2H-indazole in accordance with the general synthesis mentioned. This gave 1.67 g (60% yield of theory; purity according to HPLC-MS 98%) of the title compound.
APCI MS, m/z=311 [M+H]⁺

Step 2

Under an atmosphere of protective gas (argon), the tert-butyl (2-hetaryl)-2H-indazol-5-yl)carbamates were dissolved in dried tetrahydrofuran (20 ml/mmol), and 2.5 equiv. of lithium aluminium hydride were then added a little at a time. The reaction mixture was then stirred at reflux temperature for 10 hours, another 1 equiv. of lithium aluminium hydride was added and the mixture was stirred at reflux temperature for a further 20 hours. 1M aqueous sodium hydroxide solution (1 ml/mmol) was then added, and the mixture was filtered. The filtrate was concentrated under reduced pressure and the residue that remained was taken up in dichloromethane (10 ml/mmol). The resulting solution was washed with aqueous sodium carbonate solution (10 ml/mmol), dried over magnesium sulphate, filtered and concentrated under reduced pressure. The crude product that remained was purified on a silica gel column; the mobile phase used was a gradient from 0% to 5% methanol in dichloromethane.

N-Methyl-(2-pyridin-3-yl)-2H-indazole-5-amines of the Formula (I, A=pyridin-3-yl-; $R^1$=H, $R^2$=$NH_2$)

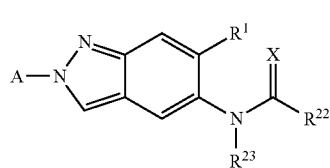

This compound was prepared, for example, from 1.67 g (5.4 mmol) of tert-butyl (2-(2-pyridin-3-yl)-2H-indazol-5-yl)carbamate in accordance with the general synthesis mentioned. This gave 686 mg (57% yield of theory; purity according to HPLC-MS 93%) of the title compound.

APCI MS, m/z=225 $[M+H]^+$

General Synthesis of Compounds of the Formula (I-g)

Method A:

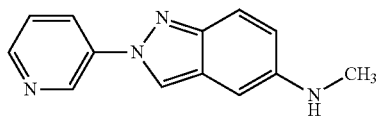

The respective N-methyl-2-(hetaryl)-2H-indazole-5-amines of the formula (I, A=hetaryl; $R^1$=H, $R^2$=NH—$CH_3$) were dissolved in dried dichloromethane (5 ml/mmol) and, at 0° C. and with stirring, 1.2 equiv. of the appropriate acids, 2.4 equiv. of diisopropylethylamine (Hünig base) and 1.5 equiv. of a 50% strength solution of propylphosphonic anhydride (T3P) in tetrahydrofuran were added. The reaction mixture was then stirred at 0° C. for a further 30 minutes and subsequently at room temperature for 20 hours. After the reaction had ended, the reaction mixture was dissolved in dichloromethane (5 ml/mmol) and washed first with aqueous potassium carbonate solution (5 ml/mmol) and then with water (5 ml/mmol). The organic phase was dried over magnesium sulphate, filtered and concentrated under reduced pressure. The crude product that remained was purified on a silica gel column; the mobile phase used was a gradient from 0% to 5% methanol in dichloromethane.

Example 105: N,2-Dimethyl-N-(2-(1-methyl-1H-pyrazol-4-yl)-2H-indazol-5-yl)-3-(methylthio) propanamide

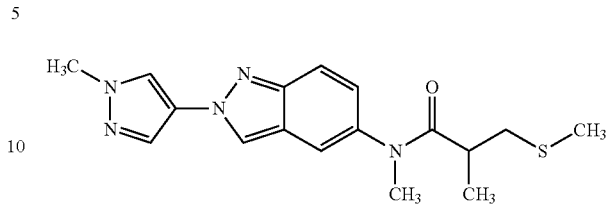

This compound was prepared, for example, from 300 mg (1.3 mmol) of 2-(1-methyl-1H-pyrazol-4-yl)-2H-indazole-5-amine in accordance with the general synthesis mentioned. This gave 389 mg (86% yield of theory; purity according to HPLC-MS 98%) of the title compound.

APCI MS, m/z=344 $[M+H]^+$ $^1$H NMR (300 MHz, DMSO-$d_6$) δ=0.99 (3H, d, J=6.4 Hz), 1.79 (3H, s), 2.30 (1H, dd, J1=11.8 Hz, J2=4.9 Hz), 2.57-2.77 (2H, m), 3.21 (3H, s), 3.93 (3H, s), 7.22 (1H, dd, J1=9.0 Hz, J2=1.7 Hz), 7.71-7.81 (2H, m), 8.08 (1H, s), 8.43 (1H, s), 8.86 (1H, s) ppm.

Method B:

At 0° C., 1.2 equiv. of pyridine were added to the respective N-methyl-2-(hetaryl)-2H-indazole-5-amines of the formula (I, A=hetaryl; $R^1$=H, $R^2$=NH—$CH_3$) in dried dichloromethane (10 ml/mmol). 1.1 equiv. of the appropriate acid chloride were then added dropwise and the reaction mixture was stirred at room temperature for 2 hours. The reaction mixture was then washed with water (2×5 ml/mmol). The organic phase was dried, filtered through magnesium sulphate and concentrated under reduced pressure. The crude product that remained was purified by HPLC.

Example 106: N-Methyl-N-(2-(1-methyl-1H-pyrazol-4-yl)-2H-indazol-5-yl)-3-(methylthio) propanamide

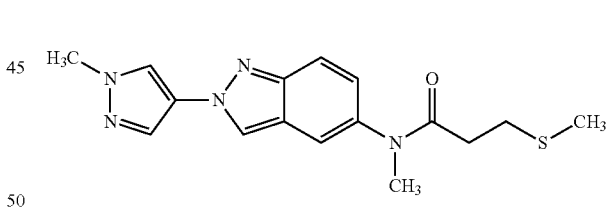

This compound was prepared, for example, from 300 mg (1.3 mmol) of 2-(1-methyl-1H-pyrazol-4-yl)-2H-indazole-5-amine in accordance with the general synthesis mentioned. This gave 452 mg (100% yield of theory; purity according to HPLC-MS 97%) of the title compound.

APCI MS, m/z=330 [M+H]

$^1$H NMR (300 MHz, DMSO-$d_6$) δ=1.88 (3H, s), 2.34 (2H, t, J=7.1 Hz), 2.62 (2H, t, J=7.1 Hz), 3.20 (3H, s), 3.93 (3H, s), 7.21 (1H, dd, J1=8.9 Hz, J2=1.5 Hz), 7.70-7.79 (2H, m), 8.08 (1H, s), 8.44 (1H, s), 8.85 (1H, s).

The compounds 107 to 113 listed in Tables 1 and 2 were prepared in an analogous manner.

Method C:

The respective N-methyl-2-(hetaryl)-2H-indazole-5-amines of the formula (I, A=hetaryl; $R^1$=H, $R^2$=NH—$CH_3$) were stirred in N,N-dimethylformamide (3 ml/mmol), 1.0 equiv. of the appropriate carboxylic acid, 1.1 equiv. of 1-hydroxybenzotriazole (HOBt), 1.1 equiv. of diisopropylethylamine (Hünig base) and 1.1 equiv. of 1-ethyl-3-(3-dimethylaminopropyl)carbodimide (EDCI) were added and the mixture was stirred at 60° C. for 8 hours. The reaction mixture is then dissolved in dichloromethane (5 ml/mmol) and washed with water (3×5 ml/mmol). The organic phase was dried, filtered through magnesium sulphate and concentrated under reduced pressure. The crude product that remained was purified by HPLC.

The compounds 114 to 118 listed in Tables 1 and 2 were prepared in an analogous manner.

General Sulphonyl Oxidation Method 0.9 equiv. of sodium perborate hydrate ($NaBO_3$ $4H_2O$) were added to a solution of the respective amide in glacial acetic acid (5 ml/mmol), and the reaction mixture was stirred at 60° C. for 1 hour. Saturated sodium bicarbonate solution was then added until the evolution of gas had ceased. The reaction mixture was then extracted with ethyl acetate (3×5 ml/mmol). The organic phase was dried, filtered through magnesium sulphate and concentrated under reduced pressure. The crude product that remained was purified on a silica gel column; the mobile phase used was a gradient from 0% to 5% methanol in dichloromethane.

Example 119: N-Methyl-N-(2-(1-methyl-1H-pyrazol-4-yl)-2H-indazol-5-yl)-3-(methylsulphinyl) propanamide

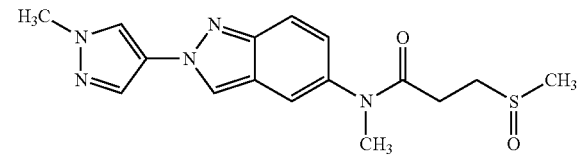

This compound was prepared, for example, from 80 mg (0.24 mmol) of N-methyl-N-(2-(1-methyl-1H-pyrazol-4-yl)-2H-indazol-5-yl)-3-(methylthio)propanamide in accordance with the general synthesis mentioned. This gave 71 mg (85% yield of theory; purity according to HPLC-MS 86%) of the title compound.

APCI MS, m/z=346 [M+H]$^+$ $^1$H NMR (300 MHz, DMSO-d$_6$) δ=2.55 (3H, s), 2.59-2.72 (2H, m), 2.79-2.90 (1H, m), 3.05-318 (1H, m), 3.33 (3H, s), 4.00 (3H, s), 7.10 (1H, dd, J1=9.0 Hz, J2=1.9 Hz), 7.54 (1H, d, J=1.3 Hz), 7.80 (1H, d, J=9.0 Hz), 7.89 (1H, s), 7.94 (1H, s), 8.22 (1H, s) ppm.

The compounds 120 to 124 listed in Tables 1 and 2 were prepared in an analogous manner.

General Sulphonyl Oxidation Method 2.2 equiv. of sodium perborate hydrate ($NaBO_3$ $4H_2O$) were added to a solution of the respective amide in glacial acetic acid (5 ml/mmol), and the reaction mixture was stirred at 60° C. for 1 hour. Saturated sodium bicarbonate solution was then added until the evolution of gas had ceased. The reaction mixture was then extracted with ethyl acetate (3×5 ml/mmol). The organic phase was dried, filtered through magnesium sulphate and concentrated under reduced pressure. The crude product that remained was purified on a silica gel column; the mobile phase used was a gradient from 0% to 5% methanol in dichloromethane.

Example 125: N-Methyl-N-(2-(1-methyl-1H-pyrazol-4-yl)-2H-indazol-5-yl)-3-(methylsulphonyl) propanamide

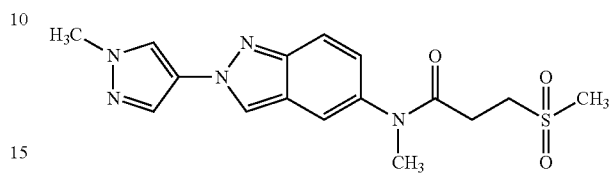

This compound was prepared, for example, from 80 mg (0.24 mmol) of N-methyl-N-(2-(1-methyl-1H-pyrazol-4-yl)-2H-indazol-5-yl)-3-(methylthio)propanamide in accordance with the general synthesis mentioned. This gave 60 mg (68% yield of theory; purity according to HPLC-MS 97%) of the target compound.

APCI MS, m/z=362 [M+H]$^+$ $^1$H NMR (300 MHz, DMSO-d$_6$) δ=2.70 (2H, t, J=7.2 Hz), 2.94 (3H, s), 3.35 (3H, s), 3.40 (2H, t, J=7.2 Hz), 4.03 (3H, s), 7.12 (1H, dd, J1=9.0 Hz, J2=1.6 Hz), 7.57 (1H, s), 7.83 (1H, d, J=8.8 Hz), 7.92 (1H, s), 7.97 (1H, s), 8.25 (1H, s) ppm.

The compounds 126 to 130 listed in Tables 1 and 2 were prepared in an analogous manner.

Synthesis of the Intermediates

4-Bromo-1-[(methylsulphanyl)methyl]-1H-pyrazole

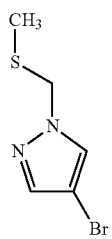

At 0° C., 41 mg (1.02 mmol) of sodium hydride were added a little at a time to a solution of 100 mg (0.68 mmol) of 4-bromo-1H-pyrazole in absolute dimethylformamide. The reaction mixture was stirred at room temperature for 15 min, 0.11 ml (1.4 mmol) of chlorodimethyl sulphide were added and the mixture was stirred at room temperature overnight. Water was then added, and the mixture was extracted repeatedly with ethyl acetate. The combined organic phases were dried with sodium sulphate and filtered and the solvent was removed under reduced pressure. This gave 100 mg (93% pure, 66% yield) of 4-bromo-1-[(methylsulphanyl)methyl]-1H-pyrazole.

$^1$H-NMR (400.0 MHz, d$_6$-DMSO): $^1$H-NMR (400.0 MHz, d$_6$-DMSO): δ=8.069 (4.4); 7.591 (3.9); 5.242 (10.2); 3.319 (8.9); 2.502 (15.8); 2.157 (0.5); 2.121 (16.0); 2.029 (0.4); 2.024 (0.5); 1.236 (0.4); 0.002 (7.1); 0.000 (10.0)

Methyl 4-methyl-3-((2,2,2-trifluoroethyl)sulphinyl)benzoate

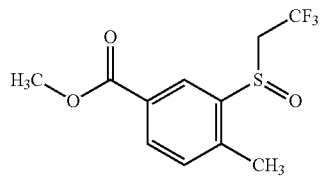 [SMILES: COC(=O)c1ccc(C)c(S(=O)CC(F)(F)F)c1]

Step 1: Synthesis of methyl 4-methyl-3-((2,2,2-trifluoroethyl)thio)benzoate 1.07 g (7.8 mmol) of potassium carbonate and 5.61 µl (1.1 mmol) of 2,2,2-trifluoroethyl iodide were added to a solution of 943 mg (5.17 mmol) of methyl 3-mercapto-4-methylbenzoate (see preparation in WO 2010/094695 A1) in 15 ml of DMF. The reaction mixture was then stirred at room temperature for 20 hours. The reaction mixture was then diluted with 50 ml of water and extracted twice with 50 ml of dichloromethane. The combined organic phases were dried with magnesium sulphate and filtered and the solvent was removed under reduced pressure. The crude product that remained was purified by flash chromatography; the mobile phase used was a gradient from 0% to 10% ethyl acetate in n-heptane. This gave 990 mg (purity: 93%; 72% yield) of methyl 4-methyl-3-((2,2,2-trifluoroethyl)thio)benzoate.

APCI MS, m/z=265 [M+H]$^+$

Step 2

559 mg (3.6 mmol; 1.0 equiv.) of sodium perborate hydrate (NaBO$_3$ 4H$_2$O) were added to a solution of 960 mg (3.6 mmol) of methyl 4-methyl-3-((2,2,2-trifluoroethyl)thio)benzoate in 27 ml of, and the reaction mixture was stirred at 60° C. for 1 hour. Saturated sodium bicarbonate solution was then added until the evolution of gas had ceased. The reaction mixture was then extracted with ethyl acetate (3×30 ml/mmol). The organic phase was dried, filtered through magnesium sulphate and concentrated under reduced pressure. This gave 1.08 g (purity: 96%; 100% yield) of methyl 4-methyl-3-((2,2,2-trifluoroethyl)thio)benzoate.

APCI MS, m/z=281 [M+H]$^+$

Compounds of the formula (I) and also those not embraced by formula (I) are listed in the table below. The compounds not embraced by formula (I) also form part of the subject-matter of the invention.

TABLE 1 compounds of the formula

[indazole core structure with A—N, R$^1$, R$^2$ substituents]

| Compound No. | A | R$^1$ | R$^2$ | Yield [in mg] | Purity: [in %] |
|---|---|---|---|---|---|
| 1 | 3-pyridyl | H | –C(O)N(CH$_3$)$_2$ | 105.6 | 94.4 |
| 2 | 3-pyridyl | H | –C(O)NH–S(O)$_2$–CH$_3$ | 89.4 | 94.7 |
| 3 | 3-pyridyl | H | –C(O)NH–CH$_2$–CHF$_2$F (2,2,2-trifluoroethyl) | 144.4 | 97.7 |
| 4 *) | 3-pyridyl | H | –C(O)NH–CH$_2$CH$_3$ | 11.5 | 98.9 |
| 5 *) | 3-pyridyl | H | –C(O)NH–S(O)$_2$–N(CH$_3$)$_2$ | 17.2 | 86.4 |

TABLE 1-continued compounds of the formula

[Structure: 2H-indazole with A on N2, R¹ at 6-position, R² at 5-position]

| Compound No. | A | R¹ | R² | Yield [in mg] | Purity: [in %] |
|---|---|---|---|---|---|
| 6 *) | pyridin-3-yl | H | -CF₃ (C(F)(F)F attached) | 30.0 | 99.1 |
| 7 *) | pyridin-3-yl | H | -C(O)NH-CH₂-CF₂-CH₃ | 51.3 | 98.4 |
| 8 *) | pyridin-3-yl | H | -C(O)NH-CH(CH₃)₂ | 32.6 | 99.4 |
| 9 *) | pyridin-3-yl | H | -C(O)-N(CH₃)-OCH₃ | 43.6 | 97.2 |
| 10 *) | pyridin-3-yl | H | -C(O)NH-cyclopropyl | 33.7 | 99.3 |
| 11 *) | pyridin-3-yl | H | -C(O)NH-CH₃ | 54.4 | 99.9 |
| 12 *) | pyridin-3-yl | H | -C(O)NH-C(CN)(cyclopropyl) | 56.7 | 99.2 |
| 13 *) | pyridin-3-yl | H | -C(O)NH-CH₂-CHF₂ | 41.2 | 99.1 |
| 14 *) | 5-fluoropyridin-3-yl | H | -C(O)NH-CH₂-CF₂-CH₃ | 41.5 | 99.8 |

TABLE 1-continued compounds of the formula

| Compound No. | A | R¹ | R² | Yield [in mg] | Purity: [in %] |
|---|---|---|---|---|---|
| 15 *) | 5-fluoropyridin-3-yl | H | C(O)NH-cyclopropyl | 41.6 | 99.0 |
| 16 | 5-fluoropyridin-3-yl | H | CF₃ | 45.9 | 96.9 |
| 17 | 5-fluoropyridin-3-yl | H | C(O)NHS(O)₂CH₃ | 97.5 | 97.1 |
| 18 | 5-fluoropyridin-3-yl | H | C(O)N(CH₃)₂ | 138.4 | 96.3 |
| 19 | 5-fluoropyridin-3-yl | H | C(O)NHCH₂CF₃ | 96.3 | 98.5 |
| 20 *) | 5-fluoropyridin-3-yl | H | C(O)NHCH₂CH₃ | 32.1 | 95.8 |
| 21 *) | 5-fluoropyridin-3-yl | H | C(O)NH-(1-cyanocyclopropyl) | 23.8 | 95.9 |
| 22 *) | 5-fluoropyridin-3-yl | H | C(O)NHCH(CH₃)₂ | 55.2 | 98.7 |
| 23 *) | 5-fluoropyridin-3-yl | H | C(O)N(CH₃)OCH₃ | 40.2 | 98.2 |

TABLE 1-continued compounds of the formula

[Structure: A—N(pyrazole fused to benzene ring with R¹ at 6-position and R² at 5-position of indazole)]

| Compound No. | A | R¹ | R² | Yield [in mg] | Purity: [in %] |
|---|---|---|---|---|---|
| 24 *) | 3-fluoropyridin-5-yl | H | —C(O)NH-CH₂-CHF₂ | 33.1 | 96.6 |
| 25 *) | 3-fluoropyridin-5-yl | H | —C(O)NH-CH₃ | 67.3 | 100 |
| 26 | pyrimidin-5-yl | H | —C(O)NH-CH₂-CF₃ | 64.3 | 91.8 |
| 27 | pyrimidin-5-yl | H | —C(O)N(CH₃)₂ | 45.6 | 96.5 |
| 28 | pyrimidin-5-yl | H | —C(O)NH-S(O)₂-CH₃ | 67.2 | 96.8 |
| 29 | pyrimidin-5-yl | H | —C(O)NH-CH₂CH₃ | 35.6 | 85.8 |
| 30 | pyrimidin-5-yl | H | —C(O)NH-CH₂-CHF₂ | 10.9 | 87.1 |
| 31 | pyrimidin-5-yl | H | —C(O)NH-CH₃ | 14.3 | 85.8 |
| 32 | pyrimidin-5-yl | H | —C(O)N(CH₃)-O-CH₃ | 11.7 | 86.5 |

TABLE 1-continued compounds of the formula

| Compound No. | A | R¹ | R² | Yield [in mg] | Purity: [in %] |
|---|---|---|---|---|---|
| 33 | pyrimidinyl | H | -C(O)NH-CH₂-CF₂-CH₃ | 12.6 | 94.0 |
| 34 | pyrazinyl | H | -C(O)-N(CH₃)₂ | 76.2 | 94.4 |
| 35 | pyrazinyl | H | -C(O)NH-CH₂-CF₃ | 106.5 | 98.4 |
| 36 | pyrazinyl | H | -C(O)NH-S(O)₂-CH₃ | 259.8 | 91.9 |
| 37 | 1-methylpyrazol-4-yl | H | -C(O)NH-CH₂-CF₃ | 78.7 | 96.7 |
| 38 | 1-methylpyrazol-4-yl | H | -C(O)-N(CH₃)₂ | 80.5 | 99.7 |
| 39 | 1-methylpyrazol-4-yl | H | -C(O)NH-S(O)₂-CH₃ | 51.8 | 92.8 |
| 40 | 1-methylpyrazol-4-yl | H | -C(O)NH-cyclopropyl | 53.7 | 99.2 |
| 41 | 1-methylpyrazol-4-yl | H | -C(O)NH-CH₃ | 60.4 | 99.6 |

TABLE 1-continued compounds of the formula

| Compound No. | A | R¹ | R² | Yield [in mg] | Purity: [in %] |
|---|---|---|---|---|---|
| 42 | 1-methylpyrazol-4-yl | H | -C(O)NH-S(O)₂-N(CH₃)₂ | 37.7 | 100 |
| 43 | 1-methylpyrazol-4-yl | H | -C(O)NH-CH₂-C(F)₂-CH₃ | 67.4 | 99.4 |
| 44 | 1-methylpyrazol-4-yl | H | -C(O)NH-CH₂-CHF₂ | 78.3 | 98.5 |
| 45 | 1-methylpyrazol-4-yl | H | -C(O)-N(CH₃)-OCH₃ | 64.7 | 98.6 |
| 46 | 1-methylpyrazol-4-yl | H | -C(O)NH-C(CN)(cyclopropyl) | 78.5 | 98.7 |
| 47 | 1-methylpyrazol-4-yl | H | -C(O)NH-CH₂CH₃ | 62.7 | 99.4 |
| 48 | 1-methylpyrazol-4-yl | H | -C(O)NH-CH(CH₃)₂ | 65.3 | 98.4 |
| 49 | pyridin-3-yl | H | 4-fluoro-2-methyl-5-(2,2,2-trifluoroethylthio)phenyl | 392 | 93 |
| 50 | pyridin-3-yl | H | 4-methyl-3-(2,2,2-trifluoroethylthio)phenyl | 149 | 97 |

TABLE 1-continued compounds of the formula

[structure: 2H-indazole with A—N on N2, R¹ at 6-position, R² at 5-position]

| Compound No. | A | R¹ | R² | Yield [in mg] | Purity: [in %] |
|---|---|---|---|---|---|
| 51 | pyridin-3-yl | H | 2,5-dimethyl-4-(2,2,2-trifluoroethylthio)phenyl | 37 | 98 |
| 52 | pyridin-3-yl | H | 4-fluoro-2-methyl-5-(2,2,2-trifluoroethylsulfinyl)phenyl | 60 | 100 |
| 53 | pyridin-3-yl | H | 2-methyl-5-(2,2,2-trifluoroethylsulfinyl)phenyl | 64 | 100 |
| 54 | pyridin-3-yl | H | 2,5-dimethyl-4-(2,2,2-trifluoroethylsulfinyl)phenyl | 54 | 100 |
| 55 | pyridin-3-yl | H | 4-(trifluoromethyl)-1H-pyrazol-1-yl | 17 | 94 |
| 56 | pyridin-3-yl | H | 3-(trifluoromethyl)-1H-pyrazol-1-yl | 167 | 100 |
| 57 | pyridin-3-yl | H | pyridin-3-yl | 80 | 100 |
| 58 | pyridin-3-yl | H | 1-methyl-1H-pyrazol-4-yl | 26 | 100 |

TABLE 1-continued compounds of the formula

A—N-N (2H-indazole core with R¹ at 5-position and R² at 6-position)

| Compound No. | A | R¹ | R² | Yield [in mg] | Purity: [in %] |
|---|---|---|---|---|---|
| 59 | pyridin-3-yl | H | pyridin-2-yl | 25 | 100 |
| 60 | pyridin-3-yl | H | pyrimidin-2-yl | 60 | 96 |
| 61 | pyridin-3-yl | H | 6-chloropyridin-2-yl | 56 | 100 |
| 62 | pyridin-3-yl | H | 1-(methylthiomethyl)-1H-pyrazol-3-yl | 10 | 97 |
| 63 | pyridin-3-yl | H | 1-(methylthiomethyl)-1H-pyrazol-4-yl | 62 | 100 |
| 64 | pyridin-3-yl | H | 6-methylpyridin-2-yl | 34 | 96 |
| 65 | pyridin-3-yl | H | 5-methylpyridin-2-yl | 40 | 98 |

TABLE 1-continued compounds of the formula

| Compound No. | A | R¹ | R² | Yield [in mg] | Purity: [in %] |
|---|---|---|---|---|---|
| 66 | 3-pyridyl | H | 4-methyl-2-pyridyl | 49 | 100 |
| 67 | 3-pyridyl | H | 5-chloro-2-pyridyl | 73 | 97 |
| 68 | 3-pyridyl | H | 3-chloro-2-pyridyl | 55 | 97 |
| 69 | 3-pyridyl | H | 4-chloro-2-pyridyl | 46 | 100 |
| 71 | 3-pyridyl | H | 1-methyl-1H-pyrazol-3-yl | 39 | 98 |
| 73 | 3-pyridyl | H | 1-ethyl-1H-pyrazol-4-yl | 21 | 100 |
| 74 | 3-pyridyl | H | 1-((methylsulfinyl)methyl)-1H-pyrazol-4-yl | 55 | 91 |
| 75 | 3-pyridyl | H | N-cyclopropyl-N-methylcarbamoyl | 43 | 100 |

TABLE 1-continued compounds of the formula

A—N(pyrazolo-indazole core)—R¹, R²

| Compound No. | A | R¹ | R² | Yield [in mg] | Purity: [in %] |
|---|---|---|---|---|---|
| 76 | 3-pyridyl | H | 4-(ethylthio)pyridin-2-yl (with CH₃ on S-ethyl) | 38 | 100 |
| 77 | 3-pyridyl | H | 3-(ethylthio)pyridin-2-yl | 37 | 100 |
| 79 | 3-pyridyl | H | 6-(ethylthio)pyridin-2-yl | 100 | 96 |
| 80 | 3-pyridyl | H | 5-(ethylthio)pyridin-2-yl | 32 | 97 |
| 81 | 3-pyridyl | H | N-(2,4-dimethyl-5-((2,2,2-trifluoroethyl)thio)phenyl)carboxamide | 28 | 90 |

TABLE 1-continued compounds of the formula

[Structure: 2H-indazole with A-N at position 2, R¹ at position 6, R² at position 5]

| Compound No. | A | R¹ | R² | Yield [in mg] | Purity: [in %] |
|---|---|---|---|---|---|
| 82 | pyridin-3-yl | H | -C(O)-NH-(4-methyl-3-(SCH₂CF₃)phenyl) | 32 | 99 |
| 85 | pyridin-3-yl | H | -C(O)-NH-CH₂CH₂-S-CH₃ | 48 | 100 |
| 86 | pyridin-3-yl | H | -C(O)-N(CH₃)-CH₂-CHF₂ | 55 | 100 |
| 87 | pyridin-3-yl | H | -C(O)-morpholin-4-yl | 81 | 100 |
| 88 | pyridin-3-yl | H | -C(O)-pyrrolidin-1-yl | 11 | 100 |
| 89 | pyridin-3-yl | H | -C(O)-N(CH₂CH₃)₂ | 12 | 100 |
| 90 | pyridin-3-yl | H | -C(O)-N(CH₃)-CH₂-CF₃ | 65 | 100 |

TABLE 1-continued compounds of the formula

[Structure: 2H-indazole with A—N on N2, R¹ at 6-position, R² at 5-position]

| Compound No. | A | R¹ | R² | Yield [in mg] | Purity: [in %] |
|---|---|---|---|---|---|
| 91 | pyridin-3-yl | H | —C(=O)NH-(2-fluoro-4-methyl-5-(2,2,2-trifluoroethylthio)phenyl) | 93 | 99 |
| 92 | pyridin-3-yl | H | —C(=O)-thiomorpholin-4-yl | 79 | 100 |
| 93 | pyridin-3-yl | H | —C(=O)-thiomorpholin-4-yl 1,1-dioxide | 49 | 100 |
| 94 | pyridin-3-yl | H | —C(=O)NH-(4-methyl-3-(2,2,2-trifluoroethylsulfinyl)phenyl) | 37 | 95 |
| 95 | pyridin-3-yl | H | —C(=O)NH-CH₂CH₂-S(=O)₂-CH₃ | 59 | 100 |

TABLE 1-continued compounds of the formula

| Compound No. | A | R¹ | R² | Yield [in mg] | Purity: [in %] |
|---|---|---|---|---|---|
| 96 | 3-pyridyl | H | 2-fluoro-4-methyl-5-(2,2,2-trifluoroethylsulfinyl)phenylaminocarbonyl | 51 | 95 |
| 97 | 3-pyridyl | H | 2,4-dimethyl-5-(2,2,2-trifluoroethylsulfinyl)phenylaminocarbonyl | 15 | 97 |
| 98 | 3-pyridyl | H | 1H-pyrazol-4-yl | 35 | 100 |
| 99 | 3-pyridyl | H | 1-(2,2,2-trifluoroethyl)-1H-pyrazol-4-yl | 35 | 100 |
| 101 | 3-pyridyl | H | 4-fluoropyridin-2-yl | | |
| 104 | 3-pyridyl | H | 6-fluoropyridin-2-yl | | |

TABLE 1-continued compounds of the formula

A—N(indazole with R¹, R²)

| Compound No. | A | R¹ | R² | Yield [in mg] | Purity: [in %] |
|---|---|---|---|---|---|
| 105 | 1-methyl-pyrazol-4-yl | H | —N(CH₃)C(O)CH(CH₃)CH₂SCH₃ | 40.8 | 98 |
| 106 | 1-methyl-pyrazol-4-yl | H | —N(CH₃)C(O)CH₂CH₂SCH₃ | 54.5 | 97 |
| 107 | 1-methyl-pyrazol-4-yl | H | —N(CH₃)C(O)CH₂C(F)(F)CH₃ | 59.7 | 98 |
| 108 | 5-fluoropyridin-3-yl | H | —N(CH₃)C(O)CH₂CH₂SCH₃ | 58.4 | 98 |
| 109 | 5-fluoropyridin-3-yl | H | —N(CH₃)C(O)CH(CH₃)CH₂SCH₃ | 41.3 | 100 |
| 110 | pyridin-3-yl | H | —N(CH₃)C(O)CH(CH₃)CH₂SCH₃ | 50.9 | 97 |
| 111 | pyridin-3-yl | H | —N(CH₃)C(O)CH₂CH₂SCH₃ | 42.1 | 98 |
| 112 | pyridin-3-yl | H | —N(CH₃)C(O)CH₂C(F)(F)CH₃ | 44.4 | 99 |
| 113 | 5-fluoropyridin-3-yl | H | —N(CH₃)C(O)CH₂C(F)(F)CH₃ | 34.2 | 89 |

TABLE 1-continued
compounds of the formula
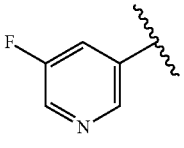
| Compound No. | A | R¹ | R² | Yield [in mg] | Purity: [in %] |
|---|---|---|---|---|---|
| 114 | 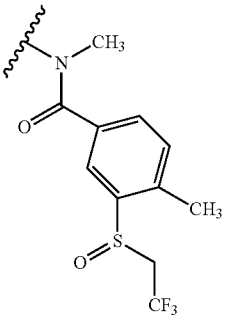 [SMILES: *N(C)C(=O)c1ccc(C)c(S(=O)CC(F)(F)F)c1] | H | 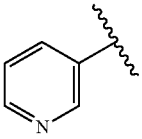 [SMILES: *c1cccnc1] | 42.4 | 89 |
| 115 | 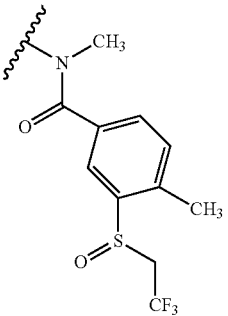 [SMILES: *N(C)C(=O)c1ccc(C)c(S(=O)CC(F)(F)F)c1] | H | 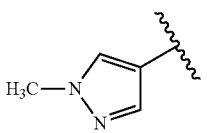 [SMILES: *c1cnn(C)c1] | 44 | 99 |
| 116 | 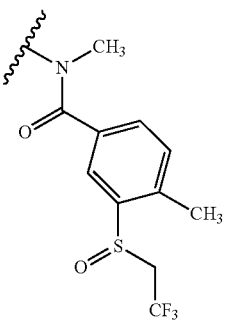 [SMILES: *N(C)C(=O)c1ccc(C)c(S(=O)CC(F)(F)F)c1] | H | 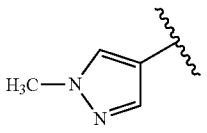 [SMILES: *c1cnn(C)c1] | 42.4 | 89 |
| 117 | 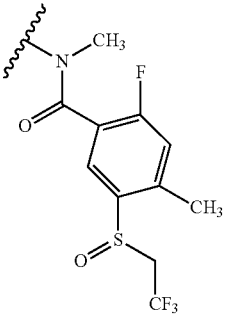 [SMILES: *N(C)C(=O)c1cc(S(=O)CC(F)(F)F)c(C)cc1F] | H |  | 45.5 | 96 |

TABLE 1-continued compounds of the formula

| Compound No. | A | R¹ | R² | Yield [in mg] | Purity: [in %] |
|---|---|---|---|---|---|
| 118 | 5-fluoropyridin-3-yl | H | N-methyl-2-fluoro-4-methyl-5-(2,2,2-trifluoroethylsulfinyl)benzamide | 42.9 | 94 |
| 119 | 1-methyl-1H-pyrazol-4-yl | H | N-methyl-3-(methylsulfinyl)propanamide | 43.7 | 86 |
| 120 | 1-methyl-1H-pyrazol-4-yl | H | N,2-dimethyl-3-(methylsulfinyl)propanamide | 60.1 | 95 |
| 121 | 5-fluoropyridin-3-yl | H | N-methyl-3-(methylsulfinyl)propanamide | 45.6 | 85 |
| 122 | 5-fluoropyridin-3-yl | H | N,2-dimethyl-3-(methylsulfinyl)propanamide | 42.6 | 99 |
| 123 | pyridin-3-yl | H | N-methyl-3-(methylsulfinyl)propanamide | 42.9 | 98 |
| 124 *) | pyridin-3-yl | H | N,2-dimethyl-3-(methylsulfinyl)propanamide | 55.7 | 100 |
| 125 | 1-methyl-1H-pyrazol-4-yl | H | N-methyl-3-(methylsulfonyl)propanamide | 59.9 | 97 |

TABLE 1-continued compounds of the formula

[Structure: A-N(N=)-benzene fused, with R¹ and R² substituents on a 2H-indazole]

| Compound No. | A | R¹ | R² | Yield [in mg] | Purity: [in %] |
|---|---|---|---|---|---|
| 126 **) | 5-fluoropyridin-3-yl | H | -N(CH₃)-C(=O)-CH(CH₃)-CH₂-S(=O)₂-CH₃ | 73.3 | 97 |
| 127 **) | 1-methylpyrazol-4-yl | H | -N(CH₃)-C(=O)-CH(CH₃)-CH₂-S(=O)₂-CH₃ | 54 | 98 |
| 128 | 5-fluoropyridin-3-yl | H | -N(CH₃)-C(=O)-CH₂-CH₂-S(=O)₂-CH₃ | 44.2 | 95 |
| 129 | pyridin-3-yl | H | -N(CH₃)-C(=O)-CH₂-CH₂-S(=O)₂-CH₃ | 41.3 | 100 |
| 130 | pyridin-3-yl | H | -N(CH₃)-C(=O)-CH(CH₃)-CH₂-S(=O)₂-CH₃ | 42.7 | 100 |

*) crystallizes with 1 × HCOOH; **) crystallizes with 1 × CH₃COOH

TABLE 2

Analytical data for the compounds 1-48 and 105-128 reported

| Ex. No. | Retention time [min] | $^1$H NMR [δ (ppm)] or LC-MS [m/z] |
|---|---|---|
| 1 | 1.725 | $^1$H-NMR (400.0 MHz, d$_6$-DMSO): δ = 3.01 (s, 6H, 2 × CH₃); 7.36; 7.67; 7.79; 7.88; 8.50; 8.67; 9.29; 9.34 (8H, =CH, aryl/hetaryl). LC-MS = 267.1 (M + 1); 266.29 (calculated) |
| 2 | 1.203 | $^1$H-NMR (400.0 MHz, d$_6$-DMSO): δ = 3.23 (s, 3H, CH₃); 7.66; 7.76; 7.86; 7.52; 8.68; 9.36; 9.44 (8H, =CH, aryl/hetaryl); 12.4 (br. 1H, NH). LC-MS = 317.1 (M + 1); 316.33 (calculated) |
| 3 | 1.203 | $^1$H-NMR (400.0 MHz, d$_6$-DMSO): δ = 4.13 (m, 2H, CH₂); 7.67; 7.83; 8.51; 8.54; 8.69; 9.17; 9.36; 9.45 (8H, =CH, aryl/hetaryl). LC-MS = 320.9 (M⁺); 320.26 (calculated) |
| 4 | 2.391 | $^1$H-NMR (400.0 MHz, d$_6$-DMSO): δ = 1.15; 3.4 (t + m, 5H, CH₂CH₃); 7.66; 7.78; 8.36; 8.53; 8.67; 9.35; 9.39 (8H, =CH, aryl/hetaryl). LC-MS = 267.3 (M + 1) [without HCOOH] |
| 5 | 2.875 | $^1$H-NMR (400.0 MHz, d$_6$-DMSO): δ = 3.34 (s, 3H, CH₃); 7.67; 7.81; 8.53; 8.58; 8.68; 9.36; 9.48 (8H, =CH, aryl/hetaryl); 11.9 (br. 1H, NH). LC-MS = 346.1 (M + 1) [without HCOOH] |
| 6 | 2.881 | $^1$H-NMR (400.0 MHz, CDCl₃): δ = 7.53; 7.90; 8.11; 8.31; 8.61; 8.73; 9.21 (8H, =CH, aryl/hetaryl). LC-MS = 364.0 (M + 1); 263.21 (calculated) |

TABLE 2-continued

Analytical data for the compounds 1-48 and 105-128 reported

| Ex. No. | Retention time [min] | $^1$H NMR [δ (ppm)] or LC-MS [m/z] |
|---|---|---|
| 7 | 2.319 | $^1$H-NMR (400.0 MHz, d$_6$-DMSO): δ = 1.64; 3.76 (t + m, 5H, CH$_2$CF$_2$CH$_3$); 7.66; 7.81; 8.45; 8.52; 8.68; 8.92; 9.36; 9.42 (8H, =CH, aryl/hetaryl).<br>LC-MS = 317.1 (M + 1) [without HCOOH] |
| 8 | 2.536 | $^1$H-NMR (400.0 MHz, d$_6$-DMSO): δ = 1.19; 4.12 (d + m, 7H, CH(CH$_3$)); 7.67; 7.79; 8.31; 8.37; 8.51; 8.67; 9.37 (8H, =CH, aryl/hetaryl).<br>LC-MS = 281.3 (M + 1) [without HCOOH] |
| 9 | 2.448 | $^1$H-NMR (400.0 MHz, d$_6$-DMSO): δ = 3.34; 3.57 (2s 6H, 2 × CH$_3$); 7.53; 7.66; 7.76; 8.13; 8.50; 8.67; 9.33 (8H, =CH, aryl/hetaryl).<br>LC-MS = 283.2 (M + 1) [without HCOOH] |
| 10 | 2.422 | $^1$H-NMR (400.0 MHz, d$_6$-DMSO): δ = 0.60; 0.69; 2.86 (3m 5H, Cyclopropyl); 7.65; 7.76; 8.33; 8.51; 8.66; 9.35; 9.38 (8H, =CH, aryl/hetaryl).<br>LC-MS = 279.3 (M + 1) [without HCOOH] |
| 11 | 2.261 | $^1$H-NMR (400.0 MHz, d$_6$-DMSO): δ = 2.81 (s 3H, CH$_3$); 7.66; 7.78; 8.35; 8.51; 8.67; 9.35; 9.40 (8H, =CH, aryl/hetaryl).<br>LC-MS = 253.2 (M + 1) [without HCOOH] |
| 12 | 2.017 | $^1$H-NMR (400.0 MHz, d$_6$-DMSO): δ = 2.81 (s 3H, CH$_3$); 7.67; 7.79; 8.40; 8.52; 8.68; 9.36; 9.40; 9.44 (8H, =CH, aryl/hetaryl).<br>LC-MS = 304.2 (M + 1) [without HCOOH] |
| 13 | 2.497 | $^1$H-NMR (400.0 MHz, d$_6$-DMSO): δ = 3.72; 6.16 (2m 3H, CH$_2$CHF$_2$); 7.67; 7.82; 8.44; 8.53; 8.68; 8.95; 9.36; 9.43 (8H, =CH, aryl/hetaryl).<br>LC-MS = 303.2 (M + 1) [without HCOOH] |
| 14 | 2.342 | $^1$H-NMR (400.0 MHz, d$_6$-DMSO): δ = 1.64; 3.76 (t + m 5H, CH$_2$CF$_2$CH$_3$); 7.79; 7.83; 8.44; 8.54; 8.71; 8.91; 9.29; 9.46 (8H, =CH, aryl/hetaryl).<br>LC-MS = 335.1 (M + 1) [without HCOOH] |
| 15 | 3.106 | $^1$H-NMR (400.0 MHz, d$_6$-DMSO): δ = 0.60; 0.70; 2.86 (3m 5H, Cyclopropyl); 7.74; 7.78; 8.33; 8.55; 8.71; 9.28; 9.42 (7H, =CH, aryl/hetaryl).<br>LC-MS = 297.0 (M + 1) [without HCOOH] |
| 16 | 2.902 | $^1$H-NMR (400.0 MHz, CDCl$_3$): δ = 7.53; 7.88; 8.10; 8.14; 8.58; 8.63; 9.04 (7H, =CH, aryl/hetaryl).<br>LC-MS = 282.0 (M + 1); 281.20 (calculated) |
| 17 | 3.142 | $^1$H-NMR (400.0 MHz, d$_6$-DMSO): δ = 3.1 (s, 3H, CH$_3$); 7.72; 7.91; 8.49; 8.55; 8.71; 9.29; 9.45 (7H, =CH, aryl/hetaryl), 12.3 (br, 1H, NH).<br>LC-MS = 335.0 (M + 1); 334.32 (calculated) |
| 18 | 1.983 | $^1$H-NMR (400.0 MHz, d$_6$-DMSO): δ = 3.01 (s, 6H, 2 × CH$_3$); 7.37; 7.79; 7.89; 8.54; 8.72; 9.28; 9.35 (7H, =CH, aryl/hetaryl).<br>LC-MS = 385.1 (M + 1); 284.28 (calculated) |
| 19 | 2.745 | $^1$H-NMR (400.0 MHz, d$_6$-DMSO): δ = 4.13 (m, 2H, CH$_2$); 7.83; 8.47; 8.56; 8.72; 9.18; 9.30; 9.48 (7H, =CH, aryl/hetaryl).<br>LC-MS = 339.1 (M + 1); 338.25 (calculated) |
| 20 | 2.962 | $^1$H-NMR (400.0 MHz, d$_6$-DMSO): δ = 1.15; 3.31 (t + q, 5H, CH$_2$CH$_3$); 7.76; 7.80; 8.36; 8.53; 8.71; 9.29; 9.43 (7H, =CH, aryl/hetaryl).<br>LC-MS = 285.0 (M + 1) [without HCOOH] |
| 21 | 2.248 | $^1$H-NMR (400.0 MHz, d$_6$-DMSO): δ = 1.32; 1.58 (2m, 4H, CH$_2$CH$_2$); 8.54; 8.55; 8.57; 8.73; 9.29; 9.41; 9.48 (7H, =CH, aryl/hetaryl).<br>LC-MS = 322.2 (M + 1) [without HCOOH] |
| 22 | 2.820 | $^1$H-NMR (400.0 MHz, d$_6$-DMSO): δ = 1.19; 4.12 (d + m, 7H, CH(CH$_3$)); 7.76; 7.81; 8.37; 8.56; 8.71; 9.29; 9.42 (7H, =CH, aryl/hetaryl).<br>LC-MS = 299.2 (M + 1) [without HCOOH] |
| 23 | 2.732 | $^1$H-NMR (400.0 MHz, d$_6$-DMSO): δ = 3.30; 3.57 (d + m, 7H, CH(CH$_3$)); 7.53; 7.76; 8.13; 8.54; 8.72; 9.27; 9.39 (7H, =CH, aryl/hetaryl).<br>LC-MS = 301.2 (M + 1) [without HCOOH] |
| 24 | 2.781 | $^1$H-NMR (400.0 MHz, d$_6$-DMSO): δ = 3.70; 6.16 (2m 3H, CH$_2$CHF$_2$); 7.82; 8.44; 8.56; 8.72; 8.96; 9.29; 9.47 (7H, =CH, aryl/hetaryl).<br>LC-MS = 321.2 (M + 1) [without HCOOH] |
| 25 | 2.344 | $^1$H-NMR (400.0 MHz, d$_6$-DMSO): δ = 2.81 (s, 3H, CH$_3$); 7.78; 7.82; 8.35; 8.55; 8.71; 9.28; 9.44 (7H, =CH, aryl/hetaryl).<br>LC-MS = 271.0 (M + 1) [without HCOOH] |

TABLE 2-continued

Analytical data for the compounds 1-48 and 105-128 reported

| Ex. No. | Retention time [min] | $^1$H NMR [δ (ppm)] or LC-MS [m/z] |
|---|---|---|
| 26 | 2.132 | $^1$H-NMR (400.0 MHz, d$_6$-DMSO): δ = 4.14 (m, 2H, CH$_2$); 7.83; 8.49; 9.18; 9.30; 9.37; 9.51; 9.58 (7H, =CH, aryl/hetaryl). LC-MS = 322.0 (M + 1); 321.25 (calculated) |
| 27 | 1.768 | $^1$H-NMR (400.0 MHz, d$_6$-DMSO): δ = 2.99 (s, 6H, 2 × CH$_3$); 7.35; 7.37; 7.78; 7.89; 9.27; 9.34; 9.54 (7H, =CH, aryl/hetaryl). LC-MS = 268.1 (M + 1); 267.28 (calculated) |
| 28 | 2.349 | $^1$H-NMR (400.0 MHz, d$_6$-DMSO): δ = 2.87 (s, 3H, CH$_3$); 7.63; 7.98; 8.40; 9.26; 9.37; 9.55 (7H, =CH, aryl/hetaryl). LC-MS = 318.2 (M + 1); 317.32 (calculated) |
| 29 | 1.872 | $^1$H-NMR (400.0 MHz, d$_6$-DMSO): δ = 2.87 (s, 3H, CH$_3$); 7.80; 8.38; 8.56; 9.29; 9.46; 9.57 (7H, =CH, aryl/hetaryl). LC-MS = 268.2 (M + 1); 267.28 (calculated) |
| 30 | 1.969 | $^1$H-NMR (400.0 MHz, d$_6$-DMSO): δ = 2.87 (s, 3H, CH$_3$); 7.83; 8.45; 8.95; 9.29; 9.49; 9.57 (7H, =CH, aryl/hetaryl). LC-MS = 304.2 (M + 1); 303.26 (calculated) |
| 31 | 1.967 | $^1$H-NMR (400.0 MHz, d$_6$-DMSO): δ = 2.81 (s, 3H, CH$_3$); 7.80; 8.37; 8.52; 9.28; 9.46; 9.56 (7H, =CH, aryl/hetaryl). LC-MS = 254.1 (M + 1); 253.25 (calculated) |
| 32 | 1.895 | $^1$H-NMR (400.0 MHz, d$_6$-DMSO): δ = 3.30; 3.57 (2s, 6H, 2 × CH$_3$); 7.55; 8.79; 8.15; 9.29; 9.40; 9.55 (7H, =CH, aryl/hetaryl). LC-MS = 284.2 (M + 1); 283.28 (calculated) |
| 33 | 2.031 | $^1$H-NMR (400.0 MHz, d$_6$-DMSO): δ = 1.64; 3.77 (t + m, 5H, CH$_2$CF$_2$CH$_3$); 7.82; 8.46; 8.92; 9.29; 9.48; 9.57 (7H, =CH, aryl/hetaryl). LC-MS = 318.1 (M + 1); 317.29 (calculated) |
| 34 | 2.034 | $^1$H-NMR (400.0 MHz, d$_6$-DMSO): δ = 3.00 (s, 6H, 2 × CH$_3$); 7.38; 7.80; 7.91; 8.71; 8.79; 9.34; 9.50 (7H, =CH, aryl/hetaryl). LC-MS = 268.0 (M + 1); 267.28 (calculated) |
| 35 | 2.322 | $^1$H-NMR (400.0 MHz, d$_6$-DMSO): δ = 4.12 (m, 2H, CH$_2$); 7.83; 7.48; 7.72; 8.80; 9.20; 9.50 (7H, =CH, aryl/hetaryl). LC-MS = 322.1 (M + 1); 321.25 (calculated) |
| 36 | 2.042 | $^1$H-NMR (400.0 MHz, d$_6$-DMSO): δ = 2.86 (s, 3H, CH$_3$); 7.63; 7.97; 8.46; 8.68; 8.76; 9.35; 9.48 (7H, =CH, aryl/hetaryl). LC-MS = 318.0 (M + 1); 317.32 (calculated) |
| 37 | 2.447 | $^1$H-NMR (400.0 MHz, d$_6$-DMSO): δ = 3.92 (s, 3H, CH$_3$); 4.11 (m, 2H, CH$_2$); 7.71; 7.77; 8.10; 8.44; 9.02; 9.09 (6H, =CH, aryl/hetaryl). LC-MS = 324.0 (M + 1); 323.27 (calculated) |
| 38 | 1.690 | $^1$H-NMR (400.0 MHz, d$_6$-DMSO): δ = 2.99 (s, 6H, 2 × CH$_3$); 3.92 (s, 3H, CH$_3$); 7.29; 7.68; 7.82; 8.08; 8.43; 8.87 (6H, =CH, aryl/hetaryl). LC-MS = 270.1 (M + 1); 269.30 (calculated) |
| 39 | 1.037 | $^1$H-NMR (300.0 MHz, d$_6$-DMSO): δ = 3.39; 3.93 (2s, 6H, 2 × CH$_3$); 7.74; 8.12; 8.48; 8.53; 9.09 (6H, =CH, aryl/hetaryl). LC-MS = 320.0 (M + 1); 319.33 (calculated) |
| 40 | 1.997 | $^1$H-NMR (400.0 MHz, d$_6$-DMSO): δ = 0.59; 0.69; 2.85 (3m, 5H, Cyclopropyl); 3.92 (s, 3H, CH$_3$); 7.66; 7.73; 8.09; 8.27; 8.45; 8.96 (6H, =CH, aryl/hetaryl). LC-MS = 282.1 (M + 1); 281.31 (calculated) |
| 41 | 1.843 | $^1$H-NMR (400.0 MHz, d$_6$-DMSO): δ = 2.80; 3.92; (2s, 6H, 2 × CH$_3$); 7.67; 7.73; 8.09; 8.29; 8.45; 8.98 (6H, =CH, aryl/hetaryl). LC-MS = 282.1 (M + 1); 255.27 (calculated) |
| 42 | 1.695 | $^1$H-NMR (400.0 MHz, d$_6$-DMSO): δ = 2.89; 3.92; (2s, 6H, 2 × CH$_3$); 7.71; 7.75; 7.76; 8.12; 8.48; 9.06 (6H, =CH, aryl/hetaryl), 11.79 (br, 1H, NH). LC-MS = 349.1 (M + 1); 348.38 (calculated) |
| 43 | 2.350 | $^1$H-NMR (400.0 MHz, d$_6$-DMSO): δ = 1.63; 3.76 (t + m, 5H, CH$_2$CF$_2$CH$_3$); 3.92 (s, 1H, CH$_3$); 7.74; 8.10; 8.38; 8.46; 8.84; 9.00 (6H, =CH, aryl/hetaryl). LC-MS = 320.1 (M + 1); 319.3093 |
| 44 | 2.454 | $^1$H-NMR (400.0 MHz, d$_6$-DMSO): δ = 3.68; 6.14 (2m, 3H, CH$_2$CHF$_2$); 3.92 (s, 1H, CH$_3$); 7.75; 8.10; 8.37; 8.45; 8.88; 9.01 (6H, =CH, aryl/hetaryl). LC-MS = 306.1 (M + 1); 305.28 (calculated) |

TABLE 2-continued

Analytical data for the compounds 1-48 and 105-128 reported

| Ex. No. | Retention time [min] | $^1$H NMR [δ (ppm)] or LC-MS [m/z] |
|---|---|---|
| 45 | 2.033 | $^1$H-NMR (400.0 MHz, d$_6$-DMSO): δ = 3.28; 3.33; 3.92 (2s, 9H, 3 × CH$_3$); 3.92 (s, 1H, CH$_3$); 7.49; 7.68; 8.09; 8.44; 8.93 (6H, =CH, aryl/hetaryl). LC-MS = 286.1 (M + 1); 285.30 (calculated) |
| 46 | 2.053 | $^1$H-NMR (400.0 MHz, d$_6$-DMSO): δ = 1.29; 1.56; (2m, 4H, 2 × CH$_2$); 3.92 (s, 1H, CH$_3$); 7.71; 8.10; 8.34; 8.46; 9.02; 9.34 (6H, =CH, aryl/hetaryl). LC-MS = 307.1 (M + 1); 306.32 (calculated) |
| 47 | 1.968 | $^1$H-NMR (400.0 MHz, d$_6$-DMSO): δ = 1.14; 3.29; (t + q, 5H, CH$_2$CH$_3$); 3.92 (s, 1H, CH$_3$); 7.67; 7.75; 8.09; 8.30; 8.49; 8.97 (6H, =CH, aryl/hetaryl). LC-MS = 270.1 (M + 1); 269.30 (calculated) |
| 48 | 2.127 | $^1$H-NMR (400.0 MHz, d$_6$-DMSO): δ = 1.18; 4.13 (d + m, 5H, CH(CH$_3$)$_2$); 3.92 (s, 3H, CH$_3$); 7.70; 8.09; 8.24; 8.31; 8.45; 8.95 (6H, =CH, aryl/hetaryl). LC-MS = 284.2 (M + 3); 283.32 (calculated) |
| 105 | | $^1$H NMR (300 MHz, DMSO-d$_6$) δ = 0.99 (3H, d, J = 6.4 Hz), 1.79 (3H, s), 2.30 (1H, dd, J1 = 11.8 Hz, J2 = 4.9 Hz), 2.57-2.77 (2H, m), 3.21 (3H, s), 3.93 (3H, s), 7.22 (1H, dd, J1 = 9.0 Hz, J2 = 1.7 Hz), 7.71-7.81 (2H, m), 8.08 (1H, s), 8.43 (1H, s), 8.86 (1H, s). |
| 106 | 1.10 | $^1$H NMR (300 MHz, DMSO-d$_6$) δ = 1.88 (3H, s), 2.34 (2H, t, J = 7.1 Hz), 2.62 (2H, t, J = 7.1 Hz), 3.20 (3H, s), 3.93 (3H, s), 7.21 (1H, dd, J1 = 8.9 Hz, J2 = 1.5 Hz), 7.70-7.79 (2H, m), 8.08 (1H, s), 8.44 (1H, s), 8.85 (1H, s). LC-MS = 330.2 (M + 1); 329.42 (calculated) |
| 108 | 1.20 | $^1$H-NMR (300.0 MHz, d$_6$-DMSO): δ = 1.22; 1.89; 2.34; 2.62; 3.21 (alkyl); 7.30; 7.83; 5.52; 8.70; 9.26; 9.30 (7H, =CH, aryl/hetaryl). LC-MS = 345.2 (M + 1); 344.41 (calculated) |
| 109 | 1.26 | $^1$H-NMR (300.0 MHz, d$_6$-DMSO): δ = 0.99; 1.02; 1.81; 2.69-2.73; 3.21 (alkyl); 7.29; 7.32; 7.82; 7.84; 7.87; 8.51; 8.54; 8.71; 8.72; 9.27; 9.32 (7H, =CH, aryl/hetaryl). LC-MS = 359.2 (M + 1); 358.44 (calculated) |
| 119 | 1.16 | $^1$H NMR (300 MHz, DMSO-d$_6$) δ = 2.55 (3H, s), 2.59-2.72 (2H, m), 2.79-2.90 (1H, m), 3.05-318 (1H, m), 3.33 (3H, s), 4.00 (3H, s), 7.10 (1H, dd, J1 = 9.0 Hz, J2 = 1.9 Hz), 7.54 (1H, d, J = 1.3 Hz), 7.80 (1H, d, J = 9.0 Hz), 7.89 (1H, s), 7.94 (1H, s), 8.22 (1H, s). LC-MS = 346.2 (M + 1); 345.42 (calculated) |
| 120 | 0.86 | $^1$H-NMR (300.0 MHz, d$_6$-CDCl$_3$): δ = 1.13; 1.21; 2.50; 3.14; 3.25; 3.33; 3.99 (alkyl); 7.12-7.18; 7.55-7.8; 8.23 (6H, = CH, aryl/hetaryl). LC-MS = 360.2 (M + 1); 359.45 (calculated) |
| 121 | 0.94 | $^1$H-NMR (300.0 MHz, d$_6$-CDCl$_3$): δ = 1.25; 1.62; (alkyl); 7.14; 7.60; 7.84; 8.09; 8.12; 8.51; 8.56; 9.02 (7H, =CH, aryl/hetaryl). LC-MS = 361.2 (M + 1); 360.41 (calculated) |
| 125 | 0.90 | $^1$H NMR (300 MHz, DMSO-d$_6$) δ = 2.70 (2H, t, J = 7.2 Hz), 2.94 (3H, s), 3.35 (3H, s), 3.40 (2H, t, J = 7.2 Hz), 4.03 (3H, s), 7.12 (1H, dd, J1 = 9.0 Hz, J2 = 1.6 Hz), 7.57 (1H, s), 7.83 (1H, d, J = 8.8 Hz), 7.92 (1H, s), 7.97 (1H, s), 8.25 (1H, s) LC-MS = 362.2 (M + 1); 361.42 (calculated) |
| 126 | 1.05 | $^1$H-NMR (300.0 MHz, d$_6$-DMSO): δ = 1.05; 1.07; 1.76; 2.86; 3.21 (alkyl); 7.32; 7.35; 7.85; 7.88; 8.51; 8.55; 8.71; 9.27; 9.34 (7H, =CH, aryl/hetaryl). LC-MS = 490.1 (M + 1); [without CH$_3$COOH] |
| 127 | 0.92 | $^1$H-NMR (300.0 MHz, d$_6$-DMSO): δ = 1.04; 1.78; 2.96; 3.92 (alkyl); 7.24; 7.75; 7.78; 8.08; 8.43; 8.88 (6H, =CH, aryl/hetaryl). LC-MS = 376.1 (M + 1); [without CH$_3$COOH] |
| 128 | 2.12 | $^1$H-NMR (300.0 MHz, d$_6$-CDCl$_3$): δ = 2.69; 2.94; 3.38; 3.42 (alkyl); 7.15; 7.60; 7.86; 7.89; 8.12; 8.55; 9.01 (7H, =CH, aryl/hetaryl). LC-MS = 377.1 (M + 1); 376.41 (calculated) |

TABLE 3

Analytical data for the compounds 49-104 reported

| Ex. No. | logP[a] | logP[b] | $^1$H NMR [δ (ppm)] or LC-MS [m/z] |
|---|---|---|---|
| 49 | 4.23 | 4.11 | $^1$H-NMR(400.0 MHz, d$_6$-DMSO): δ = 9.374 (3.5); 9.367 (3.5); 9.306 (5.9); 9.305 (5.9); 8.686 (2.4); 8.682 (2.6); 8.674 (2.5); 8.671 (2.6); 8.541 (1.3); 8.537 (1.5); 8.534 (1.5); 8.531 (1.3); 8.520 (1.5); 8.516 (1.5); 8.513 (1.7); 8.510 (1.4); 8.228 (0.3); 7.975 (3.7); 7.860 (2.7); 7.837 (3.1); 7.774 (3.1); 7.754 (3.2); 7.687 (1.9); 7.675 (1.9); 7.666 (1.9); 7.655 (1.9); 7.558 (1.3); 7.553 (2.2); 7.549 (1.3); 7.535 (1.1); 7.531 (2.0); 7.527 (1.1); 7.338 (2.8); 7.309 (2.7); 4.066 (1.3); 4.040 (4.2); 4.014 (4.4); 3.988 (1.5); 3.335 (28.4); 2.893 (0.4); 2.528 (0.5); 2.514 (12.2); 2.510 (24.6); 2.505 (32.5); 2.501 (24.0); 2.496 (11.9); 2.453 (16.0); 2.406 (0.4); 1.397 (1.7). |
| 50 | 4.12 | 4.07 | $^1$H-NMR(400.0 MHz, d$_6$-DMSO): δ = 9.377 (3.4); 9.371 (3.5); 9.274 (5.9); 9.272 (6.2); 8.678 (2.3); 8.675 (2.6); 8.666 (2.5); 8.663 (2.7); 8.542 (1.4); 8.539 (1.6); 8.536 (1.6); 8.532 (1.4); 8.522 (1.5); 8.518 (1.6); 8.515 (1.7); 8.511 (1.5); 8.072 (4.1); 7.858 (2.7); 7.855 (2.3); 7.851 (3.7); 7.847 (3.9); 7.835 (3.6); 7.731 (2.9); 7.727 (2.9); 7.708 (2.1); 7.704 (2.1); 7.681 (1.9); 7.669 (1.9); 7.660 (1.9); 7.648 (1.9); 7.587 (1.9); 7.583 (1.9); 7.568 (2.3); 7.563 (2.3); 7.380 (3.2); 7.360 (2.6); 4.171 (1.3); 4.145 (4.3); 4.119 (4.4); 4.093 (1.5); 3.349 (0.4); 3.334 (63.3); 2.673 (0.3); 2.526 (0.8); 2.513 (18.3); 2.509 (37.9); 2.504 (50.6); 2.499 (37.8); 2.495 (19.1); 2.416 (16.0); 2.331 (0.3); 1.397 (0.4). |
| 51 | 4.42 | 4.40 | $^1$H-NMR(400.0 MHz, d$_6$-DMSO): δ = 9.366 (3.2); 9.359 (3.2); 9.247 (5.6); 9.245 (5.6); 8.679 (2.2); 8.676 (2.4); 8.667 (2.3); 8.664 (2.4); 8.533 (1.3); 8.529 (1.5); 8.526 (1.5); 8.523 (1.3); 8.512 (1.4); 8.508 (1.5); 8.505 (1.6); 8.502 (1.4); 7.810 (2.7); 7.788 (3.0); 7.706 (4.1); 7.681 (1.8); 7.670 (1.7); 7.661 (1.7); 7.649 (1.7); 7.441 (5.8); 7.352 (2.5); 7.348 (2.5); 7.329 (2.3); 7.325 (2.4); 7.236 (4.8); 3.979 (1.3); 3.953 (4.0); 3.927 (4.2); 3.901 (1.4); 3.335 (13.6); 2.528 (0.4); 2.524 (0.6); 2.515 (8.4); 2.510 (17.5); 2.506 (23.5); 2.501 (17.5); 2.497 (8.7); 2.409 (14.6); 2.242 (16.0); 0.000 (1.1). |
| 52 | 2.80 | 2.74 | $^1$H-NMR(400.0 MHz, d$_6$-DMSO): δ = 9.377 (3.5); 9.371 (3.5); 9.323 (6.1); 9.321 (5.9); 8.692 (2.5); 8.688 (2.7); 8.680 (2.6); 8.677 (2.7); 8.545 (1.4); 8.541 (1.6); 8.538 (1.5); 8.535 (1.4); 8.524 (1.6); 8.521 (1.6); 8.518 (1.7); 8.514 (1.4); 8.059 (7.0); 8.039 (3.4); 7.900 (2.8); 7.878 (3.3); 7.693 (1.9); 7.692 (1.9); 7.681 (1.8); 7.673 (1.8); 7.661 (1.8); 7.660 (1.8); 7.613 (1.3); 7.609 (2.3); 7.605 (1.3); 7.591 (1.2); 7.587 (2.0); 7.582 (1.1); 7.447 (2.6); 7.418 (2.5); 4.298 (0.5); 4.288 (0.5); 4.271 (0.7); 4.261 (1.7); 4.243 (0.4); 4.233 (2.1); 4.203 (1.8); 4.193 (0.6); 4.175 (0.6); 4.166 (0.6); 3.329 (42.3); 2.677 (0.4); 2.672 (0.5); 2.668 (0.4); 2.525 (1.4); 2.512 (28.8); 2.508 (57.1); 2.503 (74.6); 2.499 (54.0); 2.494 (25.9); 2.451 (16.0); 2.334 (0.4); 2.330 (0.5); 2.325 (0.4); 1.990 (0.7); 1.176 (0.4); 0.008 (1.4); 0.000 (41.3); −0.009 (1.3). |
| 53 | 2.72 | 2.68 | $^1$H-NMR(400.0 MHz, d$_6$-DMSO): δ = 9.379 (3.6); 9.373 (3.7); 9.294 (6.2); 9.293 (6.0); 8.686 (2.5); 8.683 (2.7); 8.674 (2.7); 8.671 (2.7); 8.546 (1.4); 8.542 (1.7); 8.539 (1.6); 8.536 (1.4); 8.525 (1.6); 8.521 (1.7); 8.518 (1.8); 8.515 (1.5); 8.196 (4.0); 8.191 (4.2); 8.144 (4.2); 7.910 (2.1); 7.900 (2.9); 7.890 (2.4); 7.885 (2.4); 7.877 (3.7); 7.778 (2.9); 7.774 (2.8); 7.755 (2.0); 7.751 (2.0); 7.689 (1.9); 7.677 (1.9); 7.669 (1.9); 7.657 (1.8); 7.485 (3.0); 7.465 (2.7); 4.257 (0.4); 4.247 (0.6); 4.230 (0.8); 4.220 (1.9); 4.206 (1.8); 4.193 (2.0); 4.178 (2.0); 4.166 (0.8); 4.151 (0.7); 4.142 (0.4); 3.331 (136.6); 2.676 (0.5); 2.672 (0.7); 2.667 (0.5); 2.525 (1.9); 2.512 (38.7); 2.507 (77.7); 2.503 (102.1); 2.498 (75.9); 2.494 (38.6); 2.437 (16.0); 2.334 (0.5); 2.330 (0.7); 2.325 (0.5); 1.989 (0.6); 0.008 (0.5); 0.000 (14.6); −0.008 (0.7). |
| 54 | 2.99 | 2.92 | $^1$H-NMR(400.0 MHz, d$_6$-DMSO): δ = 9.371 (3.3); 9.365 (3.5); 9.263 (5.7); 8.681 (2.5); 8.672 (2.5); 8.669 (2.6); 8.536 (1.6); 8.534 (1.6); 8.515 (1.7); 8.513 (1.7); 8.510 (1.4); 7.847 (2.6); 7.825 (2.9); 7.788 (4.4); 7.753 (6.3); 7.687 (1.8); 7.675 (1.8); 7.666 (1.8); 7.654 (1.7); 7.404 (2.3); 7.400 (2.4); 7.381 (2.2); 7.378 (2.2); 7.331 (4.8); 4.173 (1.1); 4.146 (3.4); 4.118 (3.5); 4.091 (1.2); 3.329 |

TABLE 3-continued

Analytical data for the compounds 49-104 reported

| Ex. No. | logP[a] | logP[b] | ¹H NMR [δ (ppm)] or LC-MS [m/z] |
|---|---|---|---|
| | | | (83.0); 2.672 (0.9); 2.562 (0.3); 2.507 (107.3); 2.503 (138.4); 2.498 (111.3); 2.403 (14.9); 2.341 (16.0); 1.989 (0.6); 0.146 (0.9); 0.000 (175.9); −0.150 (0.9). 0.000 (16.1); −0.008 (0.6) |
| 55 | 2.77 | 2.74 | ¹H-NMR(400.0 MHz, d$_6$-DMSO): δ = 9.379 (2.7); 9.361 (13.4); 9.259 (7.9); 9.210 (0.4); 8.695 (2.3); 8.686 (2.4); 8.550 (2.2); 8.547 (2.6); 8.544 (2.5); 8.541 (2.1); 8.529 (2.4); 8.526 (2.6); 8.523 (2.7); 8.520 (2.2); 8.285 (8.4); 8.237 (9.1); 7.947 (16.0); 7.943 (15.7); 7.693 (2.6); 7.681 (2.6); 7.672 (2.6); 7.660 (2.5); 5.759 (0.7); 3.333 (56.9); 2.678 (0.5); 2.673 (0.7); 2.527 (2.0); 2.513 (40.5); 2.509 (79.4); 2.505 (102.3); 2.500 (75.1); 2.336 (0.5); 2.331 (0.6); 1.245 (0.5); 1.230 (0.5); 0.146 (0.9); 0.022 (0.5); 0.008 (8.3); 0.000 (189.5); −0.009 (7.9); −0.150 (1.0). |
| 56 | 2.83 | 2.79 | ¹H-NMR(400.0 MHz, d$_6$-DMSO): δ = 9.375 (8.8); 9.368 (8.8); 9.346 (16.0); 8.809 (7.3); 8.806 (7.4); 8.699 (5.9); 8.696 (6.4); 8.688 (6.1); 8.684 (6.3); 8.547 (3.4); 8.543 (3.9); 8.540 (3.8); 8.537 (3.4); 8.526 (3.7); 8.522 (3.9); 8.519 (4.1); 8.516 (3.4); 8.318 (0.5); 8.277 (9.1); 8.274 (8.8); 7.968 (3.2); 7.944 (11.9); 7.930 (9.9); 7.925 (9.3); 7.907 (2.6); 7.902 (2.8); 7.695 (4.7); 7.683 (4.6); 7.674 (4.6); 7.662 (4.4); 7.076 (8.5); 7.070 (8.5); 3.332 (215.6); 2.677 (0.9); 2.673 (1.2); 2.669 (0.9); 2.526 (3.4); 2.513 (66.6); 2.508 (131.4); 2.504 (171.9); 2.499 (127.4); 2.335 (0.8); 2.331 (1.2); 2.326 (0.8); 1.990 (0.6); 0.000 (0.7). |
| 57 | 0.88 | 1.71 | ¹H-NMR(400.0 MHz, d$_6$-DMSO): δ = 9.384 (9.1); 9.377 (9.3); 9.309 (16.0); 8.988 (8.7); 8.983 (8.9); 8.685 (5.7); 8.682 (6.6); 8.673 (6.1); 8.670 (6.6); 8.591 (5.6); 8.587 (6.3); 8.579 (6.0); 8.575 (6.2); 8.554 (3.3); 8.550 (3.9); 8.547 (4.0); 8.544 (3.5); 8.533 (3.6); 8.529 (4.0); 8.527 (4.3); 8.523 (3.6); 8.318 (0.3); 8.179 (3.3); 8.173 (4.8); 8.169 (3.6); 8.154 (15.7); 7.898 (6.3); 7.876 (8.7); 7.754 (7.1); 7.750 (7.3); 7.732 (5.3); 7.727 (5.5); 7.686 (5.1); 7.674 (5.0); 7.665 (5.0); 7.653 (4.8); 7.528 (4.8); 7.516 (4.7); 7.508 (4.6); 7.496 (4.4); 3.332 (103.5); 2.677 (0.7); 2.673 (0.9); 2.669 (0.7); 2.526 (2.4); 2.508 (102.3); 2.504 (136.8); 2.499 (104.3); 2.335 (0.6); 2.331 (0.9); 2.326 (0.7); 1.990 (0.4); 1.259 (0.4); 1.250 (0.3); 1.230 (0.5); 0.000 (5.7). |
| 58 | 1.51 | 1.57 | ¹H-NMR(400.0 MHz, d$_6$-DMSO): δ = 9.349 (2.4); 9.343 (2.4); 9.149 (4.2); 9.147 (4.1); 8.656 (1.7); 8.653 (1.8); 8.645 (1.8); 8.641 (1.8); 8.511 (1.0); 8.507 (1.2); 8.504 (1.1); 8.501 (1.0); 8.490 (1.1); 8.486 (1.2); 8.483 (1.2); 8.480 (1.0); 8.199 (4.4); 7.943 (4.6); 7.942 (4.5); 7.913 (3.2); 7.757 (1.8); 7.735 (2.5); 7.664 (1.3); 7.663 (1.3); 7.652 (1.3); 7.643 (1.3); 7.631 (1.3); 7.630 (1.3); 7.618 (2.1); 7.614 (2.1); 7.596 (1.6); 7.592 (1.6); 3.885 (16.0); 3.334 (44.0); 2.526 (0.9); 2.512 (17.3); 2.508 (34.2); 2.504 (44.4); 2.499 (32.6); 2.495 (16.2); 1.232 (0.8); 0.000 (7.6). |
| 59 | 1.13 | 1.93 | ¹H-NMR(400.0 MHz, d$_6$-DMSO): δ = 9.378 (9.5); 9.371 (9.4); 9.330 (15.8); 9.329 (16.0); 8.697 (5.2); 8.695 (5.4); 8.684 (11.3); 8.681 (10.9); 8.672 (6.8); 8.669 (6.8); 8.548 (3.8); 8.544 (4.4); 8.541 (4.4); 8.537 (4.3); 8.527 (14.6); 8.520 (5.2); 8.517 (3.9); 8.318 (0.6); 8.167 (6.3); 8.163 (6.1); 8.144 (7.2); 8.140 (7.2); 8.078 (6.7); 8.058 (8.6); 7.926 (3.6); 7.921 (3.6); 7.906 (5.6); 7.902 (5.5); 7.887 (3.1); 7.883 (3.1); 7.856 (8.5); 7.833 (7.4); 7.686 (5.2); 7.675 (5.0); 7.666 (5.0); 7.654 (4.8); 7.373 (4.1); 7.371 (4.3); 7.359 (4.5); 7.355 (4.3); 7.353 (4.0); 7.342 (3.8); 7.340 (3.8); 3.336 (231.2); 2.677 (1.2); 2.672 (1.6); 2.668 (1.2); 2.526 (4.3); 2.512 (90.3); 2.508 (177.5); 2.503 (229.6); 2.499 (167.1); 2.495 (82.5); 2.335 (1.1); 2.330 (1.5); 2.326 (1.1); 2.237 (0.6); 0.008 (2.4); 0.000 (66.9); −0.008 (2.5). |
| 60 | 1.72 | 1.73 | ¹H-NMR(400.0 MHz, d$_6$-DMSO): δ = 9.408 (7.7); 9.406 (7.6); 9.373 (4.0); 9.367 (4.0); 8.934 (14.4); 8.922 (16.0); 8.918 (6.0); 8.915 (4.4); 8.695 (2.8); 8.691 (3.0); 8.683 (2.9); 8.679 (3.0); 8.544 (1.8); 8.541 (2.1); 8.538 (2.0); 8.534 (1.8); 8.524 (2.0); 8.520 (2.1); 8.517 (2.2); 8.513 (1.9); 8.418 (3.6); 8.414 (3.5); 8.395 (3.9); 8.391 (3.9); 7.871 (4.3); 7.848 (4.0); 7.694 (2.3); 7.693 (2.3); 7.682 (2.3); 7.681 (2.3); 7.673 (2.3); 7.672 (2.3); 7.661 (2.2); 7.660 (2.2); 7.456 (3.9); 7.443 (7.3); 7.431 (3.8); 5.761 (0.7); 3.340 (50.8); 2.529 (0.6); 2.524 (0.9); 2.516 (14.0); 2.511 (28.9); 2.507 (38.4); 2.502 (27.9); 2.498 (13.6); 0.000 (5.9). |

TABLE 3-continued

Analytical data for the compounds 49-104 reported

| Ex. No. | logP[a] | logP[b] | ¹H NMR [δ (ppm)] or LC-MS [m/z] |
|---|---|---|---|
| 61 | 2.79 | 2.80 | ¹H-NMR(400.0 MHz, d₆-DMSO): δ = 9.372(9.4); 9.366 (9.6); 9.351(16.0); 9.350(15.8); 8.692(6.4); 8.688(7.0); 8.680(6.8); 8.677(7.0); 8.555(11.1); 8.542(4.0); 8.538(4.4); 8.535(4.2); 8.532(3.8); 8.521(4.1); 8.517(4.4); 8.514(4.6); 8.511(3.9); 8.315 (0.5); 8.104(8.0); 8.098(6.9); 8.094(6.6); 8.085(10.7); 8.075(7.8); 8.071(7.8); 7.985(7.3); 7.965(12.8); 7.946(6.1); 7.875(9.0); 7.852(7.4); 7.691(5.0); 7.690(5.0); 7.679(4.9); 7.670(4.9); 7.658 (4.7); 7.477(10.2); 7.458(9.4); 3.320(58.1); 2.677(0.8); 2.672 (1.1); 2.668(0.8); 2.525(2.9); 2.512(61.4); 2.508(125.1); 2.503 (166.2); 2.499(123.8); 2.494(62.2); 2.334(0.8); 2.330(1.1); 2.325 (0.8); 1.398(4.1); 0.146(0.4); 0.008(3.0); 0.000(90.2); −0.008 (3.8); −0.150(0.4) |
| 62 | 1.97 | 2.11 | ¹H-NMR(601.6 MHz, CDCl₃): δ = 9.216(1.9); 9.212(1.9); 9.199(0.3); 8.704(1.3); 8.702(1.4); 8.697 (1.4); 8.694(1.3); 8.554(3.4); 8.553(3.3); 8.440(0.5); 8.323(0.8); 8.320(0.9); 8.318(0.9); 8.316(0.8); 8.309(0.9); 8.306(1.1); 8.304 (1.0); 8.302(0.9); 7.900(3.0); 7.882(1.7); 7.867(1.8); 7.854 (0.5); 7.814(0.6); 7.596(2.8); 7.593(2.8); 7.537(1.1); 7.529(1.2); 7.523(1.0); 7.515(1.2); 7.464(1.7); 7.462(1.6); 7.449(1.5); 7.447 (1.5); 7.261(23.5); 6.412(2.9); 6.409(2.8); 5.220(8.1); 5.210(0.6); 5.196(1.3); 5.082(0.5); 2.289(16.0); 2.248(0.8); 2.228(0.9); 2.200(2.2); 1.574(8.2); 0.005(0.8); 0.000(21.7); −0.006(0.9) |
| 63 | 2.02 | | ¹H-NMR(400.0 MHz, d₆-DMSO): δ = 9.353(2.1); 9.347(2.1); 9.158(3.6); 8.659(1.4); 8.656(1.6); 8.648 (1.5); 8.644(1.5); 8.515(0.8); 8.511(0.9); 8.509(0.9); 8.505(0.8); 8.494(0.9); 8.491(0.9); 8.488(1.0); 8.484(0.8); 8.337(3.9); 8.031 (4.0); 7.965(2.6); 7.771(1.4); 7.748(2.0); 7.664(1.2); 7.652 (1.2); 7.645(2.3); 7.643(2.6); 7.631(1.2); 7.623(1.3); 7.619(1.3); 5.290(8.0); 3.322(10.6); 2.525(0.5); 2.512(9.7); 2.508(19.6); 2.503 (26.1); 2.499(19.5); 2.494(10.0); 2.190(16.0); 0.008(0.6); 0.000 (15.6); −0.008(0.7) |
| 64 | 1.06 | 2.41 | ¹H-NMR(600.1 MHz, CDCl₃): δ = 9.217(2.7); 9.213(2.7); 8.675(1.8); 8.674(1.8); 8.668(1.9); 8.666 (1.8); 8.532(4.8); 8.371(3.5); 8.323(1.0); 8.321(1.2); 8.320(1.2); 8.317(1.0); 8.309(1.1); 8.307(1.3); 8.306(1.3); 8.303(1.0); 8.045 (1.7); 8.042(1.7); 8.030(2.0); 8.027(2.0); 7.873(2.4); 7.858 (2.0); 7.676(1.3); 7.663(2.9); 7.650(1.8); 7.590(2.6); 7.577(1.9); 7.514(1.4); 7.506(1.4); 7.500(1.4); 7.493(1.3); 7.262(6.2); 7.118 (2.3); 7.106(2.2); 2.657(16.0); 1.652(2.9); 0.000(5.3) |
| 65 | 1.23 | 2.25 | ¹H-NMR(400.0 MHz, d₆-DMSO): □ = 9.371(3.6); 9.364(3.6); 9.299(6.0); 8.678(2.4); 8.675(2.6); 8.666 (2.5); 8.663(2.5); 8.539(1.5); 8.535(1.8); 8.528(3.7); 8.521(3.4); 8.515(1.9); 8.512(1.8); 8.508(1.4); 8.476(4.4); 8.141(2.3); 8.138 (2.2); 8.118(2.7); 8.115(2.6); 7.969(2.8); 7.949(3.3); 7.833(3.1); 7.810(2.8); 7.728(1.8); 7.723(1.9); 7.707(1.6); 7.702(1.6); 7.680(2.0); 7.669(1.9); 7.660(1.9); 7.648(1.9); 3.318(61.0); 2.675 (0.6); 2.671(0.8); 2.667(0.6); 2.506(97.9); 2.502(126.3); 2.498 (93.1); 2.353(16.0); 2.333(0.8); 2.329(0.9); 2.324(0.7); 0.146 (0.6); 0.008(5.6); 0.000(126.5); −0.008(5.1); −0.150(0.6) |
| 66 | 0.97 | 2.2 | ¹H-NMR(400.0 MHz, d₆-DMSO): δ = 9.377(3.1); 9.372(3.2); 9.309(5.4); 9.307(5.3); 8.682(2.2); 8.679 (2.4); 8.670(2.4); 8.667(2.4); 8.544(1.8); 8.540(4.4); 8.534(1.7); 8.527(3.3); 8.523(2.1); 8.520(1.8); 8.516(2.1); 8.513(4.1); 8.510 (4.1); 8.157(2.3); 8.153(2.2); 8.134(2.6); 8.130(2.6); 7.907 (3.7); 7.840(3.0); 7.817(2.6); 7.683(1.7); 7.681(1.7); 7.671(1.6); 7.670(1.6); 7.662(1.7); 7.661(1.6); 7.650(1.6); 7.649(1.6); 7.190 (2.0); 7.189(2.0); 7.178(2.0); 7.176(2.0); 3.326(10.1); 2.527(0.4); 2.514(9.5); 2.509(19.3); 2.505(25.5); 2.500(19.0); 2.496(9.5); 2.418(16.0); 0.008(1.1); 0.000(32.7); −0.008(1.5) |
| 67 | 2.8 | 2.78 | ¹H-NMR(400.0 MHz, d₆-DMSO): δ = 9.374(8.4); 9.369(8.5); 9.338(14.7); 9.336(14.2); 8.724(7.9); 8.723 (8.3); 8.718(8.4); 8.717(8.0); 8.686(6.0); 8.682(6.6); 8.674 (6.4); 8.670(6.5); 8.544(12.8); 8.542(12.8); 8.534(4.1); 8.524(3.9); 8.520(4.0); 8.517(4.3); 8.514(3.6); 8.314(0.6); 8.136(12.2); 8.132(7.9); 8.113(16.0); 8.109(8.4); 8.036(8.1); 8.029(7.8); 8.014 (5.4); 8.008(5.5); 7.862(8.2); 7.839(7.1); 7.686(4.7); 7.684(4.6); 7.674(4.5); 7.672(4.4); 7.665(4.5); 7.663(4.4); 7.653(4.5); 7.651 (4.3); 7.627(0.5); 7.615(0.3); 7.598(0.4); 3.321(179.5); 2.676 (1.0); 2.672(1.3); 2.667(1.0); 2.663(0.5); 2.525(3.2); 2.520(5.0); 2.512(71.7); 2.507(149.0); 2.503(198.9); 2.498(144.8); 2.494 (69.7); 2.338(0.4); 2.334(0.9); 2.329(1.3); 2.325(1.0); 1.989 (0.8); 1.176(0.4); 0.146(0.4); 0.008(2.9); 0.000(98.3); −0.009 (3.3); −0.150(0.4) |
| 68 | 2.17 | 2.21 | ¹H-NMR(400.0 MHz, d₆-DMSO): δ = 9.371(8.7); 9.365(8.7); 9.336(15.4); 9.334(16.0); 8.689(6.1); 8.686 (6.8); 8.678(6.6); 8.674(7.4); 8.671(8.5); 8.667(8.2); 8.659 |

TABLE 3-continued

Analytical data for the compounds 49-104 reported

| Ex. No. | logP[a] | logP[b] | ¹H NMR [δ (ppm)] or LC-MS [m/z] |
|---|---|---|---|
| | | | (7.9); 8.656(8.0); 8.540(3.7); 8.537(4.3); 8.534(4.2); 8.530(3.8); 8.520(4.1); 8.516(4.3); 8.513(4.6); 8.509(3.9); 8.160(7.5); 8.158 (10.3); 8.157(10.4); 8.154(8.5); 8.090(7.4); 8.086(7.8); 8.069 (8.2); 8.066(8.0); 7.851(7.4); 7.831(5.4); 7.829(9.3); 7.827(5.9); 7.689(4.8); 7.687(5.0); 7.677(4.8); 7.675(4.9); 7.665(10.3); 7.661 (8.7); 7.656(5.3); 7.655(5.1); 7.642(6.7); 7.638(6.9); 7.629(0.8); 7.617(0.4); 7.601(0.5); 7.567(0.4); 7.552(0.3); 7.549(0.3); 7.473 (8.2); 7.462(7.9); 7.453(7.6); 7.441(7.7); 5.756(7.7); 3.324 (44.9); 2.674(0.4); 2.528(1.0); 2.523(1.6); 2.514(19.5); 2.510(40.5); 2.505(55.7); 2.501(42.3); 2.496(20.8); 2.332(0.4); 1.250 (0.3); 0.008(0.5); 0.000(15.6); −0.009(0.5) |
| 69 | 2.62 | 2.66 | ¹H-NMR(400.0 MHz, d₆-DMSO): δ = 9.382(9.0); 9.376(9.2); 9.341(16.0); 8.687(6.1); 8.684(6.6); 8.676 (6.6); 8.673(6.7); 8.663(10.4); 8.650(10.4); 8.619(11.1); 8.553 (3.6); 8.549(4.2); 8.546(4.1); 8.543(3.6); 8.532(3.9); 8.528(4.3); 8.526(4.4); 8.522(3.6); 8.313(0.6); 8.231(10.8); 8.227(11.2); 8.181(6.0); 8.177(6.0); 8.158(6.9); 8.154(7.0); 7.857(8.3); 7.834 (7.3); 7.686(4.9); 7.674(4.8); 7.665(4.8); 7.653(4.6); 7.501(6.7); 7.496(6.8); 7.488(6.5); 7.483(6.5); 3.316(106.8); 2.676(0.9); 2.671(1.2); 2.667(0.9); 2.525(3.7); 2.507(133.7); 2.502(180.6); 2.498(138.2); 2.334(0.9); 2.329(1.3); 2.325(1.0); 0.008(1.2); 0.000(32.1); −0.008(1.3) |
| 71 | 1.58 | | ¹H-NMR(400.0 MHz, d₆-DMSO): δ = 9.347(2.4); 9.340(2.5); 9.190(4.2); 8.662(1.6); 8.659(1.8); 8.650 (1.7); 8.647(1.7); 8.511(0.9); 8.508(1.1); 8.505(1.1); 8.502(0.9); 8.491(1.0); 8.487(1.1); 8.484(1.1); 8.481(0.9); 8.128(3.2); 7.885 (1.4); 7.882(1.4); 7.862(2.0); 7.859(2.1); 7.763(2.5); 7.750 (3.0); 7.744(3.5); 7.666(1.3); 7.654(1.9); 7.646(1.4); 7.634(1.2); 6.770(3.2); 6.765(3.3); 6.440(0.7); 6.435(0.7); 3.904(16.0); 3.839 (3.7); 3.309(16.0); 2.670(0.4); 2.523(1.2); 2.506(48.7); 2.501 (64.0); 2.497(47.7); 2.328(0.4); 0.008(0.3); 0.000(9.5) |
| 73 | 1.81 | 1.82 | ¹H-NMR(400.0 MHz, d₆-DMSO): δ = 9.348(4.9); 9.342(4.9); 9.141(8.6); 8.652(3.6); 8.643(3.5); 8.641 (3.5); 8.506(2.3); 8.503(2.3); 8.485(2.4); 8.482(2.5); 8.252(8.9); 7.945(9.1); 7.920(6.6); 7.755(3.3); 7.732(4.7); 7.661(2.6); 7.650 (2.7); 7.640(2.7); 7.629(6.1); 7.608(2.8); 7.605(2.8); 4.196 (2.3); 4.178(7.1); 4.159(7.2); 4.141(2.4); 3.319(26.8); 2.671(0.8); 2.502(113.9); 2.329(0.7); 1.447(7.7); 1.428(16.0); 1.410(7.6); 1.336(0.4); 1.250(0.5); 0.146(0.5); 0.000(95.4); −0.150(0.5) |
| 74 | 1.17 | 1.19 | ¹H-NMR(400.0 MHz, d₆-DMSO): δ = 9.354(2.8); 9.349(3.1); 9.172(4.7); 8.658(2.2); 8.647(2.3); 8.512 (1.5); 8.491(1.6); 8.360(0.4); 8.274(4.9); 8.213(0.4); 8.175(5.0); 8.014(0.3); 7.997(3.8); 7.784(1.9); 7.761(2.7); 7.665(1.7); 7.655 (3.8); 7.645(1.8); 7.633(3.2); 5.769(0.5); 5.755(0.7); 5.545 (2.1); 5.512(2.8); 5.325(2.9); 5.293(2.2); 3.321(17.1); 3.075(1.0); 2.671(0.4); 2.596(16.0); 2.503(58.2); 2.330(0.4); 2.075(0.5); 0.000(19.0) |
| 75 | 1.47 | 1.5 | ¹H-NMR(400.0 MHz, d₆-DMSO): δ = 9.350(3.2); 9.343(3.3); 9.287(5.6); 9.285(5.5); 8.681(2.1); 8.677 (2.3); 8.669(2.3); 8.666(2.3); 8.522(1.2); 8.518(1.4); 8.515(1.4); 8.512(1.3); 8.501(1.3); 8.497(1.4); 8.495(1.5); 8.491(1.3); 7.978 (3.7); 7.761(2.5); 7.738(2.9); 7.677(1.8); 7.665(1.7); 7.656 (1.7); 7.644(1.7); 7.468(2.0); 7.465(2.0); 7.446(1.7); 7.442(1.8); 5.755(3.4); 3.319(22.1); 3.008(16.0); 2.987(1.3); 2.978(0.9); 2.970 (0.7); 2.960(0.4); 2.672(0.4); 2.525(0.7); 2.511(19.0); 2.507 (38.5); 2.503(51.1); 2.498(37.7); 2.494(18.9); 0.561(1.8); 0.547 (1.8); 0.458(2.1); 0.008(0.8); 0.000(23.7); −0.008(1.0) |
| 76 | 1.62 | 2.84 | ¹H-NMR(400.0 MHz, d₆-DMSO): δ = 9.375(4.2); 9.369(4.3); 9.309(7.2); 8.683(2.9); 8.680(3.1); 8.672 (3.1); 8.669(3.1); 8.545(6.4); 8.534(1.8); 8.523(1.9); 8.519(2.0); 8.516(2.1); 8.513(1.7); 8.486(4.3); 8.473(4.4); 8.150(2.8); 8.146 (2.7); 8.127(3.2); 8.123(3.1); 7.852(5.0); 7.850(5.1); 7.837 (4.0); 7.814(3.4); 7.685(2.3); 7.673(2.2); 7.664(2.2); 7.652(2.1); 7.236(3.1); 7.232(3.1); 7.223(3.1); 7.219(3.0); 3.318(62.4); 3.232 (2.2); 3.214(6.9); 3.195(7.1); 3.177(2.3); 2.676(0.6); 2.671(0.8); 2.667(0.6); 2.507(87.7); 2.502(113.3); 2.498(84.3); 2.333 (0.6); 2.329(0.7); 2.325(0.5); 1.363(7.6); 1.345(16.0); 1.327(7.4); 1.259(0.4); 1.250(0.7); 1.230(0.6); 0.000(2.0) |
| 77 | 2.53 | 1.93 | ¹H-NMR(400.0 MHz, d₆-DMSO): δ = 9.364(3.9); 9.358(4.0); 9.306(6.8); 9.304(6.7); 8.682(2.8); 8.678 (3.1); 8.670(3.0); 8.667(3.1); 8.534(1.6); 8.531(1.9); 8.528(1.8); 8.524(1.7); 8.514(1.8); 8.510(1.9); 8.507(2.0); 8.503(1.7); 8.461 (3.0); 8.458(3.3); 8.450(3.3); 8.446(3.3); 7.989(4.8); 7.987 (3.8); 7.883(2.7); 7.879(2.8); 7.862(3.0); 7.859(3.0); 7.819(3.3); 7.796(3.9); 7.685(2.2); 7.683(2.2); 7.673(2.1); 7.672(2.1); 7.664 (2.1); 7.663(2.1); 7.652(2.1); 7.651(2.0); 7.564(3.4); 7.560(3.4); |

TABLE 3-continued

Analytical data for the compounds 49-104 reported

| Ex. No. | logP[a] | logP[b] | ¹H NMR [δ (ppm)] or LC-MS [m/z] |
|---|---|---|---|
| | | | 7.541(2.9); 7.537(3.0); 7.396(3.2); 7.384(3.0); 7.376(2.9); 7.364 (2.9); 5.754(2.5); 3.318(64.0); 2.983(2.1); 2.965(6.8); 2.947 (6.9); 2.928(2.2); 2.676(0.5); 2.671(0.6); 2.667(0.5); 2.525(1.7); 2.520(2.7); 2.511(34.0); 2.507(69.0); 2.502(92.0); 2.498(68.4); 2.493(34.2); 2.334(0.4); 2.329(0.6); 2.324(0.4); 1.352(1.8); 1.336(1.3); 1.299(0.4); 1.259(0.7); 1.250(1.9); 1.232(1.8); 1.228 (1.8); 1.208(7.6); 1.189(16.0); 1.171(7.3); 0.000(1.9) |
| 79 | 3.57 | 3.57 | ¹H-NMR(400.0 MHz, d₆-DMSO): δ = 9.375(3.2); 9.369(3.2); 9.347(6.5); 9.346(6.7); 8.683(2.3); 8.680 (2.4); 8.671(2.4); 8.669(2.4); 8.549(5.0); 8.543(2.5); 8.539(2.1); 8.536(1.9); 8.533(1.7); 8.522(1.8); 8.518(1.9); 8.515(2.0); 8.512 (1.6); 8.314(0.4); 8.157(2.7); 8.153(2.7); 8.134(3.1); 8.130 (3.2); 7.866(3.7); 7.844(3.2); 7.788(1.7); 7.786(2.0); 7.769(4.7); 7.767(4.5); 7.751(3.8); 7.732(4.8); 7.713(1.9); 7.685(2.0); 7.673 (2.0); 7.665(2.0); 7.652(1.9); 7.240(3.4); 7.238(3.7); 7.221(3.2); 7.219(3.4); 3.319(52.8); 3.305(2.4); 3.287(6.8); 3.268(6.9); 3.250(2.2); 2.891(0.5); 2.732(0.4); 2.676(0.6); 2.671(0.8); 2.667 (0.6); 2.525(2.2); 2.511(45.8); 2.507(91.2); 2.502(119.4); 2.498 (88.9); 2.494(44.6); 2.334(0.6); 2.329(0.8); 2.325(0.6); 1.419 (7.4); 1.401(16.0); 1.383(7.2); 1.232(0.3); 0.922(0.4); 0.146(0.5); 0.008(4.1); 0.000(106.0); −0.008(4.7); −0.150(0.5) |
| 80 | 2.87 | 3.03 | ¹H-NMR(400.0 MHz, d₆-DMSO): δ = 9.371(3.9); 9.365(3.9); 9.314(6.6); 8.681(2.7); 8.678(2.9); 8.669 (2.8); 8.666(2.8); 8.618(3.8); 8.613(3.8); 8.540(1.6); 8.537(1.8); 8.534(1.7); 8.530(1.5); 8.513(6.5); 8.146(2.6); 8.142(2.4); 8.123 (2.9); 8.119(2.9); 8.039(3.0); 8.018(3.9); 7.882(3.0); 7.876 (2.9); 7.861(2.4); 7.855(2.4); 7.845(3.5); 7.822(3.0); 7.682(2.1); 7.671(2.0); 7.662(2.0); 7.650(2.0); 3.318(79.7); 3.113(2.3); 3.095 (7.4); 3.076(7.5); 3.058(2.5); 2.676(0.5); 2.671(0.8); 2.667(0.6); 2.524(2.4); 2.511(45.8); 2.507(90.2); 2.502(117.9); 2.498 (87.2); 2.493(44.0); 2.334(0.6); 2.329(0.8); 2.325(0.6); 1.352(0.9); 1.336(0.4); 1.295(7.8); 1.276(16.0); 1.258(7.8); 1.250(0.9); 1.232(1.0); 0.000(1.9) |
| 81 | 3.15 | 3.12 | ¹H-NMR(400.0 MHz, d₆-DMSO): δ = 9.967(3.6); 9.462(5.6); 9.448(0.4); 9.390(3.2); 9.384(3.3); 8.702 (2.3); 8.699(2.5); 8.690(2.4); 8.687(2.5); 8.557(5.0); 8.539(1.5); 8.536(1.8); 8.533(1.9); 8.529(1.5); 7.921(1.4); 7.918(1.3); 7.899 (2.6); 7.895(2.6); 7.851(3.5); 7.828(1.8); 7.698(1.8); 7.686 (1.8); 7.678(1.8); 7.666(1.7); 7.571(5.2); 7.208(4.7); 4.038(0.4); 4.021(0.4); 3.892(1.1); 3.866(3.5); 3.840(3.6); 3.814(1.2); 3.317 (32.3); 2.675(0.4); 2.671(0.5); 2.666(0.4); 2.524(1.5); 2.510(31.3); 2.506(61.7); 2.502(81.3); 2.497(60.7); 2.493(30.4); 2.385 (14.2); 2.333(0.5); 2.329(0.6); 2.324(0.5); 2.226(16.0); 2.204(1.4); 2.185(0.9); 1.988(1.9); 1.193(0.5); 1.175(1.0); 1.158(0.5); 0.008 (1.4); 0.000(38.9); −0.008(1.4) |
| 82 | 3.22 | 3.15 | ¹H-NMR(400.0 MHz, d₆-DMSO): δ = 10.340(4.2); 9.465(6.6); 9.464(6.2); 9.390(3.5); 9.384(3.6); 8.705 (2.5); 8.701(2.7); 8.693(2.6); 8.689(2.7); 8.559(1.5); 8.555(1.8); 8.552(1.7); 8.549(1.6); 8.538(6.1); 8.535(4.9); 8.528(1.7); 8.313 (0.4); 8.005(3.7); 8.000(3.8); 7.907(1.4); 7.903(1.3); 7.884 (3.8); 7.880(4.0); 7.861(4.6); 7.838(1.6); 7.718(2.0); 7.713(2.0); 7.699(3.3); 7.692(2.6); 7.689(2.5); 7.680(1.9); 7.668(1.9); 7.667 (1.8); 7.278(3.1); 7.257(2.8); 3.916(1.4); 3.891(4.5); 3.865(4.7); 3.839(1.6); 3.316(37.0); 2.676(0.5); 2.671(0.7); 2.667(0.5); 2.524(2.1); 2.511(39.5); 2.506(79.7); 2.502(106.8); 2.497(80.0); 2.493(39.9); 2.370(16.0); 2.333(0.6); 2.329(0.8); 2.324(0.6); 1.988(0.8); 1.176(0.4); 0.008(1.6); 0.000(47.8); −0.009(1.7) |
| 85 | 1.45 | 1.5 | ¹H-NMR(400.0 MHz, d₆-DMSO): δ = 9.411(3.6); 9.366(1.8); 9.360(1.8); 8.700(0.5); 8.690(1.8); 8.687 (2.2); 8.678(1.6); 8.675(1.7); 8.536(0.7); 8.532(0.8); 8.529(0.8); 8.526(0.7); 8.515(0.8); 8.511(0.9); 8.508(0.9); 8.505(0.7); 8.377 (2.5); 7.799(2.5); 7.795(3.6); 7.792(3.1); 7.686(1.0); 7.674 (1.0); 7.665(0.9); 7.653(0.9); 3.514(0.7); 3.498(1.5); 3.480(1.5); 3.464(0.8); 3.319(45.1); 2.704(1.8); 2.685(2.5); 2.676(0.4); 2.668 (1.8); 2.525(0.8); 2.511(17.8); 2.507(36.3); 2.502(48.0); 2.498 (35.2); 2.493(17.3); 2.122(16.0); 0.008(0.6); 0.000(20.4); −0.008 (0.8) |
| 86 | 1.55 | 1.55 | ¹H-NMR(400.0 MHz, d₆-DMSO): δ = 9.350(2.9); 9.344(3.1); 9.311(5.6); 8.687(2.3); 8.678(2.1); 8.675 (2.3); 8.524(1.2); 8.520(1.5); 8.517(1.5); 8.514(1.4); 8.503(1.3); 8.499(1.5); 8.496(1.6); 8.493(1.4); 7.912(1.3); 7.826(2.6); 7.804 (2.9); 7.683(1.7); 7.671(1.7); 7.662(1.7); 7.650(1.6); 7.366 (1.0); 7.345(0.9); 6.295(0.6); 5.755(1.1); 3.893(0.7); 3.323(9.7); 3.088(16.0); 2.508(22.2); 2.504(30.2); 2.500(24.3); 0.000(5.7) |
| 87 | 1.14 | 1.16 | ¹H-NMR(400.0 MHz, d₆-DMSO): δ = 9.346(8.9); 9.340(9.0); 9.303(15.2); 9.302(16.0); 8.686(5.7); 8.683 |

TABLE 3-continued

Analytical data for the compounds 49-104 reported

| Ex. No. | logP[a] | logP[b] | ¹H NMR [δ (ppm)] or LC-MS [m/z] |
|---|---|---|---|
| | | | (6.4); 8.674(6.0); 8.671(6.4); 8.520(3.4); 8.517(3.9); 8.514 (3.9); 8.510(3.5); 8.500(3.7); 8.496(3.9); 8.493(4.2); 8.489(3.6); 8.313(0.7); 7.896(11.8); 7.813(7.2); 7.790(8.0); 7.680(5.1); 7.668 (4.9); 7.659(4.8); 7.647(4.6); 7.377(6.8); 7.373(7.0); 7.354(6.2); 7.351(6.5); 4.056(0.4); 4.038(1.2); 4.020(1.2); 4.003(0.4); 3.628 (10.1); 3.548(4.7); 3.415(0.3); 3.355(0.4); 3.339(0.6); 3.315 (198.6); 2.716(0.5); 2.675(1.4); 2.671(1.9); 2.666(1.4); 2.662 (0.7); 2.565(0.4); 2.524(4.8); 2.510(94.3); 2.506(194.6); 2.501 (267.1); 2.497(203.5); 2.493(103.2); 2.333(1.3); 2.328(1.8); 2.324 (1.3); 1.988(5.2); 1.336(0.9); 1.299(0.3); 1.259(0.5); 1.250(1.2); 1.235(0.5); 1.193(1.4); 1.175(2.7); 1.157(1.3); 0.008(1.5); 0.000 (50.0); −0.008(1.9) |
| 88 | 1.43 | 1.48 | ¹H-NMR(400.0 MHz, d₆-DMSO): δ = 9.412(0.3); 9.348(8.9); 9.342(9.0); 9.293(16.0); 9.291(15.5); 8.683 (6.2); 8.679(6.7); 8.671(6.4); 8.668(6.6); 8.523(3.8); 8.519 (4.4); 8.516(4.2); 8.512(3.7); 8.502(4.1); 8.498(4.4); 8.495(4.6); 8.492(3.8); 8.313(1.6); 8.005(12.2); 7.781(7.8); 7.758(9.0); 7.729 (0.3); 7.678(5.1); 7.677(5.1); 7.667(5.0); 7.657(4.8); 7.646(4.7); 7.644(4.5); 7.481(7.9); 7.477(7.8); 7.459(6.7); 7.455(6.9); 7.183 (0.4); 5.920(0.5); 5.753(1.0); 3.902(1.1); 3.503(10.8); 3.492 (10.9); 3.371(0.3); 3.315(234.6); 2.675(2.4); 2.671(3.3); 2.666 (2.5); 2.595(0.5); 2.524(9.5); 2.511(169.3); 2.506(342.2); 2.502 (458.1); 2.497(343.6); 2.493(171.5); 2.333(2.1); 2.328(2.9); 2.324(2.1); 2.043(0.5); 2.009(0.5); 1.898(4.5); 1.883(4.8); 1.865 (3.8); 1.848(4.9); 1.833(4.5); 1.352(0.6); 1.336(4.4); 1.298(2.0); 1.259(3.1); 1.250(6.1); 1.235(2.8); 1.188(0.4); 0.854(0.5); 0.146 (1.1); 0.016(0.8); 0.008(9.3); 0.000(270.2); −0.009(9.9); −0.150 (1.1) |
| 89 | 1.63 | 1.65 | ¹H-NMR(400.0 MHz, d₆-DMSO): δ = 9.342(8.9); 9.336(8.9); 9.271(15.2); 9.270(16.0); 8.682(5.9); 8.678 (6.6); 8.670(6.2); 8.667(6.5); 8.517(3.5); 8.513(4.1); 8.511 (4.0); 8.507(3.6); 8.496(3.8); 8.493(4.1); 8.490(4.4); 8.486(3.6); 8.314(0.5); 7.834(0.5); 7.804(15.5); 7.803(15.6); 7.779(8.1); 7.676 (5.1); 7.665(4.9); 7.656(4.8); 7.644(4.7); 7.307(6.9); 7.303 (6.7); 7.285(6.1); 7.281(6.5); 4.303(0.5); 3.671(0.9); 3.375(2.5); 3.356(2.5); 3.345(2.4); 3.335(2.4); 3.317(58.3); 2.676(0.7); 2.671 (0.9); 2.667(0.7); 2.524(2.8); 2.507(106.2); 2.502(142.9); 2.498 (108.9); 2.494(56.1); 2.466(0.5); 2.463(0.5); 2.334(0.7); 2.329 (1.0); 2.325(0.7); 1.336(1.0); 1.299(0.5); 1.259(0.7); 1.250 (1.4); 1.233(0.7); 1.214(0.5); 1.197(0.9); 1.134(11.3); 0.146(0.8); 0.008(6.0); 0.000(158.8); −0.008(7.1); −0.150(0.8) |
| 90 | 1.84 | 1.87 | ¹H-NMR(400.0 MHz, d₆-DMSO): δ = 9.348(3.5); 9.342(3.5); 9.313(5.9); 8.693(2.4); 8.690(2.6); 8.681 (2.5); 8.678(2.5); 8.524(1.4); 8.521(1.7); 8.518(1.6); 8.514(1.4); 8.503(1.5); 8.500(1.7); 8.497(1.7); 8.493(1.4); 7.940(2.4); 7.840 (2.9); 7.817(3.1); 7.685(1.9); 7.674(1.9); 7.665(1.9); 7.653 (1.8); 7.368(1.6); 7.345(1.5); 4.425(0.4); 4.378(1.0); 4.361(1.0); 3.318(44.4); 3.143(0.4); 3.121(16.0); 2.672(0.5); 2.667(0.4); 2.507 (59.1); 2.502(76.5); 2.498(57.7); 2.333(0.4); 2.329(0.5); 2.325 (0.4); 0.000(2.5) |
| 91 | 3.22 | 3.12 | ¹H-NMR(400.0 MHz, d₆-DMSO): δ = 10.202(4.5); 9.474(6.5); 9.389(3.7); 9.383(3.8); 8.704(2.5); 8.701 (2.8); 8.693(2.7); 8.689(2.8); 8.576(4.5); 8.560(1.6); 8.556(1.8); 8.554(1.8); 8.550(1.6); 8.539(1.6); 8.536(1.8); 8.533(1.9); 8.529 (1.6); 8.313(0.3); 7.913(1.5); 7.909(1.5); 7.890(3.4); 7.886 (3.6); 7.857(4.3); 7.844(3.4); 7.834(2.3); 7.824(3.3); 7.699(2.0); 7.687(2.0); 7.678(2.0); 7.667(1.9); 7.313(2.8); 7.284(2.8); 3.918 (1.4); 3.892(4.3); 3.866(4.5); 3.840(1.6); 3.317(33.8); 2.676 (0.3); 2.671(0.5); 2.667(0.4); 2.511(26.0); 2.507(51.7); 2.502(70.1); 2.498(55.4); 2.465(0.6); 2.429(16.0); 2.333(0.4); 2.329(0.5); 2.324(0.4); 0.008(0.5); 0.000(11.8) |
| 92 | 1.5 | 1.58 | ¹H-NMR(400.0 MHz, d₆-DMSO): δ = 9.346(9.8); 9.340(10.0); 9.293(16.0); 8.682(7.3); 8.670(7.1); 8.514 (4.9); 8.493(5.0); 8.311(0.6); 7.883(13.3); 7.810(7.4); 7.788 (8.0); 7.678(5.0); 7.666(5.2); 7.657(5.0); 7.645(4.5); 7.352(7.3); 7.329(6.6); 4.056(0.6); 4.039(1.6); 4.021(1.7); 4.003(0.7); 3.768 (4.7); 3.626(0.5); 3.308(53.9); 2.671(15.8); 2.501(307.4); 2.328 (2.0); 1.988(6.2); 1.193(1.7); 1.176(3.3); 1.158(1.7); 0.000 (15.5) |
| 93 | 0.87 | 1.03 | ¹H-NMR(400.0 MHz, d₆-DMSO): δ = 9.353(9.2); 9.346(9.3); 9.323(16.0); 8.690(5.9); 8.687(6.8); 8.678 (6.2); 8.675(6.7); 8.526(3.2); 8.523(3.9); 8.520(4.0); 8.516(3.5); 8.505(3.5); 8.502(3.9); 8.499(4.3); 8.495(3.6); 8.310(0.7); 8.014 (12.3); 7.829(7.1); 7.807(8.0); 7.683(5.1); 7.671(4.9); 7.662 (4.8); 7.650(4.7); 7.457(0.4); 7.442(6.5); 7.439(6.9); 7.420(5.8); 7.417(6.3); 4.056(1.0); 4.050(0.8); 4.039(2.5); 4.021(2.6); 4.003 |

TABLE 3-continued

Analytical data for the compounds 49-104 reported

| Ex. No. | logP[a] | logP[b] | ¹H NMR [δ (ppm)] or LC-MS [m/z] |
|---|---|---|---|
| | | | (1.4); 3.920(4.2); 3.793(0.4); 3.322(349.3); 3.294(11.0); 3.282 (12.9); 2.722(0.4); 2.675(1.1); 2.671(1.6); 2.666(1.3); 2.524 (3.9); 2.506(186.6); 2.502(251.0); 2.497(188.8); 2.333(1.1); 2.328 (1.6); 2.324(1.2); 1.988(9.0); 1.193(2.4); 1.176(4.6); 1.158 (2.3); 0.008(0.4); 0.000(13.4) |
| 94 | 2.23 | 2.23 | ¹H-NMR(400.0 MHz, $d_6$-DMSO): δ = 10.618(4.2); 9.478(6.2); 9.394(3.7); 9.387(3.8); 8.706(2.5); 8.703 (2.8); 8.695(2.7); 8.691(2.9); 8.600(4.5); 8.563(1.4); 8.560(1.7); 8.557(1.6); 8.553(1.5); 8.543(1.6); 8.539(1.7); 8.536(1.8); 8.532 (1.5); 8.373(3.9); 8.368(4.2); 8.314(0.3); 8.000(1.9); 7.995 (1.9); 7.980(2.1); 7.974(2.1); 7.940(1.7); 7.936(1.8); 7.917(3.3); 7.913(3.5); 7.869(4.0); 7.847(2.1); 7.703(2.0); 7.691(1.9); 7.682 (1.9); 7.670(1.9); 7.367(3.0); 7.346(2.8); 4.181(1.0); 4.171(0.5); 4.153(1.1); 4.143(1.3); 4.126(0.5); 4.116(1.3); 4.089(0.4); 3.949 (0.3); 3.922(1.2); 3.913(0.4); 3.895(1.4); 3.885(1.1); 3.868 (0.5); 3.858(1.0); 3.832(0.3); 3.318(50.7); 2.791(0.6); 2.676(0.6); 2.671(0.8); 2.667(0.6); 2.635(0.5); 2.524(2.4); 2.511(44.9); 2.507(91.6); 2.502(122.3); 2.497(92.4); 2.493(47.8); 2.351(16.0); 2.333(0.9); 2.329(1.0); 2.324(0.8); 1.336(0.7); 1.299(0.5); 1.259 (0.8); 1.250(1.0); 1.234(0.5); 0.146(0.6); 0.008(5.1); 0.000 (138.3); −0.008(6.3); −0.150(0.6) |
| 95 | 0.9 | 0.95 | |
| 96 | 2.19 | 2.14 | ¹H-NMR(400.0 MHz, $d_6$-DMSO): δ = 10.415(4.3); 9.488(6.7); 9.391(3.8); 9.385(3.8); 8.707(2.8); 8.704 (2.7); 8.695(2.8); 8.692(2.7); 8.598(4.7); 8.562(1.5); 8.558(1.8); 8.556(1.7); 8.552(1.4); 8.541(1.6); 8.538(1.8); 8.535(1.8); 8.531 (1.4); 8.314(0.4); 8.167(3.2); 8.148(3.2); 7.923(1.5); 7.920 (1.4); 7.900(3.6); 7.897(3.5); 7.870(4.4); 7.847(1.8); 7.703(2.1); 7.691(2.0); 7.682(2.0); 7.670(1.9); 7.413(2.7); 7.385(2.7); 5.754 (0.5); 4.238(0.9); 4.229(0.5); 4.211(1.1); 4.201(1.3); 4.183(0.5); 4.174(1.3); 4.147(0.4); 4.055(0.4); 4.029(1.2); 4.020(0.4); 4.002 (1.4); 3.992(1.0); 3.974(0.5); 3.965(1.0); 3.317(62.0); 2.671 (1.7); 2.557(0.4); 2.524(3.1); 2.506(119.8); 2.502(153.5); 2.497 (112.4); 2.399(16.0); 2.333(0.7); 2.328(1.0); 2.324(0.7); 1.909 (3.4); 1.235(0.9); 0.146(1.0); 0.008(8.2); 0.000(206.2); −0.008 (8.5); −0.025(0.4); −0.150(1.0) |
| 97 | 2.2 | 2.22 | ¹H-NMR(601.6 MHz, DMF): δ = 10.128(0.3); 9.505(1.0); 9.504(0.9); 9.455(0.5); 9.451(0.5); 8.740 (0.4); 8.738(0.4); 8.732(0.4); 8.730(0.4); 8.705(0.7); 8.091(1.0); 8.052(0.4); 8.049(0.4); 8.037(0.7); 8.034(0.7); 8.024(5.2); 7.906 (0.6); 7.891(0.5); 7.326(0.8); 3.465(16.0); 2.921(2.9); 2.918 (5.7); 2.915(8.1); 2.912(5.6); 2.909(2.7); 2.751(3.1); 2.747(6.3); 2.744(9.0); 2.741(6.3); 2.738(3.1); 2.438(3.0); 2.433(2.9); 0.005 (0.5); 0.000(12.7); −0.006(0.4) |
| 98 | 1.27 | 1.30 | ¹H-NMR(400.0 MHz, $d_6$-DMSO): δ = 12.941(2.9); 9.350(9.6); 9.344(9.6); 9.136(16.0); 8.655(6.5); 8.652 (7.1); 8.643(6.8); 8.640(7.0); 8.510(3.7); 8.507(4.5); 8.505 (4.5); 8.501(3.8); 8.490(4.0); 8.486(4.6); 8.484(4.8); 8.480(3.8); 8.314(0.7); 8.257(4.7); 8.007(4.6); 7.951(12.7); 7.755(5.7); 7.732 (9.9); 7.676(8.2); 7.673(8.3); 7.662(5.6); 7.650(9.7); 7.641(5.2); 7.629(4.7); 3.321(105.7); 2.891(0.4); 2.732(0.4); 2.672(1.3); 2.507(159.7); 2.503(205.5); 2.498(160.5); 2.329(1.3); 0.000 (5.4) |
| 99 | 2.12 | 2.12 | ¹H-NMR(400.0 MHz, $d_6$-DMSO): δ = 9.356(8.4); 9.350(8.8); 9.175(14.9); 8.661(6.6); 8.649(6.7); 8.513 (4.1); 8.492(4.4); 8.349(15.0); 8.139(16.0); 7.998(11.7); 7.786 (6.0); 7.763(8.2); 7.667(4.5); 7.655(4.9); 7.646(11.1); 7.635 (4.8); 7.623(5.3); 5.206(2.9); 5.183(9.2); 5.160(9.6); 5.137(3.3); 3.323(45.8); 2.673(0.7); 2.504(114.3); 2.330(0.7); 1.990(0.9); 1.176(0.5); 0.146(0.6); 0.000(109.6); −0.150(0.6) |
| 101 | 2.04 | 2.21 | ¹H-NMR(400.0 MHz, $d_6$-DMSO): δ = 9.382(9.7); 9.375(9.6); 9.348(16.0); 8.730(5.1); 8.716(5.4); 8.707 (5.3); 8.693(5.9); 8.688(7.0); 8.685(7.1); 8.676(6.8); 8.673(6.8); 8.608(11.3); 8.551(3.6); 8.548(4.2); 8.545(4.1); 8.541(3.6); 8.531(3.9); 8.527(4.2); 8.524(4.4); 8.521(3.6); 8.315(0.4); 8.186 (6.1); 8.182(5.9); 8.163(7.0); 8.159(6.9); 8.045(5.1); 8.040(5.2); 8.017(5.3); 8.011(5.0); 7.859(8.5); 7.836(7.4); 7.686(5.0); 7.674 (4.9); 7.665(4.8); 7.653(4.7); 7.310(3.2); 7.304(3.0); 7.296 (3.3); 7.289(4.8); 7.283(3.0); 7.275(3.2); 7.269(2.8); 3.324(78.0); 3.322(83.3); 2.677(0.6); 2.673(0.8); 2.668(0.6); 2.508(103.2); 2.504(133.3); 2.499(96.6); 2.335(0.6); 2.331(0.8); 2.326(0.6); 0.008(2.0); 0.000(50.1); −0.008(2.0) |
| 104 | 2.4 | 2.44 | |

BIOLOGICAL EXAMPLES

*Myzus persicae*—Spray Test

Solvent:

78 parts by weight of acetone 1.5 parts by weight of dimethylformamide

Emulsifier: alkylaryl polyglycol ether

To produce a suitable preparation of active compound, 1 part by weight of active compound is dissolved using the specified parts by weight of solvent and made up with water containing an emulsifier concentration of 1000 ppm until the desired concentration is attained. To produce further test concentrations, the formulation is diluted with emulsifier-containing water.

Discs of Chinese cabbage leaves (*Brassica pekinensis*) infested by all stages of the green peach aphid (*Myzus persicae*) are sprayed with an active compound formulation of the desired concentration.

After 6 days, the efficacy in % is determined. 100% means that all the aphids have been killed; 0% means that no aphids have been killed.

In this test, for example, the following compounds from the preparation examples showed an efficacy of 100% at an application rate of 500 g/ha: 1, 3, 5, 7, 16, 24, 30, 32, 33, 50, 52, 61, 67, 68, 69, 74, 79, 80, 86, 87, 88, 89, 92, 96, 97, 108, 109, 112, 115, 121, 122, 128

In this test, for example, the following compounds from the preparation examples showed an efficacy of 90% at an application rate of 500 g/ha: 4, 6, 8, 9, 10, 11, 13, 14, 15, 18, 19, 20, 22, 25, 27, 31, 37, 49, 51, 53, 54, 55, 56, 57, 58, 60, 62, 63, 64, 65, 66, 71, 73, 75, 76, 77, 81, 82, 85, 90, 94, 95, 99, 101, 104, 105, 110, 111, 113, 114, 116, 118, 123, 124, 126, 129, 130

In this test, for example, the following compounds from the preparation examples show an efficacy of 100% at an application rate of 100 g/ha: 23

In this test, for example, the following compounds from the preparation examples showed an efficacy of 90% at an application rate of 100 g/ha: 26, 29, 59, 91

*Myzus persicae*—Spray Test

Solvent: 7 parts by weight of dimethylformamide

Emulsifier: alkylaryl polyglycol ether

To produce a suitable preparation of active compound, 1 part by weight of active compound is dissolved using the specified parts by weight of solvent and made up with water containing an emulsifier concentration of 1000 ppm until the desired concentration is attained. To produce further test concentrations, the formulation is diluted with emulsifier-containing water. If the addition of ammonium salts or/and penetrants is required, these are each added in a concentration of 1000 ppm to the formulation solution.

Bell pepper plants (*Capsicum annuum*) severely infested with the green peach aphid (*Myzus persicae*) are treated by spraying with the active compound formulation in the desired concentration.

After 6 days, the kill in % is determined. 100% means that all of the aphids have been killed; 0% means that none of the aphids have been killed.

In this test, for example, the following compounds from the preparation examples showed an efficacy of 100% at an application rate of 4 ppm: 51

*Phaedon cochleariae*—Spray Test

Solvent:

78.0 parts by weight of acetone 1.5 parts by weight of dimethylformamide

Emulsifier: alkylaryl polyglycol ether

To produce a suitable preparation of active compound, 1 part by weight of active compound is dissolved using the specified parts by weight of solvent and made up with water containing an emulsifier concentration of 1000 ppm until the desired concentration is attained. To produce further test concentrations, the formulation is diluted with emulsifier-containing water.

Discs of Chinese cabbage leaves (*Brassica pekinensis*) are sprayed with an active compound preparation of the desired concentration and, after drying, populated with larvae of the mustard beetle (*Phaedon cochleariae*).

After 7 days, the efficacy in % is determined. 100% means that all the beetle larvae have been killed; 0% means that no beetle larvae have been killed.

In this test, for example, the following compounds from the preparation examples showed an efficacy of 100% at an application rate of 500 g/ha: 16, 38

*Spodoptera frugiperda*—Spray Test

Solvent:

78.0 parts by weight of acetone 1.5 parts by weight of dimethylformamide

Emulsifier: alkylaryl polyglycol ether

To produce a suitable preparation of active compound, 1 part by weight of active compound is dissolved using the specified parts by weight of solvent and made up with water containing an emulsifier concentration of 1000 ppm until the desired concentration is attained. To produce further test concentrations, the formulation is diluted with emulsifier-containing water.

Leaf discs of maize (*Zea mays*) are sprayed with an active compound formulation of the desired concentration and, after drying, populated with caterpillars of the armyworm (*Spodoptera frugiperda*).

After 7 days, the efficacy in % is determined. 100% means that all the caterpillars have been killed; 0% means that no caterpillar has been killed.

In this test, for example, the following compounds from the preparation examples showed an efficacy of 100% at an application rate of 500 g/ha: 38

*Tetranychus urticae*—Spray Test, OP-Resistant

Solvent:

78.0 parts by weight of acetone 1.5 parts by weight of dimethylformamide

Emulsifier: alkylaryl polyglycol ether

To produce a suitable preparation of active compound, 1 part by weight of active compound is dissolved using the specified parts by weight of solvent and made up with water containing an emulsifier concentration of 1000 ppm until the desired concentration is attained. To produce further test concentrations, the formulation is diluted with emulsifier-containing water.

Discs of bean leaves (*Phaseolus vulgaris*) infested with all stages of the greenhouse red spider mite (*Tetranychus urticae*) are sprayed with an active compound formulation of the desired concentration.

After 6 days, the efficacy in % is determined. 100% means that all the spider mites have been killed; 0% means that no spider mites have been killed.

In this test, for example, the following compounds from the preparation examples showed an efficacy of 90% at an application rate of 500 g/ha: 117

*Aphis gossypii*—Spray Test

Solvent: 7 parts by weight of dimethylformamide
Emulsifier: alkylaryl polyglycol ether To produce a suitable preparation of active compound, 1 part by weight of active compound is dissolved using the specified parts by weight of solvent and made up with water containing an emulsifier concentration of 1000 ppm until the desired concentration is attained. To produce further test concentrations, the formulation is diluted with emulsifier-containing water. If the addition of ammonium salts or/and penetrants is required, these are each added in a concentration of 1000 ppm to the formulation solution.

Cotton plants (*Gossypium hirsutum*) which are heavily infested by the cotton aphid (*Aphis gossypii*) are sprayed with an active compound formulation of the desired concentration.

After 6 days, the kill in % is determined. 100% means that all the aphids have been killed; 0% means that no aphids have been killed.

In this test, for example, the following compound from the preparation examples showed an efficacy of 80% at an application rate of 4 ppm: 12

*Boophilus microplus*—Injection Test

Solvent: dimethyl sulphoxide

To produce a suitable preparation of active compound, 10 mg of active compound are mixed with 0.5 ml of solvent and the concentrate is diluted with solvent to the desired concentration.

1 µl of the active compound solution is injected into the abdomen of 5 engorged adult female cattle ticks (*Boophilus microplus*). The animals are transferred into dishes and kept in a climate-controlled room.

Efficacy is assessed after 7 days by laying of fertile eggs. Eggs which are not externally visibly fertile are stored in a climate-controlled cabinet until the larvae hatch after about 42 days. An efficacy of 100% means that none of the ticks has laid any fertile eggs; 0% means that all the eggs are fertile.

In this test, for example, the following compound from the preparation examples showed an efficacy of 100% at an application rate of 20 µg/animal: 52

*Cooperia curticei*—Test

Solvent: dimethyl sulphoxide

To produce a suitable preparation of active compound, 10 mg of active compound are mixed with 0.5 ml of dimethyl sulfoxide and the concentrate is diluted with "Ringer's solution" to the desired concentration.

Vessels containing the active compound preparation of the desired concentration are populated with about 40 nematode larvae (*Cooperia curticei*).

After 5 days, the kill in % is determined. 100% means that all the larvae have been killed; 0% means that none of the larvae have been killed.

In this test, for example, the following compounds of the preparation examples show an efficacy of 90% at an application rate of 20 ppm: 56, 65

In this test, for example, the following compounds of the preparation examples showed an efficacy of 80% at an application rate of 20 ppm: 57, 67, 76

*Haemonchus contortus*—Test

Solvent: dimethyl sulphoxide

To produce a suitable preparation of active compound, 10 mg of active compound are mixed with 0.5 ml of dimethyl sulfoxide and the concentrate is diluted with "Ringer's solution" to the desired concentration.

Vessels containing the active compound preparation of the desired concentration are populated with about 40 larvae of the red stomach worm (*Haemonchus contortus*).

After 5 days, the kill in % is determined. 100% means that all the larvae have been killed; 0% means that none of the larvae have been killed.

In this test, for example, the following compounds from the preparation examples showed an efficacy of 80% at an application rate of 20 ppm: 65, 67

*Meloidogyne incognita*—Test

Solvent: 125.0 parts by weight of acetone

To produce a suitable active compound preparation, 1 part by weight of active compound is mixed with the stated amount of solvent and the concentrate is diluted with water to the desired concentration.

Vessels are filled with sand, active compound solution, an egg/larvae suspension of the southern root-knot nematode (*Meloidogyne incognita*) and lettuce seeds. The lettuce seeds germinate and the plants develop. The galls develop on the roots.

After 14 days, the nematicidal efficacy in % is determined by the formation of galls. 100% means that no galls were found; 0% means that the number of galls on the treated plants corresponds to the untreated control.

In this test, for example, the following compounds from the preparation examples showed an efficacy of 90% at an application rate of 20 ppm: 99, 104

The invention claimed is:
1. A compound of formula (I),

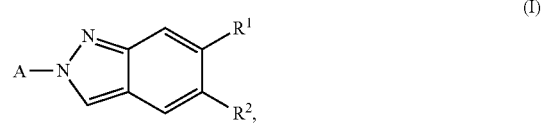

wherein
A represents an A radical selected from the group consisting of (A-b) and (A-f)

where the broken line represents the bond to the nitrogen atom of the bicycle of the formula (I),
$B^2$ represents hydrogen,
$R^1$ represents hydrogen,
$R^2$ c) represents a radical of the formula

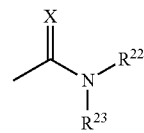

or $R^2$ d) represents a radical of the formula

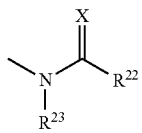

X represents oxygen,
$R^3$ represents $C_1$-$C_4$-alkyl,
$R^{22}$, if $R^2$ represents the radical c), represents a radical selected from the group consisting of $C_1$-$C_6$-alkyl, optionally cyano-substituted $C_3$-$C_6$-cycloalkyl, $C_1$-$C_6$-haloalkyl, $C_1$-$C_6$-alkoxy, $C_1$-$C_4$-alkylsulphonyl, $C_1$-$C_4$-alkylthio-$C_1$-$C_4$-alkyl, and di-($C_1$-$C_4$-alkyl)aminosulphonyl,
$R^{23}$, if $R^2$ represents the radical c), represents a radical selected from the group consisting of hydrogen and $C_1$-$C_6$-alkyl,
$R^{22}$, if $R^2$ represents the radical d), represents a radical selected from the group consisting of $C_1$-$C_4$-haloalkyl, $C_1$-$C_4$-alkylthio-$C_1$-$C_4$-alkyl, $C_1$-$C_4$-alkylsulphinyl-$C_1$-$C_4$-alkyl and $C_1$-$C_4$-alkylsulphonyl-$C_1$-$C_4$-alkyl,
$R^{23}$, if $R^2$ represents the radical d), represents a radical selected from the group consisting of hydrogen and $C_1$-$C_6$-alkyl, and
in the case $R^2$=d),
$R^{22}$ may also represent optionally halogen-, $C_1$-$C_6$-alkyl- and $C_1$-$C_6$-haloalkylsulphinyl-substituted phenyl; or
a compound of the formula (I) in which
A represents the A radical

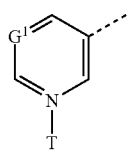 (A-a)

where the broken line represents the bond to the nitrogen atom of the bicycle of the formula (I),
$G^1$ represents N or C—$B^1$,
$B^1$ represents a radical from the group consisting of hydrogen and fluorine,
T represents an electron pair,
$R^1$ represents hydrogen,
$R^2$ aa) represents a radical from the group consisting of

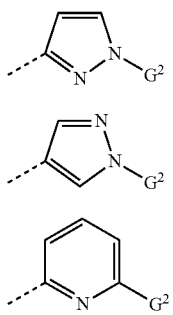

(B-3)

(B-4)

(B-21)

-continued

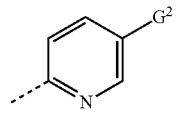

(B-22)

(B-35)

(B-36)

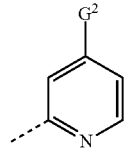

in which
$G^2$ represents a radical selected from the group consisting of halogen, $C_1$-$C_4$-alkylthio, $C_1$-$C_4$-alkyl sulphinyl, $C_1$-$C_4$-alkylsulphonyl, $C_1$-$C_4$-halo alkylthio, $C_1$-$C_4$-halo alkyl sulphinyl, $C_1$-$C_4$-haloalkylsulphonyl, $C_1$-$C_4$-alkylthio-$C_1$-$C_4$-alkyl, $C_1$-$C_4$-alkyl sulphinyl-$C_1$-$C_4$-alkyl, and $C_1$-$C_4$-alkylsulphonyl-$C_1$-$C_4$-alkyl, or
$R^2$ c) represents a radical of the formula

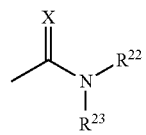

or
$R^2$ d) represents a radical of the formula

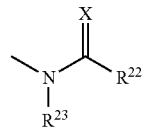

or
$R^2$ f) represents haloalkyl,
X represents oxygen,
$R^{22}$ represents a radical from the group consisting of (D-1) to (D-3)

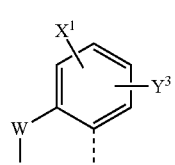

(D-1)

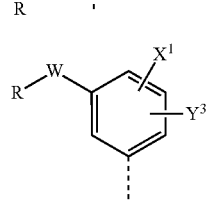

(D-2)

-continued (D-3)

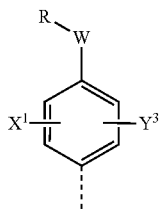

where the broken line represents the bond to the nitrogen atom in the radical c) or to the carbon atom in the radical d), R represents $C_1$-$C_4$-alkyl, in each case optionally mono-, di-, tri-, tetra- or pentasubstituted by fluorine, or chlorine, $X^1$ represents a radical selected from the group consisting of hydrogen, fluorine, chlorine, bromine, methyl and ethyl, W represents a radical from the group consisting of S, SO and $SO_2$, $Y^3$ represents a radical from the group consisting of hydrogen, fluorine, chlorine, bromine, methyl and ethyl.

2. A composition comprising at least one compound of formula (I) according to claim 1 and one or more customary extenders and/or surfactants.

3. A compound of formula (I) according to claim 1 or a composition thereof for controlling pests.

4. A compound of formula (I) according to claim 1, wherein

A represents (A-a)

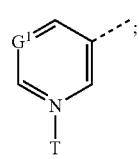

$G^1$ represents C—$B^1$;
$B^1$ represents hydrogen;
$B^2$ represents hydrogen;
T represents an electron pair;
$R^1$ represents hydrogen;
$R^2$ represents (B-4)

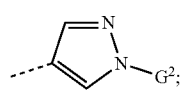

and
$G^2$ represents

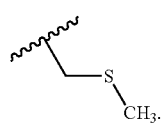

5. The compound of formula (I) according to claim 1, wherein

A represents (A-b)

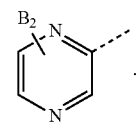

6. The compound of formula (I) according to claim 1, wherein

A represents (A-f)

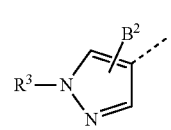

7. The compound of formula (I) according to claim 1, wherein

A represents (A-a)

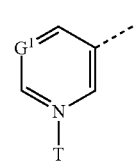

8. The compound of formula (I) according to claim 1, wherein $R^2$ represents

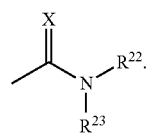

9. The compound of formula (I) according to claim 1, wherein $R^2$ represents

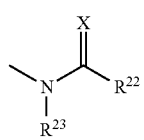

10. The compound of formula (I) according to claim 7, wherein $G^1$ represents N.

11. The compound of formula (I) according to claim 7, wherein $G^1$ represents C—$B^1$.

12. The compound of formula (I) according to claim 7, wherein $R^2$ represents

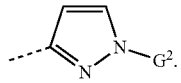

(B-3)

13. The compound of formula (I) according to claim 7, wherein $R^2$ represents

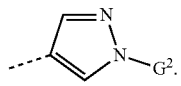

(B-4)

14. The compound of formula (I) according to claim 7, wherein $R^2$ represents

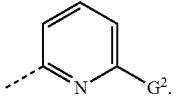

(B-21)

15. The compound of formula (I) according to claim 7, wherein $R^2$ represents

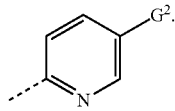

(B-22)

16. The compound of formula (I) according to claim 7, wherein $R^2$ represents

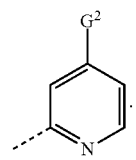

(B-35)

17. The compound of formula (I) according to claim 7, wherein $R^2$ represents

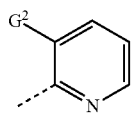

(B-36)

18. A method for controlling an animal pest comprising applying the compound of formula (I) according to claim 1 or a composition thereof to said pest and/or a habitat thereof.

* * * * *